US008124095B2

(12) United States Patent
Pardridge et al.

(10) Patent No.: US 8,124,095 B2
(45) Date of Patent: *Feb. 28, 2012

(54) FUSION PROTEINS FOR DELIVERY OF ERYTHROPOIETIN TO THE CNS

(75) Inventors: William M. Pardridge, Pacific Palisades, CA (US); Ruben J. Boado, Agoura Hills, CA (US)

(73) Assignee: ArmaGen Technologies, Inc., Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/688,842

(22) Filed: Jan. 15, 2010

(65) Prior Publication Data

US 2010/0261647 A1   Oct. 14, 2010

Related U.S. Application Data

(63) Continuation-in-part of application No. 11/245,546, filed on Oct. 7, 2005, and a continuation-in-part of application No. 12/323,232, filed on Nov. 25, 2008.

(51) Int. Cl.
A61K 39/44       (2006.01)
A61K 39/395    (2006.01)
A61K 38/18      (2006.01)
(52) U.S. Cl. ............... 424/178.1; 424/152.1; 424/143.1; 514/7.7; 514/17.7
(58) Field of Classification Search .................. None
See application file for complete search history.

(56) References Cited

U.S. PATENT DOCUMENTS

| | | | |
|---|---|---|---|
| 4,801,575 A | 1/1989 | Pardridge | |
| 4,902,505 A | 2/1990 | Pardridge et al. | |
| 5,154,924 A | 10/1992 | Friden | |
| 5,180,820 A | 1/1993 | Barde et al. | |
| 5,229,500 A | 7/1993 | Barde et al. | |
| 5,438,121 A | 8/1995 | Barde et al. | |
| 5,453,361 A | 9/1995 | Yancopoulos et al. | |
| 5,527,288 A | 6/1996 | Gross et al. | |
| 5,618,920 A | 4/1997 | Robinson et al. | |
| 5,656,284 A | 8/1997 | Balkin | |
| 5,672,683 A | 9/1997 | Friden et al. | |
| 5,693,762 A | 12/1997 | Queen et al. | |
| 5,824,782 A | 10/1998 | Holzer et al. | |
| 5,837,231 A | 11/1998 | Low et al. | |
| 5,848,991 A | 12/1998 | Gross et al. | |
| 5,977,307 A | 11/1999 | Friden et al. | |
| 5,997,501 A | 12/1999 | Gross et al. | |
| 6,041,775 A | 3/2000 | Century | |
| 6,060,069 A | 5/2000 | Hill et al. | |
| 6,153,190 A * | 11/2000 | Young et al. | ................ 424/141.1 |
| 6,165,783 A * | 12/2000 | Weiss et al. | .................... 435/325 |
| 6,284,262 B1 | 9/2001 | Place | |
| 6,287,792 B1 | 9/2001 | Pardridge et al. | |
| 6,322,808 B1 | 11/2001 | Trautman et al. | |
| 6,329,508 B1 | 12/2001 | Friden | |
| 6,348,210 B1 | 2/2002 | Gale | |
| 6,361,760 B1 | 3/2002 | Murata et al. | |
| 6,372,250 B1 | 4/2002 | Pardridge | |
| 6,375,975 B1 | 4/2002 | Modi | |
| 6,583,272 B1 | 6/2003 | Bailon | |
| 6,743,427 B1 | 6/2004 | Schenk | |
| 7,053,202 B2 | 5/2006 | O'Keefe et al. | |
| 7,078,376 B1 | 7/2006 | Thompson | |
| 7,226,758 B1 | 6/2007 | Lin et al. | |
| 7,294,704 B2 | 11/2007 | Simon et al. | |
| 7,309,687 B1 * | 12/2007 | Brines et al. | .................... 514/7.7 |
| 7,388,079 B2 | 6/2008 | Pardridge et al. | |
| 2002/0137684 A1 * | 9/2002 | Tchistiakova et al. | ........... 514/16 |
| 2002/0169109 A1 * | 11/2002 | Plata-Salaman et al. | ......... 514/2 |
| 2003/0129186 A1 | 7/2003 | Beliveau et al. | |
| 2003/0165853 A1 | 9/2003 | Pardridge et al. | |
| 2004/0072291 A1 | 4/2004 | Carr et al. | |
| 2004/0101904 A1 | 5/2004 | Pardridge et al. | |
| 2004/0102369 A1 | 5/2004 | Wu et al. | |
| 2005/0142141 A1 | 6/2005 | Pardridge | |
| 2007/0081992 A1 | 4/2007 | Pardridge et al. | |
| 2007/0082380 A1 | 4/2007 | Pardridge et al. | |
| 2007/0275882 A1 | 11/2007 | Meijer et al. | |
| 2008/0051564 A1 | 2/2008 | Pardridge et al. | |
| 2009/0068206 A1 | 3/2009 | Pardridge et al. | |
| 2009/0156498 A1 | 6/2009 | Pardridge et al. | |
| 2009/0238789 A1 | 9/2009 | Guyon et al. | |
| 2010/0172919 A1 * | 7/2010 | Grimm et al. | .............. 424/172.1 |
| 2011/0112018 A1 * | 5/2011 | Ehrenreich et al. | ............ 514/7.7 |

FOREIGN PATENT DOCUMENTS

WO    WO 00/15759 A1    3/2000

OTHER PUBLICATIONS

European search report dated Feb. 23, 2010 for Application No. 6825389.7.
International search report dated Sep. 7, 2010 for PCT Application No. US10-27882.
Office Action dated Oct. 12, 2010 U.S. Appl. No. 11/245,710.
Office Action dated Jul. 1, 2010 U.S. Appl. No. 11/245,546.
Pardridge, et al. Drug and gene targeting to the brain with molecular Trojan horses. Nat Rev Drug Discov. Feb. 2002;1(2):131-9.
Altschul et al. Basic Local Alignment Search Tool. J. Mol. Biol. 1990;215:403-410.
Altschul et al. Gapped BLAST and PSI-BLAST: a new generation of protein database search programs. Nucleic Acids Res. 1977;25:3389-3402.
Altschul, et al. Optimal sequence alignment using affine gap costs. Bulletin of. Mathematical Biology: 1986; 48(5-6):603-616.
Ausubel, et al. Current Protocols in Molecular Biology. John Wiley & Sons, New York, 1995 supplement.
Baloh, et al. Functional mapping of receptor specificity domains of glial cell line-derived neurotrophic factor (GDNF) family ligands and production of GFRalphal RET-specific agonists. J Biol Chem. Feb. 4, 2000;275(5):3412-20.
Batzer et al. Enhanced evolutionary PCR using oligonucleotides with inosine at the 3'-terminus. Nucleic Acid Res.1991;19:5081.

(Continued)

Primary Examiner — Daniel E Kolker
(74) Attorney, Agent, or Firm — Wilson Sonsini Goodrich & Rosati

(57) ABSTRACT

The invention provides compositions, methods, and kits for increasing transport of a neurotrophin (e.g., erythropoietin (EPO)) across the blood brain barrier while allowing its activity to remain substantially intact. The neurotrophin (e.g., EPO) is transported across the blood brain barrier via one or more endogenous receptor-mediated transport systems.

22 Claims, 42 Drawing Sheets

OTHER PUBLICATIONS

Boado et al. Fusion Antibody for Alzheimer's Disease with Bi-Directional Transport Across the Blood-Brain Barrier and Abeta Fibril Disaggregation. Bioconjug Chem. 2007;18(2):447-455.

Boado et al. Genetic engineering of a lysosomal enzyme fusion protein for targeted delivery across the human blood-brain barrier. Biotechnology and Bioengineering. 2008;99:475-484.

Carnicella, et al. GDNF is a fast-acting potent inhibitor of alcohol consumption and relapse. Proc Natl Acad Sci U S A. Jun. 10, 2008;105(23):8114-9.

Cassol, et al. Stability of dried blood spot specimens for detection of human immunodeficiency virus DNA by polymerase chain reaction. J Clin Microbiol. Dec. 1992;30(12):3039-42.

Eketjall, et al. Distinct structural elements in GDNF mediate binding to GFRalpha1 and activation of the GFRalpha1-c-Ret receptor complex. EMBO J. Nov. 1, 1999;18(21):5901-10.

Elliott, et al. Control of rHuEPO biological activity: the role of carbohydrate. Exp Hematol. Dec. 2004;32(12):1146-55.

Eslamboli et al. Continuous Low-Level Glial Cell Line-Derived Neurotrophic Factor Delivery Using Recombinant Adeno-Associated Viral Vectors Provides Neuroprotection and Induces Behavioral Recovery in a Primate Model of Parkinson's Disease. J. Neurosci. 2005;25:769-777.

European search report and search opinion dated Dec. 2, 2010 for Application No. 07841110.5.

Fu, et al. Neuroprotection in stroke in the mouse with intravenous erythropoietin-Trojan horse fusion protein. Brain Res. Jan. 19, 2011;1369:203-7. Epub Oct. 31, 2010.

Grasso, et al. Neuroprotection by erythropoietin administration after experimental traumatic brain injury. Brain Res. Nov. 28, 2007;1182:99-105.

Habgood, et al. Changes in blood-brain barrier permeability to large and small molecules following traumatic brain injury in mice. Eur J Neurosci. Jan. 2007;25(1):231-8.

Haisma, et al. Construction and characterization of a fusion protein of single-chain anti-CD20 antibody and human beta-glucuronidase for antibody-directed enzyme prodrug therapy. Blood. Jul. 1, 1998;92(1):184-90.

Henikoff et al. Amino acid substitution matrices from protein blocks. Proceedings of the National Academy of Sciences. 1992;89:10915.

Iwasaki, et al. Protective effect of interleukin-3 and erythropoietin on motor neuron death after neonatal axotomy. Neurol Res. Oct. 2002;24(7):643-6.

Karlin et al. Applications and statistics for multiple high-scoring segments in molecular sequences. Proc. Natl. Acad. Sci. USA. 1993;90:5873-5787.

Kastin et al. Glial cell line-derived neurotrophic factor does not enter normal mouse brain. Neuroscience Letters. 2003;340:239-241.

Kitagawa et al. Reduction of Ischemic Brain Injury by Topical Application of Glial Cell Line—Derived Neurotrophic Factor After Permanent Middle Cerebral Artery Occlusion in Rats. Stroke. 1998;29:1417-1422.

Kobayashi, et al. Intracerebral Infusion of Glial Cell Line-Derived Neurotrophic Factor Promotes Striatal Neurogenesis After Stroke in Adult Rats. Stroke. 2006;37:2361-2367.

Koehne, et al. Vascular endothelial growth factor and erythropoietin concentrations in cerebrospinal fluid of children with hydrocephalus. Childs Nerv Syst. Apr. 2002;18(3-4):137-41.

Lang et al. Randomized controlled trial of intraputamenal glial cell line-derived neurotrophic factor infusion in Parkinson disease. Annals of Neurology. 2006;59:459-466.

Lapchak et al. Glial cell line-derived neurotrophic factor attenuates behavioural deficits and regulates nigrostriatal dopaminergic and peptidergic markers in 6-hydroxydopamine-lesioned adult rats: comparison of intraventricular and intranigral delivery. Neuroscience. 1997;78:61-72.

Lin et al. GDNF: a glial cell line-derived neurotrophic factor for midbrain dopaminergic neurons. Science. 1993;260:1130-1132.

Lu et al. Cationic Liposome-Mediated GDNF Gene Transfer after Spinal Cord Injury. Journal of Neurotrauma. 2002;19:1081-1090.

Ma, et al. Erythropoietin protects PC12 cells from beta-amyloid(25-35)-induced apoptosis via PI3K/Akt signaling pathway. Neuropharmacology. May-Jun. 2009;56(6-7):1027-34.

Matis, et al. Erythropoietin in spinal cord injury. Eur Spine J. Mar. 2009;18(3):314-23.

Needleman et al. A general method applicable to the search for similarities in the amino acid sequence of two proteins. J. Mol. Biol. 1970;48:443-453.

Ng, et al. Predicting the effects of amino acid substitutions on protein function. Annual Review of Genomics and Human Genetics. 2006;7:61-80.

Office action dated Feb. 10, 2006 for U.S. Appl. No. 10/307,165.
Office action dated Feb. 22, 2006 for U.S. Appl. No. 10/307,276.
Office action dated Mar. 1, 2007 for U.S. Appl. No. 10/307,165.
Office action dated Mar. 18, 2011 for U.S. Appl. No. 12/574,571.
Office action dated Apr. 9, 2007 for U.S. Appl. No. 10/307,276.
Office action dated May 9, 2008 for U.S. Appl. No. 11/061,956.
Office action dated May 23, 2006 for U.S. Appl. No. 11/061,956.
Office action dated Jul. 19, 2006 for U.S. Appl. No. 10/307,276.
Office action dated Aug. 17, 2007 for U.S. Appl. No. 10/307,165.
Office action dated Aug. 18, 2006 for U.S. Appl. No. 10/307,165.
Office action dated Oct. 29, 2007 for U.S. Appl. No. 10/307,276.
Office action dated Nov. 13, 2007 for U.S. Appl. No. 11/061,956.
Office action dated Dec. 21, 2006 for U.S. Appl. No. 11/061,956.
Office Action dated Mar. 7, 2011 U.S. Appl. No. 12/558,348.

Ohtsuka et al. An alternative approach to deoxyoligonucleotides as hybridization probes by insertion of Deoxyinosine at Ambiguous Codon Positions. J. Biol. Chem. 1985;260:2605-2608.

Pardridge. Drug Targeting to the Brain. Pharmaceutical Research. 2007;24:1733-1744.

Patel et al. Intraputamenal infusion of glial cell line-derived neurotrophic factor in PD: A two-year outcome study. Annals of Neurology. 2005;57:298-302.

Pearson et al. Improved Tools for Biological Sequence Comparison. Proc. Nat'l Acad. Sci. USA. 1988;85:2444-2448.

Pearson. Rapid and sensitive sequence comparison with FASTP and FASTA. Meth. Enzymol. 1990;183:63-98.

Pregi, et al. TNF-alpha-induced apoptosis is prevented by erythropoietin treatment on SH-SY5Y cells. Exp Cell Res. Feb. 1, 2009;315(3):419-31. Epub Nov. 20, 2008.

Reiber, et al. Protein transfer at the blood cerebrospinal fluid barrier and the quantitation of the humoral immune response within the central nervous system. Clin Chim Acta. Mar. 30, 1987;163(3):319-28.

Rossolini et al. Use of deoxyinosine-containing primers vs degenerate primers for polymerase chain reaction based on ambiguous sequence information. Mol. Cell. Probes. 1994;8(2):91-98.

Sakanaka, et al. In vivo evidence that erythropoietin protects neurons from ischemic damage. Proc Natl Acad Sci U S A. Apr. 14, 1998;95(8):4635-40.

Sellers. On the theory and computation of evolutionary distances. SIAM Journal on Applied Mathematics. 1974;26:787.

Smith, et al. Comparison of Biosequences. Adv. Appl. Math. 1981 1 482-489.

Um, et al. A "classical" homodimeric erythropoietin receptor is essential for the antiapoptotic effects of erythropoietin on differentiated neuroblastoma SH-SY5Y and pheochromocytoma PC-12 cells. Cell Signal. Mar. 2007;19(3):634-45.

Whetstone, et al. Blood-spinal cord barrier after spinal cord injury: relation to revascularization and wound healing. J Neurosci Res. Oct. 15, 2003;74(2):227-39.

Wiesenhofer et al. Glial cell line-derived neurotrophic factor (GDNF) and its receptor (GFR-α1l) are strongly expressed in human gliomas. Acta Neuropathol. (Berl). 2000;99:131-137.

Xue, et al. Intrastriatal administration of erythropoietin protects dopaminergic neurons and improves neurobehavioral outcome in a rat model of Parkinson's disease. Neuroscience. May 25, 2007;146(3):1245-58.

Al, et al., 2003. Intraputamenal Infusion of GDNF in Aged Rhesus Monkeys: Distribution and Dopaminergic Effects. The Journal of Comparative Neurology 461: 250-261.

Airavaara, et al. Effects of repeated morphine on locomotion, place preference and dopamine in heterozygous glial cell line-derived neurotrophic factor knockout mice. Genes Brain Behav. Apr. 2007;6(3):287-98.

Albayrak, et al. 1997. Effect of transient focal ischemia on blood-brain barrier permeability in the rat: Correlation to Cell Injury. Acta Neuropathol 94: 158-163.

Alberts, et al. Molecular Biology of the Cell. 3rd Edition. Garland Publishing Inc. New York. 1994; pp. 1206-1207.

Bachis, et al. 2003. Brain-Derived Neurotropic Factor Inhibits Human Immunodeficiency Virus-1/gp 120-Mediated Cerebellar Granule Cell Death by Preventing gp 120 Internalization. The Journal of Neuroscience 23 (13): 5712-5722.

Barth et al. Boron neutron capture therapy of brain tumors: an emerging therapeutic modality. Neurosurgery. Mar. 1999;44(3):433-50; discussion 450-1.

Beck, et al. 1994. Brain-Derived Neurotropic Factor Protects Against Ischemic Cell Damage in Rat Hippocampus. Journal of Cerebral Blood Flow and Metabolism 14: 689-692.

Bifare, et al. 2005. Brain-Derived Neurotropic Factor Protects against Multiple Forms of Brain Injury in Bacterial Meningitis. The Journal of Infectious Diseases 191: 40- 45.

Boado et al, Genetic engineering, expression, and activity of a fusion protein of a human neurotrophin and a molecular Trojan horse for delivery across the human blood-brain barrier. Biotechnology and Bioengineering. 2007;97:1376-1386.

Boado et al. Humanization of anti-human insulin receptor antibody for drug targeting across the human blood-brain barrier. Biotechnology and Bioengineering. 2007;96:381-391.

Boado, et al. Engineering and expression of a chimeric transferrin receptor monoclonal antibody for blood-brain barrier delivery in the mouse. Biotechnol Bioeng. Mar. 1, 2009;102(4):1251-8.

Boado, et al. GDNF fusion protein for targeted-drug delivery across the human blood-brain barrier. Biotechnol Bioeng. Jun. 1, 2008;100(2):387-96.

Brummell, et al. Probing the combining site of an anti-carbohydrate antibody by saturation-mutagenesis: role of the heavy-chain CDR3 residues. Biochemistry. 1993; 32(4):1180-7.

Buchli, et al. Inhibition of Nogo: a key strategy to increase regeneration, plasticity and functional recovery of the lesioned central nervous system. Ann Med. 2005;37(8):556-67.

Burgess, et al. Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.

Chen, et al. In vitro scanning saturation mutagenesis of all the specificity determining residues in an antibody binding site. Protein Engineering. 1999; vol. 12, No. 4, 349-356.

Cheng, et al. 1997. Marked Age-dependent Neuroprotection by Brain-derived Neurotropic Factor Against Neonatal Hypoxic-Ischemic Brain Injury. Annals of Neurology 41 (4): 521-529.

Cheng, et al. 2004. Neuroprotection for Ischemic Stroke: Two Decades of Success and Failure. The Journal of the American Society for Experimental Neuro Therapeutics 1: 36-45.

Coloma, et al. 1999. Transport Across the Primate Blood-Brain Barrier of a Genetically Engineered Chimeric Monoclonal Antibody to the Human Insulin Receptor. Pharmaceutical Research 17 (3): 266-274.

Coloma, et al. Design and production of novel tetravalent bispecificl antibodies. Nat Biotechnol. Feb. 1997;15(2):159-63.

Coloma, et al. The hinge as a spacer contributes to covalent assembly and is required for function of IgG. J Immunol. Jan. 15, 1997;158(2):733-40.

Cowen, et al. 2004. Neuropeptides: implications for alcoholism. Journal of Neurochemistry 89: 273-285.

Dawson, et al. 2001. A comparative assessment of the efficacy and side-effect liability of the neuroprotective compounds in experimental stroke. Brain Research 892: 344-350.

Deguchi, et al. Retention of biologic activity of human epidermal growth factor following conjugation to a blood-brain barrier drug delivery vector via an extended poly(ethylene glycol) linker. Bioconjug Chem. Jan.-Feb. 1999;10(1):32-7.

Duchnowska, et al. Central nervous system metastases in breast cancer patients administered trastuzumab. Cancer Treat Rev. Jun. 2005;31(4):312-8.

Duffy, et al. 1987. Blood-brain barrier transcytosis of insulin in developing rabbits. Brain Research 420: 32-38.

Ferber, D. Bridging the blood-brain barrier: new methods improve the odds of getting drugs to the brain cells that need them. PLoS Biol. Jun. 2007;5(6):e169: 1191-1194.

Fillebeen, et al. Receptor-mediated transcytosis of lactoferrin through the blood-brain barrier. J Biol Chem. Mar. 12, 1999;274(11):7011-7017.

Forough, et al. Differential transforming abilities of non-secreted and secreted forms of human fibroblast growth factor-1. J Biol Chem. Feb. 5, 1993;268(4):2960-8.

Friden, et al. Blood-brain barrier penetration and in vivo activity of an NGF conjugate. Science. Jan. 15, 1993;259(5093):373-377.

Gennaro, 2000. Remington: The Science and Practice of Pharmacy. 20 ed.

Gillies, et al. Bi-functional cytokine fusion proteins for gene therapy and antibody-targeted tratment of cancer. 2002, Cancer Immunology and Immunotherapy, vol. 51, pp. 449-460.

Green-Sadan, et al. Transplantation of glial cell line-derived neurotrophic factor-expressing cells into the striatum and nucleus accumbens attenuates acquisition of cocaine self-administration in rats. Eur J Neurosci. Oct. 2003;18(7):2093-8.

He, et al. Autoregulation of glial cell line-derived neurotrophic factor expression: implications for the long-lasting actions of the anti-addiction drug, Ibogaine. FASEB J. Nov. 2006;20(13):E1820-E1827; 2420-2422.

He, et al. Glial cell line-derived neurotrophic factor mediates the desirable actions of the anti-addiction drug ibogaine against alcohol consumption. J Neurosci. Jan. 19, 2005;25(3):619-28.

Hetman, et al. 1999. Neuroprotection by Brain-derived Neurotropic Factor Is Mediated by Extracellular Signal-regulated Kinase and Phoshatidylinositol 3-Kinase. The Journal of Biological Chemistry 274 (32): 22569-22580.

Hoshaw, et al. 2005. Central administration of IGF-I and BDNF leads to long-lasting antidepressant-like effects. Brain Research 1037: 204-208.

http://www.amgen.com/ (accessed Dec. 16, 2005).

http://www.idecpharm.com/site/home.html (accessed Dec. 16, 2005).

Ibanez, et al. An extended surface of binding to Trk tyrosine kinase receptors in NGF and BDNF allows the engineering of a multifunctional pan-neurotrophin. EMBO J. Jun. 1993;12(6):2281-93.

Ibanez, Structure-function relationships in the neurotrophin family. J Neurobiol. Nov. 1994;25(11):1349-61.

International search report dated Feb. 27, 2009 for PCT Application No. US08/71121.

International search report dated Jul. 1, 2008 for PCT Application No. US06/38587.

International Search Report dated Sep. 16, 2008 for PCT Application no. US2007/76316.

Jefferies, et al. Analysis of lymphopoietic stem cells with a monoclonal antibody to the rat transferrin receptor. Immunology. Feb. 1985;54(2):333-41.

Jethwa, et al. 2004. Neuromedin U has a physiological role in the regulation of food intake and partially mediates the effects of leptin. American Journal of Physiology-Endocrinology and Metabolism 289: E301-E305.

Jiang, et al. 2005. BDNF Variation and Mood Disorders: A Novel Functional Promoter Polymorphism and Va166Met are Associated with Anxiety but Have Opposing Effects. Neuropsychopharmacology 30: 1353-1361.

Kido, et al. 2000. Neuroprotective effects of brain-derived neurotropic factor in eyes with NMDA-induced neuronal death. Brain Research 884: 59-67.

Kim, et al. 2003. Continuous Brain-derived Neurotropic Factor (BDNF) Infusion After Methylprednisolone Treatment in Severe Spinal Cord Injury. Journal of Korean Medical Science 19: 113-122.

Krewson, et al. 1995. Distribution of nerve growth factor following direct delivery to brain interstitium. Brain Research 680: 196-206.

Kurihara, et al. 1999. Imaging Brain Tumors by Targeting Peptide Radiopharmaceuticals through the Blood-Brain Barrier. Cancer Research 59: 6159-6163.

Lai, et al. Structural determinants of Trk receptor specificities using BDNF-based neurotrophin chimeras. J Neurosci Res. Dec. 1, 1996;46(5):618-29.

Lazar, et al. Transforming growth factor alpha: mutation of aspartic acid 47 and leucine 48 results in different biological activities. Mol Cell Biol. Mar. 1988;8(3):1247-52.

Lee, et al. 2002. Imaging Brain Amyloid of Alzheimer Disease in Vivo in Transgenic Mice With an All Peptide Radiopharmaceutical. Journal of Cerebral Blood Flow and Metabolism 22: 223-231.

Lewin, B. Genes IV. Oxford University Press. 1990. Page 810.

Lin, et al. Structure-function relationships in glucagon: properties of highly purified des-His-1-, monoiodo-, and (des-Asn-28, Thr-29)(homoserine lactone-27)-glucagon. Biochemistry. Apr. 22, 1975;14(8):1559-63.

Marvin, et al. Recombinant approaches to IgG-like bispecific antibodies. Acta Pharmacol Sin. Jun. 2005;26(6):649-58.

Mcgrath, et al. Bifunctional fusion between nerve growth factor and a transferrin receptor antibody. J Neurosci Res. Jan. 15, 1997;47(2):123-33.

McLendon et al. Radiotoxicity of systemically administered 211At-labeled human/mouse chimeric monoclonal antibody: a long-term survival study with histologic analysis. Int J Radiat Oncol Biol Phys. Sep. 1, 1999;45(2):491-9.

Menzies, et al. 1993. Contributions of ions and albumin to the formations and resolution of ischemic brain edema. Journal of Neurosurgery 78: 257-266.

Messer, et al. Role for GDNF in biochemical and behavioral adaptations to drugs of abuse. Neuron. Apr. 2000;26(1):247-57.

Mori, et al. 2004. Differential expression patterns of TrkB ligands in the macaque monkey brain. Developmental Neuroscience 15: 2507-2511.

Nutt, et al. 2003. Randomized, double-blind trial of glial cell line-derived neurotropic factor (GDNF) in PD. Neurology 60: 69-73.

Office Action dated Jan. 15, 2008 U.S. Appl. No. 11/245,710.
Office Action dated Jan. 15, 2009 U.S. Appl. No. 11/841,623.
Office Action dated Jan. 23, 2009 U.S. Appl. No. 11/245,546.
Office Action dated Apr. 13, 2007 U.S. Appl. No. 11/245,710.
Office Action dated Jun. 3, 2008 U.S. Appl. No. 11/245,710.
Office Action dated Jun. 17, 2009 U.S. Appl. No. 11/841,541.
Office Action dated Jul. 2, 2008 U.S. Appl. No. 11/245,546.
Office Action dated Jul. 2, 2009U.S. Appl. No. 11/245,710.
Office Action dated Jul. 31, 2009 U.S. Appl. No. 12/179,806.
Office Action dated Aug. 20, 2009 U.S. Appl. No. 12/323,232.
Office Action dated Sep. 20, 2007 U.S. Appl. No. 11/245,710.
Office Action dated Sep. 24, 2009 U.S. Appl. No. 11/841,623.
Office Action dated Oct. 15, 2007 U.S. Appl. No. 11/245,710.
Office Action dated Oct. 20, 2009 U.S. Appl. No. 11/245,546.
Office Action dated Oct. 30, 2009 U.S. Appl. No. 11/841,592.
Office Action dated Nov. 8, 2007 U.S. Appl. No. 11/245,546.
Office Action dated Nov. 10, 2008 U.S. Appl. No. 11/245,710.
Office Action dated Nov. 13, 2006 U.S. Appl. No. 11/245,710.
Office Action dated Dec. 16, 2009 U.S. Appl. No. 11/841,541.
Office Action dated Feb. 2, 2010 U.S. Appl. No. 11/245,710.
Office Action dated Mar. 10, 2010 U.S. Appl. No. 12/179,806.
Office Action dated Mar. 26, 2010 U.S. Appl. No. 12/323,232.
Office Action dated Mar. 26, 2010 U.S. Appl. No. 11/841,594.

Padlan, et al. Identification of specificity-determining residues in antibodies. FASEB J. 1995; 9(1):133-9.

Pardridge, 2001. Brain drug targeting: The future of brain drug development. Cambridge University Press.

Pardridge, 2002. Neurotrophins, neuroprotection and the blood-brain barrier. Current Opinion in Investigational Drugs 3 (12): 1753-1757.

Pardridge, 2003. Blood-Brain Barrier Drug Targeting: the Future of Brain Drug Development. Molecular Interventions 3: 90-105.

Pardridge, 2005. The Blood-Brain Barrier and Neurotherapeutics. NeuroRx: The Journal of the American Society for Experimental NeuroTherapeutics 2 (1): 1-2.

Pardridge, 2001. Neuroprotection in stroke: is it time to consider large-molecule drugs? Drug Discovery Today 6: 751-753.

Pardridge, 2005. The Blood-Brain Barrier: Bottleneck in Brain Drug Development. NeuroRx: The Journal of the American Society for Experimental NeuroTherapeutics 2: 3-14.

Pardridge, et al. 1987. Human Blood-Brain Barrier Transferrin Receptor. Metabolism 36: 892-895.

Pardridge, et al. 1993. Transport of Human Recombinant Brain-Derived Neurotrophic Factor (BDNF) Through the Rat Blood-Brain Barrier in Vivo Using Vector-Mediated Peptide Drug Delivery. Pharmaceutical Research 11 (5): 738-746.

Pardridge, et al. 1995. Human Insulin Receptor Monoclonal Antibody Undergoes High Affinity Binding to Human Brain Capillaries in Vitro and Rapid Transcytosis Through the Blood-Brain Barrier in Vivo in the Primate. Pharmaceutical Research 12.(6); 807-816.

Pardridge, et al. 1998, Combined Use of Carboxyl-Directed Protein Pegylation and Vector-Mediated Blood-Brain Barrier Drug Delivery System Optimizes Brain Uptake of Brain-Derived Neurotrophic Factor Following Intravenous Administration. Pharmaceutical Research 15 (4): 576-582.

Park, et al. Production and characterization of fusion proteins containing transferrin and nerve growth factor. J Drug Target. 1998;6(1):53-64.

Pencea, et al. 2001. Infusion of Brain-Derived Neurotrophic Factor into the Lateral Ventricle of the Adult Rat Leads to New Neurons in the Parenchyma of the Striatum, Septum, Thalamus, and Hypothalamus. The Journal of Neuroscience 21 (17): 6706-6717.

Penichet, et al. An antibody-avidin fusion protein specific for the transferrin receptor serves as a delivery vehicle for effective brain targeting: initial applications in anti-HIV antisense drug delivery to the brain. J Immunol. Oct. 15, 1999;163(8):4421-4426.

Preston, et al. 1997. Evidence for pore-like opening of the blood-brain barrier following forebrain ischemia in rats. Brain Research 761: 4-10.

Raghavan, et al. Analysis of the pH dependence of the neonatal Fc receptor/immunoglobulin G interaction using antibody and receptor variants. Biochemistry. Nov. 14, 1995;34(45):14649-57.

Ratliff-Schaub, et al. 2005. Randomized controlled trial of transdermal secretion on behavior of children with autism. Autism 9 (3): 256-265.

Robinson, et al. 1999. The structures of the neurotrophin 4 homodimer and the brain-derived neurotrophic factor / neurotrophin 4 heterodimer reveal a common Trk-binding site. Protein Science 8: 2589-2597.

Rudikoff, et al. Single amino acid substitution altering antigen-binding specificity. Proc Natl Acad Sci U S A. Mar. 1982;79(6):1979-83.

Ruiz-Leon, et al. 2003. Induction of Tyrosine Kinase Receptor B by Retinoic Acid Allows Brain-Derived Neurotrophic Factor-Induced Amyloid Precursor Protein Gene Expression in Human SHSY5Y Neuroblastoma Cells. Neuroscience 120: 1019-1026.

Sakane, et al. 1997. Carboxyl-directed Pegylation of Brain-derived Neurotrophic Factor Markedly Reduces Systemic Clearance with Minimal Loss of Biologic Activity. Pharmaceutical Research 14 (8): 1085-1091.

Schabitz, et al. 1997. Intraventricular Brain-Derived Neurotrophic Factor Reduces Infarct Size After Focal Cerebral Ischemia in Rats. Journal of Cerebral Blood Flow and Metabolism 17: 500-506.

Schlachetzki, et al. Expression of the neonatal Fc receptor (FcRn) at the blood-brain barrier. J Neurochem. Apr. 2002;81(1):203-6.

Schwartz, et al. A superactive insulin: [B10-aspartic acid]insulin(human). Proc Natl Acad Sci U S A. Sep. 1987;84(18):6408-11.

Selmayr, et al. Induction of tumor immunity by autologous B lymphoma cells expressing a genetically engineered idiotype. Gene Ther. May 1999;6(5):778-84.

Shin, et al. Transferrin-antibody fusion proteins are effective in brain targeting, Proceedings of the Natinal Academy of Sciences, 1995. vol. 92, pp. 2820-2824.

Siren, et al., Erythropoetin prevents neuronal apoptosis after cerebral ischemia and metabolic stress. Proc Natl Acad Sci U S A. Mar. 27, 2001;98(7):4044-9.

Skolnick, et al. From genes to protein structure and function: novel applications of computational approaches in the genomic era. Trends Biotechnol. Jan. 2000;18(1):34-9. Review.

Spina, et al. 1992. Brain-Derived Neurotrophic Factor Protects Dopamine Neurons Against 6-Hydroxydopamine and N-Methyl-4-Phenylpyridinium Ion Toxicity: Involvement of the Glutathione System. Journal of Neurochemistry 59 (1): 99-106.

Strauss, et al. 2005. Brain-derived neurotrophic factor variants are associated with childhood-onset mood disorder: confirmation in a Hungarian sample. Molecular Psychiartry 10: 861-867.

Takahashi, et al. 1991. Inhibition of cell growth and tumorigenesis of human glioblastoma cells by a neutralizing antibody against human basic fibroblast growth factor. Federation of European Biochemical Societies 288 (1,2): 65-71.

The BDNF Study Group (Phase III). 1999. A controlled trial of recombinant methionyl human BDNF in ALS. Neurology 52: 1427-1433.

Thoenen, et al. 2002. Neurotrophins: from enthusiastic expectations through sobering experiences to rational therapeutic approaches. Nature Neuroscience Supplement 5: 1046-1050.

Triguero et al. Capillary depletion method for quantification of blood-brain barrier transport of circulating peptides and plasma proteins. J Neurochem. 1990; 54(6):1882-8.

Tsukahara, et al. 1994. The Role of Brain-derived Neurotrophic Factor in Transient Forebrain Ischemia in the Rat Brain. Neurosurgery 34 (2): 323-331.

Weich, et al. Interleukin-3/erythropoietin fusion proteins: in vitro effects on hematopoietic cells. Exp Hematol. May 1993;21(5):647-55.

Wu, et al. 1999. Neuroprotection with noninvasive neurotrophin delivery to the brain. Proceedings of the National Academy of Sciences of the USA: Neurobiology 96: 254-259.

Wu, et al. Drug targeting of a peptide radiopharmaceutical through the primate blood-brain barrier in vivo with a monoclonal antibody to the human insulin receptor. J Clin Invest. Oct. 1, 1997;100(7):1804-12.

Yamashita, et al. 1997. Post-Occlusion Treatment with BDNF Reduces Infarct Size in a Model of Permanent Occlusion of the Middle Cerebral Artery in Rat. Metabolic Brain Disease 12 (4): 271-280.

Yan, et al. 1994. Distribution of Intracerebral Ventricularly Administered Neurotrophins in Rat Brain and Its Correlation with Trk Receptor Expression. Experimental Neurology 127: 23-36.

Yan, et al. Enduring vulnerability to reinstatement of methamphetamine-seeking behavior in glial-cell-line-derived neurotrophic factor mutant mice. FASEB J. Jul. 2007;21(9):1994-2004.

Yip, et al. Three-dimensional structural interactions of insulin and its receptor. J Biol Chem. Jul. 25, 2003;278(30):27329-32.

Zhang, et al. 2001. Conjugation of brain-derived neurotrophic factor to a blood-brain barrier drug targeting system enables neuroprotection in regional brain ischemia following intrvenous injection of the neurotrophin. Brain Research 889: 49-56.

Zhang, et al. 2001. Neuroprotection in Transient Focal Brain Ischemia After Delayed Intravenous Administration of Brain-Derived Neurotrophic Factor Conjugated to a Blood-Brain Barrier Drug Targeting System. Stroke 32: 1378-1384.

Zhang, et al. 2003. Global Non-Viral Gene Transfer to the Primate Brain Following Intravenous Administration. Molecular Therapy 7 (1): 11-18.

Zhang, et al. Mediated efflux of IgG molecules from brain to blood across the blood-brain barrier. J Neuroimmunol. Mar. 1, 2001;114(1-2):168-72.

Brines, et al. Erythropoetin crosses the blood-brain barrier to protect against experimental brain injury, Proc Natl Acad Sci USA. 2000; 97:10526-10531.

Juul, et al. Erythropoietin concentrations in cerebrospinal fluid of nonhuman primates and fetal sheep following high-dose recombinant erythropoietin, Biol. Neonate. 2004;85:138-144.

Dreier, et al. Recombinant immunocytokines targeting the mouse transferrin receptor: construction and biological activities. Bioconjug Chem. Jul.-Aug. 1998;9(4):482-9.

International search report and written opinion dated Apr. 8, 2011 for PCT Application No. US11/21418.

Martell, et al. Efficacy of transferrin receptor-targeted immunotoxins in brain tumor cell lines and pediatric brain tumors. Cancer Res. Mar. 15, 1993;53(6):1348-53.

Notice of Allowance dated Aug. 9, 2011 for U.S. Appl. No. 11/245,710.
Office action dated Feb. 16, 2011 for U.S. Appl. No. 11/893,281.
Office action dated Feb. 16, 2011 for U.S. Appl. No. 12/150,983.
Office action dated Apr. 6, 2011 for U.S. Appl. No. 11/245,710.
Office action dated May 12, 2010 for U.S. Appl. No. 11/893,281.
Office action dated Sep. 15, 2010 for U.S. Appl. No. 12/150,983.
Office action dated Oct. 13, 2009 for U.S. Appl. No. 11/893,281.
Office action dated Jun. 27, 2011 for U.S. Appl. No. 11/245,710.

Sariola, et al. Novel functions and signalling pathways for GDNF. J Cell Sci. Oct. 1, 2003;116(Pt 19):3855-62.

Shanafelt, et al. Identification of critical amino acid residues in human and mouse granulocyte-macrophage colony-stimulating factor and their involvement in species specificity. J Biol Chem. Jul. 25, 1991;266(21):13804-10.

Wang, et al. Identification of the key amino acids of glial cell line-derived neurotrophic factor family. receptor alpha1 involved in its biological function. J Biol Chem. Jan. 2, 2004;279(1):109-16.

Office action dated Oct. 18, 2011 for U.S. Appl. No. 11/245,546.
Office action dated Dec. 14, 2011 for U.S. Appl. No. 12/574,571.
Notice of Allowance dated Oct. 31, 2011 for U.S. Appl. No. 11/245,546.

\* cited by examiner

Engineering of intron-based expression vector for fusion protein heavy chain

Figure 2

Engineering of vBDNF

A. 5'-end linker (Table 2)

pHTBS01 [Xho BsiWI Bpl BamH — hBDNF]

BamHI
BpII
T4 ligase

Clone 412 (5'-engineered) [XhoI BsiWI BpII NruI-BamHI — vBDNF]

B. 3'-end linker (Table 2)

XhoI
BsiWI
T4 ligase

Clone 413 (5'- & 3'-engineered) [XhoI-NruI BsiWI BpII NruI-BamHI — vBDNF]

NruI

Insertion of vBDNF at SspI in clone 405

Figure 4
Engineered cDNA and amino acid sequence corresponding to the end of CH3, CH3-vBDNF linker and vBDNF, of the fusion protein
(S

Figure 5
Nucleotide Sequence of Fusion Protein Heavy Chain Gene Derived from Clone 416
(2711nt)
(SEQ ID NO. 23)

```
TAGTCTTTCTCTTCAGTGACAAACACAGACATAGGATATTCCACCATGGAATGCAGCTGGGTCATGCTCTTCCTCCTGTCAGGAACTGCAGG
TGTCCATTGCCAGGTTCAGCTGCAGCAGTCTGGACCTGAGCTGGTGAAGCCTGGGGCTTTAGTGAAGATATCCTGCAAGGCTTCTGGTTACA
CCTTCACAAACTACGATATACACTGGGTGAAGCAGAGGCCTGGACAGGGACTTGAGTGGATTGGATGGATTTATCCTGGAGATGGTAGTACT
AAGTACAATGAGAAATTCAAGGGCAAGGCCACACTGACTGCAGACAAATCCTCCAGCACAGCCTACATGCACCTCAGCAGCCTGACTTCTGA
GAAATCTGCAGTCTATTTCTGTGCAAGAGAGTGGGCTTACTGGGGCCAAGGGACTCTGGTCACTGTCTCTGCAGCTAGCACCAAGGGCCCAT
CGGTCTTCCCCCTGGCACCCTCCTCCAAGAGCACCTCTGGGGGCACAGCGGCCCTGGGCTGCCTGGTCAAGGACTACTTCCCCGAACCGGTG
ACGGTGTCGTGGAACTCAGGCGCCCTGACCAGCGGCGTGCACACCTTCCCGGCTGTCCTACAGTCCTCAGGACTCTACTCCCTCAGCAGCGT
GGTGACCGTGCCCTCCAGCAGCTTGGGCACCCAGACCTACATCTGCAACGTGAATCACAAGCCCAGCAACACCAAGGTGGACAAGAAAGTTG
GTGAGAGGCCAGCACAGGGAGGGAGGGTGTCTGCTGGAAGCCAGGCTCAGCGCTCCTGCCTGGACGCATCCCGGCTATGCAGCCCCAGTCCA
GGGCAGCAAGGCAGGCCCCGTCTGCCTCTTCACCCGGAGGCCTCTGCCCGCCCCACTCATGCTCAGGGAGAGGGTCTTCTGGCTTTTTCCCC
AGGCTCTGGGCAGGCACAGGCTAGGTGCCCCTAACCCAGGCCCTGCACACAAAGGGGCAGGTGCTGGGCTCAGACCTGCCAAGAGCCATATC
CGGGAGGACCCTGCCCCTGACCTAAGCCCACCCCAAAGGCCAAACTCTCCACTCCCTCAGCTCGGACACCTTCTCTCCTCCCAGATTCCAGT
AACTCCCAATCTTCTCTCTGCAGAGCCCAAATCTTGTGACAAAACTCACACATGCCCACCGTGCCCAGGTAAGCCAGCCCAGGCCTCGCCCT
CCAGCTCAAGGCGGGACAGGTGCCCTAGAGTAGCCTGCATCCAGGGACAGGCCCCAGCCGGGTGCTGACACGTCCACCTCCATCTCTTCCTC
AGCACCTGAACTCCTGGGGGGACCGTCAGTCTTCCTCTTCCCCCCAAAACCCAAGGACACCCTCATGATCTCCCGGACCCCTGAGGTCACAT
GCGTGGTGGTGGACGTGAGCCACGAAGACCCTGAGGTCAAGTTCAACTGGTACGTGGACGGCGTGGAGGTGCATAATGCCAAGACAAAGCCG
CGGGAGGAGCAGTACAACAGCACGTACCGTGTGGTCAGGGTCCTCACCGTCCTGCACCAGGACTGGCTGAATGGCAAGGAGTACAAGTGCAA
GGTCTCCAACAAAGCCCTCCCAGCCCCCATCGAGAAAACCATCTCCAAAGCCAAAGGTGGGACCCGTGGGGTGCGAGGGCCACATGGACAGA
GGCCGGCTCGGCCCACCCTCTGCCCTGAGAGTGACCGCTGTACCAACCTCTGTCCCTACAGGGCAGCCCCGAGAACCACAGGTGTACACCCT
GCCCCCATCCCGGGATGAGCTGACCAAGAACCAGGTCAGCCTGACCTGCCTGGTCAAAGGCTTCTATCCCAGCGACATCGCCGTGGAGTGGG
AGAGCAATGGGCAGCCGGAGAACAACTACAAGACCACGCCTCCCGTGCTGGACTCCGACGGCTCCTTCTTCCTCTACAGCAAGCTCACCGTG
GACAAGAGCAGGTGGCAGCAGGGGAACGTCTTCTCATGCTCCGTGATGCATGAGGCTCTGCACAACCACTACACGCAGAAGAGCCTCTCCCT
GTCTCCGGGTAAATCGAGTATGCACTCTGACCCTGCCCGTCGAGGTGAGCTGAGCGTGTGTGACAGTATTAGTGAGTGGGTAACGGCGGCAG
ACAAAAAGACTGCAGTGGACATGTCGGGCGGGACGGTCACAGTCCTTGAAAAGGTCCCTGTATCAAAAGGCCAACTGAAGCAATACTTCTAC
GAGACCAAGTGCAATCCCATGGGTTACACAAAAGAAGGCTGCAGGGGCATAGACAAAAGGCATTGGAACTCCCAGTGCCGAACTACCCAGTC
GTACGTGCGGGCCCTTACCATGGATAGCAAAAAGAGAATTGGCTGGCGATTCATAAGGATAGACACTTCTTGTGTATGTACATTGACCATTA
AAAGGTGATCGATTTTGCGACGGCCGGCAAGCCCCCGCTCCCCGGGCTCTCGCGGTCGCACGAGGATGCTTGGCACGTACCCCCTGTACATA
CTTCCCGGGCGCCCAGCATGGAAATAAAGCACCCAGCGCTGCCCTGGGCCCCTGCGAGACTGTGATGGTTCTTTCCACGGGTCAGGCCGAGT
CTGAGGCCTGAGTGGCATGAGGGAGGCAGAGCGGGTCCCACTGTCCCCACACTGGCCCAGGCTGTGCAGGTGTGCCTGGGCCGCCTAGGGTG
GGGCTCAGCCAGGGGCTGCCCTCGGCAGGGTGGGGATTTGCC
```

Figure 6

Amino Acid Sequence of Heavy Chain of Fusion Protein (SEQ ID NO. 24)

NH2-
MECSWVMLFLLSGTAGVHCQVQLQQSGPELVKPGALVKISCKASGYTFTNYDIHWVKQRPGQGLE
WIGWIYPGDGSTKYNEKFKGKATLTADKSSSTAYMHLSSLTSEKSAVYFCAREWAYWGQGTLVTV
SAASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFLFPP
KPKDTLMISRTPEVTCVVVDVSHEDPEVKFNWYVDGVEVHNAKTKPREEQYNSTYRVVȒVLTVLH
QDWLNGKEYKCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMHEALHNHYTQKS
LSLSPGKSSMHSDPARRGELSVCDSISEWVTAADKKTAVDMSGGTVTVLEKVPVSKGQLKQYFYE
TKCNPMGYTKEGCRGIDKRHWNSQCRTTQSYVRALTMDSKKRIGWRFIRIDTSCVCTLTIKR-
COOH

Figure 7

Amino acid sequence of the fusion protein heavy chain

(SEQ. ID NO. 25)

Signal peptide:
MECSWVMLFLLSGTAGVHC

FR1:
QVQLQQSGPELVKPGALVKISCKAS

CDR1:
GYTFTNYDIH

FR2:
WVKQRPGQGLEWIG

CDR2:
WIYPGDGSTKYNEKFKG

FR3:
KATLTADKSSSTAYMHLSSLTSEKSAVYFCAR

CDR3:
EWAY

FR4:
WGQGTLVTVSA

CH1:
ASTKGPSVFPLAPSSKSTSGGTAALGCLVKDYFPEPVTVSWNSGALTSGVHTFPAVLQSSGLYSLSSVVTVPSSSLGTQTYICNVNHKPSNT
KVDKKV

Hinge:
EPKSCDKTHTCP

CH2:
PCPAPELLGGPSVFLFPPKPKDTLMISRTPEVTCVVVDVSHEDPEVKFNWYVDGVEVHNAKTKPREEQYNSTYRVVSVLTVLHQDWLNGKEY
KCKVSNKALPAPIEKTISKAK

CH3:
GQPREPQVYTLPPSRDELTKNQVSLTCLVKGFYPSDIAVEWESNGQPENNYKTTPPVLDSDGSFFLYSKLTVDKSRWQQGNVFSCSVMHEAL
HNHYTQKSLSLSPGK linker:
SSM vBDNF:
HSDPARRGELSVCDSISEWVTAADKKTAVDMSGGTVTVLEKVPVSKGQLKQYFYETKCNPMGYTKEGCRGIDKRHWNSQCRTTQSYVRALTM
DSKKRIGWRFIRIDTSCVCTLTIKR

Engineering of intronless pCD-HC-120 expression

Figure 9A

Nucleotide sequence of fusion protein heavy chain cDNA in clone 422a

(SEQ ID NO. 26)

ATTCCACCATGGAATGCAGCTGGGTCATGCTCTTCCTCCTGTCAGGAACTGCAGGTGTCCATTGCCAGGTTCAGCTGCAGCAGTCTGGACCT
GAGCTGGTGAAGCCTGGGGCTTTAGTGAAGATATCCTGCAAGGCTTCTGGTTACACCTTCACAAACTACGATATACACTGGGTGAAGCAGAG
GCCTGGACAGGGACTTGAGTGGATTGGATGGATTTATCCTGGAGATGGTAGTACTAAGTACAATGAGAAATTCAAGGGCAAGGCCACACTGA
CTGCAGACAAATCCTCCAGCACAGCCTACATGCACCTCAGCAGCCTGACTTCTGAGAAATCTGCAGTCTATTTCTGTGCAAGAGAGTGGGCT
TACTGGGGCCAAGGGACTCTGGTCACTGTCTCTGCAGCTAGCACCAAGGGCCCATCGGTCTTCCCCCTGGCACCCTCCTCCAAGAGCACCTC
TGGGGGCACAGCGGCCCTGGGCTGCCTGGTCAAGGACTACTTCCCCGAACCGGTGACGGTGTCGTGGAACTCAGGCGCCCTGACCAGCGGCG
TGCACACCTTCCCGGCTGTCCTACAGTCCTCAGGACTCTACTCCCTCAGCAGCGTGGTGACCGTGCCCTCCAGCAGCTTGGGCACCCAGACC
TACATCTGCAACGTGAATCACAAGCCCAGCAACACCAAGGTGGACAAGAAAGTTGAGCCCAAATCTTGTGACAAAACTCACACATGCCCACC
GTGCCCAGCACCTGAACTCCTGGGGGGACCGTCAGTCTTCCTCTTCCCCCCAAAACCCAAGGACACCCTCATGATCTCCCGGACCCCTGAGG
TCACATGCGTGGTGGTGGACGTGAGCCACGAAGACCCTGAGGTCAAGTTCAACTGGTACGTGGACGGCGTGGAGGTGCATAATGCCAAGACA
AAGCCGCGGGAGGAGCAGTACAACAGCACGTACCGTGTGGTCAGCGTCCTCACCGTCCTGCACCAGGACTGGCTGAATGGCAAGGAGTACAA
GTGCAAGGTCTCCAACAAAGCCCTCCCAGCCCCCATCGAGAAAACCATCTCCAAAGCCAAAGGGCAGCCCCGAGAACCACAGGTGTACACCC
TGCCCCCATCCCGGGATGAGCTGACCAAGAACCAGGTCAGCCTGACCTGCCTGGTCAAAGGCTTCTATCCCAGCGACATCGCCGTGGAGTGG
GAGAGCAATGGGCAGCCGGAGAACAACTACAAGACCACGCCTCCCGTGCTGGACTCCGACGGCTCCTTCTTCCTCTACAGCAAGCTCACCGT
GGACAAGAGCAGGTGGCAGCAGGGGAACGTCTTCTCATGCTCCGTGATGCATGAGGCTCTGCACAACCACTACACGCAGAAGAGCCTCTCCC
TGTCTCCGGGTAAATCGAGTATGCACTCTGACCCTGCCCGTCGAGGTGAGCTGAGCGTGTGTGACAGTATTAGTGAGTGGGTAACGGCGGCA
GACAAAAAGACTGCAGTGGACATGTCGGGCGGGACGGTCACAGTCCTTGAAAAGGTCCCTGTATCAAAAGGCCAACTGAAGCAATACTTCTA
CGAGACCAAGTGCAATCCCATGGGTTACACAAAAGAAGGCTGCAGGGGCATAGACAAAAGGCATTGGAACTCCCAGTGCCGAACTACCCAGT
CGTACGTGCGGGCCCTTACCATGGATAGCAAAAAGAGAATTGGCTGGCGATTCATAAGGATAGACACTTCTTGTGTATGTACATTGACCATT
AAAAGGTGA

<u>ATT</u>: ½ SspI
CCACC: Kozak

Figure 9B
Deduced amino acid sequence of fusion protein heavy chain cDNA in clone 422a
(SEQ ID NO. 27 and 28)

```
atggaatgcagctgggtcatgctcttcctcctgtcaggaactgca
 M   E   C   S   W   V   M   L   F   L   L   S   G   T   A
ggtgtccattgccaggttcagctgcagcagtctggacctgagctg
 G   V   H   C   Q   V   Q   L   Q   Q   S   G   P   E   L
gtgaagcctggggcttlagtgaagatatcctgcaaggcttctggt
 V   K   P   G   A   L   V   K   I   S   C   K   A   S   G
tacaccttcacaaactacgatatacactgggtgaagcagaggcct
 Y   T   F   T   N   Y   D   I   H   W   V   K   Q   R   P
ggacagggacttgagtggattggatggatttatcctggagatggt
 G   Q   G   L   E   W   I   G   W   I   Y   P   G   D   G
agtactaagtacaatgagaaattcaagggcaaggcacactgact
 S   T   K   Y   N   E   K   F   K   G   K   A   T   L   T
gcagacaaatcctccagcacagcctacatgcacctcagcagcctg
 A   D   K   S   S   T   A   Y   M   H   L   S   S   L
acttctgagaaatctgcagtctatttctgtgcaagagagtgggct
 T   S   E   K   S   A   V   Y   F   C   A   R   E   W   A
tactggggccaagggactctggtcactgtctctgcagctagcacc
 Y   W   G   Q   G   T   L   V   T   V   S   A   A   S   T
aagggcccatcggtcttccccctggcaccctcctccaagagcacc
 K   G   P   S   V   F   P   L   A   P   S   S   K   S   T
tctgggggcacagcggccctgggctgcctggtcaaggactacttc
 S   G   G   T   A   A   L   G   C   L   V   K   D   Y   F
cccgaaccggtgacggtgtcgtggaactcaggcgccctgaccagc
 P   E   P   V   T   V   S   W   N   S   G   A   L   T   S
ggcgtgcacaccttcccggctgtcctacagtcctcaggactctac
 G   V   H   T   F   P   A   V   L   Q   S   S   G   L   Y
tccctcagcagcgtggtgaccgtgcctccagcagcttgggcacc
 S   L   S   S   V   V   T   V   P   S   S   S   L   G   T
cagacctacatctgcaacgtgaatcacaagcccagcaacaccaag
 Q   T   Y   I   C   N   V   N   H   K   P   S   N   T   K
gtggacaagaaagttgagcccaaatcttgtgacaaaactcacaca
 V   D   K   K   V   E   P   K   S   C   D   K   T   H   T
tgcccaccgtgcccagcacctgaactcctgggggaccgtcagtc
 C   P   P   C   P   A   P   E   L   L   G   G   P   S   V
ttcctcttccccccaaaacccaaggacaccctcatgatctcccgg
 F   L   F   P   P   K   P   K   D   T   L   M   I   S   R
acccctgaggtcacatgcgtggtggtggacgtgagccacgaagac
 T   P   E   V   T   C   V   V   V   D   V   S   H   E   D
cctgaggtcaagttcaactggtacgtggacggcgtggaggtgcat
 P   E   V   K   F   N   W   Y   V   D   G   V   E   V   H
aatgccaagacaaagccgcgggaggagcagtacaacagcacgtac
 N   A   K   T   K   P   R   E   E   Q   Y   N   S   T   Y
cgtgtggtcagcgtcctcaccgtcctgcaccaggactggctgaat
 R   V   V   S   V   L   T   V   L   H   Q   D   W   L   N
ggcaaggagtacaagtgcaaggtctccaacaaagcccccagcc
 G   K   E   Y   K   C   K   V   S   N   K   A   L   P   A
cccatcgagaaaaccatctccaaagccaaagggcagccccgagaa
 P   I   E   K   T   I   S   K   A   K   G   Q   P   R   E
ccacaggtgtacaccctgcccccatcccgggatgagctgaccaag
 P   Q   V   Y   T   L   P   P   S   R   D   E   L   T   K
aaccaggtcagcctgacctgcctggtcaaaggcttctatcccagc
 N   Q   V   S   L   T   C   L   V   K   G   F   Y   P   S
gacatcgccgtggagtgggagagcaatgggcagccggagaacaac
 D   I   A   V   E   W   E   S   N   G   Q   P   E   N   N
tacaagaccacgcctcccgtgctggactccgacggctccttcttc
 Y   K   T   T   P   P   V   L   D   S   D   G   S   F   F
ctctacagcaagctcaccgtggacaagagcaggtggcagcagggg
 L   Y   S   K   L   T   V   D   K   S   R   W   Q   Q   G
aacgtcttctcatgctccgtgatgcatgaggctctgcacaaccac
 N   V   F   S   C   S   V   M   H   E   A   L   H   N   H
tacacgcagaagagcctctccctgtctccgggtaaatcgagtatg
 Y   T   Q   K   S   L   S   L   S   P   G   K   S   S   M
cactctgaccctgccgtcgaggtgagctgagcgtgtgtgacagt
 H   S   D   P   A   R   R   G   E   L   S   V   C   D   S
attagtgagtgggtaacggcggcagacaaaaagactgcagtggac
 I   S   E   W   V   T   A   A   D   K   K   T   A   V   D
atgtcgggcgggacggtcacagtccttgaaaggtccctgtatca
 M   S   G   G   T   V   T   V   L   E   K   V   P   V   S
aaaggccaactgaagcaatacttctacgagaccaagtgcaatccc
 K   G   Q   L   K   Q   Y   F   Y   E   T   K   C   N   P
atgggttacacaaaagaaggctgcaggggcatagacaaaaggcat
 M   G   Y   T   K   E   G   C   R   G   I   D   K   R   H
tggaactcccagtgccgaactaccccagtcgtacgtgcgggccctt
 W   N   S   Q   C   R   T   T   Q   S   Y   V   R   A   L
accatggatagcaaaaagagaattggctggcgattcataaggata
 T   M   D   S   K   K   R   I   G   W   R   F   I   R   I
gacacttcttgtgtatgtacattgaccattaaaaggtga  1757
 D   T   S   C   V   C   T   L   T   I   K   R   *
```

Engineering of intronless pCD-LC-1 expression

Figure 11A

Nucleotide sequence of fusion protein light chain cDNA in clone 423a

(SEQ ID NO. 29)

GATATCACCATGGAGACAGACACACTCCTGCTATGGCTCTTGTTGCTCATGTTTCCAGGTACCAGATG
TGACATCCAGATGACCCAGTCTCCATCCTCCTTATCTGCCTCTCTGGGAGAAAGAGTCAGTCTCACTT
GTCGGGCAAGTCAGGACATTGGTGGTAACTTATACTGGCTTCAGCAGGGACCAGATGGAACTATTAA
ACGCCTGATCTACGCCACATCCAGTTTAGATTCTGGTGTCCCCAAAAGGTTCAGTGGCAGTAGGTCTG
GGTCAGATTATTCTCTCACCATCAGCAGCCTTGAGTCTGAAGATTTTGTAGACTATTACTGTCTACAG
TATTCTAGTTCTCCGTGGACGTTCGGTGGAGCGACAAAGATGGAAATAAAACGAACTGTGGCTGCAC
CATCTGTCTTCATCTTCCCGCCATCTGATGAGCAGTTGAAATCTGGAACTGCCTCTGTTGTGTGCCTGC
TGAATAACTTCTATCCCAGAGAGGCCAAAGTACAGTGGAAGGTGGATAACGCCCTCCAATCGGGTAA
CTCCCAGGAGAGTGTCACAGAGCAGGACAGCAAGGACAGCACCTACAGCCTCAGCAGCACCCTGAC
GCTGAGCAAAGCAGACTACGAGAAACACAAAGTCTACGCCTGCGAAGTCACCCATCAGGGCCTGAG
CTCGCCCGTCACAAAGAGCTTCAACAGGGGAGAGTGTTAG

GATATC: EcoRV
CACC: Kozak

Figure 11B

Deduced amino acid sequence of fusion protein light chain in clone 423a

(SEQ ID NO. 30 and 31)

```
atggagacagacacactcctgctatggctcttgttgctcatgttt
 M  E  T  D  T  L  L  L  W  L  L  L  M  F
ccaggtaccagatgtgacatccagatgacccagtctccatcctcc
 P  G  T  R  C  D  I  Q  M  T  Q  S  P  S  S
ttatctgcctctctgggagaaagagtcagtctcacttgtcgggca
 L  S  A  S  L  G  E  R  V  S  L  T  C  R  A
agtcaggacattggtggtaacttatactggcttcagcagggacca
 S  Q  D  I  G  G  N  L  Y  W  L  Q  Q  G  P
gatggaactattaaacgcctgatctacgccacatccagtttagat
 D  G  T  I  K  R  L  I  Y  A  T  S  S  L  D
tctggtgtccccaaaaggttcagtggcagtaggtctgggtcagat
 S  G  V  P  K  R  F  S  G  S  R  S  G  S  D
tattctctcaccatcagcagccttgagtctgaagattttgtagac
 Y  S  L  T  I  S  S  L  E  S  E  D  F  V  D
tattactgtctacagtattctagttctccgtggacgttcggtgga
 Y  Y  C  L  Q  Y  S  S  S  P  W  T  F  G  G
gcgacaaagatggaaataaaacgaactgtggctgcaccatctgtc
 A  T  K  M  E  I  K  R  T  V  A  A  P  S  V
ttcatcttcccgccatctgatgagcagttgaaatctggaactgcc
 F  I  F  P  P  S  D  E  Q  L  K  S  G  T  A
tctgttgtgtgcctgctgaataacttctatcccagagaggccaaa
 S  V  V  C  L  L  N  N  F  Y  P  R  E  A  K
gtacagtggaaggtggataacgccctccaatcgggtaactcccag
 V  Q  W  K  V  D  N  A  L  Q  S  G  N  S  Q
gagagtgtcacagagcaggacagcaaggacagcacctacagcctc
 E  S  V  T  E  Q  D  S  K  D  S  T  Y  S  L
agcagcaccctgacgctgagcaaagcagactacgagaaacacaaa
 S  S  T  L  T  L  S  K  A  D  Y  E  K  H  K
gtctacgcctgcgaagtcacccatcagggcctgagctcgcccgtc
 V  Y  A  C  E  V  T  H  Q  G  L  S  S  P  V
acaaagagcttcaacaggggagagtgttag
 T  K  S  F  N  R  G  E  C  *
```

Engineering of fusion protein tandem expression vector

Figure 13A
Nucleotide sequence of the fusion protein heavy chain (HC) and light chain (LC) genes, and the DHFR gene in the tandem vector
(SEQ ID NO. 32)

HC gene (forward)

```
CGATGTACGGGCCAGATATACGCGTTGACATTGATTATTGACTAGTTATTAATAGTAATCAATTACGGGGTCATTAGTTCATAGCCCATATATGGAGTTCCGCGTTACATAACTT
ACGGTAAATGGCCCGCCTGGCTGACCGCCCAACGACCCCCGCCCATTGACGTCAATAATGACGTATGTTCCCATAGTAACGCCAATAGGGACTTTCCATTGACGTCAATGGGTGG
AGTATTTACGGTAAACTGCCCACTTGGCAGTACATCAAGTGTATCATATGCCAAGTACGCCCCCTATTGACGTCAATGACGGTAAATGGCCCGCCTGGCATTATGCCCAGTACAT
GACCTTATGGGACTTTCCTACTTGGCAGTACATCTACGTATTAGTCATCGCTATTACCATGGTGATGCGGTTTTGGCAGTACATCAATGGGCGTGGATAGCGGTTTGACTCACGG
GGATTTCCAAGTCTCCACCCCATTGACGTCAATGGGAGTTTGTTTTGGCACCAAAATCAACGGGACTTTCCAAAATGTCGTAACAACTCCGCCCATTGACGCAAATGGGCGGTA
GGCGTGTACGGTGGGAGGTCTATATAAGCAGAGCTCTCTGGCTAACTAGAGAACCCACTGCTTACTGGCTTATCGAAATTAATACGACTCACTATAGGGAGACCCTTGCTAGCGA
TATTCCACCATGGAATGCAGCTGGGTCATGCTCTTCCTCCTGTCAGGAACTGCAGGTGTCCATTGCCAGGTTCAGCTGCAGCAGTCTGGACCTGAGCTGGTGAAGCCTGGGGCTT
TAGTGAAGATATCCTGCAAGGCTTCTGGTTACACCTTCACAAACTACGATATACACTGGGTGAAGCAGAGGCCTGGACAGGGACTTGAGTGGATTGGATGGATTTATCCTGGAGA
TGGTAGTACTAAGTACAATGAGAAATTCAAGGGCAAGGCCACACTGACTGCAGACAAATCCTCCAGCACAGCCTACATGCACCTCAGCAGCCTGACTTCTGAGAAATCTGCAGTC
TATTTCTGTGCAAGAGAGTGGGCTTACTGGGGCCAAGGGACTCTGGTCACTGTCTCTGCAGCTAGCACCAAGGGCCCATCGGTCTTCCCCCTGGCACCCTCCTCCAAGAGCACCT
CTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCT
ACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGAC
AAGAAAGTTGAGCCCAAATCTTGTGACAAAACTCACACATGCCCACCGTGCCCAGCACCTGAACTCCTGGGGGGACCGTCAGTCTTCCTCTTCCCCCCAAAACCCAAGGACACCC
TCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGAC
AAAGCCGCGGGAGGAGCAGTACAACAGCACGTACCGTGTGGTCAGCGTCCTCACCGTCCTGCACCAGGACTGGCTGAATGGCAAGGAGTACAAGTGCAAGGTCTCCAACAAAGCC
CTCCCAGCCCCCATCGAGAAAACCATCTCCAAAGCCAAAGGGCAGCCCCGAGAACCACAGGTGTACACCCTGCCCCCATCCCGGGATGAGCTGACCAAGAACCAGGTCAGCCTGA
CCTGCCTGGTCAAAGGCTTCTATCCCAGCGACATCGCCGTGGAGTGGGAGAGCAATGGGCAGCCGGAGAACAACTACAAGACCACGCCTCCCGTGCTGGACTCCGACGGCTCCTT
CTTCCTCTACAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCC
CTGTCTCCGGGTAAATCGAGTATGCACTCTGACCCTGCCCGTCGAGGTGAGCTGAGCGTGTGTGACAGTATTAGTGAGTGGGTAACGGCGGCAGACAAAAAGACTGCAGTGGACA
TGTCGGGCGGGACGGTCACAGTCCTTGAAAAGGTCCCTGTATCAAAAGGCCAACTGAAGCAATACTTCTACGAGACCAAGTGCAATCCCATGGGTTACACAAAAGAAGGCTGCAG
GGGCATAGACAAAAGGCATTGGAACTCCCAGTGCCGAACTACCCAGTCGTACGTGCGGGCCCTTACCATGGATAGCAAAAAGAGAATTGGCTGGCGATTCATAAGGATAGACACT
TCTTGTGTATGTACATTGACCATTAAAAGGTGAGGATCCCTCGAGCATGCATCTAGAGGGCCCTATTCTATAGTGTCACCTAAATGCTAGAGCTCGCTGATCAGCCTCGACTGTG
CCTTCTAGTTGCCAGCCATCTGTTGTTTGCCCCTCCCCCGTGCCTTCCTTGACCCTGGAAGGTGCCACTCCCACTGTCCTTTCCTAATAAAATGAGGAAATTGCATCGCATTGTC
TGAGTAGGTGTCATTCTATTCTGGGGGGTGGGGTGGGGCAGGACAGCAAGGGGGAGGATTGGGAAGACAATAGCAGGCATGCTGGGGATGCGGTGGGCTCTATGGCTTCTGAGGC
GGAAAGAACCAGTGGCGGTAATACGGTTATCCACAGAATCAGGGGATAACGCAGGAAAGAACATGTGAGCAAAAGGCCAGCAAAAGGCCAGGAACC
```

LC gene (forward)

```
GAATTCGATATTCCATACACATACTTCTGTGTTCCTTTGAAAGCTGGACTTTTGCAGGCTCCACCAGACCTCTCTAGATCAATTCCTTTGCCTAATTTCGCTTACAATTTACGCG
CGCGTTGACATTGATTATTGACTAGTTATTAATAGTAATCAATTACGGGGTCATTAGTTCATAGCCCATATATGGAGTTCCGCGTTACATAACTTACGGTAAATGGCCCGCCTGG
CTGACCGCCCAACGACCCCCGCCCATTGACGTCAATAATGACGTATGTTCCCATAGTAACGCCAATAGGGACTTTCCATTGACGTCAATGGGTGGAGTATTTACGGTAAACTGCC
CACTTGGCAGTACATCAAGTGTATCATATGCCAAGTACGCCCCCTATTGACGTCAATGACGGTAAATGGCCCGCCTGGCATTATGCCCAGTACATGACCTTATGGGACTTTCCTA
CTTGGCAGTACATCTACGTATTAGTCATCGCTATTACCATGGTGATGCGGTTTTGGCAGTACATCAATGGGCGTGGATAGCGGTTTGACTCACGGGGATTTCCAAGTCTCCACCC
CATTGACGTCAATGGGAGTTTGTTTTGGCACCAAAATCAACGGGACTTTCCAAAATGTCGTAACAACTCCGCCCATTGACGCAAATGGGCGGTAGGCGTGTACGGTGGGAGGTC
TATATAAGCAGAGCTCTCTGGCTAACTAGAGAACCCACTGCTTACTGGCTTATCGAAATTAATACGACTCACTATAGGGAGACCCAAGCTGGCTAGCGATATCACCATGGAGACA
GACACACTCCTGCTATGGCTCTTGTTGCTCATGTTTCCAGGTACCAGATGTGACATCCAGATGACCCAGTCTCCATCCTCCTTATCTGCCTCTCTGGGAGAAAGAGTCAGTCTCA
CTTGTCGGGCAAGTCAGGACATTGGTGGTAACTTATACTGGCTTCAGCAGGGACCAGATGGAACTATTAAACGCCTGATCTACGCCACATCCAGTTTAGATTCTGGTGTCCCCAA
AAGGTTCAGTGGCAGTAGGTCTGGGTCAGATTATTCTCTCACCATCAGCAGCCTTGAGTCTGAAGATTTTGTAGACATTATTACTGTCTACAGTATTCTAGTTCTCCGTGGACGTTC
GGTGGAGCGACAAAGATGGAAATAAAACGAACTGTGGCTGCACCATCTGTCTTCATCTTCCCGCCATCTGATGAGCAGTTGAAATCTGGAACTGCCTCTGTTGTGTGCCTGCTGA
ATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCT
CAGCAGCACCCTGACGCTGAGCAAAGCAGACTACGAGAAACACAAAGTCTACGCCTGCGAAGTCACCCATCAGGGCCTGAGCTCGCCCGTCACAAAGAGCTTCAACAGGGGAGAG
TGTTAGCTCGAGTCTAGAGGGCCCGTTTAAACCCGCTGATCAGCCTCGACTGTGCCTTCTAGTTGCCAGCCATCTGTTGTTTGCCCCTCCCCCGTGCCTTCCTTGACCCTGGAAG
```

Figure 13B

```
GTGCCACTCCCACTGTCCTTTCCTAATAAAATGAGGAAATTGCATCGCATTGTCTGAGTAGGTGTCATTCTATTCTGGGGGGTGGGGTGGGGCAGGACAGCAAGGGGGAGGATTG
GGAAGACAATAGCAGGCATGCTGGGGATGCGGTGGGCTCTATGGCTTCTGAGGCGGAAAGAACCAGTGGCGGTAATACGGTTATCCACAGAATCAGGGGATAACGAAATGAGGAC
TTAACCTGTGGAAATATCAAGCTT
```

LC gene-DHFR gene linker
```
GCGGCCGCGTA
```

DHFR gene (reverse)
```
TCGACGCTCTCCCTTATGCGACTCCTGCATTAGGAAGCAGCCCAGTAGTAGGTTGAGGCCGTTGAGCACCGCCGCCGCAAGGAATGGTGCATGCAAGGAGATGGCGCCCAACAGT
CCCCCGGCCACGGGGCCTGCCACCATACCCACGCCGAAACAAGCGCTCATGAGCCCGAAGTGGCGAGCCCGATCTTCCCCATCGGTGATGTCGGCGATATAGGCGCCAGCAACCG
CACCTGTGGCGCCGGTGATGCCGGCCACGATGCGTCCGGCGTAGAGGATCTCTGACGGAAGGAAAGAAGTCAGAAGGCAAAAACGAGAGTAACTCCACAGTAGCTCCAAATTCTT
TATAAGGGTCAATGTCCATGCCCCAAAGCCACCCAAGGCACAGCTTGGAGGCTTGAACAGTGGGACATGTACAAGAGATGATTAGGCAGAGGTGAAAAAGTTGCATGGTGCTGGT
GCGCAGACCAATTTATGCCTACAGCCTCCTAATACAAAGACCTTTAACCTAATCTCCTCCCCCAGCTCCTCCCAGTCCTTAAACACACAGTCTTTGAAGTAGGCCTCAAGGTCGG
TCGTTGACATTGCTGGGAGTCCAAGAGTCCTCTTATGTAAGACCTTGGGCAGGATCTGATGGGCGTTCACGGTGGTCTCCATGCAACGTGCAGAGGTGAAGCGAAGTGCACACGG
ACCGGCAGATGAGAAGGCACAGACGGGGAGACCGCGTAAAGAGAGGTGCGCCCCGTGGTCGGCTGGAACGGCAGACGGAGAAGGGGACGAGAGAGTCCCAAGCGGCCCCGCGAGG
GGTCGTCCGCGGGATTCAGCGCCGACGGGACGTAAACAAAGGACGTCCCGCGAAGGATCTAAAGCCAGCAAAAGTCCCATGGTCTTATAAAAATGCATAGCTTTAGGAGGGGAGC
AGAGAACTTGAAAGCATCTTCCTGTTAGTCTTTCTTCTCGTAGACTTCAAACTTATACTTGATGCCTTTTTCCTCCTGGACCTCAGAGAGGACGCCTGGGTATTCTGGGAGAAGT
TTATATTTCCCCAAATCAATTTCTGGGAAAAACGTGTCACTTTCAAATTCCTGCATGATCCTTGTCACAAAGAGTCTGAGGTGGCCTGGTTGATTCATGGCTTCCTGGTAAACAG
AACTGCCTCCGACTATCCAAACCATGTCTACTTTACTTGCCAATTCCGGTTGTTCAATAAGTCTTAAGGCATCATCCAAACTTTTGGCAAGAAAATGAGCTCCTCGTGGTGGTTC
TTTGAGTTCTCTACTGAGAACTATATTAATTCTGTCCTTTAAAGGTCGATTCTTCTCAGGAATGGAGAACCAGGTTTTCCTACCCATAATCACCAGATTCTGTTTACCTTCCACT
GAAGAGGTTGTGGTCATTCTTTGGAAGTACTTGAACTCGTTCCTGAGCGGAGGCCAGGGTCGGTCTCCGTTCTTGCCAATCCCCATATTTTGGGACACGGCGACGATGCAGTTCA
ATGGTCGAACCATGATGGCAAATTCTAGAATCGATAAGCTTTTTGCAAAAGCCTAGGCCTCCAAAAAAGCCTCCTCACTACTTCTGGAATAGCTCAGAGGCCGAGGCGGCCTCGG
CCTCTGCATAAATAAAAAAAATTAGTCAGCCATGGGCGGAGAATGGGCGGAACTGGGCGGAGTTAGGGGCGGGATGGGCGGAGTTAGGGGCGGGACTATGGTTGCTGACTAATT
GAGATGCAGATCTCGAGCTAGCACGCGTAAGAGCTCGGTACCTCCCTAC
```

Figure 14
Nucleotide and deduced amino acid sequence of heavy chain of fusion protein cDNA and protein encoded by tandem vector
(SEQ ID NO. 33 and 34)

```
atggaatgcagctgggtcatgctcttcctcctgtcaggaactgca
 M  E  C  S  W  V  M  L  F  L  L  S  G  T  A
ggtgtccattgccaggttcagctgcagcagtctggacctgagctg
 G  V  H  C  Q  V  Q  L  Q  Q  S  G  P  E  L
gtgaagcctggggcttagtgaagatatcctgcaaggcttctggt
 V  K  P  G  A  L  V  K  I  S  C  K  A  S  G
tacaccttcacaaactacgatatacactgggtgaagcagaggcct
 Y  T  F  T  N  Y  D  I  H  W  V  K  Q  R  P
ggacagggacttgagtggattggatggatttatcctggagatggt
 G  Q  G  L  E  W  I  G  W  I  Y  P  G  D  G
agtactaagtacaatgagaaattcaagggcaaggccacactgact
 S  T  K  Y  N  E  K  F  K  G  K  A  T  L  T
gcagacaaatcctccagcacagcctacatgcacctcagcagcctg
 A  D  K  S  S  S  T  A  Y  M  H  L  S  S  L
acttctgagaaatctgcagtctatttctgtgcaagagagtgggct
 T  S  E  K  S  A  V  Y  F  C  A  R  E  W  A
tactgggccaagggactctggtcactgtctctgcagctagcacc
 Y  W  G  Q  G  T  L  V  T  V  S  A  A  S  T
aagggcccatcggtcttccccctggcaccctcctccaagagcacc
 K  G  P  S  V  F  P  L  A  P  S  S  K  S  T
tctgggggcacagcggccctgggctgcctggtcaaggactacttc
 S  G  G  T  A  A  L  G  C  L  V  K  D  Y  F
cccgaaccggtgacggtgtcgtggaactcaggcgccctgaccagc
 P  E  P  V  T  V  S  W  N  S  G  A  L  T  S
ggcgtgcacaccttcccggctgtcctacagtcctcaggactctac
 G  V  H  T  F  P  A  V  L  Q  S  S  G  L  Y
tccctcagcagcgtggtgaccgtgcctccagcagcttgggcacc
 S  L  S  S  V  V  T  V  P  S  S  S  L  G  T
cagacctacatctgcaacgtgaatcacaagcccagcaacaccaag
 Q  T  Y  I  C  N  V  N  H  K  P  S  N  T  K
gtggacaagaaagttgagcccaaatcttgtgacaaaactcacaca
 V  D  K  K  V  E  P  K  S  C  D  K  T  H  T
tgcccaccgtgcccagcacctgaactcctggggggaccgtcagtc
 C  P  P  C  P  A  P  E  L  L  G  G  P  S  V
ttcctcttccccccaaaacccaaggacaccctcatgatctcccgg
 F  L  F  P  P  K  P  K  D  T  L  M  I  S  R
acccctgaggtcacatgcgtggtggtggacgtgagccacgaagac
 T  P  E  V  T  C  V  V  V  D  V  S  H  E  D
cctgaggtcaagttcaactggtacgtggacggcgtggaggtgcat
```

```
                                                  P  E  V  K  F  N  W  Y  V  D  G  V  E  V  H
aatgccaagacaaagccgcgggaggagcagtacaacagcacgtac
 N  A  K  T  K  P  R  E  E  Q  Y  N  S  T  Y
cgtgtggtcagcgtcctcaccgtcctgcaccaggactggctgaat
 R  V  V  S  V  L  T  V  L  H  Q  D  W  L  N
ggcaaggagtacaagtgcaaggtctccaacaaagcccctcccagcc
 G  K  E  Y  K  C  K  V  S  N  K  A  L  P  A
cccatcgagaaaaccatctccaaagccaaagggcagccccgagaa
 P  I  E  K  T  I  S  K  A  K  G  Q  P  R  E
ccacaggtgtacaccctgcccccatcccgggatgagctgaccaag
 P  Q  V  Y  T  L  P  P  S  R  D  E  L  T  K
aaccaggtcagcctgacctgcctggtcaaaggcttctatcccagc
 N  Q  V  S  L  T  C  L  V  K  G  F  Y  P  S
gacatcgccgtggagtgggagagcaatgggcagccggagaacaac
 D  I  A  V  E  W  E  S  N  G  Q  P  E  N  N
tacaagaccacgcctcccgtgctggactccgacggctccttcttc
 Y  K  T  T  P  P  V  L  D  S  D  G  S  F  F
ctctacagcaagctcaccgtggacaagagcaggtggcagcaggggg
 L  Y  S  K  L  T  V  D  K  S  R  W  Q  Q  G
aacgtcttctcatgctccgtgatgcatgaggctctgcacaaccac
 N  V  F  S  C  S  V  M  H  E  A  L  H  N  H
tacacgcagaagagcctctccctgtctccgggtaaatcgagtatg
 Y  T  Q  K  S  L  S  L  S  P  G  K  S  S  M
cactctgacccctgcccgtcgaggtgagctgagcgtgtgtgacagt
 H  S  D  P  A  R  R  G  E  L  S  V  C  D  S
attagtgagtgggtaacggcggcagacaaaaagactgcagtggac
 I  S  E  W  V  T  A  A  D  K  K  T  A  V  D
atgtcgggcgggacggtcacagtccttgaaaaggtccctgtatca
 M  S  G  G  T  V  T  V  L  E  K  V  P  V  S
aaaggccaactgaagcaatacttctacgagaccaagtgcaatccc
 K  G  Q  L  K  Q  Y  F  Y  E  T  K  C  N  P
atgggttacacaaaagaaggctgcaggggcatagacaaaaggcat
 M  G  Y  T  K  E  G  C  R  G  I  D  K  R  H
tggaactcccagtgcgaactacccagtcgtacgtgcgggcctt
 W  N  S  Q  C  R  T  T  Q  S  Y  V  R  A  L
accatggatagcaaaaagagaattggctggcgattcataaggata
 T  M  D  S  K  K  R  I  G  W  R  F  I  R  I
gacacttcttgtgtatgtacattgaccattaaaaggtga  2448
 D  T  S  C  V  C  T  L  T  I  K  R  *
```

Figure 15

Nucleotide and deduced amino acid sequence of light chain encoded by tandem vector

(SEQ ID NO. 35 and 36)

```
atggagacagacacactcctgctatggctcttgttgctcatgttt
 M   E   T   D   T   L   L   W   L   L   L   M   F
ccaggtaccagatgtgacatccagatgacccagtctccatcctcc
 P   G   T   R   C   D   I   Q   M   T   Q   S   P   S   S
ttatctgcctctctgggagaaagagtcagtctcacttgtcgggca
 L   S   A   S   L   G   E   R   V   S   L   T   C   R   A
agtcaggacattggtggtaacttatactggcttcagcagggacca
 S   Q   D   I   G   G   N   L   Y   W   L   Q   Q   G   P
gatggaactattaaacgcctgatctacgccacatccagtttagat
 D   G   T   I   K   R   L   I   Y   A   T   S   S   L   D
tctggtgtccccaaaaggttcagtggcagtaggtctgggtcagat
 S   G   V   P   K   R   F   S   G   S   R   S   G   S   D
tattctctcaccatcagcagccttgagtctgaagattttgtagac
 Y   S   L   T   I   S   S   L   E   S   E   D   F   V   D
tattactgtctacagtattctagttctccgtggacgttcggtgga
 Y   Y   C   L   Q   Y   S   S   S   P   W   T   F   G   G
gcgacaaagatggaaataaaacgaactgtggctgcaccatctgtc
 A   T   K   M   E   I   K   R   T   V   A   A   P   S   V
ttcatcttcccgccatctgatgagcagttgaaatctggaactgcc
 F   I   F   P   P   S   D   E   Q   L   K   S   G   T   A
tctgttgtgtgcctgctgaataacttctatcccagagaggccaaa
 S   V   V   C   L   L   N   N   F   Y   P   R   E   A   K
gtacagtggaaggtggataacgccctccaatcgggtaactcccag
 V   Q   W   K   V   D   N   A   L   Q   S   G   N   S   Q
gagagtgtcacagagcaggacagcaaggacagcacctacagcctc
 E   S   V   T   E   Q   D   S   K   D   S   T   Y   S   L
agcagcaccctgacgctgagcaaagcagactacgagaaacacaaa
 S   S   T   L   T   L   S   K   A   D   Y   E   K   H   K
gtctacgcctgcgaagtcacccatcagggcctgagctcgcccgtc
 V   Y   A   C   E   V   T   H   Q   G   L   S   S   P   V
acaaagagcttcaacaggggagagtgttag
 T   K   S   F   N   R   G   E   C   *
```

Figure 16

Nucleotide and deduced amino acid sequence of DHFR encoded by tandem vector

(SEQ ID NO. 37 and 38)

```
atggttcgaccattgaactgcatcgtcgccgtgtcccaaaatatg
 M   V  R  P  L  N  C  I  V  A  V  S  Q  N  M
gggattggcaagaacggagaccgaccctggcctccgctcaggaac
 G   I  G  K  N  G  D  R  P  W  P  P  L  R  N
gagttcaagtacttccaaagaatgaccacaacctcttcagtggaa
 E   F  K  Y  F  Q  R  M  T  T  T  S  S  V  E
ggtaaacagaatctggtgattatgggtaggaaaacctggttctcc
 G   K  Q  N  L  V  I  M  G  R  K  T  W  F  S
attcctgagaagaatcgacctttaaaggacagaattaatatagtt
 I   P  E  K  N  R  P  L  K  D  R  I  N  I  V
ctcagtagagaactcaaagaaccaccacgaggagctcatttctt
 L   S  R  E  L  K  E  P  P  R  G  A  H  F  L
gccaaaagtttggatgatgccttaagacttattgaacaaccggaa
 A   K  S  L  D  D  A  L  R  L  I  E  Q  P  E
ttggcaagtaaagtagacatggtttggatagtcggaggcagttct
 L   A  S  K  V  D  M  V  W  I  V  G  G  S  S
gtttaccaggaagccatgaatcaaccaggccacctcagactcttt
 V   Y  Q  E  A  M  N  Q  P  G  H  L  R  L  F
gtgacaaggatcatgcaggaatttgaaagtgacacgttttccca
 V   T  R  I  M  Q  E  F  E  S  D  T  F  F  P
gaaattgatttggggaaatataaacttctcccagaatacccaggc
 E   I  D  L  G  K  Y  K  L  L  P  E  Y  P  G
gtcctctctgaggtccaggaggaaaaaggcatcaagtataagttt
 V   L  S  E  V  Q  E  E  K  G  I  K  Y  K  F
gaagtctacgagaagaaagactaa
 E   V  Y  E  K  K  D  *
```

Fusion Protein

Figure 24
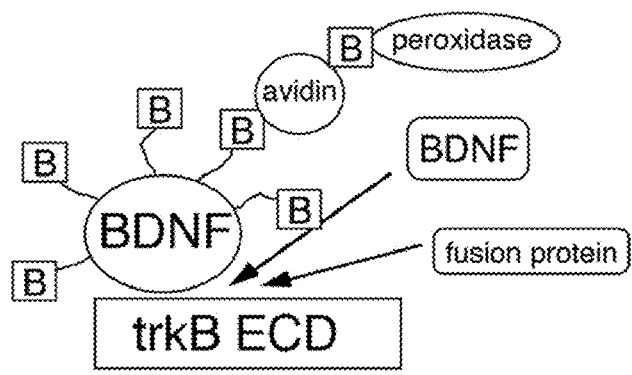
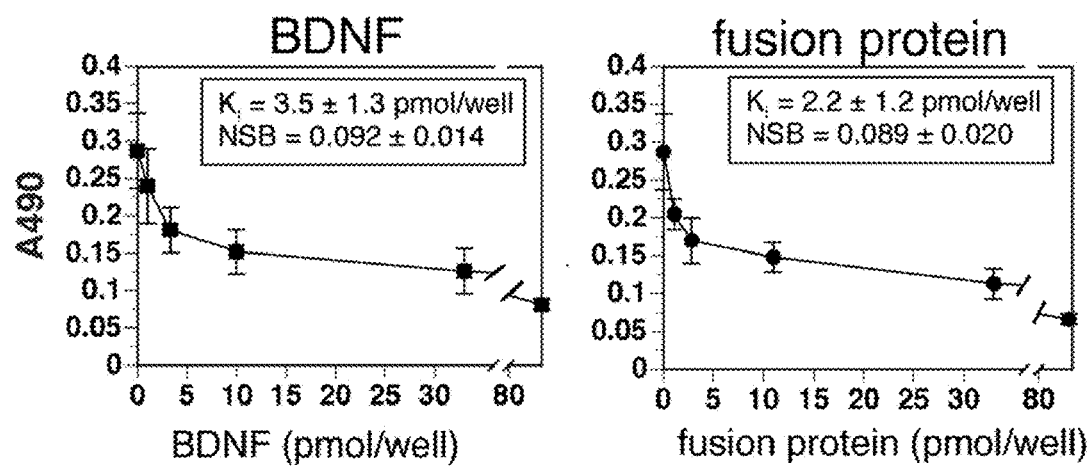

FUSION PROTEINS FOR DELIVERY OF ERYTHROPOIETIN TO THE CNS

CROSS-REFERENCE TO RELATED APPLICATIONS

This application in a continuation-in-part of U.S. patent application Ser. No. 11/245,546 filed Oct. 7, 2005, and of U.S. patent application Ser. No. 12/323,232, filed Nov. 25, 2008, the contents of which are incorporated herein by reference in their entirety.

SEQUENCE LISTING

The instant application contains a Sequence Listing which has been submitted via EFS-Web and is hereby incorporated by reference in its entirety. Said ASCII copy, created on May 4, 2010, is named 28570701.txt and is 105,032 bytes in size.

BACKGROUND OF THE INVENTION

Neurological disorders represent a major cause of mortality and disability worldwide. Despite extensive progress, current treatment options remain limited in some aspects. One major reason for this limitation is that the brain is unique in allowing only select access to molecules. While this is a useful protective mechanism, it also means that many potentially beneficial molecular entities do not have access to the central nervous system (CNS), and thus are unable to exert a therapeutic effect in many neurological disorders or other conditions of the CNS. The present invention represents an advance in providing accessibility of the CNS for molecular entities whose ability to cross the blood brain barrier is limited.

SUMMARY OF THE INVENTION

In one aspect, the invention provides a composition comprising a neurotherapeutic peptide comprising a mature human erythropoietin (EPO) polypeptide covalently linked to a structure that is capable of crossing the blood brain barrier (BBB). In some embodiments, the structure that is capable of crossing the BBB crosses the BBB on an endogenous BBB receptor. In some embodiments, the endogenous BBB receptor is selected from the group consisting of the insulin receptor, transferrin receptor, leptin receptor, lipoprotein receptor, and the IGF receptor. In further embodiments, the endogenous BBB receptor mediated transport system is the insulin BBB receptor mediated transport system.

In some embodiments, the structure that is capable of crossing the BBB is an antibody. In some embodiments, said structure is a monoclonal antibody (MAb). In some embodiments, the MAb is a chimeric MAb. In some embodiments, the structure that crosses the BBB on an endogenous BBB receptor mediated transport system is an antibody that, in some embodiments, is a monoclonal antibody (MAb). In some embodiments, the MAb is a chimeric MAb. In some embodiments, the chimeric antibody contains at least 80% human sequence.

In some embodiments and aspects, the mature human EPO polypeptide is covalently linked at its amino terminus to the carboxy terminus of the antibody. In some embodiments, the mature human EPO polypeptide is covalently linked at its amino terminus to the carboxy terminus of the MAb. In some embodiments, the mature human EPO polypeptide is covalently linked at its amino terminus to the carboxy terminus of the heavy chain of the MAb.

In some embodiments, after peripheral administration, the mature human EPO polypeptide has a plasma area under the concentration curve (AUC) that is at least 5-fold lower than the plasma AUC of a human EPO polypeptide that is not linked to said structure that is capable of crossing the BBB. In some embodiments, the composition is capable of crossing the BBB in an amount that is effective in treating the neurological disorder.

In a further aspect of the invention disclosed herein, the composition is a recombinant mammalian cell comprising the composition of claim 1.

In yet another aspect, the invention provides methods for treating a CNS disorder in an individual comprising peripherally administering to the individual an effective amount of a composition described herein. In some embodiments, the administering is selected from the group consisting of oral, intravenous, intramuscular, subcutaneous, intraperitoneal, rectal, transbuccal, intranasal, transdermal, and inhalation administration. In some embodiments, the CNS disorder is an acute CNS disorder. In some embodiments, the acute CNS disorder is selected from the group consisting of spinal cord injury, brain injury, focal brain ischemia and global brain ischemia. Often, the CNS disorder is a chronic disorder.

In some embodiments, the chronic disorder is a chronic neurodegenerative disease.

In some embodiments, the chronic neurodegenerative disease is selected from the group consisting of Parkinson's disease and a motor neuron disease. In some embodiments, the effective amount is about 1 ug to 10 mg.

In another aspect, the invention provides a composition comprising a neurotherapeutic peptide comprising an amino acid sequence which is at least 80% (e.g., 95%) identical to the amino acid sequence of mature human erythropoietin (EPO) (SEQ ID NO:48) covalently linked to a structure that is capable of crossing the blood brain barrier (BBB) (e.g., an antibody). In one aspect, the invention provides a composition comprising a neurotherapeutic peptide comprising an amino acid sequence which is at least 80% (e.g., 95%) identical to the amino acid sequence of mature human erythropoietin (EPO) (SEQ ID NO:48) covalently linked to a structure that is capable of crossing the blood brain barrier (BBB) (e.g., an antibody). In some embodiments, the structure that is capable of crossing the BBB crosses the BBB on an endogenous BBB receptor. In some embodiments, the endogenous BBB receptor is the insulin receptor, transferrin receptor, leptin receptor, lipoprotein receptor, and the IGF receptor. In some embodiments, the structure that is capable of crossing the BBB is a monoclonal antibody. In some embodiments, the monoclonal antibody is a chimeric monoclonal antibody. In one embodiment, the chimeric antibody contains sufficient human sequences to avoid significant immunogenic reaction when administered to a human. In some embodiments, the above-mentioned neurotherapeutic peptide is covalently linked at its amino terminus to the carboxy terminus of the heavy chain of the MAb. In one embodiment, the neurotherapeutic peptide of the above-mentioned composition comprises the amino acid sequence of mature human EPO.

In a further aspect provided herein is a composition for treating a neurological disorder comprising a neurotherapeutic peptide comprising an amino acid sequence which is at least 80% identical to the amino acid sequence of mature human EPO covalently linked to an immunoglobulin that is capable of crossing the blood brain barrier, wherein the composition is capable of crossing the BBB in an amount that is effective in treating the neurological disorder. In some embodiments provided herein is a mammalian cell comprising the just-mentioned composition.

In another aspect provided herein is a method of transport of a neurotherapeutic peptide comprising an amino acid sequence which is at least 80% identical to the amino acid sequence of mature human EPO (SEQ ID NO:48) from the peripheral circulation across the BBB in an effective amount, comprising peripherally administering to an individual the EPO covalently attached to a structure that crosses the BBB, under conditions where the agent covalently attached to a structure that crosses the BBB is transported across the BBB in an effective amount.

In yet another aspect provided herein is a method for treating a CNS disorder in an individual comprising peripherally administering to the individual an effective amount of a composition comprising a neurotherapeutic peptide comprising an amino acid sequence which is at least 80% (e.g., 95%) identical to the amino acid sequence of human EPO covalently attached to a structure capable of crossing the BBB. In one embodiment, the neurotherapeutic peptide comprises the amino acid sequence of human EPO. In some embodiments, the administering is oral, intravenous, intramuscular, subcutaneous, intraperitoneal, rectal, transbuccal, intranasal, transdermal, or inhalation administration. In some embodiments, the CNS disorder is an acute CNS disorder (e.g., spinal cord injury, brain injury focal brain ischemia and global brain ischemia). In other embodiments, the CNS disorder is a chronic CNS disorder (e.g., a chronic neurodegenerative disease). In some embodiments, the chronic neurodegenerative disease is Parkinson's disease or a motor neuron disease (e.g., amyotrophic lateral sclerosis). In some embodiments, the individual to be treated is administered about 0.1 to about 100 ug of the IgG-EPO fusion protein used in above-mentioned method.

In yet another aspect provided herein is a composition comprising a neurotherapeutic peptide comprising an amino acid sequence which is at least 80% identical to the amino acid sequence of human EPO covalently linked to an immunoglobulin, wherein the IgG-EPO fusion protein has a plasma area under the concentration curve (AUC) that is at least about 5-fold less than the plasma AUC of the EPO alone. In some embodiments, the immunoglobulin is an antibody to an endogenous BBB receptor (e.g., the insulin receptor, transferrin receptor, leptin receptor, lipoprotein receptor, or the IGF receptor). In one embodiment, the neurotherapeutic peptide comprises the amino acid sequence of human EPO.

In a further aspect provided herein is a method for treating substance abuse in an individual, comprising administering to the individual an effective amount of a composition comprising a neurotherapeutic peptide comprising an amino acid sequence which is at least 80% identical to the amino acid sequence of mature human EPO (SEQ ID NO:48) covalently attached to a structure capable of crossing the BBB.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2. Diagram showing genetic engineering of a bacterial expression plasmid encoding vBDNF cDNA with modified 5'- and 3'-linkers.

FIG. 4. Nucleotide (SEQ ID NO: 21) and amino acid (SEQ ID NO: 22) sequence of fusion site between carboxyl terminus of the fusion protein HC and the amino terminus of the vBDNF. The 3-amino acid linker between the HIRMAb HC and the vBDNF is shown, as well as the new stop codon at the carboxyl terminus of vBDNF.

FIG. 5. Nucleotide sequence (SEQ ID NO: 23) of fusion protein HC gene cloned into plasmid 416. Italics: human IgG1 constant region introns; bold font: human IgG1 exon sequence; underline font: vBDNF.

FIG. 6. Amino acid sequence (SEQ ID NO: 24) of the fusion protein HC. The 19 amino acid signal peptide is underlined, as is the 3-amino acid linker between the CH3 region and the vBDNF. The N-linked glycosylation consensus sequence within CH2 is underlined.

FIG. 7. The amino acid sequence (SEQ ID NO: 25) of the different domains of the fusion protein HC are shown.

FIG. 9. (A) Nucleotide sequence (SEQ ID NO: 26) of the fusion protein HC cDNA inserted in clone 422a. (B) (SEQ ID NOS 27 & 28) Amino acid sequence of the fusion protein HC that is deduced from the nucleotide sequence shown in panel A. The sequence of the signal peptide is underlined.

FIG. 11. (A) Nucleotide sequence (SEQ ID NO: 29) of the fusion protein LC cDNA inserted in clone 423a. (B) (SEQ ID NOS 30 & 31) Amino acid sequence of the fusion protein LC that is deduced from the nucleotide sequence shown in panel A. The sequence of the signal peptide is underlined.

FIGS. 13A and 13B. Nucleotide sequence (SEQ ID NO: 32) of the fusion protein HC gene and LC gene, and the DHFR genes incorporated in the tandem vector.

FIG. 14. Deduced amino acid sequence of the fusion protein HC based on tandem vector nucleotide sequence analysis (SEQ ID NOS 33 & 34). The signal peptide sequence is underlined.

FIG. 15. Deduced amino acid sequence of the fusion protein LC based on tandem vector nucleotide sequence analysis (SEQ ID NO 35 & 36). The signal peptide sequence is underlined.

FIG. 16. Deduced amino acid sequence of the DHFR based on tandem vector nucleotide sequence analysis (SEQ ID NO 37 & 38).

FIG. 24. (A) Design of trkB competitive ligand binding assay (CLBA). The advantage of the PEG linker is that this modification eliminates the high non-specific binding (NSB) of the cationic BDNF to the ELISA wells, which gives an assay with a high signal/noise ratio. The binding of the BDNF-PEG$^{2000}$-biotin to the trkB ECD was detected with a peroxidase system using avidin and biotinylated peroxidase. (B) The binding of the BDNF-PEG$^{2000}$-biotin to the trkB ECD is competitively displaced by recombinant BDNF. This binding data was analyzed by non-linear regression analysis to yield the $K_1$ of BDNF binding, 3.5±1.3 pmol/well and the NSB parameter. (C) The binding of the BDNF-PEG$^{2000}$-biotin to the trkB ECD is competitively displaced by the fusion protein. This binding data was analyzed by non-linear regression analysis to yield the $K_1$ of fusion protein binding, 2.2±1.2 pmol/well, which is not significantly different than the $K_1$ for native BDNF. These data show that the affinity of the fusion protein for the trkB receptor is equal to that of native BDNF.

DETAILED DESCRIPTION OF THE INVENTION

Figure 1:
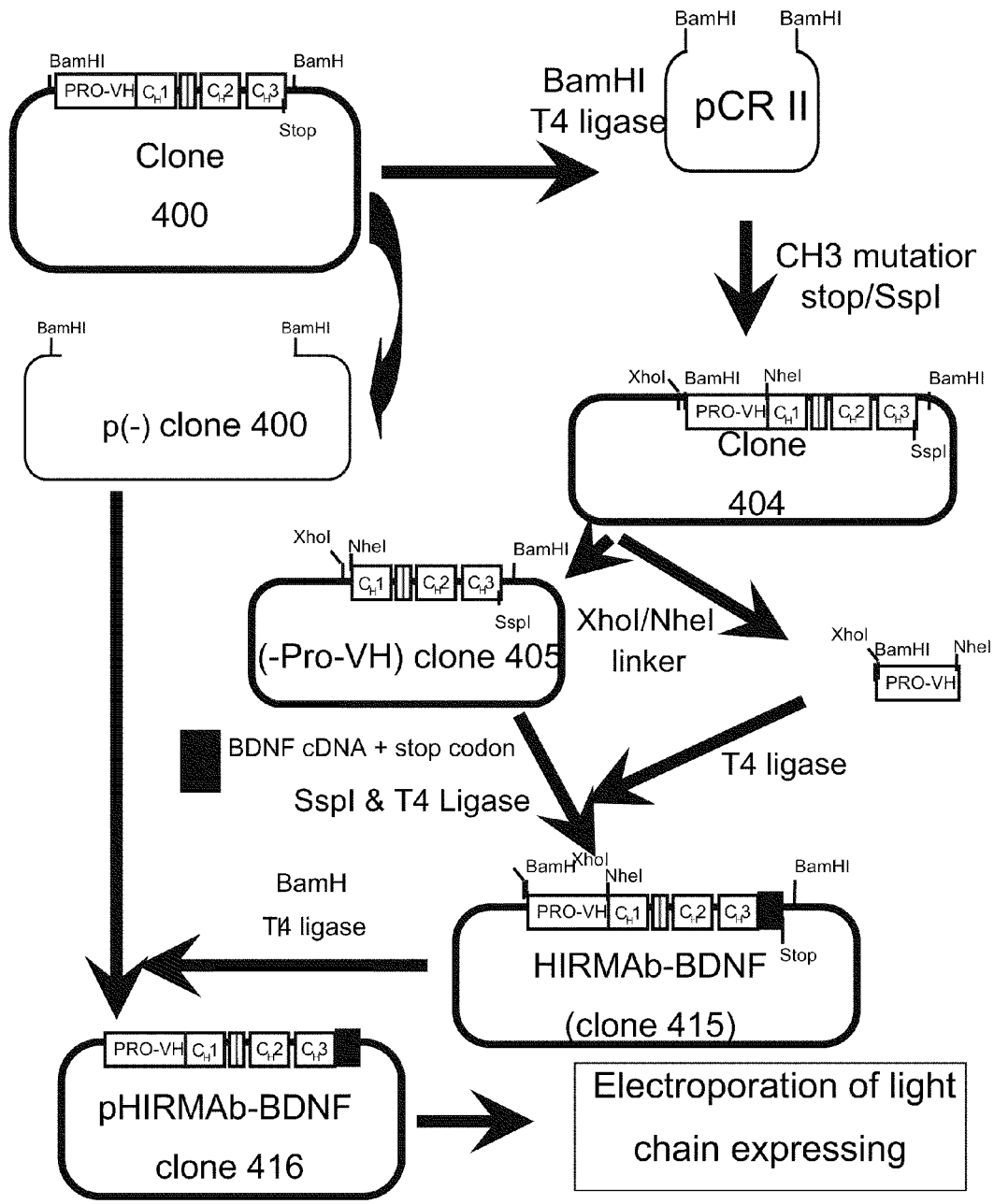
FIG. 1. Diagram showing genetic engineering of a eukaryotic expression vector encoding a fusion gene comprised of the variable region of the heavy chain (VH) of the chimeric HIRMAb, a genomic fragment encoding the constant region of human IgG1, which is comprised of 4 regions (CH1, hinge, CH2, and CH3), and the cDNA for the BDNF variant (vBDNF). Transcription of the gene is driven by the human IgG1 promoter (PRO). This vector produces the heavy chain (HC) of the fusion protein.

I. Introduction
II. Definitions
III. The blood brain barrier
   A. Transport systems
   B. Structures that bind to a blood brain barrier receptor-mediated transport system
IV. Agents for transport across the blood brain barrier
   A. Neurotrophins
   B. Brain-derived neurotrophic factor
   C. Erythropoietin
V. Compositions
VI. Nucleic acids, vecors, cells, and manufacture
   A. Nucleic acids
   B. Vectors
   C. Cells
   D. Manufacture
VII. Methods
VIII. Kits
Abbreviations
AA amino acid
ALS amyotrophic lateral sclerosis AP alkaline phosphatase
AUC area under the plasma concentration curve
BBB blood-brain barrier
BCA bicinchoninic acid
BDNF brain derived neurotrophic factor
BGH bovine growth hormone
Bmax dose causing maximal effect
BSA bovine serum albumin
BSCB blood-spinal cord barrier
C cysteine
CDR compementarity determining region
CED convection enhanced diffusion
CHO Chinese hamster ovary
CL clearance
CMV cytomegalovirus
CNTF ciliary neurotrophic factor
CNS central nervous system
CPW cell per well
CSF cerebrospinal fluid
DC dilutional cloning
DHFR dihydrofolate reductase
ECD extracellular domain
ED50 effective dose causing 50% saturation
EP electroporation
EPO erythropoietin
EPOR EPO receptor
FR framework region
FS flanking sequence
FWD forward
GDNF glial derived neurotrophic factor
GFR GDNF receptor
GM-CSF granulocyte-macrophage colony stimulating factor
HC heavy chain
HIR human insulin receptor
HIRMAb MAb to HIR
HIRMAb-EPO fusion protein of HIRMAb and EPO
HPLC high pressure liquid chromatography
HT hypoxanthine-thymidine
ICV intra-cerebroventricular
ID injected dose
IGF insulin-like growth factor
IgG immunoglobulin G
KD dissociation constant
LC light chain
LDL low density lipoprotein
LSC liquid scintillation counter
MAb monoclonal antibody
MAH mouse anti-human IgG
MCAO middle cerebral artery occlusion
MRT mean residence time
MTH molecular Trojan horse
MTX methotrexate
MW molecular weight
N asparagine
NSP N-succinimidy propionate
nt nucleotide
ODN oligodeoxynucleotide
pA poly-adenylation
PAGE polyacrylamide gel electrophoresis
PBS phosphate buffered saline
PBST PBS plus Tween-20
PCR polymerase chain reaction
PD Parkinson's disease
pI isoelectric point
PK pharmacokinetics
PS permeability-surface area
RAG rabbit anti-goat IgG
REV reverse
RNase A ribonuclease A
RRA radio-receptor assay
RT reverse transcriptase
RT room temperature
SDM site-directed mutagenesis
SDS sodium dodecyl sulfate
SEC size exclusion chromatography
Ser serine
SFM serum free medium
SMA spinal muscular atrophy
TBI traumatic brain injury
TCA trichloroacetic acid
TH tyrosine hydroxylase
TTC triphenyltetrazolium chloride
TV tandem vector
UTV universal TV
Vc central volume of distribution
VD volume of distribution
Vss steady state volume of distribution
VH variable region of heavy chain
VL variable region of light chain I. Introduction The blood brain barrier is a limiting factor in the delivery of many peripherally-administered agents to the central nervous system. The present invention addresses two factors that are important in delivering EPO across the BBB to the CNS: 1) modification of the agent to allow it to cross the BBB; and 2) retention of activity of the agent once across the BBB. Various aspects of the invention address these factors, by providing fusion structures (e.g., fusion proteins) of an agent (e.g., a therapeutic agent) covalently linked to a structure that causes the agent to have increased serum half life, to be transported across the BBB, and/or to retain some or all of its activity in the brain while still attached to the structure.

Accordingly, in one aspect, the invention provides compositions and methods that utilize an agent covalently linked to a structure capable of crossing the blood brain barrier (BBB). The compositions and methods are useful in transporting agents, e.g., therapeutic agents such as neurotherapeutic agents, from the peripheral blood and across the BBB into the CNS. Neurotherapeutic agents useful in the invention include neurotrophins, e.g., EPO. In some embodiments, the structure that is capable of crossing the BBB is capable of binding to an endogenous BBB receptor mediated transport system and crossing the BBB. In some embodiments, the structure that is capable of crossing the BBB is an antibody, e.g., a monoclonal antibody (MAb) such as a chimeric MAb.

In some embodiments, the invention provides a fusion protein that includes a structure capable of crossing the BBB covalently linked to a peptide that is active in the central nervous system (CNS), where the structure capable of crossing the blood brain barrier and the peptide that is active in the central nervous system each retain a proportion (e.g., 10-100%) of their activities or their binding affinities for their respective receptors, compared to their activities or their binding affinities for their respective receptors as separate entities.

In another aspect, the invention provides a composition of an IgG-EPO fusion protein containing a form of EPO that is rapidly cleared from plasma compared to EPO alone, wherein the IgG-EPO fusion protein has a plasma area under the concentration curve (AUC) that is at least about 5-fold less than the plasma AUC of the EPO alone. The effect of EPO on hematopoiesis is proportional to the plasma AUC. Therefore, the re-engineering of EPO as the IgG-EPO fusion protein described herein results in a form of EPO that is selectively active in the brain as compared to the hematopoietic tissues outside of brain.

The invention also provides nucleic acids coding for peptides and proteins. In some embodiments, the invention provides a single nucleic acid sequence that contains a gene coding for a light chain of an immunoglobulin and a gene coding for a fusion protein made up of a heavy chain of the immunoglobulin covalently linked to a peptide. In some embodiments the peptide of the fusion protein is a therapeutic peptide, e.g., a neurotherapeutic peptide such as a neurotrophin. The invention also provides vectors containing the nucleic acids of the invention, and cells containing the vectors. Further provided are methods of manufacturing an immunoglobulin fusion protein, where the fusion protein contains an immunoglobulin heavy chain fused to a therapeutic agent, where the methods include integrating into a eukaryotic cell a single tandem expression vector in which both the immunoglobulin light chain gene and the gene for the immunoglobulin heavy chain fused to the therapeutic agent are incorporated into a single piece of DNA.

The invention further provides therapeutic compositions, such as pharmaceutical compositions that contain an agent covalently linked to a structure capable of crossing the blood brain barrier (BBB) and a pharmaceutically acceptable excipient. In some embodiments, the invention provides a composition for treating a neurological disorder that includes human EPO covalently linked to an immunoglobulin that is capable of crossing the blood brain barrier, wherein the composition is capable of crossing the BBB in an amount that is effective in treating the neurological disorder.

The invention also provides methods for treating a neurological disorder in an individual that include peripherally administering to the individual an effective amount of one or more of the compositions of the invention, optionally in combination with other therapy for the disorder.

II. Definitions

As used herein, an "agent" includes any substance that is useful in producing an effect, including a physiological or biochemical effect in an organism. A "therapeutic agent" is a substance that produces or is intended to produce a therapeutic effect, i.e., an effect that leads to amelioration, prevention, and/or complete or partial cure of a disorder. A "therapeutic effect," as that term is used herein, also includes the production of a condition that is better than the average or normal condition in an individual that is not suffering from a disorder, i.e., a supranormal effect such as improved cognition, memory, mood, or other characteristic attributable at least in part to the functioning of the CNS, compared to the normal or average state. A "neurotherapeutic agent" is an agent that produces a therapeutic effect in the CNS. A "therapeutic peptide" includes therapeutic agents that consists of a peptide. A "cationic therapeutic peptide" encompasses therapeutic peptides whose isoelectric point is above about 7.4, in some embodiments, above about 8, 8.5, 9, 9.5, 10, 10.5, 11, 11.5, 12, or above about 12.5. A subcategory of cationic therapeutic peptides is cationic neurotherapeutic peptides.

As used herein, a "peptide that is active in the central nervous system (CNS)" includes peptides that have an effect when administered to the CNS. The effect may be a therapeutic effect or a non-therapeutic effect, e.g., a diagnostic effect or an effect useful in research. If the effect is a therapeutic effect, then the peptide is also a therapeutic peptide. A therapeutic peptide that is also a peptide that is active in the CNS is encompassed by the term "neurotherapeutic peptide," as used herein.

"Treatment" or "treating" as used herein includes achieving a therapeutic benefit and/or a prophylactic benefit. By therapeutic benefit is meant eradication or amelioration of the underlying disorder or condition being treated. For example, in an individual with a neurological disorder, therapeutic benefit includes partial or complete halting of the progression of the disorder, or partial or complete reversal of the disorder. Also, a therapeutic benefit is achieved with the eradication or amelioration of one or more of the physiological or psychological symptoms associated with the underlying condition such that an improvement is observed in the patient, notwithstanding the fact that the patient may still be affected by the condition. A prophylactic benefit of treatment includes prevention of a condition, retarding the progress of a condition (e.g., slowing the progression of a neurological disorder), or decreasing the likelihood of occurrence of a condition. As used herein, "treating" or "treatment" includes prophylaxis.

As used herein, the term "effective amount" can be an amount sufficient to effect beneficial or desired results, such as beneficial or desired clinical results, or enhanced cognition, memory, mood, or other desired CNS results. An effective amount is also an amount that produces a prophylactic effect, e.g., an amount that delays, reduces, or eliminates the appearance of a pathological or undesired condition. Such conditions of the CNS include dementia, neurodegenerative diseases as described herein, suboptimal memory or cognition, mood disorders, general CNS aging, or other undesirable conditions. An effective amount can be administered in one or more administrations. In terms of treatment, an "effective amount" of a composition of the invention is an amount that is sufficient to palliate, ameliorate, stabilize, reverse or slow the progression of a disorder, e.g., a neurological disorder. An "effective amount" may be of any of the compositions of the invention used alone or in conjunction with one or more agents used to treat a disease or disorder. An "effective amount" of a therapeutic agent within the meaning of the present invention will be determined by a patient's attending physician or veterinarian. Such amounts are readily ascertained by one of ordinary skill in the art and will a therapeutic effect when administered in accordance with the present invention. Factors which influence what a therapeutically effective amount will be include, the specific activity of the therapeutic agent being used, the type of disorder (e.g., acute vs. chronic neurological disorder), time elapsed since the initiation of the disorder, and the age, physical condition, existence of other disease states, and nutritional status of the individual being treated. Additionally, other medication the patient may be receiving will affect the determination of the therapeutically effective amount of the therapeutic agent to administer.

A "subject" or an "individual," as used herein, is an animal, for example, a mammal. In some embodiments a "subject" or an "individual" is a human. In some embodiments, the subject suffers from a neurological disorder.

In some embodiments, an agent is "administered peripherally" or "peripherally administered." As used herein, these terms refer to any form of administration of an agent, e.g., a therapeutic agent, to an individual that is not direct administration to the CNS, i.e., that brings the agent in contact with the non-brain side of the blood-brain barrier. "Peripheral administration," as used herein, includes intravenous, subcutaneous, intramuscular, intraperitoneal, transdermal, inhalation, transbuccal, intranasal, rectal, and oral administration.

A "pharmaceutically acceptable carrier" or "pharmaceutically acceptable excipient" herein refers to any carrier that does not itself induce the production of antibodies harmful to the individual receiving the composition. Such carriers are well known to those of ordinary skill in the art. A thorough discussion of pharmaceutically acceptable carriers/excipients can be found in *Remington's Pharmaceutical Sciences*, Gennaro, A R, ed., 20th edition, 2000: Williams and Wilkins P A, USA. Exemplary pharmaceutically acceptable carriers can include salts, for example, mineral acid salts such as hydrochlorides, hydrobromides, phosphates, sulfates, and the like; and the salts of organic acids such as acetates, propionates, malonates, benzoates, and the like. For example, compositions of the invention may be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used buffers include histidine, acetate, phosphate, or citrate.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally occurring amino acid, e.g., an amino acid analog. As used herein, the terms encompass amino acid chains of any length, including full length proteins (i.e., antigens), wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof, including, but not limited to, degenerate codon substitutions, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res*. (1991) 19:5081; Ohtsuka et al., *J. Biol. Chem*. (1985) 260: 2605-2608; and Cassol et al. (1992); Rossolini et al., *Mol. Cell. Probes* 8:91-98 (1994)).

The terms "isolated" and "purified" refer to a material that is substantially or essentially removed from or concentrated in its natural environment. For example, an isolated nucleic acid may be one that is separated from the nucleic acids that normally flank it or other nucleic acids or components (proteins, lipids, etc. . . . ) in a sample. In another example, a polypeptide is purified if it is substantially removed from or concentrated in its natural environment. Methods for purification and isolation of nucleic acids and peptides are well known in the art.

III. The Blood Brain Barrier

In one aspect, the invention provides compositions and methods that utilize an agent covalently linked to a structure capable of crossing the blood brain barrier (BBB). The compositions and methods are useful in transporting agents, e.g., therapeutic agents such as neurotherapeutic agents, from the peripheral blood and across the BBB into the CNS. As used herein, the "blood-brain barrier" refers to the barrier between the peripheral circulation and the brain and spinal cord which is formed by tight junctions within the brain capillary endothelial plasma membranes, creates an extremely tight barrier that restricts the transport of molecules into the brain, even molecules as small as urea, molecular weight of 60 Da. The blood-brain barrier within the brain, the blood-spinal cord barrier within the spinal cord, and the blood-retinal barrier within the retina, are contiguous capillary barriers within the central nervous system (CNS), and are collectively referred to as the blood-brain barrier or BBB.

The BBB is a limiting step in the development of new neurotherapeutics, diagnostics, and research tools for the brain and CNS. In general, large molecule therapeutics such as recombinant proteins, antisense drugs, gene medicines, monoclonal antibodies, or RNA interference (RNAi)-based drugs, do not cross the BBB in pharmacologically significant amounts. While it is generally assumed that small molecule drugs can cross the BBB, in fact, <2% of all small molecule drugs are active in the brain owing to the lack transport across the BBB. A molecule must be lipid soluble and have a molecular weight less than 400 Daltons (Da) in order to cross the BBB in pharmacologically significant amounts, and the vast majority of small molecules do not have these dual molecular characteristics. Therefore, most potentially therapeutic, diagnostic, or research molecules do not cross the BBB in pharmacologically active amounts. So as to bypass the BBB, invasive transcranial drug delivery strategies are used, such as intracerebro-ventricular (ICV) infusion, intracerebral (IC) administration, and convection enhanced diffusion (CED). Transcranial drug delivery to the brain is expensive, invasive, and largely ineffective. The ICV route delivers BDNF only to the ependymal surface of the brain, not into brain parenchyma, which is typical for drugs given by the ICV route. The IC administration of a neurotrophin, such as nerve growth factor (NGF), only delivers drug to the local injection site, owing to the low efficiency of drug diffusion within the brain. The CED of neurotrophin results in preferential fluid flow through the white matter tracts of brain, which causes demyelination, and astrogliosis.

The present invention offers an alternative to these highly invasive and generally unsatisfactory methods for bypassing the BBB, allowing agents, e.g., neuroprotective factors to cross the BBB from the peripheral blood. It is based on the use of endogenous transport systems present in the BBB to provide a mechanism to transport a desired substance from the peripheral blood to the CNS.

A. Transport Systems

In some embodiments, the invention provides compositions that include a structure that binds to a BBB receptor mediated transport system, coupled to an agent for which transport across the BBB is desired, e.g., a neurotherapeutic agent. The compositions and methods of the invention may utilize any suitable structure that is capable of transport by the selected endogenous BBB receptor-mediated transport system, and that is also capable of attachment to the desired agent. In some embodiments, the structure is an antibody. In some embodiment the antibody is a monoclonal antibody (MAb), e.g., a chimeric MAb.

Endogenous BBB receptor-mediated transport systems The BBB has been shown to have specific receptors that allow the transport from the blood to the brain of several macromolecules; these transporters are suitable as transporters for compositions of the invention. Endogenous BBB receptor-mediated transport systems useful in the invention include those that transport insulin, transferrin, insulin-like growth factors 1 and 2 (IGF1 and IGF2), leptin, and lipoproteins. In some embodiments, the invention utilizes a structure that is capable of crossing the BBB via the endogenous insulin BBB receptor-mediated transport system, e.g., the human endogenous insulin BBB receptor-mediated transport system.

B. Structures that Bind to a BBB Receptor Mediated Transport System

One noninvasive approach for the delivery of drugs to the CNS is to attach the agent of interest to a structure, e.g., molecule that binds with receptors on the BBB. The structure then serves as a vector for transport of the agent across the BBB. Such structures are referred to herein as "molecular Trojan horses (MTH)." Typically, though not necessarily, a MTH is an exogenous peptide or peptidomimetic moiety (e.g., a MAb) capable of binding to an endogenous BBB receptor mediated transport system that traverses the BBB on the endogenous BBB receptor-mediated transport system. In certain embodiments, the MTH can be an antibody to a receptor of the transport system, e.g., the insulin receptor. In some embodiments, the antibody is a monoclonal antibody (MAb). In some embodiments, the MAb is a chimeric MAb. Thus, despite the fact that Abs normally are excluded from the brain, they can be an effective vehicle for the delivery of molecules into the brain parenchyma if they have specificity for receptors on the BBB.

Accordingly, antibodies are particularly useful in embodiments of the invention, especially MAbs. Certain receptor-specific MAbs may mimic the endogenous ligand and function as a MTH and traverse a plasma membrane barrier via transport on the specific receptor system. In certain embodiments, the MTH is a MAb to the human insulin receptor (HIR) on the human BBB. The HIR MAb binds an exofacial epitope on the human BBB HIR and this binding enables the MAb to traverse the BBB via a transport reaction that is mediated by the human BBB insulin receptor.

An "antibody," as that term is used herein, includes reference to any molecule, whether naturally-occurring, artificially induced, or recombinant, which has specific immunoreactive activity. Generally, though not necessarily, an antibody is a protein that includes two molecules, each molecule having two different polypeptides, the shorter of which functions as the light chains of the antibody and the longer of which polypeptides function as the heavy chains of the antibody. Normally, as used herein, an antibody will include at least one variable region from a heavy or light chain. Additionally, the antibody may comprise combinations of variable regions. The combination may include more than one variable region of a light chain or of a heavy chain. The antibody may also include variable regions from one or more light chains in combination with variable regions of one or more heavy chains. An antibody can be an immunoglobulin molecule obtained by in vitro or in vivo generation of the humoral response, and includes both polyclonal and monoclonal antibodies. Furthermore, the present invention includes antigen binding fragments of the antibodies described herein, such as Fab, Fab', F(ab)$_2$, and Fv fragments, fragments comprised of one or more CDRs, single-chain antibodies (e.g., single chain Fv fragments (scFv)), disulfide stabilized (dsFv) Fv fragments, heteroconjugate antibodies (e.g., bispecific antibodies), pFv fragments, heavy chain monomers or dimers, light chain monomers or dimers, and dimers consisting of one heavy chain and one light chain. Such antibody fragments may be produced by chemical methods, e.g., by cleaving an intact antibody with a protease, such as pepsin or papain, or via recombinant DNA techniques, e.g., by using host cells transformed with truncated heavy and/or light chain genes. Synthetic methods of generating such fragments are also contemplated. Heavy and light chain monomers may similarly be produced by treating an intact antibody with a reducing agent, such as dithiothreitol or beta-mercaptoethanol, or by using host cells transformed with DNA encoding either the desired heavy chain or light chain or both. An antibody immunologically reactive with a particular antigen can be generated in vivo or by recombinant methods such as selection of libraries of recombinant antibodies in phage or similar vectors.

A "chimeric" antibody includes an antibody derived from a combination of different mammals. The mammal may be, for example, a rabbit, a mouse, a rat, a goat, or a human. The combination of different mammals includes combinations of fragments from human and mouse sources.

In some embodiments, an antibody of the present invention is a monoclonal antibody (MAb), typically a human monoclonal antibody. Such antibodies are obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas.

For use in humans, a chimeric MAb is preferred that contains enough human sequence that it is not significantly immunogenic when administered to humans, e.g., at least about 80% human and about 20% mouse, or about 85% human and about 15% mouse, or about 90% human and about 10% mouse, or about 95% human and 5% mouse, or greater than about 95% human and less than about 5% mouse. Chimeric antibodies to the human BBB insulin receptor with sufficient human sequences for use in the invention are described in, e.g., Coloma et al., Pharm. Res. (2000) 17: 266-274, which is incorporated by reference herein in its entirety. A more highly humanized form of the HIR MAb can also be engineered, and the humanized HIRMAb has activity comparable to the murine HIRMAb and can be used in embodiments of the invention. See, e.g., U.S. Patent Application Publication No. 20040101904, filed Nov. 27, 2002, incorporated by reference herein in its entirety.

Antibodies used in the invention may be glycosylated or non-glycosylated. If the antibody is glycosylated, any pattern of glycosylation that does not significantly affect the function of the antibody may be used. Glycosylation can occur in the pattern typical of the cell in which the antibody is made, and may vary from cell type to cell type. For example, the glycosylation pattern of a monoclonal antibody produced by a mouse myeloma cell can be different than the glycosylation pattern of a monoclonal antibody produced by a transfected Chinese hamster ovary (CHO) cell. In some embodiments, the antibody is glycosylated in the pattern produced by a transfected Chinese hamster ovary (CHO) cell.

Accordingly, in some embodiments, a genetically engineered HIR MAb, with the desired level of human sequences, is fused to an agent for which transport across the BBB is desired, e.g., a neurotherapeutic agent such as a neurotrophin such as human EPO, to produce a recombinant fusion protein that is a bi-functional molecule. The recombinant therapeutic neuroprotective factor/HIRMAb is able to both (i) cross the human BBB, via transport on the BBB HIR, and (ii) activate the factor's target, e.g., EPO receptor (EPOR), to cause neurotherapeutic effects once inside the brain, following peripheral administration.

IV. Agents for Transport Across the BBB

The agent for which transport across the BBB is desired may be any suitable substance for introduction into the CNS. Generally, the agent is a substance for which transport across the BBB is desired, which does not, in its native form, cross the BBB in significant amounts. The agent may be, e.g., a therapeutic agent, a diagnostic agent, or a research agent. Diagnostic agents include peptide radiopharmaceuticals, such as radiolabeled epidermal growth factor (EGF) for imaging brain cancer (Kurihara and Pardridge, Canc. Res. (1999) 54: 6159-6163), and amyloid peptides for imaging brain amyloid such as in Alzheimers disease (Lee et al. (2002) J. Cereb. Blood Flow Metabol. 22: 223-231). In some embodiments, the agent is a therapeutic agent, such as a neurotherapeutic agent. Apart from neurotrophins, potentially useful therapeutic protein agents include recombinant enzymes for lysosomal storage disorders (see, e.g., U.S. Patent Application Publication No. 20050142141, filed Feb. 17, 2005, incorporated by reference herein in its entirety), monoclonal antibodies that either mimic an endogenous peptide or block the action of an endogenous peptide, polypeptides for brain disorders, such as secretin for autism (Ratliff-Schaub et al., Autism (2005) 9: 256-265), opioid peptides for drug or alcohol addiction (Cowen et al., J. Neurochem. (2004) 89: 273-285), or neuropeptides for appetite control (Jethwa et al., Am. J. Physiol. (2005) 289: E301-305). In some embodiments, the agent is a neurotrophic factor, also referred to herein as a "neurotrophin." Thus, in some embodiments, the invention provides compositions and methods that utilize a neurotrophin. In some embodiments, a single neurotrophin may be used. In others, combinations of neurotrophins are used. In others, combinations of neurotrophins are used. In some embodiments, the invention utilizes erythropoietin (EPO).

A. Neurotrophins

Many neurotrophic factors are neuroprotective in brain, but do not cross the blood-brain barrier. These factors are suitable for use in the compositions and methods of the invention and include brain-derived neurotrophic factor (BDNF), nerve growth factor (NGF), neurotrophin-4/5, fibroblast growth factor (FGF)-2 and other FGFs, neurotrophin (NT)-3, erythropoietin (EPO), hepatocyte growth factor (HGF), epidermal growth factor (EGF), transforming growth factor (TGF)-α, TGF-β, vascular endothelial growth factor (VEGF), interleukin-1 receptor antagonist (IL-1ra), ciliary neurotrophic factor (CNTF), glial-derived neurotrophic factor (GDNF), neurturin, platelet-derived growth factor (PDGF), heregulin, neuregulin, artemin, persephin, interleukins, granulocyte-colony stimulating factor (CSF), granulocyte-macrophage-CSF, netrins, cardiotrophin-1, hedgehogs, leukemia inhibitory factor (LIF), midkine, pleiotrophin, bone morphogenetic proteins (BMPs), netrins, saposins, semaphorins, and stem cell factor (SCF). Particularly useful in some embodiments of the invention utilizing neurotrophins that are used as precursors for fusion proteins that cross the BBB are those that naturally form dimeric structures, similar to BDNF. Certain neurotrophins such as BDNF or NT-3 may form hetero-dimeric structures, and in some embodiments the invention provides a fusion protein constructed of one neurotrophin monomer fused to one chain (e.g., a light or heavy chain) of an antibody, e.g., of the HIRMAb, and another neurotrophin monomer fused to the second chain (e.g., a light or heavy chain) of the antibody. Typically, the molecular weight range of recombinant proteins that may be fused to the molecular Trojan horse ranges from 1000 Daltons to 500,000 Daltons.

B. Brain-Derived Neurotrophic Factor

One particularly useful neurotrophin in embodiments of the invention is brain-derived neurotrophic factor (BDNF). In experimental models of chronic neurodegenerative disease such as prion diseases, Alzheimer's disease (AD), Parkinson's disease (PD), Huntington's disease (HD), or amyotrophic lateral sclerosis (ALS), the direct intracerebral injection of BDNF is neuroprotective.

In studies demonstrating the pharmacologic efficacy of BDNF in experimental brain disease, it is necessary to administer the neurotrophin directly into the brain following a transcranial drug delivery procedure. The transcranial drug delivery is required because BDNF does not cross the brain capillary wall, which forms the blood-brain barrier (BBB) in vivo. Owing to the lack of transport of BDNF across the BBB, it is not possible for the neurotrophin to enter the CNS, including the brain or spinal cord, following a peripheral administration unless the BBB is experimentally disrupted. Clinical trials showed that subcutaneous administration of BDNF was not effective in the treatment of chronic neurodegenerative conditions, which derives from the lack of transport of BDNF across the BBB. The lack of utility of BDNF as a CNS therapeutic following peripheral administration is expected and follows from the limiting role that is played by the BBB in the development of neurotherapeutics, especially large molecule drugs such as BDNF. BDNF does not cross the BBB, and the lack of transport of the neurotrophin across the BBB prevents the molecule from being pharmacologically active in the brain following peripheral administration. The lack of BDNF transport across the BBB means that the neurotrophin must be directly injected into the brain across the skull bone to be pharmacologically active in the CNS. However, when the BDNF is fused to a Trojan horse such as the HIR MAb, this neurotrophin is now able to enter brain from blood following a non-invasive peripheral route of administration such as intravenous intramuscular, subcutaneous, intraperitoneal, or even oral administration. Owing to the BBB transport properties of this new class of molecule, it is not necessary to administer the BDNF directly into the CNS with an invasive delivery procedure requiring penetration of the skull or spinal canal. The reformulated fusion protein of the BDNF variant and the HIR MAb now enables entry of BDNF into the brain from the blood, and the development of BDNF as a neurotherapeutic for human diseases.

The forms of BDNF used in various embodiments of the invention may include pharmaceutically acceptable salts and prodrugs, and prodrugs of the salts, polymorphs, hydrates, solvates, biologically-active fragments, biologically active variants and stereoisomers of the naturally-occurring BDNF, as well as agonist, mimetic, and antagonist variants of the naturally-occurring BDNF and polypeptide fusions thereof. Variants that include one or more deletions, substitutions, or insertions in the natural sequence of the BDNF, in particular truncated versions of the native BDNF comprising deletion of one or more amino acids at the amino terminus, carboxyl terminus, or both, may also be used in certain embodiments.

In some embodiments, the invention utilizes a carboxy-truncated variant of the native BDNF, e.g., a variant in which 1, 2, 3, 4, 5, 6, 7, 8, 9, 10, or more than 10 amino acids are absent from the carboxy-terminus of the BDNF. BDNF variants include the complete 119 amino acid BDNF, the 117 or 118 amino acid variant with a truncated carboxyl terminus, variants with a truncated amino terminus, or variants with up to about a 20, 30, or 40% change in amino acid composition, as long as the fusion protein variant still binds to the brain neuroprotection receptor with high affinity. When an Ab, e.g., a MAb such as HIRMAb is used, additional fusion protein variants can be produced with the substitution of amino acids within either the framework region (FR) or the complementarity determining region (CDR) of either the light chain or the heavy chain of the Ab, e.g., HIRMAb, as long as the fusion protein binds with high affinity to the endogenous receptor, e.g., HIR to promote transport across the human BBB. Additional fusion protein variants can be produced by changing the composition or length of the linker peptide separating the fusion protein from the HIRMAb.

In some embodiments, the full-length 119 a.a. sequence of BDNF is utilized. In some embodiments, a one amino-acid carboxy-truncated variant of BDNF is utilized (amino acids 1-118). In some embodiments, a two amino-acid carboxy-truncated variant of BDNF is utilized (amino acids 1-117). In some embodiments, a three amino-acid carboxy-truncated variant of BDNF is utilized (amino acids 1-116). In some embodiments, a four amino-acid carboxy-truncated variant of BDNF is utilized (amino acids 1-115). In some embodiments, a five amino-acid carboxy-truncated variant of BDNF is utilized (amino acids 1-114).

In some embodiments, the invention utilizes a BDNF that is about 60, 70, 80, 90, 95, 99, or 100% identical with the sequence of human BDNF, or a truncated version thereof, e.g., the 117 or 118 amino acid variant with a one- or two-amino acid truncated carboxyl terminus, or variants with a truncated amino terminus. In some embodiments, the invention utilizes a two amino-acid carboxy-truncated 117 amino acid variant human BDNF with a sequence that is at least about 60, 70, 80, 90, 95, 99 or 100% identical to the sequence of amino acids 466-582 of SEQ ID NO: 24. In some embodiments, the invention utilizes a two amino-acid carboxy-truncated human 117 amino acid BDNF with a sequence that includes amino acids 466-582 of SEQ ID NO: 24.

Accordingly, BDNFs useful in the invention include peptides having at least about 60%, at least about 70%, at least about 80%, at least about 90%, at least about 95%, at least about 99%, or greater than 95% or greater than 99% sequence identity, e.g., 100% sequence identity, to the amino acid sequences disclosed herein.

C. Erythropoietin

One particularly useful neurotrophin in embodiments of the invention is erythropoietin (EPO). In experimental models of chronic neurodegenerative disease such as Parkinson's disease (PD), the direct intracerebral injection of EPO is neuroprotective. In experimental models of acute brain disease, where the BBB is prematurely disrupted, such as acute stroke, or acute brain injury, the peripheral administration of EPO is neuroprotective.

EPO has the characteristics of a classical neurotrophin. The EPO receptor (EPOR) and EPO are both expressed in brain (Sakanaka, M., Wen, T. C., Matsuda, S., Masuda, S., Morishita, E., Nagao, M., et al., In vivo evidence that erythropoietin protects neurons from ischemic damage, *Proc Natl Acad Sci USA*, (1998) 95: 4635-4640). EPO has the same characteristics as other neurotrophins, as EPO is neuroprotective in neural cells exposed to cytokines, such as tumor necrosis factor (TNF)-alpha (Pregi, N., Wenker S., Vittori D., Leiros C P., Nesse A., TNF-alpha-induced apoptosis is prevented by erythropoietin treatment on SH-SY5Y cells, *Exp Cell Res.* (2009) 315:419-431), or toxins such as the Abeta amyloid peptide (Ma, R., Xiong, N., Huang, C., Tang, Q., Hu, B., Xiang, J., Li, G., Erythropoietin protects PC12 cells from beta-amyloid (25-35)-induced apoptosis via PI3K/Akt signaling pathway, *Neuropharmacology* (2009) 56: 1027-1034). The EPOR that mediates neuroprotection in brain is the same classical EPOR expressed in peripheral tissues (Um, M., Gross, A. W., Lodish, H. F., A "classical" homodimeric erythropoietin receptor is essential for the antiapoptotic effects of erythropoietin on differentiated neuroblastoma SH-SY5Y and pheochromocytoma PC-12 cells, *Cell Signal* (2007) 19: 634-645). EPO is neuroprotective in acute and chronic brain disease. EPO is neuroprotective in acute brain disease such as transient forebrain ischemia, such as occurs after acute cardiac arrest, following the direct intra-cerebral injection of the neurotrophin (Sakanaka, M., Wen, T. C., Matsuda, S., Masuda, S., Morishita, E., Nagao, M., et al., In vivo evidence that erythropoietin protects neurons from ischemic damage, *Proc Natl Acad Sci USA* (1998) 95: 4635-4640). EPO is neuroprotective in chronic brain disease such as Parkinson's disease (PD) (Xue, Y. Q., Zhao, L. R., Guo, W. P., Duan, W. M., Intrastriatal administration of erythropoietin protects dopaminergic neurons and improves neurobehavioral outcome in a rat model of Parkinson's disease, *Neuroscience* (2007) 146: 1245-1258).

Several studies have suggested that EPO is capable of crossing the BBB, and therefore may be administered peripherally without any further alteration to enable transport across the BBB.

In the present work, we make the surprising finding that EPO does not cross the BBB following peripheral administration into the bloodstream. We then re-engineer EPO by fusion of the EPO to a BBB transport delivery system, the HIRMAb, and we observe that EPO is still biologically active following fusion to the IgG. In fact, EPO retains high affinity binding for the EPOR in both receptor binding assay using recombinant human EPOR, and in a tissue culture bio-assay using human cells. We then show that EPO is transported across the primate BBB in pharmacologically significant amounts following intravenous administration of the HIRMAb-EPO fusion protein in the adult Rhesus monkey. We also show that the plasma area under the concentration curve (AUC) for EPO is reduced >10-fold following fusion to the HIRMAb, compared to the plasma AUC of native EPO. Since the stimulation of hematopoiesis by EPO is proportional to the plasma AUC, our findings indicate that fusion of EPO to the HIRMAb has 2 major effects: (a) delivery across the BBB to allow for drug action in the CNS, and (b) reduced delivery to peripheral tissues, which will lower the unwanted side effects of EPO administration for the treatment of brain disorders.

The term EPO as used in various embodiments of the invention may include pharmaceutically acceptable salts and prodrugs, and prodrugs of the salts, polymorphs, hydrates, solvates, biologically-active fragments, biologically active variants and stereoisomers of the naturally-occurring EPO, as well as agonist, mimetic, and antagonist variants of the naturally-occurring EPO and polypeptide fusions thereof. Variants that include one or more deletions, substitutions, or insertions in the natural sequence of the EPO, in particular truncated versions of the native EPO comprising deletion of one or more amino acids at the amino terminus, carboxyl terminus, or both, may also be used in certain embodiments. A number of recombinant human EPO (EPO biosimilars) products are available for use, including Epoetin alfa, Epoetin beta, Epoetin delta, Epoietin Omega (see U.S. Pat. No. 7,078, 376, filed Aug. 11, 2000) and darbepoetin, all of which have differing glycan structures. EPO mutant proteins useful in the methods of the invention include but are not limited to Synthetic Erythropoiesis Protein (SEP, Gryphon Therapeutics), and Continuous Erythropoietin Receptor Activator (CERA, Roche). CERA is pegylated recombinant EPO. Another pegylated analogue is Hematide™ wherein two erythropoiesis stimulating agent (ESA) peptides are fused as a dimer to the polyethyleneglycol (PEG). EPO fusion proteins, and dimerized protein/peptide segments are also available for use in the methods of the invention. Additionally, EPO mimetics, including but not limited to ERP (QRVEILEGRTECVKSNLRGRTRY (SEQ ID NO: 57), a linear peptide, can be used in the present invention. Furthermore, CNTO-528 or CNTO-530 are Fc fusion proteins of an EPO-mimetic peptide (EMP), designated EMP-1, which is a 20 amino acid sequence peptide. In some embodiments of the present invention, EMP-1 is substituted for EPO. Of note, CNTO-528 comprises EMP-1 fused to the Fc of human IgG1, and CNTO-530 comprises EMP-1 fused to the Fc of human IgG4. In both cases, EMP is fused to the amino terminus of the Fc fragment. In contrast, the instant disclosure provides for, inter alia, EPO fused to the carboxyl terminus of the IgG constant region.

In some cases, an antibody against the EPO receptor, which has agonist properties and mimics EPO action, could be engineered as a single chain Fv (scFv) antibody and substituted for the EPO used in the present invention.

In some embodiments, when an Ab, (e.g., a MAb such as HIRMAb) is used, additional fusion protein variants can be produced with the substitution of amino acids within either the framework region (FR) or the complementarity determining region (CDR) of either the light chain or the heavy chain of the Ab, e.g., HIRMAb, as long as the fusion protein binds with high affinity to the endogenous receptor, e.g., HIR to promote transport across the human BBB. Additional fusion protein variants can be produced by changing the composition or length of the linker peptide separating the fusion protein from the HIRMAb.

Human mature EPO lacks the 27 a.a. signal peptide that is present in full-length EPO. The sequence of human mature EPO, without its 27 a.a. signal peptide is given in SEQ ID NO: 48. In some embodiments, the full 166 a.a. sequence of mature EPO is utilized. In some embodiments, the invention utilizes a EPO that is about 60, 70, 80, 90, 95, 99, or 100% identical with the sequence of human mature EPO given SEQ ID NO: 48. In some embodiments, the invention utilizes a EPO that is the full-length 193 a.a. human EPO, that is provided in SEQ ID NO:56. In some embodiments, the invention utilizes an EPO that is about 60, 70, 80, 90, 95, 99, or 100% identical with the sequence of the full-length EPO provided in SEQ ID NO:56.

Accordingly, EPO polypeptides useful in the invention include peptides having at least about 60%, at least about 70%, at least about 80%, at least about 90%, at least about 95%, at least about 99%, or greater than 95% or greater than 99% sequence identity, e.g., 100% sequence identity, to the amino acid sequences disclosed herein.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.). The percent identity is then calculated as: ([Total number of identical matches]/[length of the longer sequence plus the number of gaps introduced into the longer sequence in order to align the two sequences])(100).

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of another peptide. The FASTA algorithm is described by Pearson and Lipman, *Proc. Nat'l Acad. Sci. USA* 85:2444 (1988), and by Pearson, *Meth. Enzymol.* 183:63 (1990). Briefly, FASTA first characterizes sequence similarity by identifying regions shared by the query sequence (e.g., SEQ ID NO:44 or SEQ ID NO: 45) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, SIAM J. *Appl. Math.* 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

The present invention also includes peptides having a conservative amino acid change, compared with an amino acid sequence disclosed herein. Many such changes have been described specifically. More generally, for example, variants can be obtained that contain one or more amino acid substitutions of SEQ ID NO:48, or truncated versions thereof In some embodiments sequence variants include conservative amino acid substitutions, e.g., an alkyl amino acid is substituted for an alkyl amino acid in a EPO peptide amino acid sequence, an aromatic amino acid is substituted for an aromatic amino acid in a EPO peptide amino acid sequence, a sulfur-containing amino acid is substituted for a sulfur-containing amino acid in a EPO peptide amino acid sequence, a hydroxy-containing amino acid is substituted for a hydroxy-containing amino acid in a EPO peptide amino acid sequence, an acidic amino acid is substituted for an acidic amino acid in a EPO peptide amino acid sequence, a basic amino acid is substituted for a basic amino acid in EPO peptide amino acid sequence, or a dibasic monocarboxylic amino acid is substituted for a dibasic monocarboxylic amino acid in a EPO peptide amino acid sequence. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

It also will be understood that amino acid sequences may include additional residues, such as additional N- or C-terminal amino acids, and yet still be essentially as set forth in one of the sequences disclosed herein, so long as the sequence retains sufficient biological protein activity to be functional in the compositions and methods of the invention.

In some embodiments, where EPO sequence variants (e.g., variants of SEQ ID NO:48) are to be utilized, mutation tolerance prediction programs can be used to greatly reduce the number of non-functional sequence variants that would be generated by strictly random mutagenesis. Various programs for predicting the effects of amino acid substitutions in a protein sequence on protein function (e.g., SIFT, PolyPhen, PANTHER PSEC, PMUT, and TopoSNP) are described in, e.g., Henikoff et al., *Annu. Rev. Genomics Hum. Genet.*, (2006) 7:61-80.

V. Compositions

Compositions of the invention are useful in one or more of: decreasing serum half-life of EPO, transporting an agent across the BBB, and/or retaining activity of the agent once transported across the BBB. Accordingly, in some embodiments, the invention provides compositions containing a neurotherapeutic agent (e.g., EPO) covalently linked to a structure that is capable of crossing the blood brain barrier (BBB), where the composition is capable of producing an average elevation of concentration in the brain of the neurotherapeutic agent of at least about 1, 2, 3, 4, 5, 10, 20, 30, 40, or 50 ng/gram brain following peripheral administration. The invention also provides compositions containing an agent that is covalently linked to a chimeric MAb to the human BBB insulin receptor. The invention further provides a fusion protein containing a structure capable of crossing the BBB, covalently linked to a peptide that is active in the central nervous system (CNS), where the structure capable of crossing the blood brain barrier and the peptide that is active in the central nervous system each retain an average of at least about 10, 20, 30, 40, 50, 60, 70, 80, 90, 95, 99, or 100% of their activities, compared to their activities as separate entities. In certain embodiments, the invention further provides compositions that decrease the serum half-life of EPO. The invention also provides pharmaceutical compositions that contain one or more compositions of the invention and a pharmaceutically acceptable excipient.

In some embodiments, the invention provides compositions containing a neurotherapeutic agent covalently linked to a structure that is capable of crossing the blood brain barrier (BBB), where the composition is capable of producing an average elevation of concentration in the brain of the neurotherapeutic agent of at least about 1, 2, 3, 4, 5, 10, 20, 30, 40, or 50 ng/gram brain following peripheral administration.

"Elevation" of the agent is an increase in the brain concentration of the agent compared to the concentration of the agent administered alone (i.e., not covalently linked to a structure that is capable of crossing the BBB). In the case of agents for which only a small amount of the agent alone normally crosses the BBB, "elevation" may be an increase in the agent compared to resting brain levels. "Average" refers to the mean of at least three, four, five, or more than five measurements, preferably in different individuals. The individual in which the elevation is measured is a mammal, such as a rat, or, preferably, a primate, e.g., a monkey. An example of measurements of elevation of the level of a neurotherapeutic agent (EPO) is given in Example 21.

In some embodiments, the structure that is capable of crossing the BBB utilizes an endogenous BBB receptor mediated transport system, such as a system that utilizes the insulin receptor, transferrin receptor, leptin receptor, LDL receptor, or IGF receptor. In some embodiments, the endogenous BBB receptor mediated transport system is the insulin BBB receptor mediated transport system. In some embodiments, the structure that is capable of crossing the BBB is an antibody, e.g., a monoclonal antibody (MAb) such as a chimeric MAb. The antibody can be a chimeric antibody with sufficient human sequence that it is suitable for administration to a human. The antibody can be glycosylated or nonglycosylated; in some embodiments, the antibody is glycosylated, e.g., in a glycosylation pattern produced by its synthesis in a CHO cell. In embodiments in which the structure is an antibody, the covalent linkage between the antibody and the neurotherapeutic agent may be a linkage between any suitable portion of the antibody and the neurotherapeutic agent, as long as it allows the antibody-agent fusion to cross the blood brain barrier and the neurotherapeutic agent to retain a therapeutically useful portion of its activity within the CNS. In certain embodiments, the covalent link is between one or more light chains of the antibody and the neurotherapeutic agent. In the case of a peptide neurotherapeutic agent (e.g., a neurotrophin such as EPO), the peptide can be covalently linked by its carboxy or amino terminus to the carboxy or amino terminus of the light chain (LC) or heavy chain (HC) of the antibody. Any suitable linkage may be used, e.g., carboxy terminus of light chain to amino terminus of peptide, carboxy terminus of heavy chain to amino terminus of peptide, amino terminus of light chain to amino terminus of peptide, amino terminus of heavy chain to amino terminus of peptide, carboxy terminus of light chain to carboxy terminus of peptide, carboxy terminus of heavy chain to carboxy terminus of peptide, amino terminus of light chain to carboxy terminus of peptide, or amino terminus of heavy chain to carboxy terminus of peptide. In some embodiments, the linkage is from the carboxy terminus of the HC to the amino terminus of peptide. It will be appreciated that a linkage between terminal amino acids is not required, and any linkage which meets the requirements of the invention may be used; such linkages between non-terminal amino acids of peptides are readily accomplished by those of skill in the art.

In some embodiments, the invention utilizes EPO, either the native form or truncated variants. Strikingly, it has been found that fusion proteins of these forms of EPO retain full transport and activity. This is surprising because the neurotrophin is translated in vivo in cells as a pro form and the pro-EPO is then converted into mature EPO following cleavage of the signal peptide from the amino terminus of the EPO. In order to preserve the pro form of the EPO, and the subsequent cleavability of the pro peptide, it would seem to be necessary to fuse the pro EPO to the amino terminus of either the HC or the LC of the targeting MAb. This could, however, inhibit the binding of the MAb for the target antigen, since the complementarity determining regions (CDR) of the heavy chain or light chain of the MAb molecule, which comprise the antigen binding site of the MAb, are situated near the amino terminus of the heavy chain or light chains of the antibody. Therefore, fusion of the pro-EPO to the amino terminus of the antibody chains is expected to result in not only impairment of antibody activity, but also an impairment of antibody folding following translation. The present invention shows the unexpected finding that it is possible to fuse the mature form of EPO, to the carboxyl terminus of the heavy chain of the HIR MAb. The production of this new genetically engineered fusion protein creates a bi-functional molecule that binds with high affinity to both the HIR and the EPO receptors.

In other embodiments, the invention utilizes EPO (e.g., mature human EPO) or a sequence variant of the EPO as described herein.

In some embodiments, more than one molecule of the same neurotherapeutic agent is attached to the structure that crosses the BBB. For example, in compositions of the invention where a single neurotrophin is attached to an antibody, one molecule of the neurotrophin is attached to each heavy chain, naturally producing a structure that is ideal for homodimer formation. This is the case for compositions containing EPO. Neurotrophins such as EPO bind to the EPOR in a receptor dimeric configuration.

In some embodiments, more than one type of neurotherapeutic agent can be attached to the structure that is capable of crossing the blood brain barrier. In some embodiments, 2, 3, 4, 5, 6, 7, 8, 9, 10, or more than 10 different neurotherapeutic agents may be attached to the structure that is capable of crossing the blood brain barrier. In certain embodiments, 2 different neurotrophins are attached to an antibody to an endogenous BBB receptor-mediated transport system. Any combination of neurotrophins may be used. Particularly useful in some embodiments of the invention are neurotrophins used as precursors for fusion proteins that cross the BBB are those that naturally form dimeric structures, similar to EPO. Typically, the molecular weight range of recombinant proteins that may be fused to the molecular Trojan horse ranges from 1000 Daltons to 500,000 Daltons.

In some embodiments, more than one type of structure capable of crossing the BBB, e.g., molecular Trojan horse, may be used. The different structures may be covalently attached to a single neurotherapeutic agent, e.g., a single neurotrophin such as EPO, or multiple neurotherapeutics, e.g., multiple neurotrophins, or any combination thereof. Thus, for example, in some embodiments either with the same neurotrophin attached to each MTH or a different neurotrophin attached, or combinations of neurotrophins attached. Thus the neuroprotective recombinant protein can be fused to multiple molecular Trojan horses that undergo receptor-mediated transport across the blood-brain barrier, including monoclonal antibodies to the insulin receptor, transferrin receptor, insulin-like growth factor (IGF) receptor, or the low density lipoprotein (LDL) receptor or the endogenous ligand, including insulin, transferrin, the IGFs, or LDL. Ligands that traverse the blood-brain barrier via absorptive-mediated transport may also be used as molecular Trojan horses including cationic proteins, or carbohydrate bearing proteins that bind to membrane lectins. The molecular weight range of molecular Trojan horses is 1000 Daltons to 500,000 Daltons.

The covalent linkage between the structure capable of crossing the BBB and the neurotherapeutic agent may be direct, e.g., a peptide bond between the terminal amino acid of one peptide and the terminal amino acid of the other peptide to which it is linked, or indirect, via a linker If a linker is used, it may be any suitable linker, e.g., a peptide linker. If a peptide linker is used, it may be 1, 2, 3, 4, 5, 6, 7, 8, 9, 10, or more than 10 amino acids in length. In some embodiments, a three amino acid linker is used. In some embodiments, the linker has the sequence ser-ser-met. The covalent linkage may be cleavable, however this is not a requirement for activity of the system in some embodiments; indeed, an advantage of these embodiments of the present invention is that the fusion protein, without cleavage, is partially or fully active both for transport and for activity once across the BBB.

In some embodiments, the invention provides compositions containing a neurotherapeutic agent covalently linked to a structure that is capable of crossing the BBB where the composition is capable of producing an average elevation of concentration in the brain of the neurotherapeutic agent of at least about 1, 2, 3, 4, 5, 10, 20, 30, 40, or 50 ng/gram brain following peripheral administration, where the neurotherapeutic agent is a neurotrophin and the structure that is capable of crossing the BBB is a MAb to an endogenous BBB receptor mediated transport system. The antibody can be glycosylated or nonglycosylated; in some embodiments, the antibody is glycosylated, e.g., in a glycosylation pattern produced by its synthesis in a CHO cell. In certain embodiments, the neurotrophin is EPO, e.g., a mature human EPO (SEQ ID NO:48) or a sequence variant thereof. The MAb can be an antibody to the insulin BBB receptor mediated transport system, e.g., a chimeric MAb. The antibody can be a chimeric antibody with sufficient human sequence that it is suitable for administration to a human, e.g., at least about 80% human sequence, e.g., 85%, 90%, 95%, or another percent human amino acid sequence from about 80% to about 100% human sequence. In some embodiments, the insulin receptor is a human insulin receptor and the EPO is a human EPO. In some embodiments, the EPO contains a sequence that is about 60, 70, 80, 90, 95, 99, or 100% identical to the sequence of SEQ ID NO: 48. The EPO can be covalently linked at its amino terminus to the carboxy terminus of the heavy chain of the MAb, optionally with a linker between the termini, such as the three amino-acid linker ser-ser-ser. In some embodiments, the heavy chain of the MAb contains a sequence that is about 60, 70, 80, 90, 95, 99, or 100% identical to amino acids 20-462 of SEQ ID NO: 46. In some embodiments, the light chain of the MAb contains a sequence that is about 60, 70, 80, 90, 95, 99, or 100% identical to amino acids 21-234 of SEQ ID NO: 47.

The invention also provides compositions containing an agent that is covalently linked to a chimeric MAb to the human BBB insulin receptor. In some embodiments, the heavy chain of the MAb is covalently linked to the agent to form a fusion protein. The agent can be any agent described herein, i.e., any agent for which transport across the BBB is desired. In some embodiments, the agent is a therapeutic agent, such as a neurotherapeutic agent as described herein, e.g., a neurotrophin such as EPO.

Strikingly, it has been found that multifunctional fusion proteins of the invention, e.g., difunctional fusion proteins, retain a high proportion of the activity of the separate portions, e.g., the portion that is capable of crossing the BBB and the portion that is active in the CNS. Accordingly, the invention further provides a fusion protein containing a structure capable of crossing the BBB, covalently linked to a peptide that is active in the central nervous system (CNS), where the structure capable of crossing the BBB and the peptide that is active in the central nervous system each retain an average of at least about 10, 20, 30, 40, 50, 60, 70, 80, 90, 95, 99, or 100% of their activities, compared to their activities as separate entities. In some embodiments, the structure capable of crossing the BBB, and the peptide that is active in the central nervous system each retain about 20% to about 80% of their activities (e.g., about 30% to about 70, or about 40% to about 60%) compared to their activities as separate entities. In some embodiments, the invention provides a fusion protein containing a structure capable of crossing the BBB, covalently linked to a peptide that is active in the central nervous system (CNS), where the structure capable of crossing the blood brain barrier and the peptide that is active in the central nervous system each retain an average of at least about 50% of their activities, compared to their activities as separate entities. In some embodiments, the invention provides a fusion protein containing a structure capable of crossing the BBB, covalently linked to a peptide that is active in the central nervous system (CNS), where the structure capable of crossing the blood brain barrier and the peptide that is active in the central nervous system each retain an average of at least about 60% of their activities, compared to their activities as separate entities. In some embodiments, the invention provides a fusion protein containing a structure capable of crossing the BBB, covalently linked to a peptide that is active in the central nervous system (CNS), where the structure capable of crossing the blood brain barrier and the peptide that is active in the central nervous system each retain an average of at least about 70% of their activities, compared to their activities as separate entities. In some embodiments, the invention provides a fusion protein containing a structure capable of crossing the BBB, covalently linked to a peptide that is active in the central nervous system (CNS), where the structure capable of crossing the blood brain barrier and the peptide that is active in the central nervous system each retain an average of at least about 80% of their activities, compared to their activities as separate entities. In some embodiments, the invention provides a fusion protein containing a structure capable of crossing the BBB, covalently linked to a peptide that is active in the central nervous system (CNS), where the structure capable of crossing the blood brain barrier and the peptide that is active in the central nervous system each retain an average of at least about 90% of their activities, compared to their activities as separate entities. In some embodiments, the structure capable of crossing the blood brain barrier retains at least about 10, 20, 30, 40, 50, 60, 70, 80, 90, 95, 99, or 100% of its activity, compared to its activity as a separate entity, and the peptide that is active in the central nervous system retains at least about 10, 20, 30, 40, 50, 60, 70, 80, 90, 95, 99, or 100% of its activity, compared to its activity as a separate entity.

As used herein, "activity" includes physiological activity, e.g., ability to cross the BBB and/or therapeutic activity and also binding affinity of the structures for their respective receptors.

Transport of the structure capable of crossing the BBB across the BBB may be compared for the structure alone and for the structure as part of a fusion structure of the invention by standard methods. For example, pharmacokinetics and brain uptake of the fusion structure, e.g., fusion protein, by a model animal, e.g., a mammal such as a primate, may be used. Such techniques are illustrated in Example 21, which demonstrates pharmacokinetics and brain uptake of a fusion protein of the invention by the adult Rhesus monkey. Similarly, standard models for the function of an agent, e.g., the therapeutic or protective function of a therapeutic agent, may also be used to compare the function of the agent alone and the function of the agent as part of a fusion structure of the invention. See, e.g., Example 19, which demonstrates the activity of EPO bound to a fusion protein in a model system (human cell activation). In Example 18, the fusion protein of the invention retained a high degree of the transport ability and the therapeutic function of its individual components, i.e., a structure capable of crossing the BBB (a MAb to the human insulin receptor) and a therapeutic agent (EPO).

Alternatively, binding affinity for receptors may be used as a marker of activity. Binding affinity for the receptor is compared for the structure alone and for the structure when part of the fusion protein. A suitable type of binding affinity assay is enzyme linked immunoabsorbent assay (ELISA). For example, for fusion proteins containing MAbs to endogenous BBB receptor-mediated transport systems fused to a neurotrophin, a ELISA may be used both to assay the affinity of the MAb for its receptor and the neurotrophin for its receptor, either as part of the fusion protein or as separate entities, and percentage affinity calculated.

In embodiments of the above fusion proteins, the structure capable of crossing the blood brain barrier crosses the BBB on an endogenous BBB receptor-mediated transporter, such as a transporter selected from the group consisting of the insulin transporter, the transferrin transporter, the leptin transporter, the LDL transporter, and the IGF receptor. In some embodiments, the endogenous BBB receptor-mediated transporter is selected from the group consisting of the insulin transporter and the transferrin transporter. In some embodiments, the endogenous BBB receptor-mediated transporter is the insulin transporter, e.g., the human insulin transporter. The structure capable of crossing the BBB can be an antibody, e.g., a MAb such as a chimeric MAb. The antibody can be an antibody to an endogenous BBB receptor-mediated transporter, as described herein. The peptide that is active in the CNS can be a neurotherapeutic agent, e.g., a neurotrophin. In some embodiments, the neurotrophin is erythropoietin (EPO). In some embodiments, the neurotrophin is EPO such as a truncated EPO, e.g., a carboxyl-truncated EPO. The carboxyl-truncated EPO is lacking the one or more carboxyl terminal amino acids in some embodiments. The structure capable of crossing the BBB and the neurotherapeutic agent are covalently linked by a peptide linker in some embodiments.

In certain embodiments, the invention provides compositions that decrease the serum half-life of EPO. The work in Example 21 shows that when EPO is re-engineered as an IgG fusion protein, the plasma pharmacokinetics is dominated by the IgG moiety, and that EPO fused to the IgG is cleared from blood much faster than is EPO alone. The effect of EPO on hematopoiesis is proportional to the plasma AUC. If EPO has a lower plasma AUC, ie, because the EPO is cleared from blood faster, than the effect of the modified EPO on hematopoiesis in the peripheral tissues is reduced. Therefore, the re-engineering of EPO as the IgG-EPO fusion protein described herein results in a form of EPO that is selectively active in the brain as compared to the hematopoietic tissues outside of brain Accordingly, in some embodiments, the invention provides composition comprising an EPO covalently linked to an immunoglobulin, wherein the EPO in the composition has a plasma AUC that is an average of at least about 1.5, 2, 3, 4, 5, 6, 7, 8, 9, or 10-fold lower than the plasma AUC of the EPO alone. In some embodiments, the invention provides a composition comprising an EPO covalently linked to an immunoglobulin, wherein the EPO in the composition has a mean residence time (MRT) in the serum that is an average of at least about 1.5, 2, 3, 4, or more than about 5-fold lower than the MRT of the EPO alone. In some embodiments, the invention provides composition comprising an EPO covalently linked to an immunoglobulin, wherein the EPO in the composition has a systemic clearance rate that is an average of at least about 1.5, 2, 3, 4, 5, 6, 7, 8, 9, or more than about 10-fold faster than the systemic clearance rate of the EPO alone.

In some embodiments, the immunoglobulin is an antibody to an endogenous BBB receptor-mediated transport system. In some embodiments, the endogenous BBB receptor-mediated transport system is selected from the group consisting of the insulin BBB transport system, the BBB transferrin receptor, the BBB leptin receptor, the BBB IGF receptor, or the BBB lipoprotein receptor. In some embodiments, the antibody is an antibody to the endogenous insulin BBB receptor-mediated transport system. Antibodies can be any suitable antibody as described herein.

Pharmaceutical compositions The invention also provides pharmaceutical compositions that contain one or more compositions of the invention and a pharmaceutically acceptable excipient. A thorough discussion of pharmaceutically acceptable carriers/excipients can be found in *Remington's Pharmaceutical Sciences*, Gennaro, A R, ed., 20th edition, 2000: Williams and Wilkins PA, USA. Pharmaceutical compostions of the invention include compositions suitable for administration via any peripheral route, including intravenous, subcutaneous, intramuscular, intraperitoneal injection; oral, rectal, transbuccal, pulmonary, transdermal, intranasal, or any other suitable route of peripheral administration.

The compostions of the invention are particular suited for injection, e.g., as a pharmaceutical composition for intravenous, subcutaneous, intramuscular, or intraperitonal administration. Aqueous compositions of the present invention comprise an effective amount of a composition of the present invention, which may be dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, e.g., a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Exemplary pharmaceutically acceptable carriers for injectable compositions can include salts, for example, mineral acid salts such as hydrochlorides, hydrobromides, phosphates, sulfates, and the like; and the salts of organic acids such as acetates, propionates, malonates, benzoates, and the like. For example, compositions of the invention may be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used buffers include histidine, acetate, phosphate, or citrate. Under ordinary conditions of storage and use, these preparations can contain a preservative to prevent the growth of microorganisms. The prevention of the action of microorganisms can be brought about by various antibacterial and antifungal agents, for example, parabens, chlorobutanol; phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate, and gelatin.

For human administration, preparations meet sterility, pyrogenicity, general safety, and purity standards as required by FDA and other regulatory agency standards. The active compounds will generally be formulated for parenteral administration, e.g., formulated for injection via the intravenous, intramuscular, subcutaneous, intralesional, or intraperitoneal routes. The preparation of an aqueous composition that contains an active component or ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, methods of preparation include vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed The term "unit dose" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the protection desired. The person responsible for administration will, in any event, determine the appropriate dose for the individual subject.

The active therapeutic agents may be formulated within a mixture to comprise about 0.1 to 100 ug/kg. Multiple doses can also be administered. In some embodiments, a dosage of about 0.3 to about 3 ug/kg of a fusion protein of the invention is used as a unit dose for administration to a human, e.g., about 0.3 to about 3 ug/kg of a fusion protein of EPO and a HIR MAb.

In addition to the compounds formulated for parenteral administration, such as intravenous or intramuscular injection, other alternative methods of administration of the present invention may also be used, including but not limited to intradermal administration (See U.S. Pat. Nos. 5,997,501; 5,848,991; and 5,527,288), pulmonary administration (See U.S. Pat. Nos. 6,361,760; 6,060,069; and 6,041,775), buccal administration (See U.S. Pat. Nos. 6,375,975; and 6,284, 262), transdermal administration (See U.S. Pat. Nos. 6,348, 210; and 6,322,808) and transmucosal administration (See U.S. Pat. No. 5,656,284). All such methods of administration are well known in the art. One may also use intranasal administration of the present invention, such as with nasal solutions or sprays, aerosols or inhalants. Nasal solutions are usually aqueous solutions designed to be administered to the nasal passages in drops or sprays. Nasal solutions are prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and include, for example, antibiotics and antihistamines and are used for asthma prophylaxis.

Additional formulations, which are suitable for other modes of administration, include suppositories and pessaries. A rectal pessary or suppository may also be used. Suppositories are solid dosage forms of various weights and shapes, usually medicated, for insertion into the rectum or the urethra. After insertion, suppositories soften, melt or dissolve in the cavity fluids. For suppositories, traditional binders and carriers generally include, for example, polyalkylene glycols or triglycerides; such suppositories may be formed from mixtures containing the active ingredient in any suitable range, e.g., in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations, or powders. In certain defined embodiments, oral pharmaceutical compositions will comprise an inert diluent or assimilable edible carrier, or they may be enclosed in a hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations can contain at least 0.1% of active compound. The percentage of the compositions and preparations may, of course, be varied, and may conveniently be between about 2 to about 75% of the weight of the unit, or between about 25-60%. The amount of active compounds in such therapeutically useful compositions is such that a suitable dosage will be obtained.

The tablets, troches, pills, capsules and the like may also contain the following: a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent, methylene and propyl parabens as preservatives, a dye and flavoring, such as cherry or orange flavor. In some embodiments, an oral pharmaceutical composition may be enterically coated to protect the active ingredients from the environment of the stomach; enteric coating methods and formulations are well-known in the art.

VI. Nucleic Acids, Vectors, Cells, and Manufacture

The invention also provides nucleic acids, vectors, cells, and methods of production.

A. Nucleic Acids

In some embodiments, the invention provides nucleic acids that code for proteins or peptides of the invention. In certain embodiments, the invention provides a single nucleic acid sequence containing a first sequence coding for a light chain of an immunoglobulin and second sequence coding a heavy chain of the immunoglobulin, where either the first sequence also codes for a peptide that is expressed as a fusion protein of the peptide covalently linked to the light chain, or the second sequence also codes for a peptide that is expressed as a fusion protein of the peptide covalently linked to the heavy chain. In some embodiments, the invention provides nucleic acid sequences, and in some embodiments the invention provides nucleic acid sequences that are at least about 60, 70, 80, 90, 95, 99, or 100% identical to a particular nucleotide sequence. For example, in some embodiments, the invention provides a nucleic acid containing a first sequence that is at least about 60, 70, 80, 90, 95, 99, or 100% identical to SEQ ID NO:51 and a second sequence that is at least about 60, 70, 80, 90, 95, 99, or 100% identical to nucleotides 1-1896 of SEQ ID NO: 52.

In other embodiments, the invention provides a nucleic acid containing a sequence that is at least about 60, 70, 80, 90, 95, 99, or 100% identical to nucleotides 58-1896 of SEQ ID NO: 52

For sequence comparison, of two nucleic acids, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, including but not limited to, by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

One example of an algorithm that is suitable for determining percent sequence identity and sequence similarity are the BLAST and BLAST 2.0 algorithms, which are described in Altschul et al. (1977) *Nuc. Acids Res.* 25: 3389-3402, and Altschul et al. (1990) *J. Mol. Biol.* 215: 403-410, respectively. Software for performing BLAST analyses is publicly available through the National Center for Biotechnology Information. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. The BLAST algorithm is typically performed with the "low complexity" filter turned off. The BLAST algorithm also performs a statistical analysis of the similarity between two sequences (see, e.g., Karlin and Altschul (1993) *Proc. Natl. Acad. Sci. USA* 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The invention provides nucleic acids that code for any of the peptides of the invention. In some embodiments, the invention provides a single nucleic acid sequence containing a gene coding for a light chain of an immunoglobulin and a gene coding for a fusion protein, where the fusion protein includes a heavy chain of the immunoglobulin covalently linked to a peptide. In some embodiments, the peptide is mature human EPO. In some embodiments, the peptide is a neurotherapeutic peptide, e.g., mature human EPO. In some embodiments, the immunoglobulin is an IgG. In some embodiments, the IgG is a MAb, such as a chimeric MAb. The antibody can be an antibody to a transport system, e.g., an endogenous BBB receptor-mediated transport system such as the endogenous BBB receptor-mediated insulin transport system. In some embodiments, the endogenous BBB receptor-mediated insulin transport system is a human endogenous BBB receptor-mediated insulin transport system and wherein the peptide to which the immunoglobulin heavy chain is covalently linked is human EPO. Any suitable form of EPO, antibody, monoclonal antibody, or chimeric antibody, as described herein, may be coded for by the nucleic acid, combined as a fusion protein and coded for in a single nucleic acid sequence. As is well-known in the art, owing to the degeneracy of the genetic code, any combination of suitable codons may be used to code for the desired fusion protein. In addition, other elements useful in recombinant technology, such as promoters, termination signals, and the like, may also be included in the nucleic acid sequence. Such elements are well-known in the art. In addition, all nucleic acid sequences described and claimed herein include the complement of the sequence.

In some embodiments the nucleic acid codes for a human mature EPO as a component of the fusion protein, which also comprises an immunoglobulin sequence. In some embodiments, the EPO contains a sequence that is about 60, 70, 80, 90, 95, 99, or 100% identical to the sequence of amino acids 466-631 of SEQ ID NO: 49. In some embodiments, the EPO contains a sequence that is at least about 60, 70, 80, 90, 95, 99, or 100% identical to the sequence of SEQ ID NO:48. In some embodiments, the amino acid sequence of the encoded EPO consists essentially of SEQ ID NO:48. In some embodiments, the nucleic acid codes for a fusion protein comprising an amino acid sequence that is at least about 60, 70, 80, 90, 95, 99, or 100% identical to the sequence of SEQ ID NO:49. In some embodiments, the encoded nucleic acid comprises the amino acid sequence of SEQ ID NO:49. In some embodiments, the EPO is linked at its amino terminus to carboxy terminus of the heavy chain of the immunoglobulin, e.g., MAb. The heavy chain of the MAb can comprise a sequence that is about 60, 70, 80, 90, 95, 99 or 100% identical to amino acids 20-462 of SEQ ID NO: 46. In some embodiments, the light chain of the immunoglobulin, e.g., MAb, comprises a sequence that is about 60, 70, 80, 90, 95, 99 or 100% identical to amino acids 21-234 of SEQ ID NO: 47. The nucleic acid can further contain a nucleic acid sequence that codes for a peptide linker between the heavy chain of the MAb and the EPO. In some embodiments, the linker is S—S—S. The nucleic acid may further contain a nucleic acid sequence coding for a signal peptide, wherein the signal peptide is linked to the heavy chain. Any suitable signal peptide, as known in the art or subsequently developed, may be used. In some embodiments, the signal peptide attached to the heavy chain comprises a sequence that is about 60, 70, 80, 90, 95, 99, or 100% identical to amino acids 1-19 of SEQ ID NO: 46. In some embodiments, the nucleic acid contains a nucleic acid sequence coding for another signal peptide, wherein the other signal peptide is linked to the light chain. The signal peptide linked to the light chain can comprise a sequence that is about 60, 70, 80, 90, 95, 99, or 100% identical to amino acids 1-20 of SEQ ID NO: 47. The nucleic acid can contain a nucleic acid sequence coding for a selectable marker. In some embodiments the selectable marker is DHFR. The sequence of the DHFR can be about 60, 70, 80, 90, 95, 99, or 100% identical to amino acids 1-187 of SEQ ID NO: 55.

In certain embodiments, the invention provides a nucleic acid comprising a first sequence that codes for a neurotrophin such as EPO, in the same open reading frame as a second sequence that codes for an immunoglobulin component. The immunoglobulin component can be, e.g., a light chain or a heavy chain, e.g., that is at least about 60, 70, 80, 90, 95, 99, or 100% identical to nucleotides 58-1386-of SEQ ID NO: 52 and a second sequence that is at least about 60, 70, 80, 90, 95, 99, or 100% identical to nucleotides 1396-1896 of SEQ ID NO: 52. In some embodiments, the nucleic acid also contains a third sequence that is at least about 60, 70, 80, 90, 95, 99, or 100% identical to nucleotides 61-714 of SEQ ID NO: 51. In some embodiments, the nucleic acid further contains a fourth sequence that codes for a first signal peptide and a fifth sequence that codes for a second signal peptide. In some embodiments, the fourth sequence is at least about 60, 70, 80, 90, 95, 99, or 100% identical to nucleotides 1-57 of SEQ ID NO: 52 and the fifth sequence is at least about 60, 70, 80, 90, 95, 99, or 100% identical to nucleotides 1-60 of SEQ ID NO: 51. In some embodiments, the nucleic acid further contains a sequence that codes for a selectable marker, such as dihydrofolate reductase (DHFR). In some embodiments, the sequence that codes for the DHFR is at least about 60, 70, 80, 90, 95, 99, or 100% identical to nucleotides 1-564 of SEQ ID NO: 53.

B. Vectors

The invention also provides vectors. The vector can contain any of the nucleic acid sequences described herein. In some embodiments, the invention provides a single tandem expression vector containing nucleic acid coding for an antibody heavy chain fused to a peptide, e.g., a therapeutic peptide such as a neurotrophin, and nucleic acid coding for a light chain of the antibody, all incorporated into a single piece of nucleic acid, e.g., a single piece of DNA. The single tandem vector can also include one or more selection and/or amplification genes. A method of making an exemplary vector of the invention is provided in the Examples. However, any suitable techniques, as known in the art, may be used to construct the vector.

The use of a single tandem vector has several advantages over previous techniques. The transfection of a eukaryotic cell line with immunoglobulin G (IgG) genes generally involves the co-transfection of the cell line with separate plasmids encoding the heavy chain (HC) and the light chain (LC) comprising the IgG. In the case of a IgG fusion protein, the gene encoding the recombinant therapeutic protein may be fused to either the HC or LC gene. However, this co-transfection approach makes it difficult to select a cell line that has equally high integration of both the HC and LC-fusion genes, or the HC-fusion and LC genes. The approach to manufacturing the fusion protein utilized in certain embodiments of the invention is the production of a cell line that is stably transfected with a single plasmid DNA that contains all the required genes on a single strand of DNA, including the HC-fusion protein gene, the LC gene, the selection gene, e.g., neo, and the amplification gene, e.g., the dihydrofolate reductase gene. As shown in the diagram of the fusion protein tandem vector in FIG. 15, the HC-fusion gene, the LC gene, the neo gene, and the DHFR gene are all under the control of separate, but tandem promoters and separate but tandem transcription termination sequences. Therefore, all genes are equally integrated into the host cell genome, including the fusion gene of the therapeutic protein and either the HC or LC IgG gene.

C. Cells

The invention further provides cells that incorporate one or more of the vectors of the invention. The cell may be a prokaryotic cell or a eukaryotic cell. In some embodiments, the cell is a eukaryotic cell. In some embodiments, the cell is a mouse myeloma hybridoma cell. In some embodiments, the cell is a Chinese hamster ovary (CHO) cell. Exemplary methods for incorporation of the vector(s) into the cell are given in the Examples. However, any suitable techniques, as known in the art, may be used to incorporate the vector(s) into the cell. In some embodiments, the invention provides a cell capable of expressing an immunoglobulin fusion protein, where the cell is a cell into which has been introduced a single tandem expression vector, where both the immunoglobulin light chain gene and the gene for the immunoglobulin heavy chain fused to the therapeutic agent, are incorporated into a single piece of nucleic acid, e.g., DNA. In some embodiments, the invention provides a cell capable of expressing an immunoglobulin fusion protein, where the cell is a cell into which has been stably transfected a single tandem expression vector, where both the immunoglobulin heavy chain gene and the gene for the immunoglobulin light chain fused to the therapeutic agent, are incorporated into a single piece of nucleic acid, e.g., DNA. The introduction of the tandem vector may be by, e.g., permanent integration into the chromosomal nucleic acid, or by, e.g., introduction of an episomal genetic element.

D. Methods of Manufacture

In addition, the invention provides methods of manufacture. In some embodiments, the invention provides a method of manufacturing an immunoglobulin fusion protein, where the fusion protein contains an immunoglobulin heavy chain fused to a therapeutic agent, by introducing into a eukaryotic cell a single tandem expression vector, where both the immunoglobulin light chain gene and the gene for the immunoglobulin heavy chain fused to the therapeutic agent, are incorporated into a single piece of nucleic acid, e.g., DNA. In some embodiments, the invention provides a method of manufacturing an immunoglobulin fusion protein, where the fusion protein contains an immunoglobulin light chain fused to a therapeutic agent, by ly introducing into a eukaryotic cell a single tandem expression vector, where both the immunoglobulin heavy chain gene and the gene for the immunoglobulin light chain fused to the therapeutic agent, are incorporated into a single piece of nucleic acid, e.g., DNA. In some embodiments, the introduction of the vector is accomplished by integration into the host cell genome. In some embodiments, the introduction of the vector is accomplished by introduction of an episomal genetic element containing the vector into the host cell. Episomal genetic elements are well-known in the art. In some embodiments, the therapeutic agent is a neurotherapeutic agent. In some embodiments, the single piece of nucleic acid further includes one or more genes for selectable markers. In some embodiments, the single piece of nucleic acid further includes one or more amplification genes. In some embodiments, the immunoglobulin is an IgG, e.g., a MAb such as a chimeric MAb. The methods may further include expressing the immunoglobulin fusion protein, and/or purifying the immunoglobulin fusion protein. Exemplary methods for manufacture, including expression and purification, are given in the Examples.

However, any suitable techniques, as known in the art, may be used to manufacture, optionally express, and purify the proteins. These include non-recombinant techniques of protein synthesis, such as solid phase synthesis, manual or automated, as first developed by Merrifield and described by Stewart et al. in *Solid Phase Peptide Synthesis* (1984). Chemical synthesis joins the amino acids in the predetermined sequence starting at the C-terminus. Basic solid phase methods require coupling the C-terminal protected α-amino acid to a suitable insoluble resin support. Amino acids for synthesis require protection on the α-amino group to ensure proper peptide bond formation with the preceding residue (or resin support). Following completion of the condensation reaction at the carboxyl end, the α-amino protecting group is removed to allow the addition of the next residue. Several classes of α-protecting groups have been described, see Stewart et al. in *Solid Phase Peptide Synthesis* (1984), with the acid labile, urethane-based tertiary-butyloxycarbonyl (Boc) being the historically preferred. Other protecting groups, and the related chemical strategies, may be used, including the base labile 9-fluorenylmethyloxycarbonyl (FMOC). Also, the reactive amino acid sidechain functional groups require blocking until the synthesis is completed. The complex array of functional blocking groups, along with strategies and limitations to their use, have been reviewed by Bodansky in *Peptide Synthesis* (1976) and, Stewart et al. in *Solid Phase Peptide Synthesis* (1984).

Solid phase synthesis is initiated by the coupling of the described C-terminal α-protected amino acid residue. Coupling requires activating agents, such as dicyclohexycarbodiimide (DCC) with or without 1-hydroxybenzo-triazole (HOBT), diisopropylcarbodiimide (DIIPC), or ethyldimethylaminopropylcarbodiimide (EDC). After coupling the C-terminal residue, the α-amino protected group is removed by trifluoroacetic acid (25% or greater) in dichloromethane in the case of acid labile tertiary-butyloxycarbonyl (Boc) groups. A neutralizing step with triethylamine (10%) in dichloro-methane recovers the free amine (versus the salt).

After the C-terminal residue is added to the resin, the cycle of deprotection, neutralization and coupling, with intermediate wash steps, is repeated in order to extend the protected peptide chain. Each protected amino acid is introduced in excess (three to five fold) with equimolar amounts of coupling reagent in suitable solvent. Finally, after the completely blocked peptide is assembled on the resin support, reagents are applied to cleave the peptide form the resin and to remove the side chain blocking groups Anhydrous hydrogen fluoride (HF) cleaves the acid labile tertiary-butyloxycarbonyl (Boc) chemistry groups. Several nucleophilic scavengers, such as dimethylsulfide and anisole, are included to avoid side reactions especially on side chain functional groups.

VII. Methods

The invention also provides methods. In some embodiments, the invention provides methods for transport of an agent active in the CNS across the BBB in an effective amount. In some embodiments, the invention provides therapeutic, diagnostic, or research methods. Diagnostic methods include the development of peptide radiopharmaceuticals capable of transport across the BBB, such as the fusion of a peptide ligand, or peptidomimetic MAb for an endogenous receptor in the brain, followed by the radiolabelling of the fusion protein, followed by systemic administration, and external imaging of the localization within the brain of the peptide radiopharmaceutical.

In order to achieve a neurotherapeutic effect, neurotrophins need access to the brain. In the past, in order to cross an intact BBB and achieve a therapeutic effect in the brain, neurotrophins such as EPO were injected directly into the brain, which required an invasive transcranial delivery strategy. Peripheral administration (e.g., intravenous) of a neurotrophin is ordinarily only used when the BBB is disrupted. Therefore, it is not expected that neurotrophic factors will have beneficial effects on brain disorders following the peripheral (e.g., intravenous, subcutaneous) administration of these molecules, particularly in cases where the BBB is intact.

However, neurotherapeutics can be developed as drugs for peripheral routes of administration, providing the neurotherapeutic is enabled to cross the BBB. Attachment of the neurotherapeutic, e.g., a neurotrophin such as EPO to a MTH, e.g., the chimeric HIRMAb, offers a new approach to the non-invasive delivery of neurotherapeutics to the CNS in animals, e.g., mammals such as humans for the treatment of acute brain and spinal cord conditions, such as focal brain ischemia, global brain ischemia, and spinal cord injury, and chronic treatment of neurodegenerative disease, including Alzheimer's disease (AD), Parkinson's disease (PD), ALS, multiple sclerosis.

Accordingly, in some embodiments the invention provides methods of transport of an agent active in the CNS from the peripheral circulation across the BBB in an effective amount, where the agent is covalently attached to a structure that crosses the BBB, and where the agent alone is not transported across the BBB in an effective amount. In some embodiments the invention provides methods of transport of neurotherapeutic agent from the peripheral circulation across the BBB in a therapeutically effective amount, where the neurotherapeutic agent is covalently attached to a structure that crosses the BBB, and where the neurotherapeutic agent alone is not transported across the BBB in a therapeutically effective amount.

The invention also provides, in some embodiments, methods of treatment of disorders of the CNS by peripheral administration of an effective amount of a therapeutic agent, e.g., a neurotherapeutic agent covalently linked to a structure that is capable of crossing the BBB, where the agent alone is not capable of crossing the BBB in an effective amount when administered peripherally. In some embodiments, the CNS disorder is an acute disorder, and, in some cases, may require only a single administration of the agent. In some embodiments, the CNS disorder is a chronic disorder and may require more than one administration of the agent.

In some embodiments, the effective amount, e.g., therapeutically effective amount is such that a concentration in the brain is reached of at least about 0.001, 0.01, 0.1, 0.5, 1, 2, 3, 4, 5, 6, 7, 8, 9, 10, 15, 20, 25, 30, 35, 40, 45, 50, 100, or more than 100 ng/gram brain. In some embodiments, a therapeutically effective amount, e.g., of a neurotrophin such as EPO, is such that a brain level is achieved of about 0.1 to 1000, or about 1-100, or about 5-50 ng/g brain.

In some embodiments, the invention provides methods of treating a disorder of the CNS by peripherally administering to an individual in need of such treatment an effective amount of neurotrophin (e.g., EPO), where the neurotrophin (e.g., EPO) is capable of crossing the BBB to produce an average elevation of neurotrophin (e.g., EPO) concentration in the brain of at least about 0.1, 1, 2, 3, 4, 5, 6, 7, 8, 9, 10, 15, 20, 25, 30, 35, 40, 45, 50, 100, or more than 100 ng/gram brain following said peripheral administration, and where the neurotrophin (e.g., EPO) remains at the elevated level for about 1, 2, 3, 4, 5, 6, 7, 8, 9, 10, or more than 10 days after a single administration. In some embodiments, the neurotrophin (e.g., EPO) remains at a level of greater than about 1 ng/g brain, or about 2 ng/g brain, or about 5 ng/g brain for about 2, 3, 4, 5, 6, 7, 8, 9, 10, or more than 10 days after a single administration.

In some embodiments, the invention provides methods of treating a disorder of the CNS by peripherally administering to an individual in need of such treatment an effective amount of a composition of the invention. The term "peripheral administration," as used herein, includes any method of administration that is not direct administration into the CNS, i.e., that does not involve physical penetration or disruption of the BBB. "Peripheral administration" includes, but is not limited to, intravenous intramuscular, subcutaneous, intraperitoneal, intranasal, transbuccal, transdermal, rectal, transalveolar (inhalation), or oral administration. Any suitable composition of the invention, as described herein, may be used. In some embodiments, the composition is neurotrophin (e.g., EPO) covalently linked to a chimeric HIR-MAb.

A "disorder of the CNS" or "CNS disorder," as those terms are used herein, encompasses any condition that affects the brain and/or spinal cord and that leads to suboptimal function. In some embodiments, the disorder is an acute disorder. Acute disorders of the CNS include focal brain ischemia, global brain ischemia, brain trauma, spinal cord injury, acute infections, status epilepticus, migraine headache, acute psychosis, suicidal depression, and acute anxiety/phobia. In some embodiments, the disorder is a chronic disorder. Chronic disorders of the CNS include chronic neurodegeneration, retinal degeneration, depression, chronic affective disorders, lysosmal storage disorders, chronic infections of the brain, brain cancer, stroke rehabilitation, inborn errors of metabolism, autism, mental retardation. Chronic neurodegeneration includes neurodegenerative diseases such as prion diseases, Alzheimer's disease (AD), Parkinson's disease (PD), Huntington's disease (HD), multiple sclerosis (MS), amyotrophic lateral sclerosis (ALS), transverse myelitis, motor neuron disease, Pick's disease, tuberous sclerosis, lysosomal storage disorders, Canavan's disease, Rett's syndrome, spinocerebellar ataxias, Friedreich's ataxia, optic atrophy, and retinal degeneration, and aging of the CNS.

Parkinson's disease (PD) is a neurodegenerative condition that affects the dopaminergic neurons of the nigral-striatal tract. EPO is a potent trophic factor for these dopaminergic neurons. The intra-cerebral injection of the EPO protein into the brain of rats with experimental PD can protect these neurons, and blocks further axotomy of the fibers projecting from the substantia nigra to the striatum (Xue Y. Q., Zhao L. R., Guo W. P., Duan W. M., Intrastriatal administration of erythropoietin protects dopaminergic neurons and improves neurobehavioral outcome in a rat model of Parkinson's disease, *Neuroscience* (2007) 146: 1245-1258). The peripheral administration of EPO has not been found to be therapeutically active in PD, suggesting a limitation of EPO transport across the BBB. Accordingly, in some embodiments, the compositions described herein (e.g., human mature IgG-EPO fusion proteins are used as a therapeutic for PD. In such embodiments, the IgG-EPO fusion protein is administered peripherally to a subject with PD.

Formulations and administration. Any suitable formulation, route of administration, and dose of the compositions of the invention may be used. Formulations, doses, and routes of administration are determined by those of ordinary skill in the art with no more than routine experimentation. Compositions of the invention, e.g., EPO fusion proteins are typically administered in a single dose, e.g., an intravenous dose, of about 0.01-1000 ug, or about 0.05-500 ug, or about 0.1-100 ug, or about 1-100 ug, or about 0.5-50 ug, or about 5-50 ug, or about 1, 2, 3, 4, 5, 6, 7, 8, 9, 10, 11, 12, 15, 20, 25, 30, 25, 40, 45, 50, 60, 70, 80, 90, or 100 ug. Typically, for the treatment of acute brain disease, such as stroke, cardiac arrest, spinal cord injury, or brain trauma, higher doses may be used, whereas for the treatment of chronic conditions such as Alzheimer's disease, Parkinson's disease, Huntington's disease, MS, ALS, transverse myelitis, motor neuron disease, Pick's disease, tuberous sclerosis, addiction (e.g., drug addiction), lysosomal storage disorders, Canavan's disease, Rett's syndrome, spinocerebellar ataxias, Friedreich's ataxia, optic atrophy, and retinal degeneration, and aging, lower, chronic dosing may be used. Oral administration can require a higher dosage than intravenous or subcutaneous dosing, depending on the efficiency of absorption and possible metabolism of the protein, as is known in the art, and may be adjusted from the foregoing based on routine experimentation.

For intravenous or subcutaneous administration, formulations of the invention may be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used buffers include histidine, acetate, phosphate, or citrate.

Dosages for humans can be calculated from appropriate animal data. As shown in the examples, the brain uptake of the HIRMAb-EPO fusion protein is about 2% of injected dose (ID)/100 gram brain in the adult Rhesus monkey. The brain weighs about 100 grams in the Rhesus monkey. Therefore, in a 5 kg primate, the ID may be 5 ug or 5,000 ng, and this may produce a brain concentration of HIRMAb-EPO fusion protein of 1 ng/gram brain. Since the EPO domain of the fusion protein comprises 20% of the total amino acid sequence, the administration of 1 ug/kg of the HIRMAb-EPO fusion protein may produce a concentration of fusion protein equivalent to a brain EPO concentration of 0.2 ng/gram. A dose of 3 ug/kg fusion protein may be expected to produce a concentration in brain of fusion protein equivalent to a brain EPO concentration of 0.6 ng/gram. Thus, the 1 ug/kg and 3 ug/kg doses produce EPO concentrations in brain that border a therapeutic concentration of EPO, which is about 0.4 ng/gram. In peripheral tissue, the concentration of EPO that causes a 50% increase in pharmacological effect is 12 pM (Elliott et al., 2004, Control of rHuEPO biological activity: the role of carbohydrate, Exp Hemat 32: 1146-1155), which is equal to 0.4 ng/mL, given an EPO molecular weight of 35,000 Da. Given a brain water content of 0.7 mL/gram, the therapeutic concentration of EPO in peripheral tissues is equal to 0.3 ng/gram tissue. The EPO receptor (EPOR) in the periphery is the same receptor in the brain. Therefore, doses of HIRMAb-EPO fusion protein between 1-3 ug/kg may produce EPO concentrations in brain that border the therapeutic concentration of EPO in tissues. Sub-therapeutic concentrations of EPO may be achieved by the administration of smaller doses, e.g., 0.1 or 0.3 ug/kg, and supra-therapeutic concentrations of EPO in brain may be achieved by the administration of larger doses, e.g., 10, 30, or 100 ug/kg.

The fusion protein may also be formulated for chronic use for the treatment of a chronic CNS disorder, e.g., neurodegenerative disease, stroke or brain/spinal cord injury rehabilitation, or depression. Chronic treatment may involve daily, weekly, bi-weekly administration of the composition of the invention, e.g., fusion protein either intravenously, intra-muscularly, or subcutaneous in formulations similar to that used for acute treatment. Alternatively, the composition, e.g., fusion protein may be formulated as part of a bio-degradable polymer, and administered on a monthly schedule.

Combination therapies. The composition of the invention, e.g., fusion protein may be administered as part of a combination therapy. The combination therapy involves the administration of a composition of the invention in combination with another therapy for the CNS disorder being treated. If the composition of the invention is used in combination with another CNS disorder method or composition, any combination of the composition of the invention and the additional method or composition may be used. Thus, for example, if use of a composition of the invention is in combination with another CNS disorder treatment agent, the two may be administered simultaneously, consecutively, in overlapping durations, in similar, the same, or different frequencies, etc. In some cases a composition will be used that contains a composition of the invention in combination with one or more other CNS disorder treatment agents.

Other CNS disorder treatment agents that may be used in methods of the invention include, without limitation, thromolytic therapy for stroke, amyloid-directed therapy for Alzheimers disease, dopamine restoration therapy for Parkinsons disease, RNA interference therapy for genetic disorders, cancer, or infections, and anti-convulsant therapy for epilepsy. Dosages, routes of administration, administration regimes, and the like for these agents are well-known in the art.

In some embodiments, the composition, e.g., fusion protein is co-administered to the patient with another medication, either within the same formulation or as a separate composition. For example, the fusion protein could be formulated with another fusion protein that is also designed to deliver across the human blood-brain barrier a recombinant protein other than BDNF (e.g., EPO). The fusion protein may be formulated in combination with other large or small molecules.

VIII. Kits

Compositions of the invention, e.g., fusion proteins, may be provided as a kit that includes the formulation, e.g., fusion protein in a container and in suitable packaging. The composition can be provided in a dry powder form, in solid form (i.e., lyophilized), in solution, or in suspension. If the composition is a protein, to the proteins may have been added emulsifiers, salts, preservatives, other proteins, nucleic acids, protease inhibitors, antibiotics, perfumes, polysaccharides, adhesive agents, polymers, microfibrils, oils, etc. The composition is packaged for transport, storage and/or use by a consumer. Such packaging of therapeutic compositions for transport, storage, and use is well-known in the art. Packaged compositions may include further components for the dispensing and storage of the composition, and may also include separately packaged diluent comprised of, e.g., sterile water or a suitable buffer, for solubilizing the formulation, e.g., fusion protein prior to administration to the patient. Kits of the invention may also include written materials, including instructions for use, results of clinical studies, desired outcome and expected course of treatment, information about precautions and side effects, and the like. The kits may optionally further contain other components, such as gloves, scissors, tape, implements for disposal of used vials and other waste, masks, antiseptic, antibiotics, and the like.

EXAMPLES

Example 1

Figure 3:
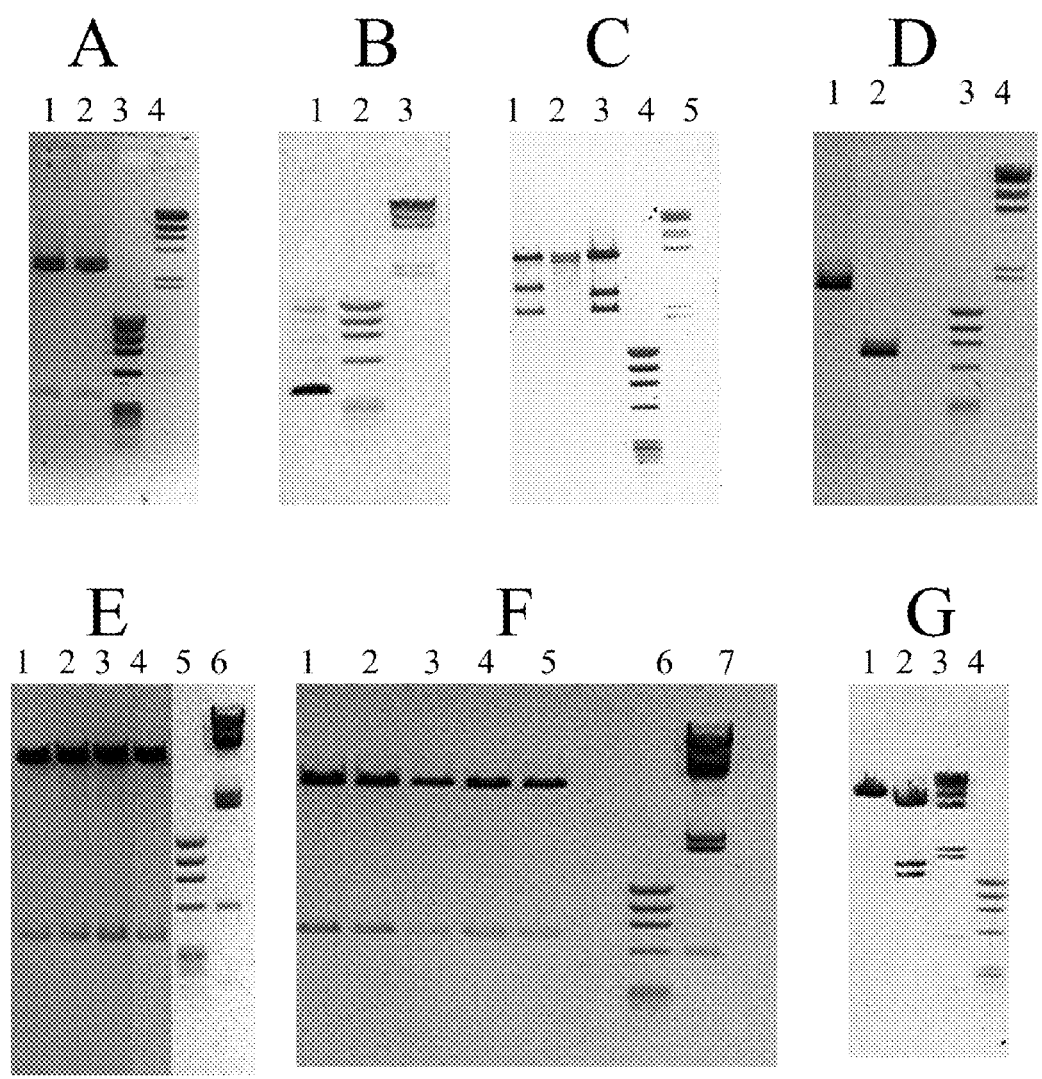
FIG. 3. Ethidium bromide stained agarose gels showing size of various constructs that are intermediates in construction of a tandem vector that produces the fusion protein. (A) Lanes 1-2: plasmid from FIG. 2 digested with NruI showing 0.4 kb vBDNF and 3.5 kb vector backbone. Lane 3: MW size standards ranging from 1.4-0.1 kb. Lane 4: MW size standards ranging from 23-0.6 kb. (B) Lane 1: the 0.4 kb vBDNF cDNA is produced by the polymerase chain reaction (PCR) using cDNA reverse transcribed from polyA+ RNA isolated from human U87 glioma cells; the PCR primer sequences are given in Table 2. Lanes 2 and 3: same MW size standards as shown in panel A. (C) lane 1: clone 416 following digestion with NheI and BamHI; lane 2: negative clone; lane 3: clone 400 following digestion with NheI and BamHI: lanes 4 and 5: same MW size standards as shown in panel A. (D) PCR fragments of DNA encoding fusion protein HC (lane 1) and LC (lane 2); lanes 3-4: same MW size standards as shown in panel A. (E) lanes 1-4: 4 different but identical copies of clone 422a following digestion with NheI, showing release of 0.4 kb fusion protein HC variable region (VH) cDNA; lanes 5-6: same MW size standards as shown in panel A. (F) lanes 1-4: 5 different but identical copies of clone 423a following digestion with EcoRV and BamHI, showing release of 0.7 kb entire LC cDNA; lanes 5-6: same MW size standards as shown in panel A. (G) Restriction endonuclease mapping of tandem vector (FIG. 12) with PvuI (lane 1), and EcoRI-HindIII (lane 2). PvuI (single cut) produced the expected linear DNA band of ~11 kb. Digestion with EcoRI and HindIII releases both the fusion protein light chain (i.e., 1.8 kb) and DHFR (i.e., 1.5 kb) expression cassettes. The ~8 kb band represents the backbone vector with the fusion protein heavy chain expression cassette; lanes 3-4: same MW size standards as shown in panel A, albeit in reverse order.

Construction of the Single Tandem Vector Containing Complete Genes for IgG-Neurotherapeutic Fusion Genetic engineering of a eukaryotic expression vector encoding the heavy chain (HC) of the fusion protein is outlined in FIG. 1. The final fusion protein HC expression vector was designated pHIRMAb-BDNF, or clone 416. This vector was designed to produce a fusion protein, comprised of a BDNF variant fused to the HC of the HIRMAb. Either BDNF or a variant of BDNF (vBDNF) can be fused to the HIRMAb. The vBDNF differs from native human BDNF by substitution of certain amino acids, such as a vBDNF where the 2 amino acids at the carboxyl terminus of BDNF are absent in vBDNF. The clone 416 plasmid was derived from clone 400, which produces the HC of the chimeric form of the HIRMAb, and a cDNA encoding mature human vBDNF, which was produced as described in FIG. 2. Clone 400 encodes a chimeric human IgG1 that is derived from a chromosomal fragment encoding the human IgG1 constant region, and is comprised of both intron and exon sequences. The HC gene of the chimeric HIRMAb in clone 400 was subcloned at the BamHI site of the pCR II plasmid to facilitate engineering of the stop codon located at the 3'-end of the CH3 region by site directed mutagenesis (SDM). The engineering of the stop codon located at the end of the CH3 region was performed by site-directed mutagenesis to produce a SspI site. The SspI site allows for insertion of the vBDNF cDNA (FIG. 3) by blunt-end ligation into clone 400 to form clone 415. SDM was performed using the QuickChange SDM kit (Stratagene, CA). Sense and complementary mutagenic primers were designed in a way that the CH3 stop codon (aaTGAg) is mutated to SspI site (aaTATt). In addition, primers contained 15 nucleotides of the stop codon 5'- and 3'-surrounding region; the sequence of these primers, designated SDM-SspI forward (FWD) and reverse (REV) are given in Table 1.

TABLE 1

Nucleotide sequence of oligodeoxynucleotides used for engineering plasmid clone 416

SDM-SspI-FWD
(SEQ ID NO. 1)
CCTGTCTCCGGGTAAATATTTGCGACGGCCGGCAAG

TABLE 1-continued

Nucleotide sequence of oligodeoxynucleotides used for engineering plasmid clone 416

SDM-SspI-REV
(SEQ ID NO. 2)
CTTGCCGGCCGTCGCAAATATTTACCCGGAGACAGG

XhoI-NheI linker FWD
(SEQ ID NO. 3)
ATG<u>CTCGAG</u>GAATTCCCATGGATGAT<u>GGCTAGC</u>AAGCTTATG XhoI-NheI linker REV
(SEQ ID NO. 4)
CATAAGCTTGCTAGCCATCATCCATGGGAATTCCTCGAGCAT XhoI-NheI (underlined) is a Universal linker that contains the following RE sites: XhoI-EcoRI-NcoI-NheI-HindIII. SDM = site-directed mutagenesis; FWD = forward; REV = reverse DNA sequence analysis of the IgG promoter region revealed the presence of additional SspI sites in this region. Therefore, it was first necessary to release the HC promoter region (PRO-VH) by digestion of clone 404 with XhoI and NheI, and the clone 404 was re-closed with a XhoI-NheI linker which produced clone 405 (-Pro-VH). The sequence of the forward and reverse ODNs used to produce the XhoI-NheI linker are given in Table 1. Plasmid clone 405 (-Pro-VH) now carries the single SspI site introduced by SDM. The human vBDNF cDNA was subcloned at SspI to form an intermediate plasmid named clone 414 (not shown). The complete fusion protein HC expression cassette was then reconstructed by subcloning of the PRO-VH fragment previously deleted to form clone 415. The fusion protein HC gene was then subcloned in the eukaryotic expression vector, clone 400, at the BamHI site to form clone 416.

The vBDNF cDNA was produced by PCR via either of 2 equivalent approaches. In one approach, a prokaryotic expression plasmid, pHTBS01, isolated as an expressed sequence tag (EST), and encoding human BDNF, was digested with BamHI and BpII, and gel purified, and re-ligated with T4 ligase and the 5'-end linker to produce clone 412 (FIG. 2). The sequence of the forward and reverse ODNs used to produce the 5'-end linker are given in Table 2.

TABLE 2

Engineering of 5'- and 3'-end linkers of vBDNF cDNA 1) 5'-end linker of vBDNF FWD-ODN
(SEQ ID NO. 5)
TCCGGATCCTCGCGAGTATGCACTCTGACCCTGCCCGTCGAGGTGAGCTG
AGCGTG 2) 5'-end linker of vBDNF REV-ODN
(SEQ ID NO. 6)
CACGCTCAGCTCACCTCGACGGGCAGGGTCAGAGTGCATACTCGCGAGGA
TCCGGA 3) 3'-end linker of vBDNF FWD-ODN
(SEQ ID NO. 7)
AGTCGTACGTGCGGGCCCTTACCATGGATAGCAAAAAGAGAATTGGCTGG
CGATTCATAAGGATAGACACTTCTTGTGTATGTACATTGACCATTAAAAG
GTGATCGCGACTCGAGATG 4) 3'-end linker of vBDNF REV-ODN
(SEQ ID NO. 8)
CATCTCGAGTCGCGATCACCTTTTAATGGTCAATGTACATACACAAGAAG
TGTCTATCCTTATGAATCGCCAGCCAATTCTCTTTTTGCTATCCATGGTA
AGGGCCCGCACGTACGACT TABLE 2-continued Engineering of 5'- and 3'-end linkers of vBDNF cDNA 5) vBDNF-PCR-U87 FWD-ODN
(SEQ ID NO. 9)
ATC<u>TCGCGA</u>GTATGCACTCTGACCCTGCC 6) vBDNF-PCR-U87 REV-ODN
(SEQ ID NO. 10)
ATC<u>TCGCGA</u>TCACCTTTTAATGGTCAA SEQ ID NO 5 and 6: Artificial forward (FWD) and reverse (REV) oligodeoxynucleotide (ODN) duplex linkers were designed to engineer a mature vBDNF cDNA that allows for insertion into the CH3 open reading frame (orf) of clone 400 heavy chain (HC) to form clone 416 (FIG. 1). The 5'-end linker is flanked by BamHI and EspI, respectively, and it reconstructs the amino terminus of the mature vBDNF. BamHI and EspI allow for directional subcloning into the vBDNF intermediate plasmid clone 413 (FIG. 2). A NruI site follows BamHI and it enables insertion of the vBDNF into the HC vector (clone 405, FIG. 1) at the SspI site. In addition, the linker also has "GT" immediately after NruI to maintain the orf of the CH3 (FIG. 1). This modification introduces a Ser-Ser-Met linker between CH3 and the vBDNF amino terminus.

SEQ ID NO 7 and 8: The 3'-end linker contains SplI and XhoI to reconstruct the COOH terminus of the mature vBDNF and introduces a stop codon "TGA". This linker has SplI, XhoI and NruI sites for directional subcloning and insertion into clone 405 (FIGS. 1 and 2).

SEQ ID NO 9 and 10: FWD ODN reconstructs the amino terminus of the mature vBDNF and introduces a Ser-Ser-Met linker. NruI site for insertion into the expression vector is underlined. REV ODN introduces the TGA stop codon. NruI site for insertion into the expression vector is underlined.

Clone 412 was then digested with XhoI and BsiWI, and gel purified, and re-ligated with T4 ligase and the 3'end linker to produce clone 413 (FIG. 2). The sequence of the forward and reverse ODNs used to produce the 3'-end linker are given in Table 2. The vBDNF cDNA, encoding the vBDNF with a reconstructed stop codon, was released from clone 413 by NruI, and gel purified; the ethidium bromide stain of the agarose gel is shown in FIG. 3A. This gel shows the expected size of the vBDNF cDNA, 0.4 kb, and the vector backbone, 3.5 kb. Alternatively, the BDNF cDNA was produced by PCR from cDNA derived by reverse transcription of polyA+RNA isolated from human U87 glioma cells, which produce neurotrophins. The primers used to produce the vBDNF by PCR from the U87-derived cDNA are given in Table 2. This PCR produced the expected 0.4 kb vBDNF cDNA (FIG. 3B). The 0.4 kb vBDNF fragment was then digested with NruI, and subcloned into clone 415, as described in FIG. 1, to produce the full fusion protein HC expression cassette, which was released by BamHI and subcloned into the original eukaryotic expression plasmid to produce clone 416 (FIG. 1), the final expression plasmid for the fusion protein HC. Clone 416 was analyzed by double digestion with NheI and BamHI and compared with that of the original clone 400, which lacks the vBDNF. The agarose gel-separated products are shown in FIG. 3C, where lanes 1 and 3 show the fragments generated from clone 416 and clone 400, respectively. Both plasmids produce a 6 kb vector backbone (upper of 3 bands in lanes 1 and 3), and a 2.5 kb promoter region (lower of 3 bands in lanes 1 and 3). However, the size of the middle band is 0.4 kb larger for clone 416, as compared to clone 400 (middle band, lanes 1 and 3). A negative clone is shown in lane 2 of FIG. 3C.

The nucleotide and amino acid sequence of the reconstructed carboxyl terminus at the CH3 region of the HIRMAb HC, a 3-amino acid linker (Ser-Ser-Met), the vBDNF sequence, followed by a stop codon is shown in FIG. 4. The entire 2711 nucleotides (nt) comprising the fusion protein HC gene of clone 416 is shown in FIG. 5. The ATG initiation codon and the TGA stop codon are underlined. The human IgG1 constant region intron and exon sequences are shown in italics and bold font, respectively, in FIG. 5. The vBDNF nt sequence in the clone 416 vector is underlined in FIG. 5. These data show that intronic sequence is found between CH1 and the hinge region, between the hinge region and CH2, and between CH2 and CH3 regions of the human IgG1 constant region. The open reading frame (orf) of the fusion protein HC gene encodes for a 563 amino acid protein, following cleavage of a 19 amino acid signal peptide, and the amino acid sequence of the fusion protein HC is shown in FIG. 6. The signal peptide is underlined; the cysteine (C) residues within the constant region that form inter- or intra-chain disulfide bridges are shown in bold font; the serine-serine-methionine (SSM) linker between the CH3 region of the IgG and the vBDNF is underlined; the single N-linked glycosylation site, at the asparagine residue within CH2 in shown by bold underlined font (FIG. 6). The amino acid sequences of the individual domains of the fusion protein HC protein are given in FIG. 7. The vBDNF domain of the fusion protein is comprised of 117 amino acids.

Clone 416 plasmid DNA was electroporated into mouse myeloma cells that had previously been transfected with an expression plasmid encoding the light chain (LC) of the chimeric HIRMAb. Since the vBDNF is fused only to the HC, there is no modification of the LC of the chimeric HIRMAb. Following selection of transfected cell lines, media from 96-well plates were screened with an ELISA comprised of 2 anti-human IgG antibodies; one antibody is directed against the heavy chain of human IgG1, and the other antibody is directed against human kappa light chains. Myeloma clones encoding for intact fusion protein were isolated, and propagated in a 10 L bioreactor. However, the production levels of the fusion protein were low. This low production was attributed to several factors, including (i) transfection of the myeloma line by 3 separate expression plasmids encoding the heavy chain gene, the light chain gene, and the antibiotic resistance gene; and (ii) the use of genomic fragment of the heavy and light chain genes with large intronic sequences. Therefore, the fusion protein expression plasmid was re-engineered with the following features:

(1) the polymerase chain reaction (PCR) was used to convert genomic fragments of the fusion protein HC and LC genes into 'intron-less' cDNA forms of the 2 genes (2) the cDNA forms the fusion protein HC and LC genes were placed on a single 'tandem vector' in which the 2 genes were placed in separate and tandem expression cassettes with separate promoters (3) the promoter driving the expression of the fusion protein HC and LC genes was changed from the human IgG promoters to the cytomegalovirus (CMV) promoter, to enable transfection of non-myeloma cells, such as Chinese hamster ovary (CHO) cells (4) the tandem vector encoding fusion protein contains a gene encoding for the dihydrofolate reductase (DHFR) gene, under a separate SV40 promoter, to allow for methotrexate (MTX) selection of CHO lines which contain amplification of the genome in the region of the insertion of the expression vector.

Figure 8:
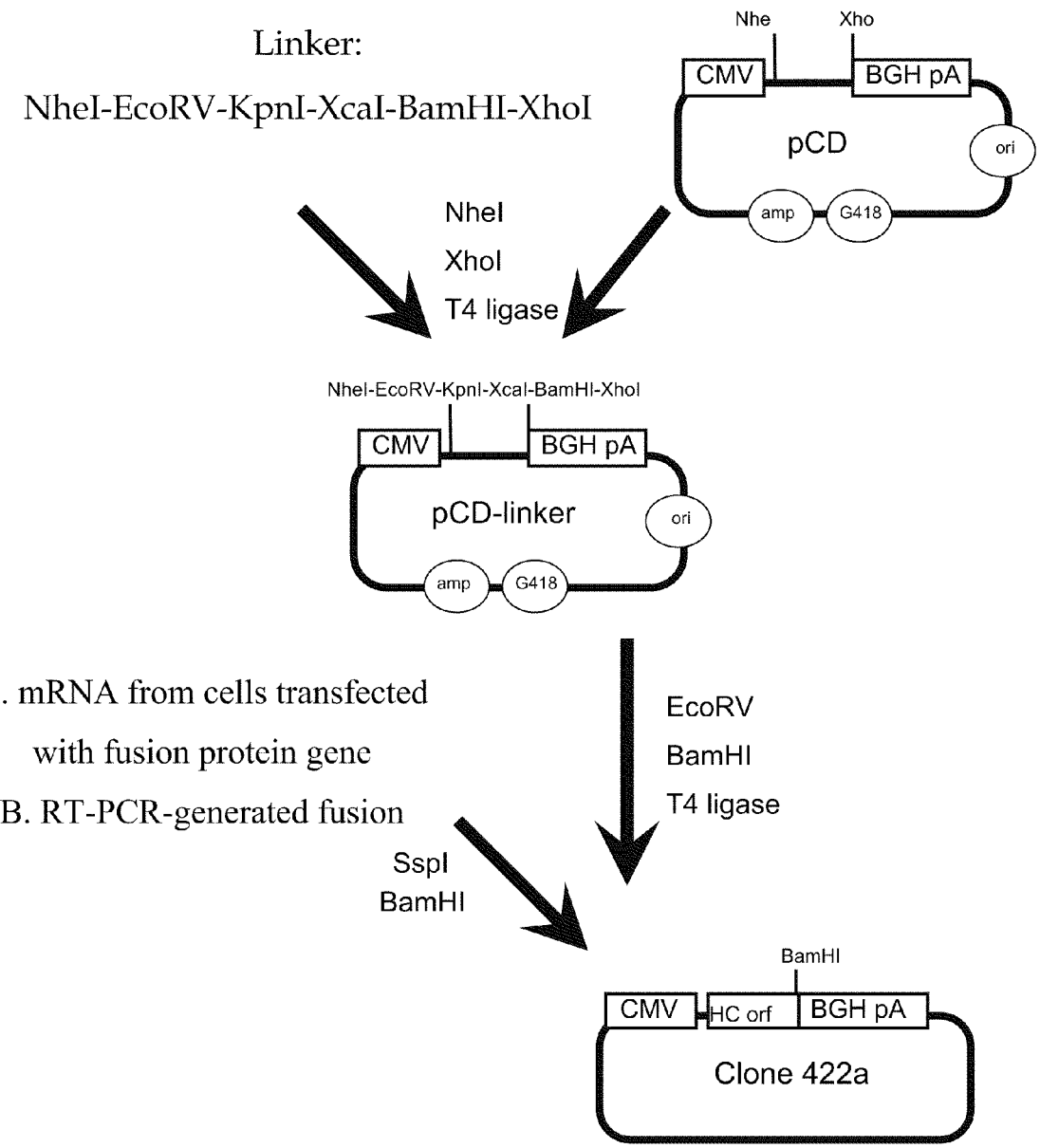
FIG. 8. Diagram showing production of the intronless eukaryotic expression vector, clone 422a, which encodes the fusion protein HC. The fusion protein HC cDNA was produced by PCR from cDNA generated by reverse transcriptase of RNA isolated from myeloma cells transfected with clone 416.

In order to produce the fusion protein tandem vector, it was first necessary to produce intermediate plasmids, which separately encode cDNA forms of the fusion protein HC and LC genes. Eukaryotic expression plasmids carrying the CMV promoter and the bovine growth hormone (BGH) poly-A (pA) transcription termination sequences, and designated pCD, were digested with NheI and XhoI and re-ligated with T4 ligase and an NheI-EcoRV-KpnI-ScaI-BamHI-XhoI linker, as shown in FIG. 8. The sequence of the forward and reverse ODNs used to produce this linker are given in Table 3.

TABLE 3

Nucleotide sequence of ODNs used for engineering of intronless expression vectors 1) Linker NheI-EcoRV-KpnI-XcaI-BamHI-XhoI FWD ODN
(SEQ ID NO. 11)
ATGGCTAGCGATATCGGTACCGTATACGGATCCCTCGAGATG 2) Linker NheI-EcoRV-KpnI-XcaI-BamHI-XhoI REV ODN
(SEQ ID NO. 12)
CATCTCGAGGGATCCGTATACGGTACCGATATCGCTAGCCAT 3) PCR cloning of LC FWD ODN primer
(SEQ ID NO. 13)
GTGACAAACACAGACATAG<u>GATATC</u>

4) PCR cloning of LC REV ODN primer
(SEQ ID NO. 14)
ATG<u>CTCGAG</u>CTAACACTCTCCCCT 5) PCR cloning of fusion protein HC FWD ODN primer
(SEQ ID NO. 15)
ATG<u>AATATT</u>CCACCATGGAATGCAGC 6) PCR cloning of fusion protein HC REV ODN primer
(SEQ ID NO. 16)
ATA<u>GGATCC</u>TCACCTTTTAATGGTCAA RE cloning sites are underlined: <u>GATATC</u>: EcoRV, <u>CTCGAG</u>: XhoI, <u>AATATT</u>: SspI, <u>GGATCC</u>: BamHI.

The resulting plasmid, designated pCD-linker (FIG. 8) was digested with EcoRV and BamHI and reclosed with T4 ligase and the fusion protein HC cDNA generated by PCR. For the PCR reaction, the above mentioned myeloma line that had been dual transfected with genomic constructs of the fusion protein HC (clone 416) and LC genes were digested and myeloma derived polyA+ RNA was produced (part A in FIG. 8). Oligodeoxythymidine (ODT) primers were used to produced myeloma cDNA with reverse transcriptase from 0.5 ug of myeloma polyA+RNA, followed by a final RNase digestion. From this cDNA, PCR was used to produce the cDNA form of the fusion protein HC gene, using the forward and reverse primers shown in Table 3, and high fidelity Pfu DNA polymerase. Similarly, the fusion protein LC cDNA was produced by PCR from the myeloma derived cDNA, and the sequences of the forward and reverse PCR primers used to amplify the fusion protein LC cDNA are given in Table 3. Following PCR, the cDNA was applied to an 0.8% agarose gel, and all amplifications yielded a single product, a 1.8 kb fusion protein HC cDNA (lane 1, FIG. 3D), and a 0.7 kb fusion protein LC cDNA (lane 2, FIG. 3D). The fusion protein HC PCR product was digested with SspI and BamHI and subcloned into CD-linker to produce the clone 422a (FIG. 8), which is an intronless eukaryotic expression plasmid encoding the fusion protein HC cDNA. Clone 422a was analyzed by restriction endonuclease using NheI; digestion with this enzyme, which has a site in the new multiple cloning region of the pCD vector, produced the expected 0.4 kb fragment corresponding to the fusion protein heavy chain variable region (VH) cDNA (lanes 1-4, FIG. 3E). The nucleotide sequence of the fusion protein HC cDNA encoded by clone 422a is shown in FIG. 9A, which shows the intron sequences present in clone 416 (FIG. 5) have been deleted by the PCR of processed myeloma RNA. The amino acid sequence encoded by the fusion protein HC cDNA is given in FIG. 9B, and this amino acid sequence is identical to that produced by the genomic fragment in clone 416 (FIG. 6).

Figure 10:
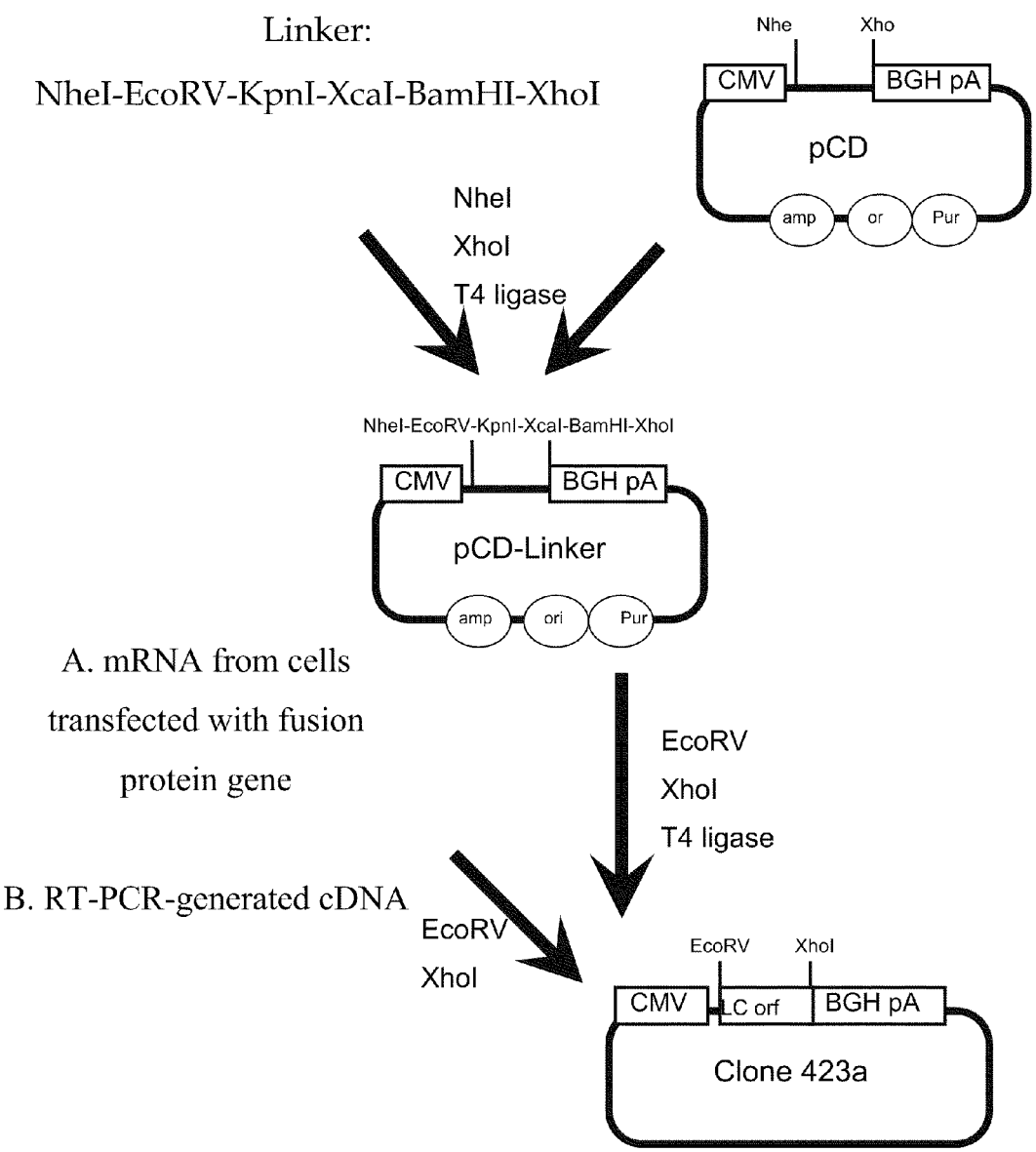
FIG. 10. Diagram showing production of the intronless eukaryotic expression vector, clone 423a, which encodes the fusion protein LC. The fusion protein LC cDNA was produced by PCR from cDNA generated by reverse transcriptase of RNA isolated from myeloma cells transfected with an expression vector producing the LC gene that was derived from chromosomal fragment encoding intron/exon sequence of the human kappa LC gene with the VL of the chimeric HIRMAb LC.

The fusion protein LC PCR product was digested with EcoRV and XhoI and subcloned into CD-linker to produce the clone 423a (FIG. 10), which is an intronless eukaryotic expression plasmid encoding the fusion protein LC cDNA. Clone 423a was analyzed by restriction endonuclease using EcoRV and BamHI; digestion with these enzymes, which have a site in the new multiple cloning region of the pCD vector, produced the expected 0.7 kb fragment corresponding to the fusion protein LC cDNA (lanes 1-5, FIG. 3F). The nucleotide sequence of the fusion protein LC cDNA encoded by clone 423a is shown in FIG. 11A, which shows the intron sequences have been deleted by the PCR of processed myeloma RNA. The amino acid sequence encoded by the fusion protein LC cDNA is shown in FIG. 11B.

Figure 12:
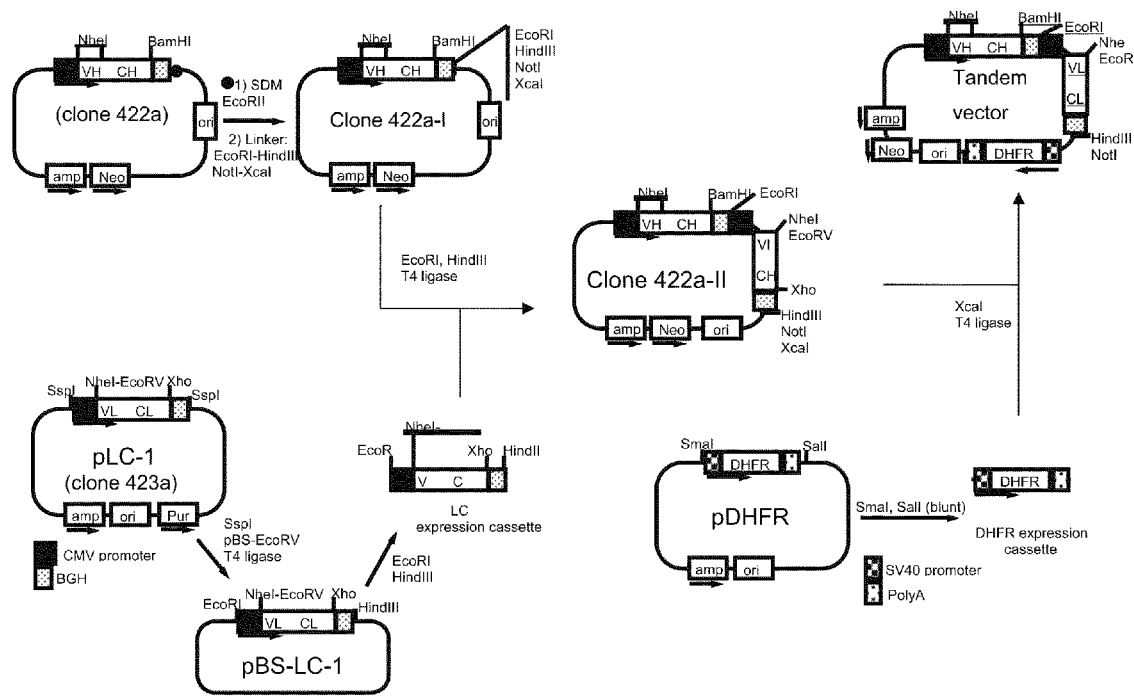
FIG. 12. Diagram showing the construction of a tandem vector encoding the HC and LC genes of the fusion protein. The TV was engineered from the cDNA expression vectors, clones 422a and 423a, for the HC and LC, respectively, as well as from a bacterial expression plasmid encoding the expression cassette for mouse DHFR.

Clones 422a and 423a were the precursors to the fusion protein tandem vector, as outlined in FIG. 12. In 2 steps, clone 422a was subjected to SDM to introduce an EcoRI site at the 3'-end of the fusion protein HC expression cassette; the sequences of the forward and reverse SDM primers are given in Table 4.

TABLE 4

Nucleotide sequences of ODNs used for engineering of TV-12

1) EcoRI-SDM FWD ODN
(SEQ ID NO. 17)
AAAAGGCCAGGAACC<u>GAATTC</u>AGATCTCGTTGCTGGCGTTTT

2) EcoRI-SDM REV ODN
(SEQ ID NO. 18)
AAAACGCCAGCAACGAGATCTGAATTCGGTTCCTGGCCTTTT

3) EcoRI linker FWD
(SEQ ID NO. 19)
ATCGAATTCAAGCTTGCGGCCGCGTATACAGATCTATC

4) EcoRI linker REV
(SEQ ID NO. 20)
GATAGATCTGTATACGCGGCCGCAAGCTTGAATTCGAT

EcoRI site in EcoRI-SDM ODN is underlined.
The EcoRI linker introduces EcoRI-HindIII-NotI-XcaI RE sites.

In step 2, the mutated clone 422a was digested with EcoRI, blunt-ended, and re-ligated with the EcoRI-HindIII-NotI-XcaI linker to produce clone 422a-I (FIG. 12). The sequence of the ODNs used to produce this EcoRI linker are given in Table 4. Clone 422a-I was digested with EcoRI and HindIII, and closed with T4 ligase in the presence of the fusion protein LC expression cassette to produce clone 422a-II (FIG. 12). The fusion protein LC expression cassette was generated by digestion of clone pBS-LC-1 with EcoRI and HindIII. Clone pBS-LC-1 was produced from EcoRV-digested pBS (Bluescript), T4 ligase, and the fusion protein LC expression cassette produced by digestion of clone 423a with SspI (FIG. 12). In parallel, a mouse DHFR expression cassette, containing the SV40 promoter and the hepatitis C virus polyA region, was produced from the pFR400 plasmid (designated pDHFR) by digestion of the plasmid with SmaI and SalI (FIG. 12). The final fusion protein tandem vector was produced by subcloning the DHFR expression cassette into XcaI digested clone 422a-II followed by closure with T4 ligase (FIG. 12). The fusion protein tandem vector was analyzed by restriction endonuclease, and the 11 kb plasmid was linearized by PvuI (lane 1, FIG. 3G). The 1.8 kb fusion protein LC and 1.5 kb DHFR expression cassettes, and the 8 kb vector backbone including the fusion protein HC expression cassette were released by digestion with EcoRI and HindIII (lane 2, FIG. 3G). The tandem vector was subjected to DNA sequencing in both directions, and the nucleotide sequence, and the deduced amino acid sequence of the fusion protein HC, the fusion protein LC, and the DHFR genes are shown in FIGS. 14, 15, and 16, respectively. The calculated MW of the fusion protein HC and LC are 62,220 and 25,760 Da, respectively, not accounting for any carbohydrate content of the fusion protein HC.

Example 2

Figure 17:
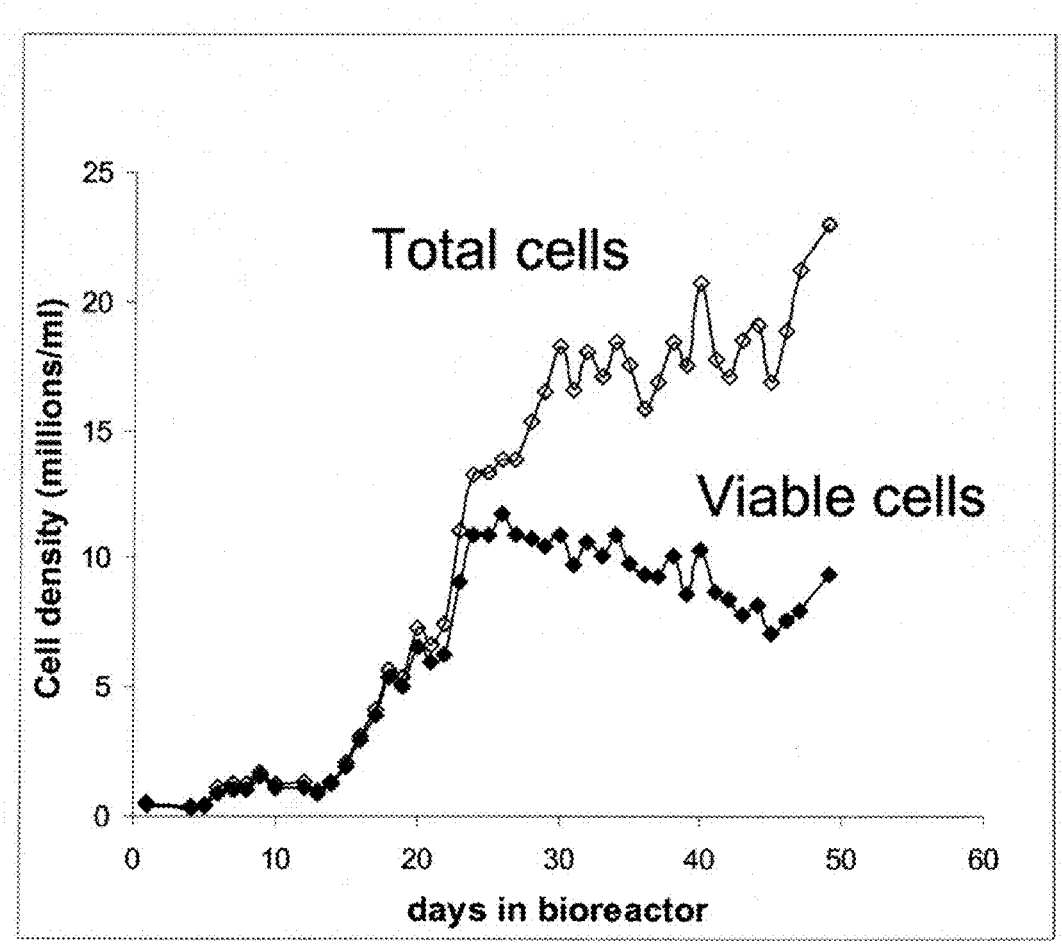
FIG. 17. Viable and total cell density of CHO cells in bioreactor maintained continuously for 50 days; the CHO cells had been stably transfected with the tandem vector encoding the fusion protein.
Figure 18:
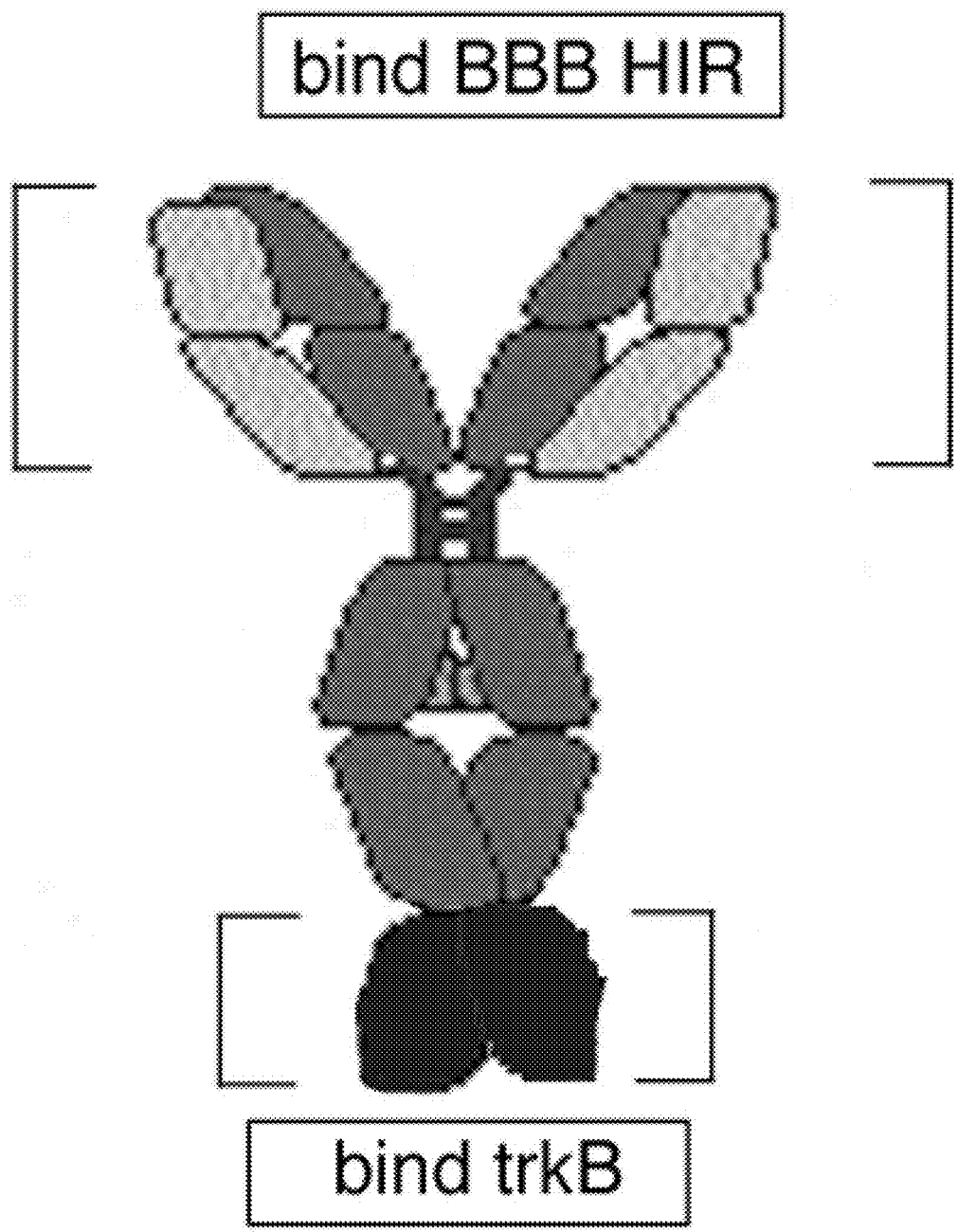
FIG. 18. Structure of fusion protein, a bi-functional molecule that both (a) binds to the human BBB human insulin receptor (HIR) to enable transport across the BBB from blood, and (b) binds to the trkB on neurons to induce neuroprotection.
Figure 19:
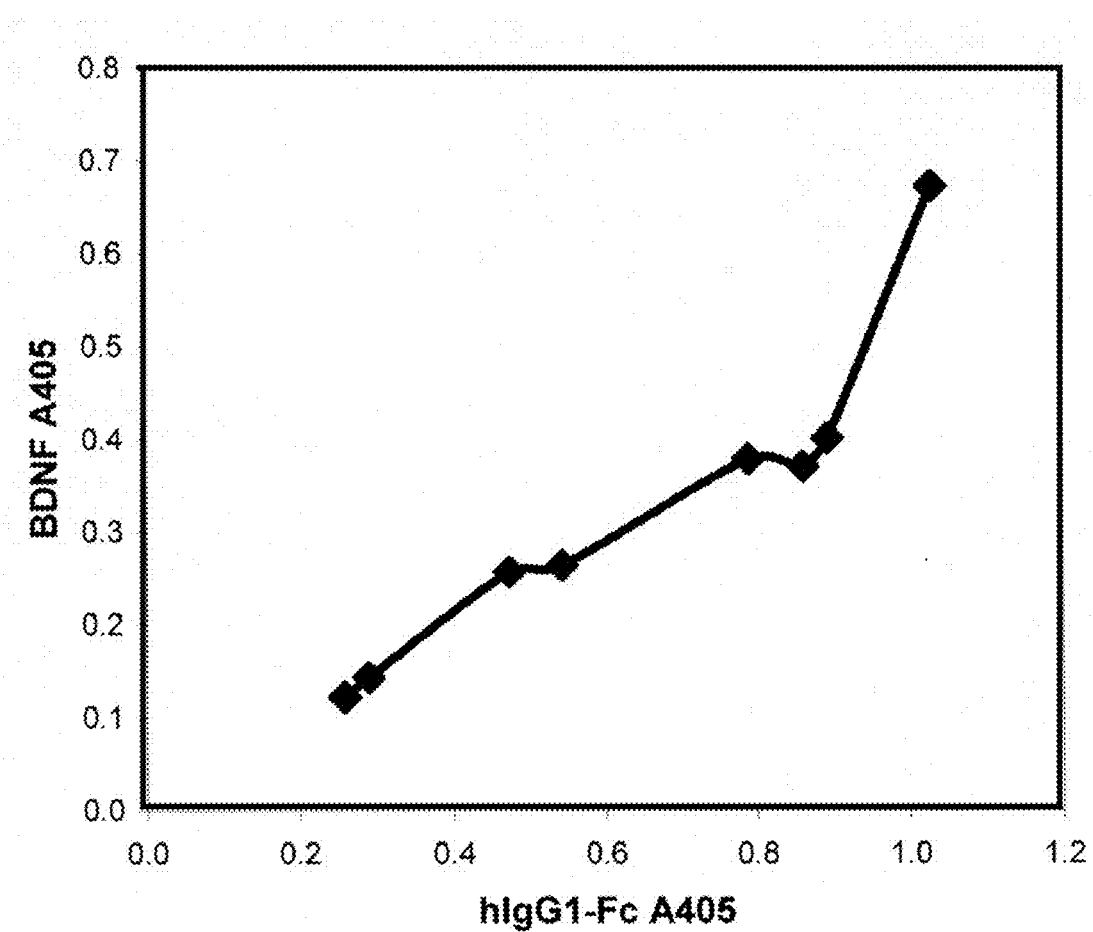
FIG. 19. Correlation of 2 different 'sandwich' immunoassays, where the secondary antibody is either directed against the Fc region of human IgG1 (x-axis) or against human BDNF (y-axis). The primary antibody in either assay is directed against the human kappa light chain. The measured level of fusion protein in CHO cell conditioned medium is the same whether the anti-Fc or the anti-BDNF antibody is used.

Electroporation of CHO Cells with Fusion Protein Tandem Vector and Cultivation in a Bioreactor The fusion protein tandem vector (FIG. 12) was linearized with PvuI and electroporated into CHO-K1 cells followed by selection with G418 (375 ug/ml) for 3 weeks. Positive clones were detected in 96 well plates with a human IgG ELISA that uses 2 primary antibodies to both the human IgG1 HC and the human kappa LC. Cell lines of high copy number of the transgene were selected by graded increases in MTX to 600 nM. The MTX-selected cell line was grown in T175 flasks and then transferred to a 20 L bioreactor with a 10 L volume of CHO cell serum free medium (SFM). As shown in FIG. 17, the CHO cells were maintained at high density in excess of 10 million viable cells/mL for nearly 50 days in perfusion mode in the bioreactor. The secretion by these cells of the fusion protein was detected by ELISA using antibodies to either human IgG or to human BDNF. As shown in FIG. 18, the fusion protein is a 1:1 fusion of the vBDNF to the carboxyl terminus of the HIRMAb heavy chain, which results in formation of the fusion protein heavy chain. This heavy chain complexes with the light chain, as shown in FIG. 18. Therefore, the fusion protein should react equally well to 3 antibodies directed against: (i) the human IgG1 HC, (ii) the human kappa LC; or (iii) human BDNF. As shown in FIG. 19, there is a direct correlation in measurement of the fusion protein in the CHO cell medium depending on whether anti-human IgG or anti-human BDNF antibodies are used in the ELISA. These ELISA results were confirmed with immunocytochemistry (ICC), which showed the CHO cells transfected with TV-120 were immunoreactive with antibodies to either human IgG or to human BDNF, and that the BDNF immune signal was eliminated by absorption of the anti-BDNF antibody with recombinant BDNF.

Example 3

Purification and Characterization of Bioreactor Produced Fusion Protein

Figure 20:
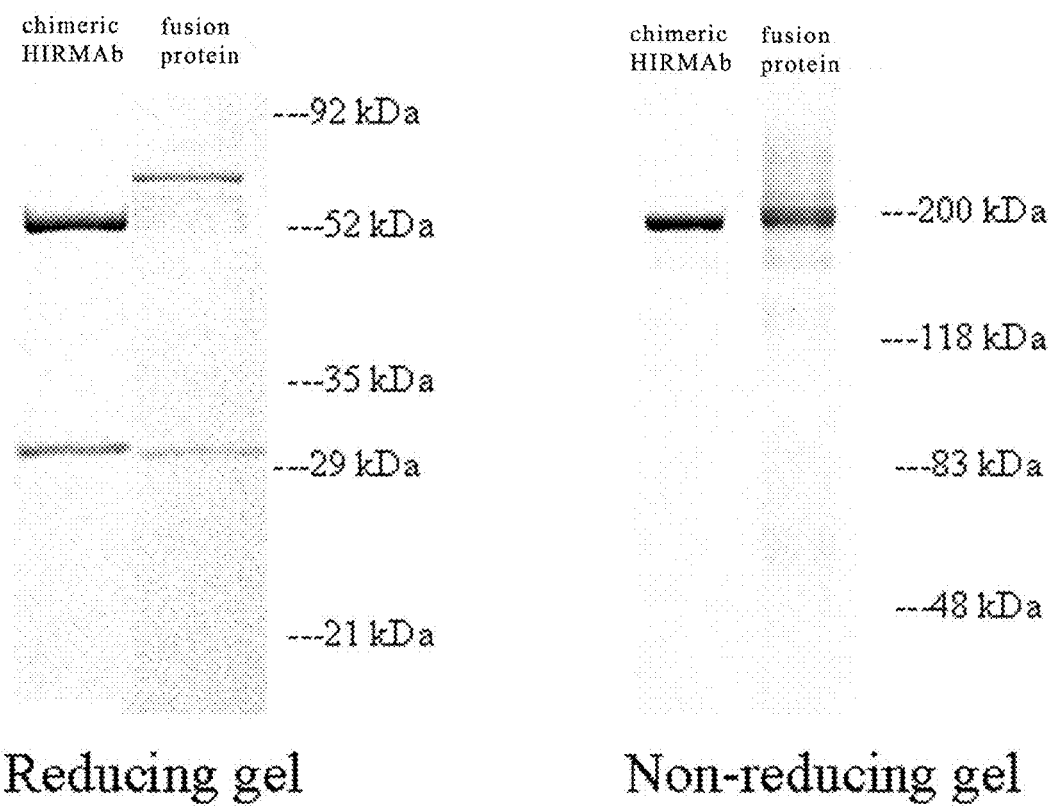
FIG. 20. Reducing (left) and non-reducing (right) sodium dodecyl sulfate polyacrylamide gel electrophoresis (SDS-PAGE) of chimeric HIRMAb and fusion protein. Under reducing conditions, the size of the light chain, 30 kDa, is identical for chimeric HIRMAb and the fusion protein; the size of the heavy chain of fusion protein is about 15 kDa larger than the chimeric HIRMAb heavy chain, owing to the presence of the BDNF. Under non-reducing conditions, the chimeric HIRMAb and the fusion protein migrate as single hetero-tetrameric species with molecular weights of 180 and 200 kDa, respectively.
Figure 21:
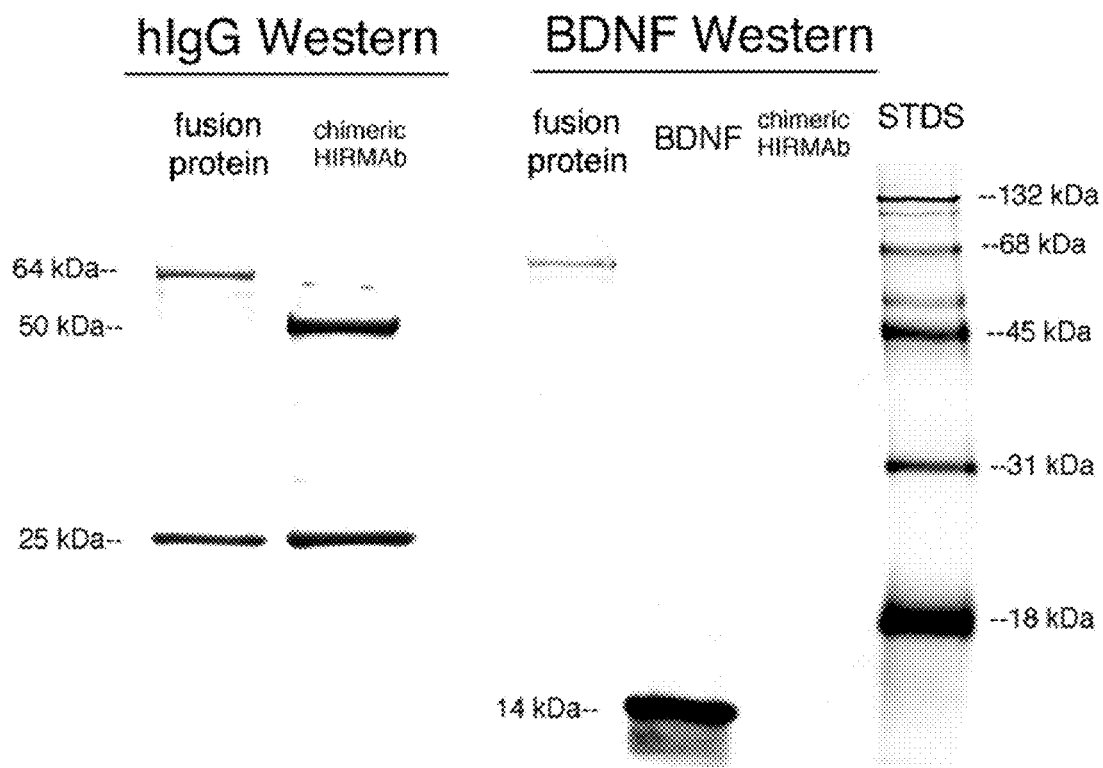
FIG. 21. (Left panel) Western blot with anti-human IgG primary antibody. The size of the heavy chain of the fusion protein and the chimeric HIRMAb is 64 kDa and 50 kDa, respectively, and the size of the light chain for either the fusion protein or the chimeric HIRMAb is 25 kDa. (Right panel) Western blot with anti-human BDNF antibody, which reacts with either fusion protein or BDNF, but not with chimeric HIRMAb. MW standards (STDS) are shown on the right side.
Figure 22:
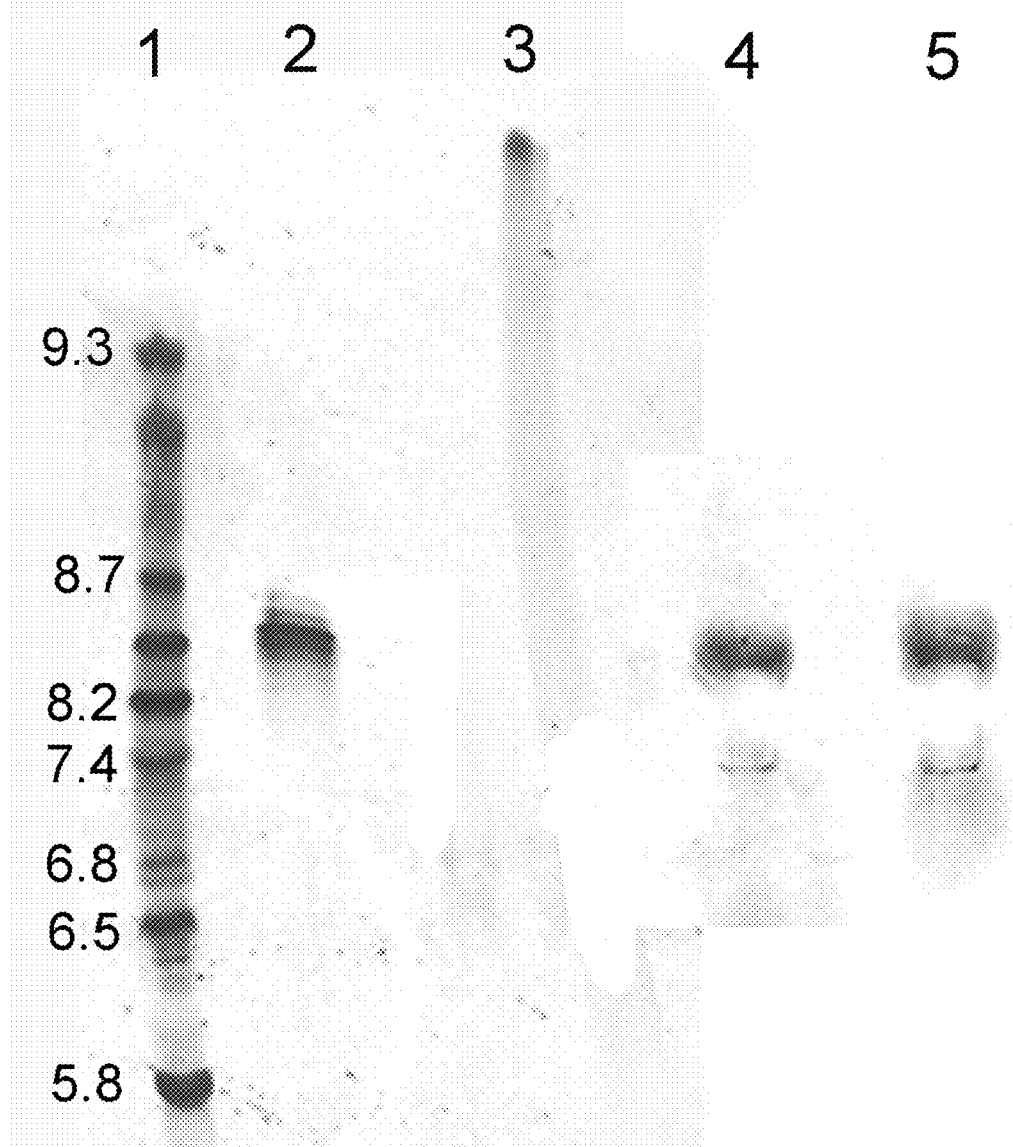
FIG. 22. Isoelectric focusing (IEF) of isoelectric point (pI) standards (lane 1), chimeric HIRMAb (lanes 2 and 4), BDNF (lane 3), and fusion protein (lane 5). Whereas BDNF is highly cationic with a pI>10, the pI of the fusion protein approximates the pI of the chimeric HIRMAb, which is about 8.5, and close to the theoretical pI of the fusion protein.

The conditioned medium obtained from the bioreactor under perfusion mode was passed through a 1 μm filter, and the medium collected in a 200 L Bioprocess container under sterile conditions, which were maintained at 4° C. in a glass door refrigerator contiguous with the bioreactor. Then, 200 L batches of conditioned medium were passed through 1 μm and 0.4 μm pre-filters for the removal of cell debris. The medium was then concentrated with tangential flow filtration (TFF). The TFF system was a Pellicon 2 model from Millipore and was comprised of five 0.5 m² filtration cassettes with a 30 kDa molecular weight cutoff and a total surface area of 2.5 m². A transmembrane gradient of 15 PSI was produced, which results in a reduction in volume of the 200 L to 2 L within 2 hours. The concentrated medium was passed through an 0.22μ filter prior to elution through 100 mL Prosep A (Millipore) recombinant protein A affinity column. Following application of the sample, the column was washed with buffer A (0.025 M NaCl, 0.025 M Tris, pH=7.4, 3 mM EDTA). The elution of CHO cell host protein (CHOP) was monitored at A280 with a Shimadzu detector. The fusion protein was eluted with 0.1 M citric acid (pH=3) in tubes containing Tris base to cause immediate neutralization to pH 7. The neutralized acid eluate pool was diluted with double distilled water until the conductivity was <7 mS, and the material was applied to a 50 mL Sepharose SP cation exchange column (Amersham) that has been equilibrated with a 0.02 M Tris, pH=7.5. Following washing in the Tris buffer, the residual CHOP was separated from the fusion protein with a linear NaCl gradient from 0 to 1 M NaCl. The fusion protein peak was pooled and buffer exchanged and concentrated with a Millipore diafiltration unit with a 30 kDa molecular weight cutoff. The final concentrated antibody solution was sterile filtered (0.22 μm) and stored at 4° C. The fusion protein was purified to homogeneity on sodium dodecyl sulfate polyacrylamide gel electrophoresis (SDS-PAGE), as demonstrated in FIG. 20. The size of the fusion protein heavy chain was 68 kDa as compared to the size of the HIRMAb heavy chain, which was 54 kDa. The difference between the size of the fusion protein and HIRMAb heavy chains reflects the added vBDNF monomer (14 kDa) fused to each heavy chain of the fusion protein. The fusion protein reacts with both anti-human IgG antibodies and anti-human BDNF antibodies on Western blotting with the expected molecular weight size of the immunoreactive bands (FIG. 21). Isoelectric focusing (IEF) shows the isoelectric point (pI) of recombinant BDNF was highly cationic with a pI>10 (FIG. 22). The observed pI of the fusion protein was 8.5, and approximates the pI of the HIRMAb (FIG. 22). The observed pI of the fusion protein, 8.5, was consistent with the calculated pI, which is 9.04 and 5.27 for the fusion protein HC and LC, respectively (http://scansite.mit.edu/).

Example 4

Figure 23:
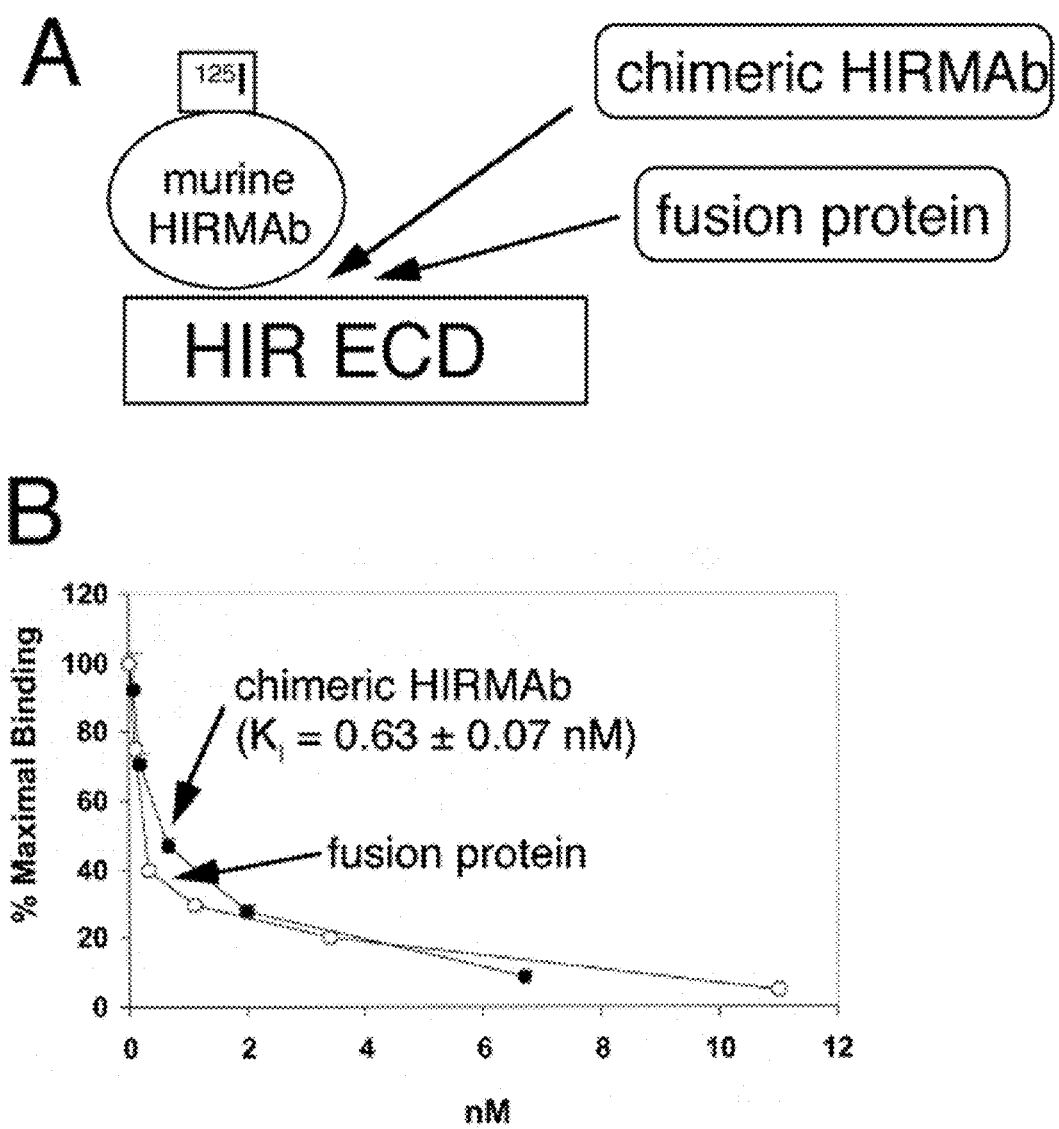
FIG. 23. (A) Outline for human insulin receptor (HIR) competitive ligand binding assay (CLBA). The HIR extracellular domain (ECD) is bound by the [$^{125}$I]-labeled murine HIRMAb, and this binding is competitively displaced by either the chimeric HIRMAb or the fusion protein, as shown in Panel B. (B) Displacement of binding of [$^{125}$I]-labeled murine HIRMAb to the HIR ECD by either chimeric HIRMAb or fusion protein. The affinity of the chimeric HIRMAb to the HIR ECD is high, and the affinity of the fusion protein for the HIR ECD is not significantly different from that of the chimeric HIRMAb. These results show that the fusion of the vBDNF to the carboxyl terminus of the chimeric HIRMAb heavy chain does not impair binding of the fusion protein to the HIR.

The Fusion Protein is Bi-Functional and Binds with High Affinity to Both the Human Insulin Receptor and to the Human trkB Receptor The affinity of the fusion protein for the HIR extracellular domain (ECD) was determined with a competitive ligand binding assay (CLBA) using the lectin affinity purified HIR ECD. CHO cells transfected with the HIR ECD were grown in serum free media (SFM), and the HIR ECD was purified with a wheat germ agglutinin affinity column. The HIR ECD was plated on Nunc-Maxisorb 96 well dishes and the binding of the murine HIRMAb to the HIR ECD was detected by radioactivity measurements following addition of [$^{125}$I] murine HIRMAb as the ligand in the binding assay (FIG. 23A). The binding of the [$^{125}$I] murine HIRMAb to the HIR ECD was displaced by the addition of unlabeled fusion protein or HIRMAb as demonstrated in FIG. 23B. The CLBA shows comparable binding of the HIRMAb or the fusion protein. A Scatchard analysis using a high affinity and low affinity binding site model and nonlinear regression analysis was performed to determine the affinity constant of the fusion protein binding to the HIR. Both the fusion protein and the HIRMAb bind equally well to the HIR with a high affinity binding constant, Ki=0.63±0.07 nM (FIG. 23B).

The TrkB CLBA was designed for measurement of the affinity of the fusion protein for recombinant human TrkB ECD. The design of a TrkB CLBA was made difficult by the cationic nature of BDNF, which causes a high degree of nonspecific binding in the assay and this reduces the sensitivity of the assay. The nonspecific binding of BDNF could be eliminated by conjugation of 2000 Da polyethyleneglycol (PEG) to the protein. A bifunctional PEG molecule, biotin-$PEG^{2000}$-hydrazide (Hz), was commercially obtained, and conjugated to BDNF to produce BDNF-$PEG^{2000}$-biotin, as outlined in FIG. 24A; this molecule was used as the "tracer" in the CLBA. The TrkB ECD was absorbed to ELISA plates and binding of BDNF-$PEG^{2000}$-biotin to the TrkB was detected colorimetrically with avidin and biotin peroxidase (FIG. 24A). Prior studies showed the ELISA signal (A490) was directly proportional to the amount of TrkB added to the well. In addition, the assay had a very low blank and the A490 was <0.04 when no TrkB is plated. The binding of the BDNF-$PEG^{2000}$-biotin to the TrkB was competitively displaced by the recombinant BDNF (FIG. 24B) or the fusion protein (FIG. 24C). The Scatchard analysis of the binding data using nonlinear regression analysis allowed for the computation of the Ki of binding of either BDNF or fusion protein to TrkB, as shown in FIGS. 24B and 24C, respectively. The affinity of the fusion protein for TrkB was not statistically different from the affinity of the recombinant BDNF (FIG. 19 B,C). The non-specific binding (NSB) of the assay was comparable for either BDNF or the fusion protein. The NSB likely represents non-linear cooperative binding of the neurotrophin to the TrkB extracellular domain. The TrkB CLBA results shown in FIG. 24 indicate the affinity of fusion protein for the TrkB receptor was not changed following fusion of the vBDNF to the carboxyl terminus of the HIRMAb heavy chain.

Neurotrophins such as BDNF require an obligatory formation of a homo-dimeric structure to be biologically active, and to bind with high affinity to the cognate receptor, e.g., TrkB. A naturally occurring homo-dimeric structure between two BDNF molecules was formed when the neurotrophin was fused to a carboxyl terminus of the CH3 region of an IgG molecule, as illustrated in FIG. 18. The surprising observation of the maintenance of the high affinity binding of BDNF for TrkB (FIG. 24), despite fusion to the HIRMAb heavy chain (FIG. 18), is consistent with the fact that BDNF normally binds to TrkB as a dimer.

Example 5

Figure 25:
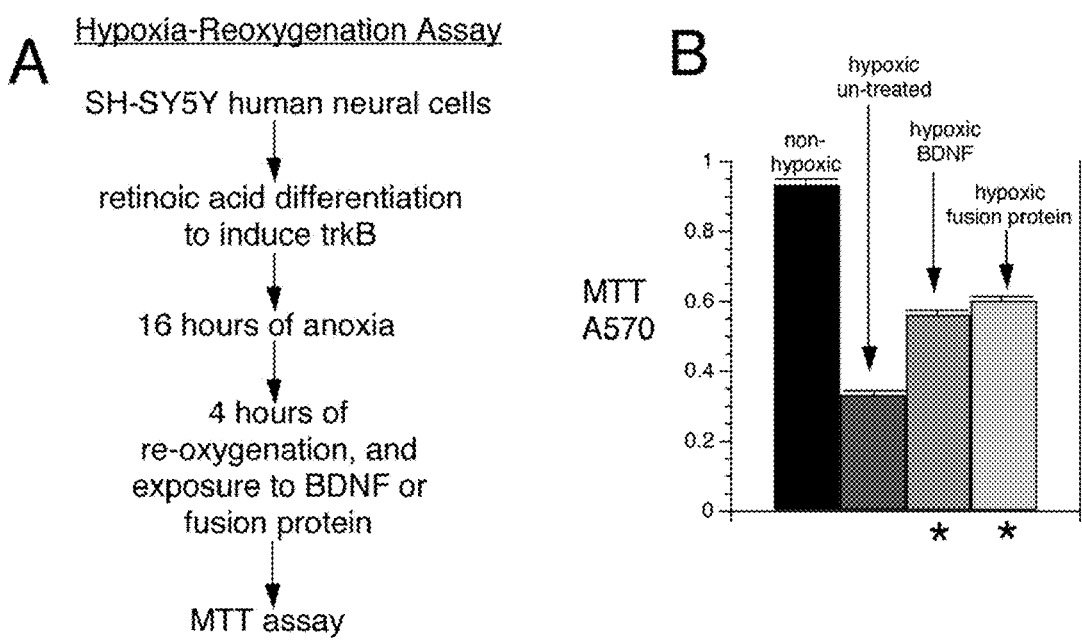
FIG. 25. (A) Design of hypoxia-reoxygenation neuroprotection assay in human neural SH-SY5Y cells. Exposure of the cells to retinoic acid for 7 days causes an up-regulation in the gene expression of trkB, the BDNF receptor. (B) Neuroprotection assay based on the measurement of mitochondrial respiration with 3-(4,5-Dimethylthiazol-2-yl)-2,5-diphenyl-2H-tetrazolium bromide (MTT). The maximal neuroprotection is established with 4 nM BDNF, and 4 nM fusion protein yields a comparable level of neuroprotection in human neural cells. The MTT level does not return to that of non-hypoxic cells, because only about 50% of the cells induce trkB in response to retinoic acid.

Human Neural Cells Subjected to Hypoxia are Neuroprotected by the Fusion Protein with Equal Activity as Recombinant BDNF Human SH-SY5Y neural cells were exposed to 10 uM retinoic acid for 7 days, which induces gene expression of trkB, the BDNF receptor. The cells were then exposed to 16 hours of oxygen deprivation in a sealed chamber, with oxygen sensor. Excitotoxic neural damage was then induced by 4 hours of re-oxygenation (FIG. 25A). During this 4 hour re-oxygenation period, the cells were exposed to either no treatment or equi-molar concentrations of human recombinant BDNF or fusion protein. As shown in FIG. 25B, the fusion protein was equipotent with native human BDNF with respect to inducing neuroprotection in human neural cells exposed to excitoxic ischemia-re-oxygenation.

Example 6

Figure 26:
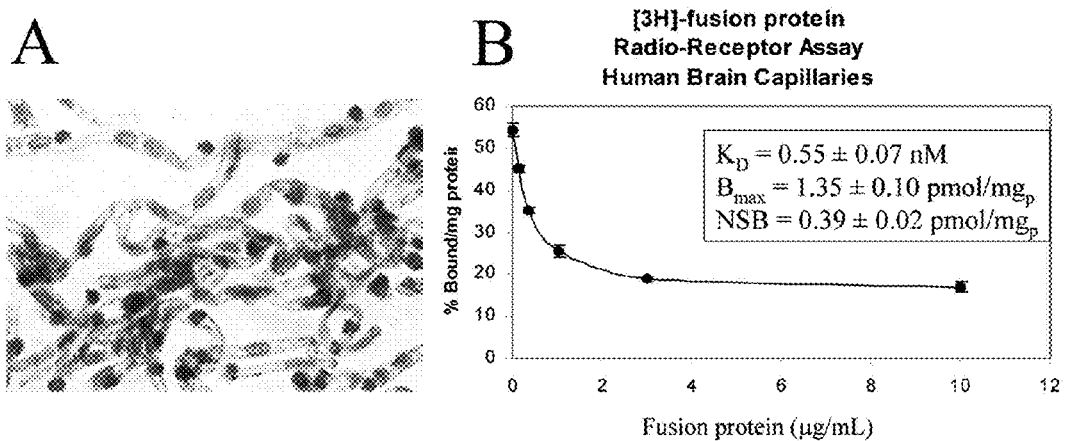
FIG. 26. (A) Light micrograph of capillaries isolated from human brain, used as an in vitro model system of the human BBB. (B) Radio-receptor assay of binding of [$^3$H]-fusion protein to the HIR on the human BBB; the binding is self-inhibited by unlabeled fusion protein. Fitting the saturation data to a Scatchard plot with a non-linear regression analysis yields the binding parameters: $K_D=0.55\pm0.07$ nM, $B_{max}=1.35\pm0.10$ pmol/mg$_p$.

High Affinity Binding of Fusion Protein to Human Blood-Brain Barrier Insulin Receptor in Isolated Human Brain Capillaries Isolated human brain capillaries are used as an in vitro model system of the human BBB (FIG. 26A). The fusion protein was radiolabeled with 3H—N-succinimidyl propionate, and added to the human brain capillaries to establish a radio-receptor assay (RRA) of fusion protein binding to the HIR of the human BBB. [$^3$H]-fusion protein is specifically bound to the BBB, as the binding is self-inhibited by unlabeled fusion protein (FIG. 26B). The fusion protein is bound by the insulin receptor of the human BBB, because the murine HIRMAb (mHIRMAb) also inhibits binding of [$^3$H]-fusion protein to the human BBB. The binding data in FIG. 26B were fit to a Scatchard plot with a non-linear regression analysis to produce the binding constants: $K_D$=0.55±0.07 nM, $B_{max}$=1.35±0.10 pmol/$mg_p$, and NSB=0.39±0.02 pmol/$mg_p$, where $K_D$ is the dissociation constant, Bmax is the maximal binding, and NSB is the non-saturable binding. The KD is <1 nM, which indicate the fusion protein binds the HIR on the human BBB with very high affinity.

Example 7

Pharmacokinetics and Brain Uptake of Fusion Protein by the Adult Rhesus Monkey

The fusion protein was tritiated with [$^3$H]—N-succinimidyl propionate to a specific activity of 2.0 µCi/µg. A 5 year old female Rhesus monkey, weighing 5.2 kg, was administered by a single intravenous injection a dose of 746 µCi (373 µg), and serum was collected at multiple time points over a 180 min period. The serum glucose of the anesthetized, overnight-fasted primate was constant throughout the 180 min study period, and averaged 72±2 mg %, which indicates that the administration of the HIRMAb based fusion protein caused no interference of the endogenous insulin receptor, and had no effect on glycemia control.

Figure 27:
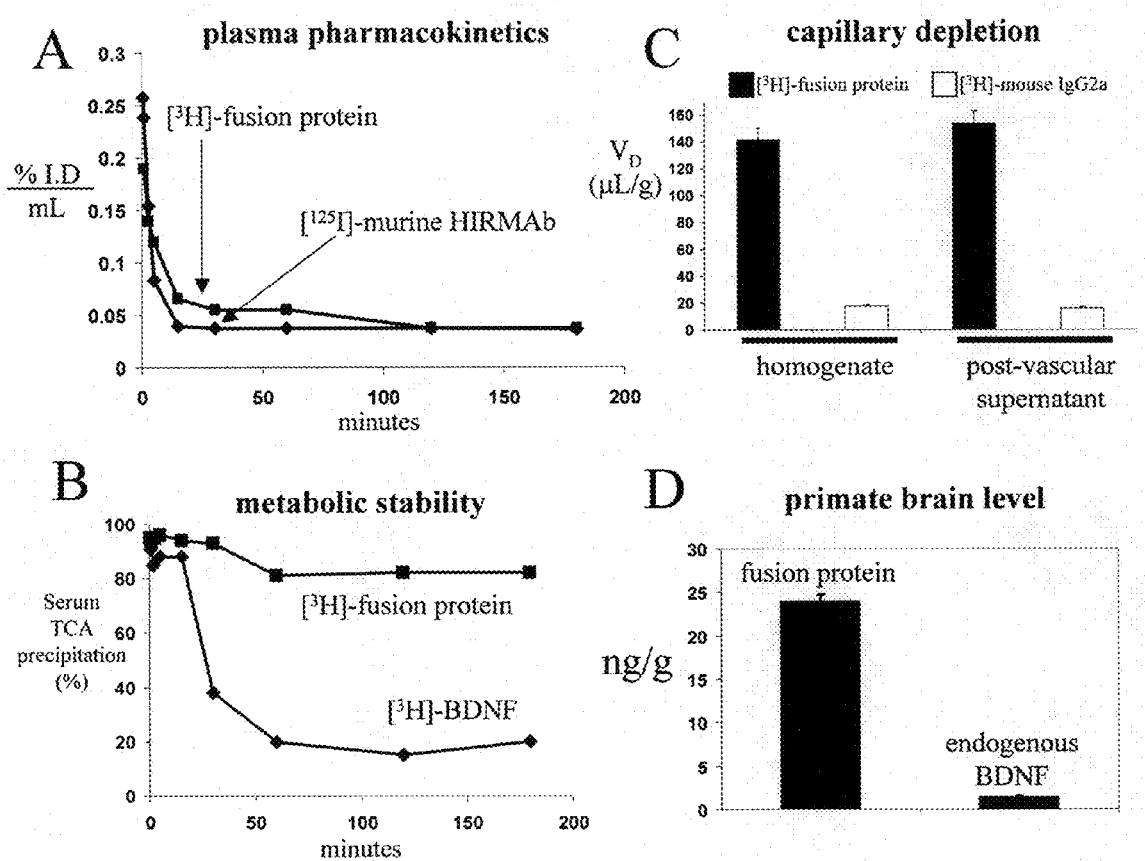
FIG. 27. Pharmacokinetics and brain uptake of fusion protein in the adult Rhesus monkey. (A) The serum concentration of [$^3$H]-fusion protein, or [$^{125}$I]-murine HIRMAb, is plotted vs. time after a single intravenous injection of either protein in anesthetized adult Rhesus monkeys. (B) The serum radioactivity that is precipitable by trichloroacetic acid (TCA) is plotted vs time after a single intravenous injection of either [$^3$H]-fusion protein in the anesthetized adult Rhesus monkey, or [$^3$H]-BDNF in the anesthetized adult rat. (C) Capillary depletion analysis of brain distribution at 180 minutes after a single intravenous injection of either [$^3$H]-fusion protein, or [$^3$H]-mouse IgG2a, in the anesthetized adult Rhesus monkey. (D) Primate brain concentrations of fusion protein at 180 minutes after an intravenous injection of 373 μg fusion protein, as compared to the endogenous primate brain concentration of BDNF.

The serum removed from the anesthetized Rhesus monkey was analyzed for total radioactivity (FIG. 27A), and radioactivity that was precipitable by trichloroacetic acid (TCA) (FIG. 27B). At 180 minutes after drug injection, the animal was euthanized, and brain radioactivity was analyzed with the capillary depletion method (FIG. 27C), similar to prior work on the brain uptake of [$^{125}$I]-labeled murine HIRMAb in the Rhesus monkey. Based on the specific activity of the [$^3$H]-fusion protein, the brain radioactivity was converted to ng per gram (g) brain, as shown in FIG. 27D, and this level was compared to the reported endogenous concentration of BDNF in the adult primate brain.

The plasma pharmacokinetics analysis (FIG. 27A) shows that the fusion protein of the genetically engineered HIRMAb and the BDNF is removed from blood at the same rate as the original murine HIRMAb. This is an important finding, because it shows that the fusion of BDNF, a highly cationic protein, to the HIRMAb does not accelerate the blood clearance of the HIRMAb. Prior work shows that the attachment of the cationic BDNF to a monoclonal antibody greatly accelerates the blood clearance of the antibody, owing to the cationic nature of the BDNF, which greatly enhances hepatic uptake. The work in FIG. 27A shows that when the cationic BDNF was re-engineered as an IgG fusion protein, the plasma pharmacokinetics was dominated by the IgG moiety, and that the blood level of the BDNF remains high for a prolonged period.

The data in FIG. 27B show that when BDNF was re-formulated as an IgG fusion protein, the metabolic stability of the neurotrophin in blood was greatly enhanced, as compared to the native BDNF. Owing to its cationic nature, the native BDNF was rapidly removed from blood, and was rapidly degraded into TCA-soluble radioactive metabolites (FIG. 27B). However, the TCA-insoluble form of the labeled fusion protein remains high during the 3 hours after an intravenous injection in the primate (FIG. 27B). The data in FIGS. 27A,B show the advantages of re-engineering a neurotrophin pharmaceutical as a fusion protein. The native neurotrophin was rapidly removed from blood and was rapidly degraded. However, the plasma pharmacokinetics profile, and metabolic stability profile, of the neurotrophin resemble those of an IgG molecule, when the IgG-neurotrophin fusion protein was produced.

Native BDNF is not transported across the BBB. Similarly, a [$^3$H]-mouse IgG2a isotype control antibody was not transported across the BBB in the adult Rhesus monkey, as the brain volume of distribution ($V_D$) of the IgG at 180 minutes after an intravenous injection was equal to the plasma volume, 18 µL/g (FIG. 27C, open bars). Conversely, the brain $V_D$ of the [$^3$H]-fusion protein exceeds 140 µl/g brain (FIG. 27C, closed bars). Capillary depletion analysis separates the brain vasculature from the post-vascular supernatant, and allows detection of the transport of a drug through the BBB and into brain, as opposed to simple sequestration of the drug by the brain vasculature. The brain $V_D$ of the post-vascular supernatant of the [$^3$H]-fusion protein was equal to the $V_D$ of the brain homogenate (FIG. 27C), which indicates the fusion protein was transported through the BBB and into brain parenchyma.

The brain $V_D$ of the fusion protein was converted into ng fusion protein per gram brain, based on the specific activity of the [$^3$H]-fusion protein, and this allowed for calculation of the total mass of fusion protein in the brain, 24±1 ng/g, as shown in FIG. 27D. This value is >10-fold higher than the endogenous brain concentration of BDNF in the adult primate (45). Therefore, the administration of a dose of 373 µg to a 5.2 kg Rhesus monkey, which is equal to a normalized dose of 72 µg/kg of fusion protein, results in a marked increase in the brain concentration of BDNF. Such an increase in brain BDNF, following intravenous administration, is not possible with native BDNF, because the native BDNF does not cross the BBB. However, when BDNF is re-engineered in the form of the fusion protein, then pharmacologically active levels of the neurotrophin in brain are achieved (FIG. 27D).

The data shows that: (1) the plasma mean residence time (MRT) of the fusion protein, 312 minutes, was 100-fold greater than the MRT for native BDNF, which was 3.0 minutes, and (2) the systemic clearance of the fusion protein, 0.94 mL/min/kg, was 39-fold slower than the systemic clearance of the BDNF, which was 37 mL/min/kg. In other words, the average blood level of the recombinant protein was up to 100-fold greater when the recombinant protein was re-formulated as an IgG fusion protein. Thus, fusion of the BDNF to the molecular Trojan horse had 2 benefits: (1) the molecular Trojan horse carried the BDNF across the blood-brain barrier (BBB), whereas the BDNF alone cannot cross the BBB, and (2) the molecular Trojan horse prevented the rapid loss from blood of the neurotrophin; BDNF by itself lasts only about 3 minutes in the blood. Both of these properties serve to enhance the pharmacological effect of the BDNF in brain following administration into the blood stream. See, e.g., Table 5.

TABLE 5

Pharmacokinetic parameters for [$^3$H]-fusion protein and [$^3$H]-BDNF

| Parameter | [$^3$H]-fusion protein | [$^3$H]-BDNF |
|---|---|---|
| $A_1$ (% ID/ml) | 0.147 ± 0.020 | 5.28 ± 0.60 |
| $A_2$ (% ID/ml) | 0.061 ± 0.005 | 2.26 ± 0.32 |
| $k_1$ (min$^{-1}$) | 0.195 ± 0.050 | 1.75 ± 0.26 |
| $k_2$ (hr$^{-1}$) | 0.186 ± 0.042 | 15.6 ± 0.6 |
| $t_{1/2}^1$ (min) | 3.5 ± 0.9 | 0.42 ± 0.07 |
| $t_{1/2}^2$ (hr) | 3.7 ± 0.9 | 0.045 ± 0.001 |
| $CL_{SS}$ (ml/min/kg) | 0.94 ± 0.16 | 37.0 ± 2.5 |
| MRT (min) | 312 ± 78 | 3.0 ± 0.3 |

$A_1$, $A_2$, $k_1$, and $k_2$ are the intercepts and slopes of the bi-exponential function describing the decay in plasma concentration with time. The parameters for the fusion protein were determined for the Rhesus monkey, and the parameters for BDNF were determined in the adult rat. All data are normalized for differences in body weight. $t_{1/2}^1$ and $t_{1/2}^2$ are computed from $k_1$ and $k_2$, respectively, and are the half-times of the decay curves for each exponent. $CL_{ss}$ and MRT are the steady state clearance and mean residence time, respectively, and are computed from $A_1$, $A_2$, $k_1$, and $k_2$ using standard pharmacokinetic formulations.

Example 8

Neuroprotection in Regional Brain Ischemia by Conjugates of BDNF and a BBB Molecular Trojan Horse Numerous attempts have been made to develop neuroprotective agents for the treatment of acute stroke. There have been no successes to date because the neuroprotective drugs are either too toxic, in the case of certain small molecules, or ineffective, because the drug does not cross the BBB. BDNF is neuroprotective when injected directly in the brain in parallel with experimental stroke in rodents and regional brain ischemia. The BDNF must be injected across the skull bone into the brain, because this large molecule drug does not cross the BBB. Since the BBB is intact in the early hours after regional brain ischemia, and since BDNF does not cross the BBB, then there is no neuroprotective effect in the ischemic brain following the intravenous administration of BDNF alone. To deliver BDNF across the BBB, the neurotrophin was attached to a mouse MAb to the rat transferrin receptor (TfR). This peptidomimetic MAb carries BDNF across the BBB, and the combined BDNF-MAb conjugate is highly neuroprotective following delayed intravenous administration in experimental stroke, because the BDNF is able to cross the BBB and enter the brain from blood. Once inside the brain, and behind the BBB, the BDNF activates its cognate receptor, trkB, which then induces neuroprotection in ischemic neurons, and stops the apoptotic death cycle. The neuroprotective effect of the BDNF-MAb conjugate demonstrates a dose response effect, a time response effect, and is long-lasting, as the neuroprotection at 7 days is identical to the neuroprotection at 1 day after a single intravenous administration of the BDNF-MAb conjugate. See, e.g., Zhang and Pardridge, *Brain Res.* (2001) 889: 49-56, and Zhang and Pardridge, *Stroke* (2001) 32: 1378-1374, which are incorporated by reference herein in their entirety. The fusion protein may also be neuroprotective in human stroke, since the BDNF is fused to an MAb to the HIR, which rapidly binds to both the human BBB in vitro, and is rapidly transported across the primate BBB in vivo.

Example 9

Neuroprotection in Global Brain Ischemia of Conjugates of BDNF and a BBB Molecular Trojan Horse The direct injection of BDNF into the brain is also neuroprotective in transient forebrain ischemia (TFI), such as might occur after a cardiac arrest. However, intravenous BDNF is not neuroprotective in TFI, because the BDNF does not cross the BBB, and because the BBB is intact in the early hours after TFI, when neuroprotection is still possible. Conversely, intravenous BDNF was neuroprotective in TFI if the BDNF was attached to a mouse MAb against the rat transferrin receptor (TfR), which acts as a molecular Trojan horse to ferry the BDNF across the BBB and into brain. Adult rats were subjected to TFI, which resulted in a flat-line electroencephalogram (EEG) for approximately a 10-minute period. The animals were resuscitated and then administered 1 of 4 different therapeutics intravenously: (a) buffer, (b) unconjugated BDNF, (c) the receptor specific MAb without the BDNF attached, and (d) the BDNF-MAb conjugate. In the case of the animals treated with saline, unconjugated BDNF, or MAb alone, there was no neuroprotection of pyramidal neurons in the CA1 sector of hippocampus. However, in the case of the BDNF-MAb conjugate, there is complete normalization of CA1 pyramidal neuron density following delayed intravenous administration. See, e.g., Wu and Pardridge (199), *PNAS (USA)* 96:254-259, which is incorporated by reference herein in its entirety. This shows that BDNF is strongly neuroprotective in global brain ischemia following delayed intravenous administration, providing the BDNF is attached to a BBB molecular Trojan horse. The recombinant fusion protein of BDNF and a receptor specific MAb could be given following cardiac arrest to prevent permanent brain damage.

Example 10

BDNF is Neuroprotective in Brain and Spinal Cord Injury if the Neurotrophin can Access Brain Cells BDNF is neuroprotective in brain injury, providing the neurotrophin is injected directly through the skull bone, because BDNF does not cross the BBB. BDNF is also neuroprotective in brain subjected to excitotoxic injury by neurotoxins, and is neuroprotective in brain infected with the human immune deficiency virus (HIV)-1. BDNF is also neuroprotective in acute spinal cord injury; however, the BDNF must be administered by direct infusion into the spinal canal, because the BDNF does not cross the blood-spinal cord barrier, which is the same as the BBB in the forebrain. In all these cases, the intravenous administration of BDNF would not be neuroprotective, because the BDNF does not cross the BBB, and the BBB is intact in brain injury in the early hours after the injury, when neuroprotection is still possible. Conversely, the BDNF fusion protein would be neuroprotective in these conditions following intravenous administration, because the BDNF is fused to the BBB molecular Trojan horse, and is able to penetrate the brain and spinal cord from the blood following peripheral administration.

Example 11

BDNF is Neuroprotective in Chronic Neurodegenerative Conditions of Brain if the Neurotrophin can Access Brain Cells Neurotrophins, such as BDNF can be developed as drugs for peripheral routes of administration, providing the neurotrophin is enabled to cross the BBB. Fusion of BDNF to the chimeric HIRMAb offers a new approach to the non-invasive delivery of BDNF to the brain in humans for the chronic treatment of neurodegenerative disease, including prion diseases, Alzheimer's disease (AD), Parkinson's disease (PD), Huntington's disease (HD), ALS, transverse myelitis, motor neuron disease, Pick's disease, tuberous sclerosis, lysosomal storage disorders, Canavan's disease, Rett's syndrome, spinocerebellar ataxias, Friedreich's ataxia, optic atrophy, and retinal degeneration, and brain aging.

Example 12

BDNF as a Therapeutic in Retinal Degeneration and Blindness

The retina, like the brain, is protected from the blood by the blood-retinal barrier (BRB). The insulin receptor is expressed on both the BBB and the BRB, and the HIRMAb has been shown to deliver therapeutics to the retina via RMT across the BRB (Zhang et al., (2003) Mol. Ther. 7: 11-18). BDNF is neuroprotective in retinal degeneration, but it was necessary to inject the neurotrophin directly into the eyeball, because BDNF does not cross the BRB. The fusion protein could be used to treat retinal degeneration and blindness with a route of administration no more invasive than an intravenous or subcutaneous injection, because the HIRMAb would deliver the BDNF across the BRB, so that the neurotrophin would be exposed to retinal neural cells from the blood compartment.

Example 13

BDNF as a Therapeutic for Depression

A subset of patients with depression may have a brain deficiency of BDNF, and the correlation of single nucleotide polymorphisms (SNPs) with affective disorders has been reported. The direct injection of BDNF into the brain has durable anti-depressant effects in rodent model. The BDNF must be injected directly into the brain, because the neurotrophin does not cross the BBB. The chronic administration of the fusion protein would provide a means for elevating the brain levels of BDNF, and may be therapeutic in those patients with depression and a reduced production of brain BDNF.

Example 14

Method of Manufacturing IgG Fusion Proteins

The transfection of a eukaryotic cell line with immunoglobulin G (IgG) genes generally involves the co-transfection of the cell line with separate plasmids encoding the heavy chain (HC) and the light chain (LC) comprising the IgG. In the case of a IgG fusion protein, the gene encoding the recombinant therapeutic protein may be fused to either the HC or LC gene. However, this co-transfection approach makes it difficult to select a cell line that has equally high integration of both the HC and LC-fusion genes, or the HC-fusion and LC genes. The preferred approach to manufacturing the fusion protein is the production of a cell line that is transfected with a single plasmid DNA that contains all the required genes on a single strand of DNA, including the HC-fusion protein gene, the LC gene, the selection gene, e.g., neo, and the amplification gene, e.g., the dihydrofolate reductase gene. As shown in the diagram of the fusion protein tandem vector in FIG. 12, the HC-fusion gene, the LC gene, the neo gene, and the DHFR gene are all under the control of separate, but tandem promoters and separate but tandem transcription termination sequences. Therefore, all genes are equally integrated into the host cell genome, including the fusion gene of the therapeutic protein and either the HC or LC IgG gene.

Example 15

Figure 28:
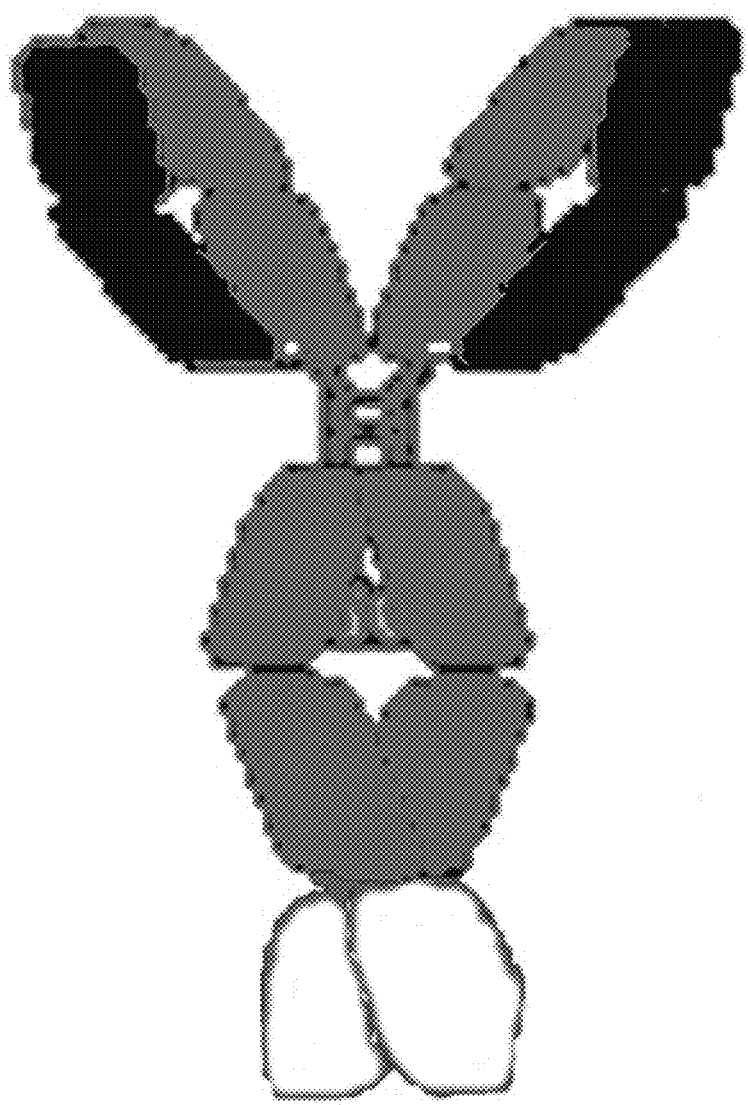
FIG. 28. The HIRMAb-EPO fusion protein is formed by fusion of the amino terminus of the mature EPO to the carboxyl terminus of the CH3 region of the heavy chain of the chimeric HIRMAb. The fusion protein is a bi-functional molecule: the fusion protein binds the HIR, at the BBB, to mediate transport into the brain, and binds the EPOR, to mediate neuroprotection in brain behind the BBB.
Figure 29:
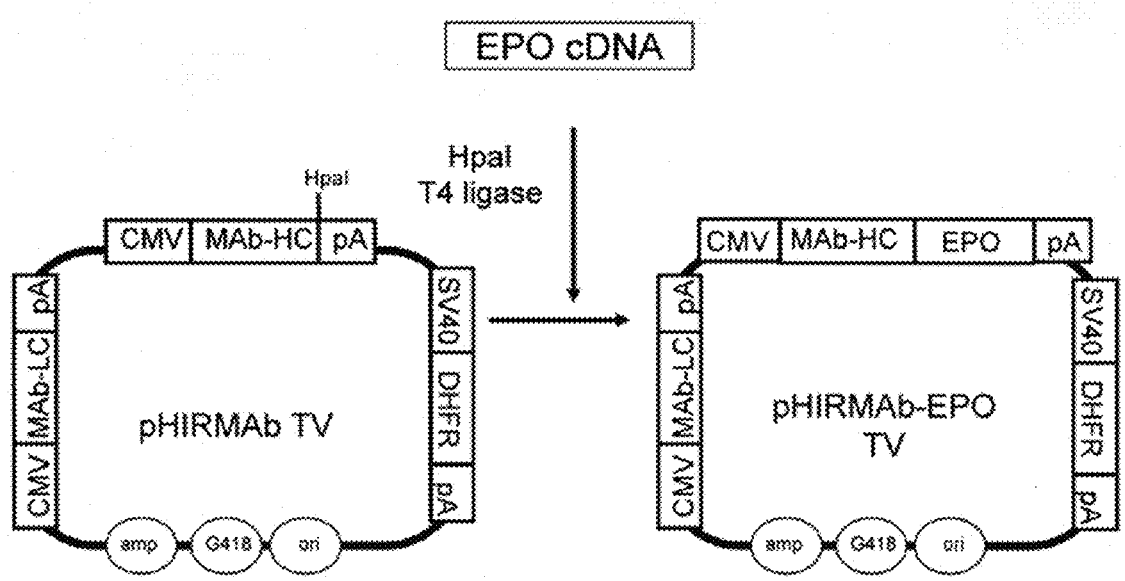
FIG. 29. Tandem vector (TV) expressing the HIRMAb-EPO fusion protein is engineered by subcloning a synthetic EPO cDNA into a unique HpaI restriction site at the 3' end of the heavy chain (HC) of the chimeric monoclonal antibody (MAb) against the human insulin receptor (HIR). The TV expressing the fusion protein is comprised of separate and tandem expression cassettes encoding the MAb HC-EPO fusion protein, the MAb light chain (LC), dihydrofolate reductase (DHFR) for methotrexate amplification of host cell lines, and the neomycin resistance gene (G418). The HC-EPO and LC open reading frames are 5'-flanked by the cytomegalovirus (CMV) promoter, and 3'-flanked by the bovine growth hormone polyA (pA) sequence. The DHFR gene is 5'-flanked by the SV40 promoter and 3'-flanked by the hepatitis B virus polyA sequence.

Construction of the Single Tandem Vector Containing Complete Genes for IgG-EPO Fusion Protein The HIRMAb-EPO fusion protein is shown in FIG. 28, and is a hetero-tetrameric fusion protein comprised of 2 heavy chains (HC) and 2 light chains (LC). In order to produce a host cell, e.g., a CHO cell, that expresses both HC and LC genes at high amounts, expression cassettes for both the HC and LC are placed on a single strand of DNA. The host cell is subjected to selection/amplification pressure, such as with methotrexate (MTX) treatment. MTX is an inhibitor of the essential enzyme, dihydrofolate reductase (DHFR). If the transfected host cell is also incorporated with exogenous DHFR, the transfected host cell will be selectively resistant to MTX treatment, as compared to non-transfected cells. Therefore, it is necessary that the DHFR expression cassette also be placed on the same single strand of DNA as contains the HC and LC genes. A universal tandem vector (TV), designated pHIRMAb TV, which is shown in FIG. 29, was engineered in which expression cassettes for the HC gene, the LC gene, and the DHFR gene are placed on the same strand of DNA. The gene encoding the HC of the chimeric HIRMAb, and the gene encoding the LC of the chimeric HIRMAb are 5'-flanked by a cytomegalovirus (CMV) promoter, and 3'-flanked by the bovine growth hormone (BGH) polyA sequence. The murine DHFR gene is 5'-flanked by the SV40 promoter, and 3'-flanked by the hepatitis B virus polyA sequence. The 3'-end of the HC open reading frame contains a unique HpaI restriction site for subcloning of the cDNA encoding the mature human EPO, as outlined in FIG. 29.

The human EPO cDNA encoding for amino acids Ala$^{28}$-Arg$^{193}$ (accession #NP_000790), and excluding the 27 amino acid signal peptide, was custom synthesized, and the nucleotide sequence is given in SEQ ID No: 50. The EPO artificial gene has a StuI site on the 5'-end followed by 'CA' to maintain the open reading frame and to introduce a Ser-Ser-Ser linker between the CH3 region of the HIRMAb heavy chain (HC) and the amino terminus of the EPO minus the EPO signal peptide. The 3'-end of the EPO cDNA was engineered with a StuI site immediately after the stop codon, TGA. An internal StuI site in the EPO cDNA was removed by use of an alternative codon for Glu$^{186}$ in the design of the synthetic EPO gene. The EPO cDNA was subcloned into the pCR-Blunt vector. The 515 nt EPO cDNA sequence was confirmed by bi-directional DNA sequencing. The EPO cDNA was released form the pCR vector with StuI and the ~500 bp EPO cDNA fragment was isolated by agarose gel electrophoresis. The EPO cDNA was inserted into the pHIRMAb TV eukaryotic tandem expression plasmid at the HpaI site, and this expression plasmid was designated pHIRMAb-EPO TV, as outlined in FIG. 29. The pHIRMAb TV expression tandem plasmid encodes the light chain (LC) of the chimeric HIRMAb, the HC of the chimeric HIRMAb, dihydrofolate reductase (DHFR), as well as the neomycin resistance gene (G418). The DHFR and G418 genes allowed for selection of high producing host cell lines with methotrexate and G418, respectively. The entire open reading frames for the LC, HC and DHFR expression cassettes of the pHIRMAb-EPO TV plasmid were confirmed by bi-directional DNA sequencing.

DNA sequencing of the pHIRMAb-EPO TV (FIG. 29) encompassed 9,036 nucleotides (nt), and the fusion heavy chain expression cassette included a 1,986 nt open reading frame (SEQ ID No:52), which encoded for a 631 amino acid fusion protein heavy chain (SEQ ID No:49), comprised of a 19 amino acid IgG signal peptide, the 443 amino acid HIRMAb HC, a 3 amino acid linker (Ser-Ser-Ser), and the 166 amino acid human EPO minus the signal peptide, which was 100% identical to the amino acid sequence from Ala$^{28}$ to Arg$^{193}$ of human EPO (NP_000790). The predicted molecular weight of the heavy chain fusion protein, minus glycosylation, is 67,226 Da, with a predicted isoelectric point (pI) of 8.75. The light chain expression cassette included a 705 nt open reading frame (SEQ ID No:51), which encoded for a 234 amino acid light chain (SEQ ID No:54), comprised of a 20 amino acid IgG signal peptide, the 214 amino acid HIRMAb LC. The DHFR expression cassette included a 564 nt open reading frame (SEQ ID No:53), which encoded for a 187 amino acid murine DHFR (SEQ ID No:55).

Example 16

Transient Expression of HIRMAb-EPO Fusion Protein in COS Cells

COS cells were transfected with pHIRMAb-EPO TV using Lipofectamine 2000, with a ratio of 1:2.5, ug DNA:uL Lipofectamine. Following transfection, the cells were cultured in serum free medium. The conditioned serum free medium was collected at 3 and 7 days. The fusion protein was purified by protein A affinity chromatography, and formulated as a sterile liquid in Tris buffered saline/pH=6.0. Transgene expression and fusion protein secretion to the medium was assayed by measurement of human IgG in the conditioned medium. Human IgG ELISA was performed in Immulon 2 high binding plates (Dynex Tech., Chantilly, Va.) with COS cell conditioned medium.

Human IgG ELISA

Human IgG ELISA was performed in Immulon 2 high binding plates (Dynex Tech., Chantilly, Va.) with COS cell conditioned medium. A goat anti-human IgG primary antibody (Zymed-Invitrogen, Carlsbad, Calif.) was plated in 0.1 M NaHCO3 (100 µl, 2 µg/ml) and incubated for overnight at 4 C. Plates were washed 0.01 M Na$_2$HPO4/0.15 M NaCl/pH=7.4/0.05% Tween-20 (PBST), and blocked with 1% gelatin in PBST for 30 min at 22° C. Plates were incubated with 100 µL/well of either human IgG1 standard or the fusion protein for 60 minutes at room temperature (RT). After washing with PBST, a goat anti-human kappa LC antibody conjugated to alkaline phosphatase was plated for 60 min at 37° C. Color development was performed with p-nitrophenyl phosphate at pH=10.4 in the dark. The reaction was stopped with NaOH, and absorbance at 405 nm was measured in a ELISA plate reader. Lipofection of COS cells with the pHIRMAb-EPO TV resulted in high medium human IgG levels (Table 1), as determined with a human Fc specific ELISA.

TABLE 6

Secretion of immunoreactive human HIRMAb-EPO fusion protein to medium of transfected COS cells

| Days | Medium IgG (ng/mL) | |
| --- | --- | --- |
| | Lipofectamine 2000 only | pHIRMAb-EPO TV |
| 3 | <3 | 1,825 ± 80 |
| 7 | <3 | 6,424 ± 596 |

Mean ± SE (n = 3 dishes).

Example 17

Biochemical Characterization of HIRMAb-EPO Fusion Protein

Figure 30:
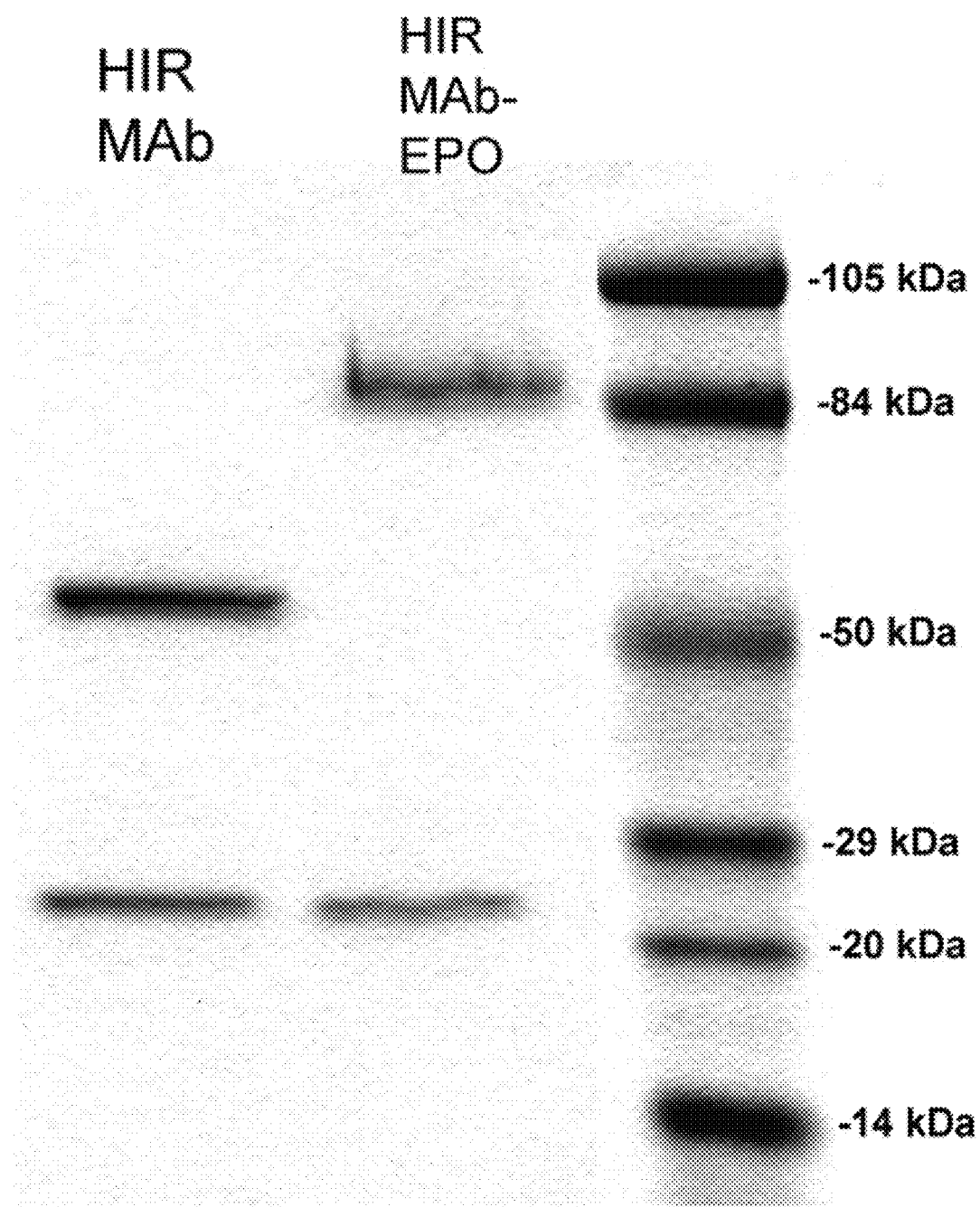
FIG. 30. Reducing SDS-PAGE and Coomasie blue staining of protein A affinity purified chimeric HIRMAb and the HIRMAb-EPO fusion protein. Both are purified to homogeneity and are comprised of a heavy chain and a light chain.
Figure 31:
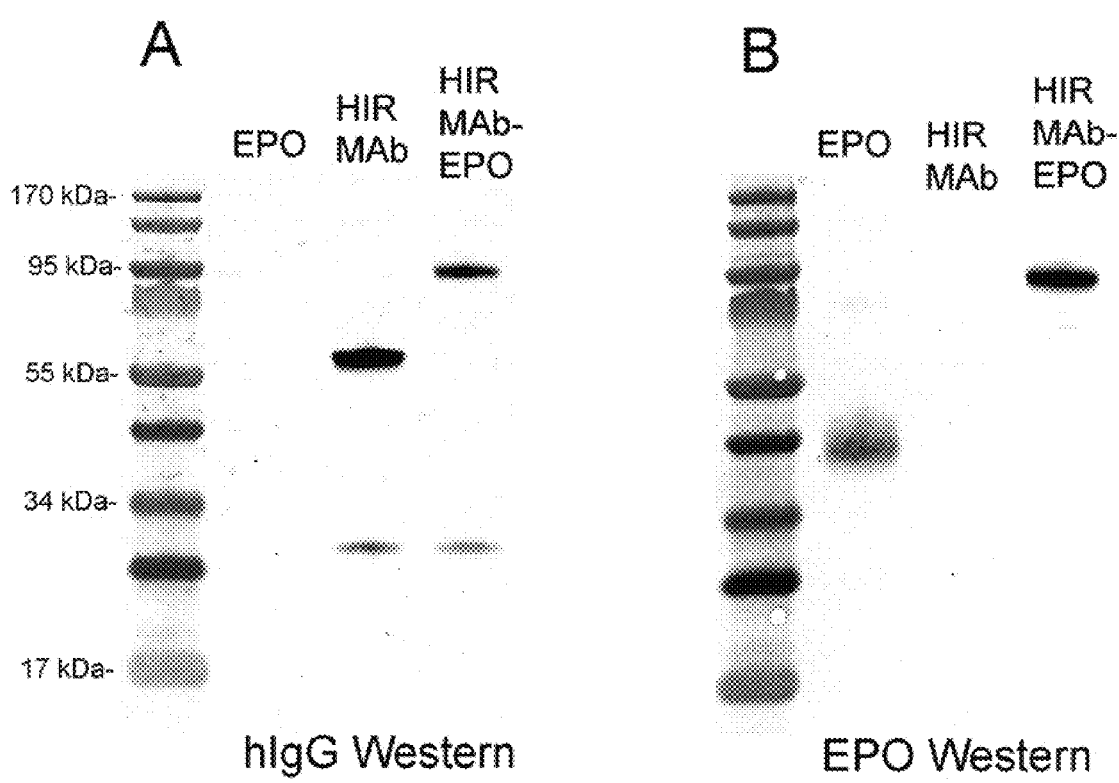
FIG. 31. Western blot with either anti-human (h) IgG primary antibody (A) or an anti-human EPO primary antiserum (B). The immunoreactivity of the HIRMAb-EPO fusion protein is compared to the chimeric HIRMAb and to recombinant EPO. Both the HIRMAb-EPO fusion protein and the HIRMAb have identical light chains on the anti-hIgG Western. The HIRMAb-EPO fusion heavy chain reacts with both the anti-hIgG and the anti-human EPO antibody, whereas the HIRMAb heavy chain only reacts with the anti-hIgG antibody. The size of the HIRMAb-EPO fusion heavy chain, ~90 kDa, is about 35 kDa larger than the size of the heavy chain of the HIRMAb, owing to the fusion of the 35 kDa EPO to the 55 kDa HIRMAb heavy chain.

The homogeneity of protein A purified fusion protein produced by COS cells was evaluated with a reducing 12% sodium dodecyl sulfate polyacrylamide gel electrophoresis (SDS-PAGE), followed by Coomasie Blue staining. For Western blotting, immunoreactivity was tested with a primary rabbit antibody to human EPO or a primary goat antiserum against human IgG heavy and light chains. Human recombinant EPO was purchased from R&D Systems. Following SDS-PAGE and Coomasie blue staining, the size of the light chain (LC) is the same for both the HIRMAb and the HIRMAb-EPO fusion protein (FIG. 30). The size of the heavy chain (HC) of the fusion protein is about 35 kDa larger than the HC of the HIRMAb (FIG. 30). On Western blotting, the LC of either the HIRMAb or the HIRMAb-EPO fusion protein react equally with a primary antibody directed against the human IgG (H+L), as shown in FIG. 31A. The size of the HC of the fusion protein is about 35 kDa larger than the size of the HC of the HIRMAb on Western blots using either the anti-human IgG primary antibody (FIG. 31A) or the anti-human EPO primary antibody (FIG. 31B). The anti-EPO primary antibody reacts with the HC of the fusion protein, and with recombinant EPO, but does not react with the HIRMAb (FIG. 31B).

Size Exclusion Chromatography

Figure 32:
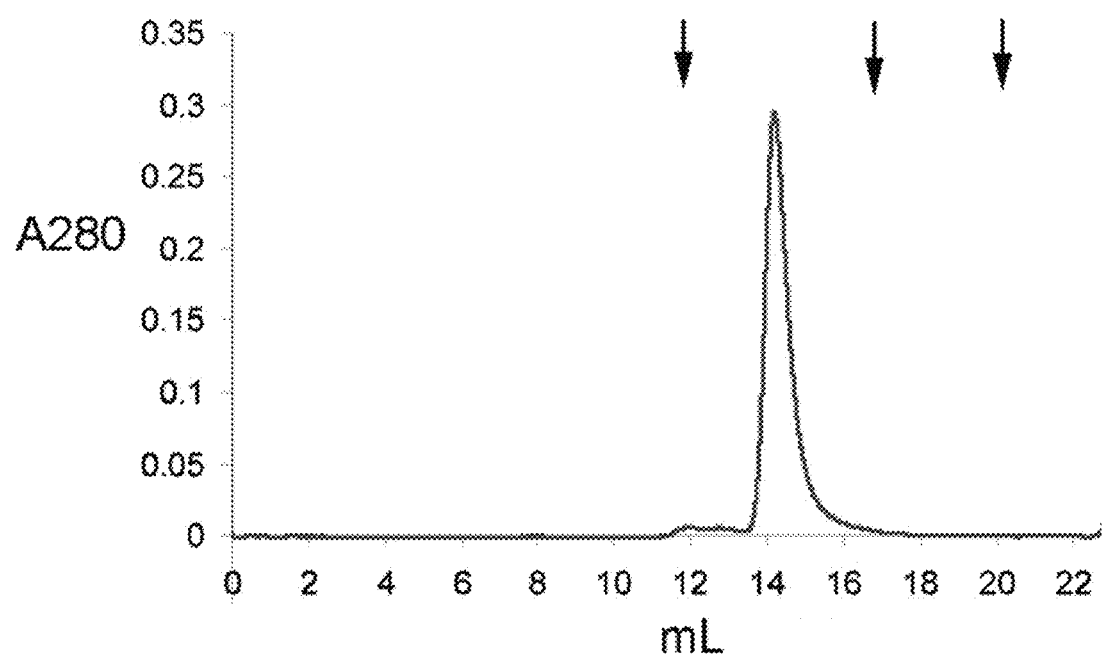
FIG. 32. HPLC size exclusion chromatography shows there is <1% aggregates in the protein A purified HIRMAb-EPO fusion protein expressed in COS cells. Migration of molecular weight standards is shown by the arrows, which represent, left-to-right, 2000 kDa blue dextran-2000, 158 kDa aldolase, and 44 kDa ovalbumin, respectively.

Size exclusion chromatography (SEC) high performance liquid chromatography of the protein A purified HIRMAb-EPO fusion protein was performed with two 7.8 mm×30 cm TSK-GEL G3000SW$_{XL}$ columns (Tosoh Bioscience, Tokyo, Japan) in series, under isocratic conditions at a flow rate of 0.5 ml/min with Perkin-Elmer Series 200 pump. The absorbance at 280 nm was detected with a Shimadzu SPD-10A UV-VIS detector and a Shimadzu CR-8 chart recorder. The elution of molecular weight (MW) standards (GE Healthcare, Buckinghamshire, UK), blue dextran-2000, aldolase, and ovalbumin was measured under the same elution conditions. The HIRMAb-EPO fusion protein eluted as a single peak, with <1% aggregation on SEC HPLC (FIG. 32).

Example 18

Figure 33:
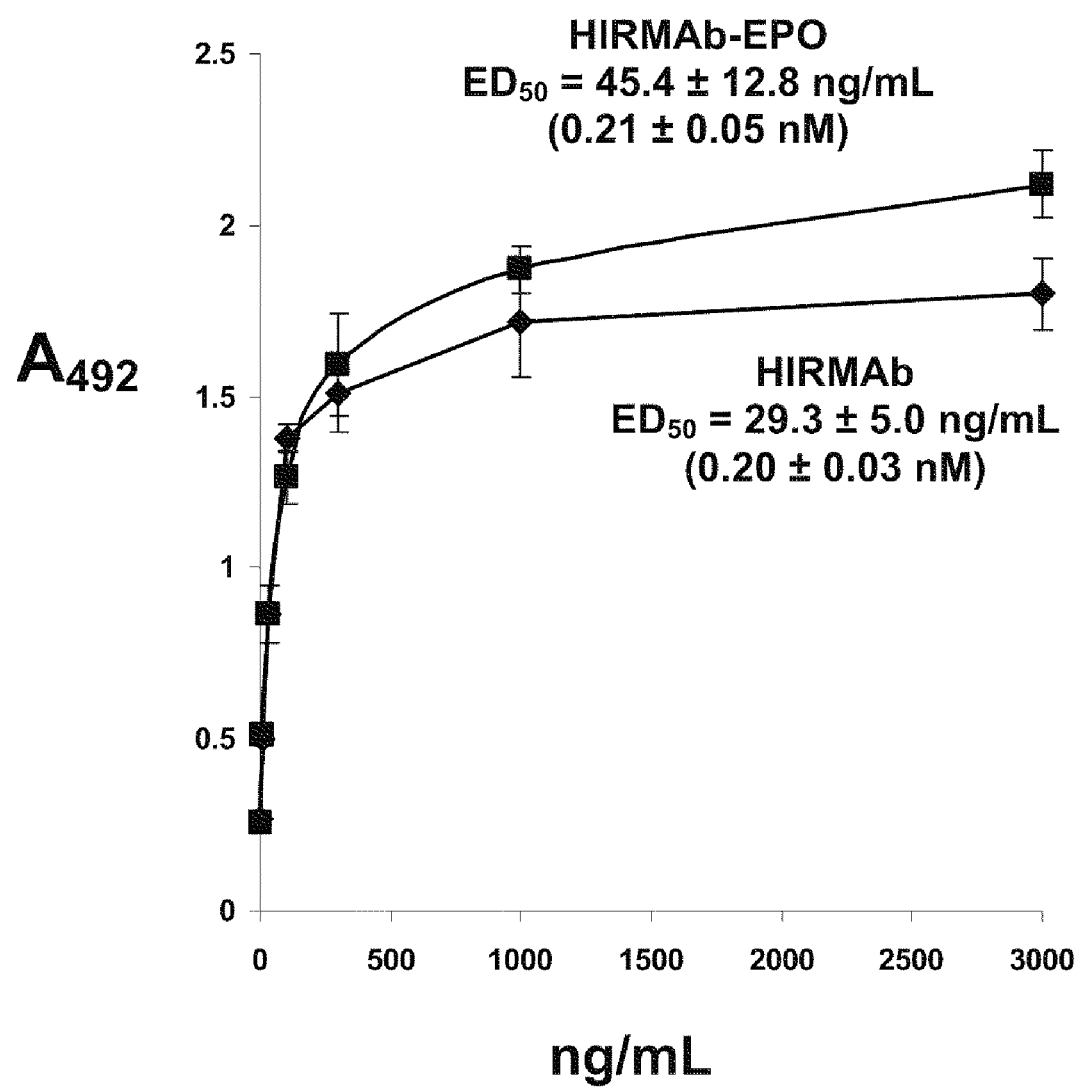
FIG. 33. Binding of either the chimeric HIRMAb or the HIRMAb-EPO fusion protein to the HIR extracellular domain (ECD) is saturable. The ED50 of HIRMAb-EPO binding to the HIR ECD is comparable to the ED50 of the binding of the chimeric HIRMAb. Data are mean±SE (n=3 dishes/point).

High Affinity Binding of the HIRMAb-EPO Fusion Protein to Both the HIR and EPOR The affinity of the fusion protein for the HIR extracellular domain (ECD) was determined with an ELISA using the lectin affinity purified HIR ECD. CHO cells permanently transfected with the HIR ECD were grown in serum free media (SFM), and the HIR ECD was purified with a wheat germ agglutinin affinity column. The HIR ECD (0.2 ug/well) was plated on Immulon 2 high binding 96-well plates, and the binding of the chimeric HIRMAb, or the HIRMAb-EPO fusion protein was detected with a biotinylated goat anti-human IgG (H+L) antibody (0.3 ug/well), and the ABC Elite detection system (Vector Labs). The concentration that caused 50% binding to the HIR ECD, the ED50, was determined by non-linear regression analysis. There is comparable binding of either the chimeric HIRMAb or the HIRMAb-EPO fusion protein to the HIR ECD with ED50 of 0.21±0.05 nM and 0.20±0.03 nM, respectively (FIG. 33).

Figure 34:
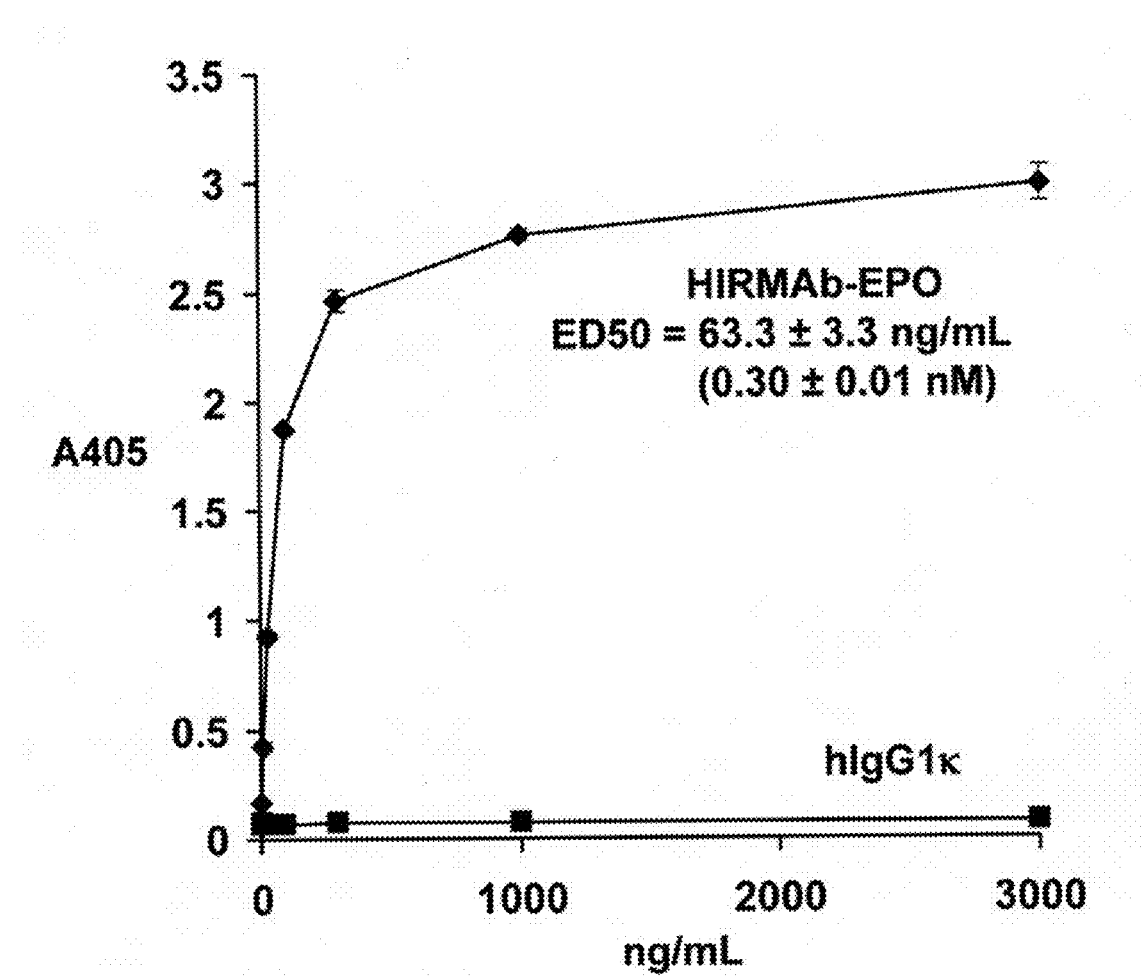
FIG. 34. Binding of either human IgG1κ or the HIRMAb-EPO fusion protein to the EPO receptor (EPOR) extracellular domain (ECD) is detected by ELISA. There is no binding to the EPOR by the human IgG1κ. Data are mean±SE (n=3 dishes/point).

Binding of the HIRMAb-EPO fusion protein to recombinant human EPOR was evaluated using a fusion protein of human IgG Fc and the ECD of recombinant human EPOR, which was obtained from R&D Systems, and plated in 96-well plates overnight at 0.2 ug/well. Wells were blocked with Tris buffered saline (TBS) and 1% bovine serum albumin (BSA). Various concentrations of HIRMAb-EPO fusion protein were plated for 2 hours at room temperature (RT). Following aspiration, the wells were washed with TBS/0.05% Tween-20 (TBST), a conjugate of alkaline phosphatase (AP) and a goat anti-human kappa light chain (GAH) antibody was plated and detection at 405 nm was performed with an ELISA plate reader after color development with para-nitrophenylphosphate. There was no binding of human IgG1k to the EPOR, whereas saturable binding of the HIRMAb-EPO fusion protein was observed (FIG. 34). The affinity of the HIRMAb-EPO fusion protein for the EPOR was high, with an ED50 of 0.30±0.01 nM (FIG. 34).

Example 19

Human Tf-1 Bio-Assay

Figure 35:
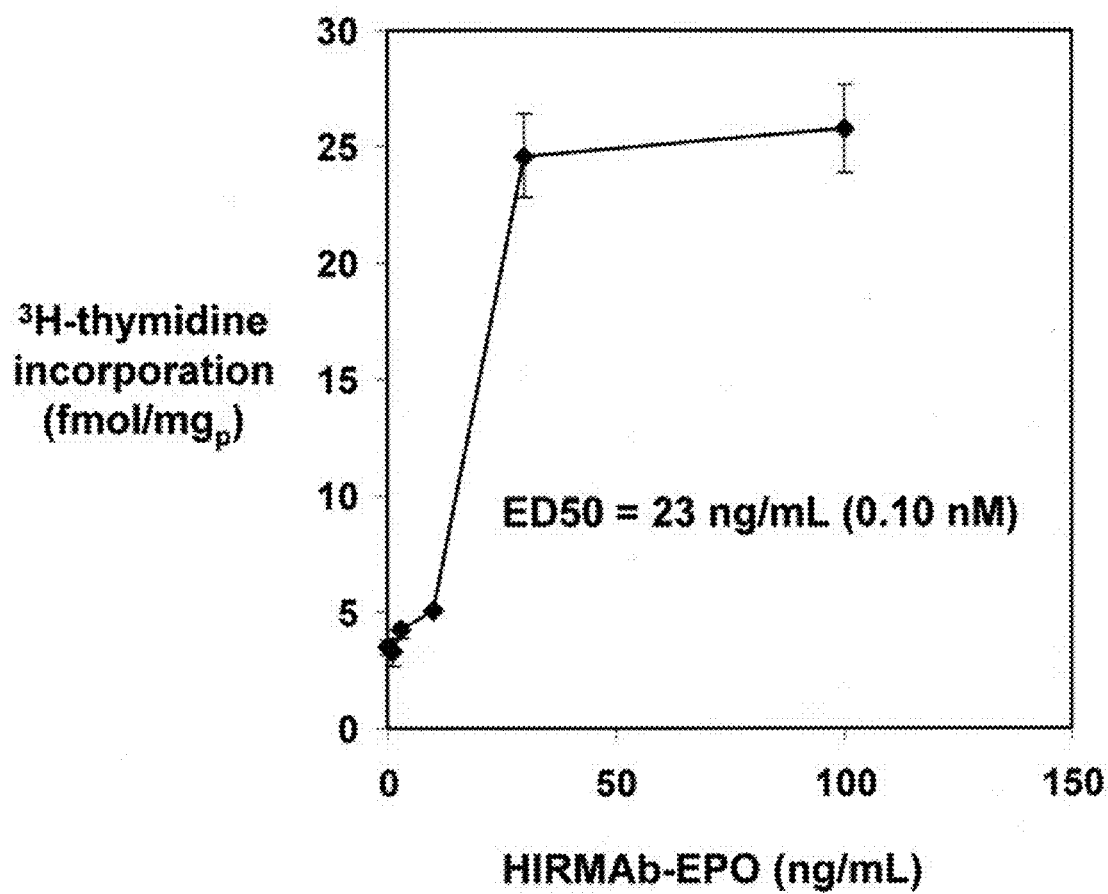
FIG. 35. EPO bio-assay in human TF-1 cells shows a saturable increase in thymidine incorporation into the cells in response to graded increases in medium concentration of HIRMAb-EPO fusion protein. Data are mean±SE (n=4 dishes/point).

Human TF-1 cells obtained from the American Type Culture Collection were cultured in RPMI-1640 medium with 10% fetal bovine serum and 2 ng/mL human recombinant granulocyte-macrophage colony stimulating factor (GM-CSF) (Peprotech, Rocky Hill, N.J.). Cells were plated in 96-well plates at 400,000 cells/well, and cultured overnight in medium containing no GM-CSF. The following day, the HIRMAb-EPO fusion protein was added followed by incubation for 44 hours. The medium was then supplemented with 3H-thymidine at a final concentration of 0.5 uCi/well. The wells were incubated at 37 C for 4 hours, and intracellular radioactivity was determined following washing of the cells in a Cell Harvester (Millipore, Billerica, Mass.) over glass fiber/C filters under vacuum. The filter was washed 3 times with cold 10% trichloroacetic acid (TCA), and the cell lysate was solubilized in 1 N NaOH. Radioactivity was determined with a Perkin Elmer liquid scintillation spectrometer, and cell protein was determined with the bicinchoninic acid (BCA) protein assay. The cell radioactivity was divided by the thymidine specific activity (6.7 uCi/nmol), and thymidine incorporation was expressed as fmol/mg protein. The biologic activity of the HIRMAb-EPO fusion protein was also evaluated with a bio-assay in human TF-1 cells. Thymidine incorporation into TF-1 cells was increased via a saturable mechanism by the HIRMAb-EPO fusion protein, with an ED50 of 0.1 nM (FIG. 35).

Example 20

Electroporation of CHO Cells

DG44 CHO cells were grown in serum-free medium (SFM), containing 1× HT supplement (hypoxanthine and thymidine). DG44 CHO cells (5×10$^6$ viable cells) were electroporated with 5 μg PvuI-linearized pHIRMAb-EPO TV plasmid DNA (FIG. 29). The cell-DNA suspension is then incubated for 10 min on ice. Cells are electroporated with pre-set protocol for CHO cells, i.e., square wave with pulse of 15 msec and 160 volts. After electroporation, cells are incubated for 10 min on ice. The cell suspension is transferred to 50 ml culture medium and plated at 125 μl per well in 40×96-well plates (10,000 cells per well), and 4,000 wells per study.

Selection and Amplification with Methotrexate and Screening IgG ELISA.

Following electroporation (EP), the CHO cells were placed in the incubator at 37° C. and 8% $CO_2$. Owing to the presence of the neo gen in the TV, transfected cell lines are initially selected with G418. The TV also contains the gene for DHFR, so the transfected cells were also selected with 20 nM methotrexate (MTX) and HT-deficient medium. Once visible colonies are detected at about 21 days after EP, the conditioned medium was sampled for human IgG by ELISA. Plates were removed from the incubator and transferred to the sterile hood where 100 μL samples were taken from each well using a Precision Pipettor system and transferred into a sterile 96-well tissue culture plate, which was then used for the human IgG ELISA. The media taken from the EP plates for the ELISA was replaced with 100 μL of SFM and cells were returned to the incubator at 37° C. and 8% $CO_2$. Wells with high human IgG signals in the ELISA were transferred from the 96-well plate to a 24-well plate with 1 mL of SFM. The 24-well plates were returned to the incubator at 37° C. and 8% $CO_2$. The following week IgG ELISA was performed on the clones in the 24-well plates. This was repeated through the 6-well plates to T75 flasks and finally to 60 mL and 125 mL square plastic bottles on an orbital shaker. After the cells adapted to the 60 mL bottle on the orbital shaker at 120 RPM they were transferred into a 125 mL plastic square bottle with 12 mL of SFM. At this stage, the final MTX concentration was 80 nM, and the medium IgG concentration, which is a measure of HIRMAb-EPO fusion protein in the medium was >10 mg/L at a cell density of $10^6$/mL.

Dilutional Cloning of CHO Cells.

Clones selected for dilutional cloning (DC) were removed from the orbital shaker in the incubator and transferred to the sterile hood. The cells were diluted to 500 mL in F-12K medium with 5% dialyzed fetal bovine serum (d-FBS) and penicillin/streptomycin, and the final dilution was 8 cells per mL, so that 4,000 wells in 40×96-well plates were plated at a cell density of 1 cell per well (CPW). After the cell suspension was prepared, within the sterile hood, a 125 μL aliquot was dispensed into each well of a 96-well plate using an 8-channel pipettor or a Precision Pipettor system. The plates were then returned to the incubator at 37° C. and 8% $CO_2$. The cells diluted to 1 cell/well cannot survive without serum. On day 6 or 7, DC plates were removed from the incubator and transferred to the sterile hood where 125 μL of F-12K medium with 5% dialyzed fetal bovine serum (d-FBS) was added to each well. After this step, the selection media contained 5% d-FBS, 30 nM MTX and 0.25 mg/mL Geneticin. On day 21 after the initial 1 CPW plating, aliquots from each of the 4,000 wells were removed for human IgG ELISA, using robotics equipment. DC plates were removed from the incubator and transferred to the sterile hood, where 100 μL of media was removed per well of the 96-well plate and transferred into a new, sterile sample 96-well plate using an 8-channel pipettor or a Precision Pipettor system.

ELISA Screening of 4,000 Wells.

On day 20 after the initial 1 CPW plating, 44 96-well Immunoassay plates were plated with 100 μL of 1 μg/mL solution of Primary antibody, a mouse anti-human IgG in 0.1M NaHCO3. Plates were incubated overnight in the 4° C. Revco refrigerator. The following day, the plates were washed with 1×TBST 5 times, and 100 μL of 1 μg/mL solution of secondary antibody and blocking buffer were added. Immulon plates were washed with 1×TBST 5 times. 100 μL of 1 mg/mL of 4-nitrophenyl phosphate di(2-amino-2-ethyl-1,3-propanediol) salt in 0.1M glycine buffer were added to the Immulon 96-well Immunoassay plates using the BioTek uFill. Plates were read on a microplate reader. The assay produced IgG output data for 4,000 wells/experiment. The highest producing 24-48 wells were selected for further propagation.

Adaptation of Cloned Cells to Serum-Free Medium (SFM).

The highest producing 24-well plates from the 1 CPW DC transferred to the sterile hood were gradually subcloned through 6-well dishes, T75 flasks, and 125 mL square plastic bottles on an orbital shaker. During this process the serum was reduced to zero, at the final stage of centrifugation of the cells and resuspension in SFM.

Second Round Dilutional Cloning.

The above procedures were repeated with a second round of dilutional cloning, again at 0.5 cells/well (CPW). At this stage, approximately 40% of the wells showed any cell growth, and all wells showing growth also secreted human IgG. These results confirmed that on average only 1 cell is plated per well with these procedures, and that the CHO cell line originated from a single cell.

Example 21

Pharmacokinetics and Brain Uptake of EPO and the HIRMAb-EPO Fusion Protein in the Rhesus Monkey EPO is believed to cross the BBB, based on the finding that EPO appears in cerebrospinal fluid (CSF) following systemic administration; accordingly, a large trial of intravenous EPO as a new treatment for stroke was designed. [Ehrenreich et al., Erythropoietin therapy for acute stroke is both safe and beneficial, *Mol Med*. (2002) 8: 495-505]. However, drug penetration into the CSF is an index of blood-CSF barrier permeability, not BBB permeability. CSF is a filtrate of plasma, and all proteins in plasma distribute into CSF, inversely related to the molecular size of the protein [Reiber and Felgenhauer, Protein transfer at the blood cerebrospinal fluid barrier and the quantitation of the humoral immune response within the central nervous system, *Clin Chim Acta* (1987) 163: 319-328]. Therefore, the detection of a peptide in CSF is not necessarily a measure of BBB transport of the peptide. In order to examine the transport of EPO across the BBB in vivo in the primate, the protein was radio-labeled with the 125I-Bolton-Hunter reagent. The biological activity of the EPO was confirmed with a radio-receptor assay (RRA). In parallel, the HIRMAb-EPO fusion protein was radiolabeled with 3H—N-succinimidy propionate (NSP). The [$^{125}$I]-EPO and the [$^3$H]-HIRMAb-EPO fusion protein were co-injected into the adult Rhesus monkey for a pharmacokinetics (PK) and brain uptake evaluation.

CHO cells stably transfected with the TV encoding the HIRMAb-EPO fusion protein were subjected to limited dilutional cloning and a high producing CHO line was isolated, and the fusion protein was purified by protein A affinity chromatography, as described above. The results of the SDS-PAGE, Western blotting, SEC HPLC, and HIR and EPO receptor binding assays were identical to the results obtained for the COS-derived fusion protein described above. The CHO-derived HIRMAb-EPO fusion protein was used for the primate brain uptake study.

Radio-labeling of proteins. [$^{125}$I]-Bolton-Hunter reagent was purchased from American Radiolabeled Chemicals (St. Louis, Mo.). Human recombinant EPO (#286-EP) was purchased from R&D Systems (Minneapolis, Minn.), and shown to be homogenous by SDS-PAGE. The EPO was radio-labeled with fresh Bolton-Hunter reagent to a specific activity of 67 uCi/ug and a trichloroacetic acid (TCA) precipitability of >99% following purification with a 1.0×28 cm column of Sephadex G-25 and elution with 0.01 M NaH2PO4/0.15 M NaCl/pH=7.4/0.05% Tween-20 (PBST). The TCA precipitation of the labeled EPO remained 99% at 24 hours after iodination, and the EPO was administered to the primate within 24 hrs of radio-labeling. [$^{3}$H]-N-succinimidyl propionate (NSP) was purchased from American Radiolabeled Chemicals. The HIRMAb-EPO fusion protein was radio-labeled with fresh NSP to a specific activity of 2.9 uCi/ug and a TCA precipitability of 96% following purification with a 1.0×28 cm column of Sephadex G-25 and elution with 0.02 M MES/0.15 M NaCl/pH=6.0/0.05% Tween-20 (MBST), where MES=4-Morpholineethanesulfonic acid. The solution was buffer exchanged with MBST/0.1% bovine serum albumin, and an Ultra-15 microconcentrator (Millipore, Bedford, Mass.), which increased the TCA precipitability to 99%. The $^{3}$H-labeled HIRMAb-EPO fusion protein was labeled in advance of the primate study and stored at −70 C.

EPO radio-receptor assay. The retention of high affinity EPOR binding by the [$^{125}$I]-EPO following radiolabeling with the Bolton-Hunter reagent was examined with a radio-receptor assay. The mouse anti-human IgG1 Fc antibody (Invitrogen/Zymed) and Fc fusion protein of the human EPOR ECD (R&D Systems) were plated as described above for the EPOR ELISA. The wells were washed with PBS, followed by the addition of 100 uL/well of a co-mixture of [$^{125}$I]-EPO at a concentration of 0.01 uCi/well (0.15 ng/well) and various concentrations of unlabeled human EPO (R&D Systems, #286-EP), followed by a 3 hour incubation at room temperature. The wells were emptied by aspiration, washed with cold PBS, and 250 uL/well of 1 N NaOH was added, followed by heating at 60 C for 30 min. Radioactivity was counted in Ultima Gold (Perkin Elmer, Downers Grove, Ill.) in a Perkin Elmer Tricarb 2100TR liquid scintillation counter, and the fractional binding per well was computed. The half-saturation constant, $K_D$, of EPO binding to the EPOR was determined by non-linear regression analysis.

Primate brain uptake and capillary depletion analysis. An adult female Rhesus monkey, 5.6 kg, was injected intravenously (IV) with 2132 uCi of [$^{3}$H]-HIRMAb-EPO fusion protein and 330 uCi of [$^{125}$I]-EPO in 3.0 mL by bolus injection over 30 seconds in the left femoral vein. The dose of HIRMAb-EPO fusion protein was 130 ug/kg, and the dose of EPO was 0.9 ug/kg, which is a therapeutic dose of EPO. The animal was initially anesthetized with intramuscular ketamine, and anesthesia was maintained by 1% isoflurane by inhalation. All procedures were carried out in accordance with the Guide for the Care and Use of Laboratory Animals as adopted and promulgated by the U.S. National Institutes of Health. Following intravenous drug administration, femoral venous plasma was obtained at 1, 2.5, 5, 15, 30, 60, and 120 min for determination of $^{3}$H and $^{125}$I radioactivity. The animal was euthanized, and samples of major organs (heart, liver, spleen, lung, skeletal muscle, kidney, and omental fat) were removed, weighed, and processed for determination of radio-activity. The cranium was opened and the brain was removed. Samples of frontal cortical gray matter, frontal cortical white matter, cerebellar gray matter, and cerebellar white matter were removed for radioactivity determination.

Samples (~2 gram) of frontal cortex were removed for capillary depletion analysis [Triguero et al., Capillary depletion method for quantifying blood-brain barrier transcytosis of circulating peptides and plasma proteins, *J Neurochem.* (1990) 54: 1882-1888]. The brain was homogenized in 8 mL cold phosphate buffered saline (PBS) in a tissue grinder. The homogenate was supplemented with 9.4 mL cold 40% dextran (70 kDa, Sigma Chemical Co.), and an aliquot of the homogenate was taken for radioactivity measurement. The homogenate was centrifuged at 3200 g at 4 C for 10 min in a fixed angle rotor. The brain microvasculature quantitatively sediments as the pellet, and the post-vascular supernatant is a measure of capillary depleted brain parenchyma. The vascular pellet and supernatant were counted for $^{3}$H and $^{125}$I radioactivity in parallel with the homogenate. The volume of distribution (VD) was determined for each of the 3 fractions from the ratio of total $^{125}$I or $^{3}$H radioactivity in the fraction divided by the total $^{125}$I or $^{3}$H radioactivity in the 120 min terminal plasma.

Plasma and tissue samples were analyzed for $^{125}$I radioactivity with a gamma counter (Wizard 1470, Perkin Elmer), and were analyzed for $^{3}$H radioactivity with a liquid scintillation counter (Tricarb 2100TR, Perkin Elmer, Downers Grove, Ill.). The $^{125}$I isotope emits radiation that is detected in the $^{3}$H channel (0-12 keV) of the liquid scintillation counter (LSC). Therefore, quench curves were produced using chloroform as the quench agent to compute the efficiency of counting of $^{125}$I in the $^{3}$H window. All samples for $^{3}$H counting were solubilized in Soluene-350 and counted in the LSC in Opti-Fluor O (Perkin Elmer).

Pharmacokinetics and organ PS product. The $^{3}$H or $^{125}$I radioactivity in plasma, DPM/mL, was converted to % injected dose (ID)/mL, and the % ID/mL was fit to a mono- or bi-exponential equation. The intercepts (A1, A2) and the slopes (k1, k2) were used to compute the median residence time (MRT), the central volume of distribution (Vc), the steady state volume of distribution (Vss), the area under the plasma concentration curve (AUC), and the systemic clearance (CL). Non-linear regression analysis used the AR subroutine of the BMDP Statistical Software (Statistical Solutions Ltd, Cork, Ireland). Data were weighted by $1/(\% \text{ID/mL})^2$.

The organ clearance (μL/min/g), also called the permeability-surface area (PS) product, is computed from the terminal organ uptake (% ID/g) and the 120 min plasma AUC (% IDmin/mL) as follows:

organ PS product=[(% ID/g)/AUC]*1000

Experimental results. The HIRMAb-EPO fusion protein was radiolabeled with [$^{3}$H] and the recombinant human EPO was radiolabeled with [$^{125}$I], and the proteins were co-injected IV into an adult Rhesus monkey. So as to confirm that radio-iodination of EPO with the [$^{125}$I]-Bolton-Hunter reagent does not affect EPO binding to the EPOR, a radio-receptor assay was performed with the [$^{125}$I]-EPO. The design of the radio-receptor assays is shown in FIG. 36A. Binding of the [$^{125}$I]-EPO to the EPOR is displaced by unlabeled EPO with a KD of 0.17±0.09 nM (FIG. 36B). This assay shows the high affinity binding of EPO to the EPOR is retained following radiolabeling with the Bolton-Hunter reagent.

Figure 37:
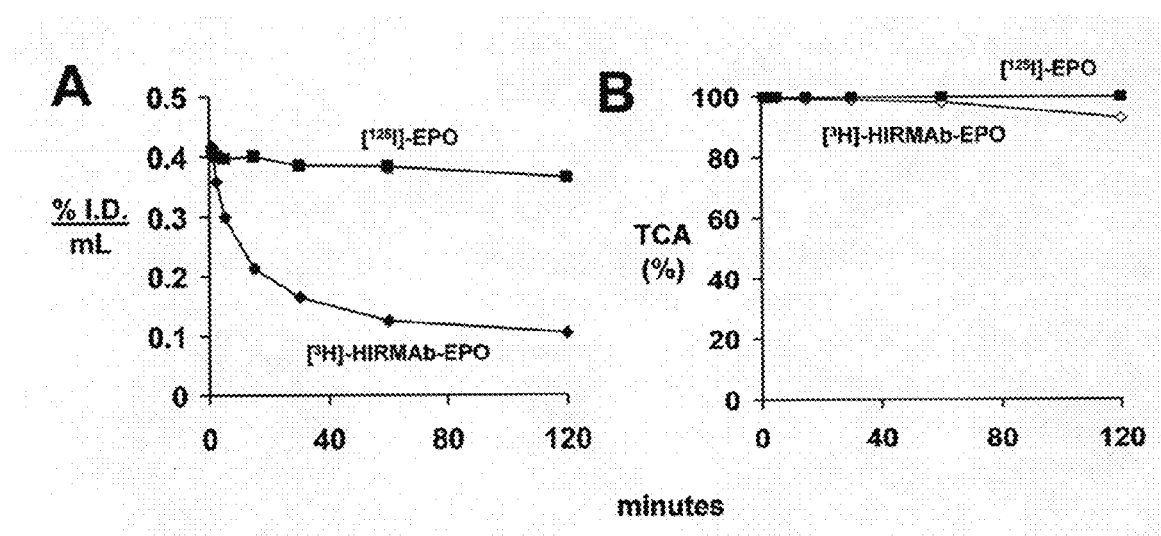
FIG. 37. (A) The plasma concentration of [$^{125}$I]-EPO and [$^3$H]-HIRMAb-EPO fusion protein is plotted vs the time after a single intravenous injection of the proteins in the adult Rhesus monkey. Data are expressed as % injected dose (I.D.)/mL. (B) The % of plasma radioactivity that is precipitable by 10% trichloroacetic acid (TCA) is plotted vs. the time after injection for both proteins. Data are mean±SE (n=3 replicates per point).

The clearance of the plasma radioactivity is shown in FIG. 37A for the [$^{125}$I]-EPO and the [$^{3}$H]-HIRMAb-EPO fusion protein, and the plasma radioactivity that was precipitable with TCA is shown in FIG. 37B. Both the HIRMAb-EPO fusion protein, and EPO, were stable in vivo as the percent of plasma radioactivity that was precipitable by TCA was >92% for both proteins at all time points (FIG. 37B). The plasma clearance profiles (FIG. 37A) were fit to a bi-exponential function for the HIRMAb-EPO fusion protein, and to a mono-exponential function for EPO, for estimation of the PK parameters, which are shown in Table 7 for each protein.

TABLE 7

Pharmacokinetic parameters

| parameter | units | [$^{125}$I]-EPO | [$^{3}$H]-HIRMAb-EPO |
| --- | --- | --- | --- |
| A1 | % ID/mL | 0.400 ± 0.002 | 0.251 ± 0.021 |
| A2 | % ID/mL | — | 0.174 ± 0.015 |
| k1 | min-1 | 0.00083 ± 0.00010 | 0.110 ± 0.025 |
| k2 | min-1 | — | 0.0049 ± 0.0010 |
| MRT | min | 1208 ± 151 | 191 ± 37 |
| Vc | mL/kg | 44 ± 1 | 42 ± 2 |
| Vss | mL/kg | — | 91 ± 7 |
| AUC|$^{120}$ | % IDmin/mL | 46.0 ± 0.2 | 18.0 ± 0.4 |
| AUCss | % IDmin/mL | 486 ± 59 | 37.5 ± 4.6 |
| CL | mL/min/kg | 0.037 ± 0.004 | 0.44 ± 0.05 |

Estimated from the plasma clearance data in FIG. 37A. Data are % ID/100 grams; mean±SE (n=3).

The uptake of the proteins by brain and peripheral organs was measured as a % ID/100 gram tissue, and these values are given in Table 8.

TABLE 8

Organ uptake of [$^{125}$I]-EPO and [$^{3}$H]-HIRMAb-EPO in the Rhesus monkey

| organ | [$^{125}$I]-EPO | [$^{3}$H]-HIRMAb-EPO |
| --- | --- | --- |
| frontal gray | 0.34 ± 0.02 | 2.1 ± 0.1 |
| frontal white | 0.17 ± 0.02 | 1.6 ± 0.1 |
| cerebellar gray | 0.34 ± 0.01 | 1.6 ± 0.1 |
| cerebellar white | 0.21 ± 0.02 | 1.2 ± 0.1 |
| heart | 2.2 ± 0.19 | 1.4 ± 0.2 |
| liver | 6.9 ± 0.3 | 17.8 ± 6.3 |
| spleen | 6.0 ± 0.1 | 15.9 ± 4.6 |
| lung | 9.5 ± 0.7 | 4.5 ± 0.6 |
| skeletal muscle | 0.39 ± 0.01 | 0.17 ± 0.03 |
| fat | 0.41 ± 0.05 | 0.26 ± 0.01 |
| kidney | 11.1 ± 0.2 | 5.2 ± 0.4 |

The brain volume of distribution (VD) of the proteins was measured with the capillary depletion method and the VD values for the homogenate, the vascular pellet, and the post-vascular supernatant are shown in Table 9. The radioactivity in the pos-vascular supernatant represents intact fusion protein as the TCA precipitability of the post-vascular supernatant is 91±1% (Table 9).

TABLE 9

Capillary depletion analysis of HIRMAb-EPO and EPO distribution in brain

| Parameter | EPO | HIRMAb-EPO |
| --- | --- | --- |
| Homogenate VD | 7.7 ± 0.7 | 260 ± 11 |
| Post-vascular supernatant VD | 6.3 ± 0.2 | 156 ± 8 |
| Brain capillary pellet VD | 0.22 ± 0.03 | 32 ± 9 |
| TCA precipitation (%) | n.m. | 91 ± 1 |

Mean ± SE (n = 3).
VD = volume of distribution (uL/g);
TCA = trichloroacetic acid;
n.m. = not measured.

Figure 38:
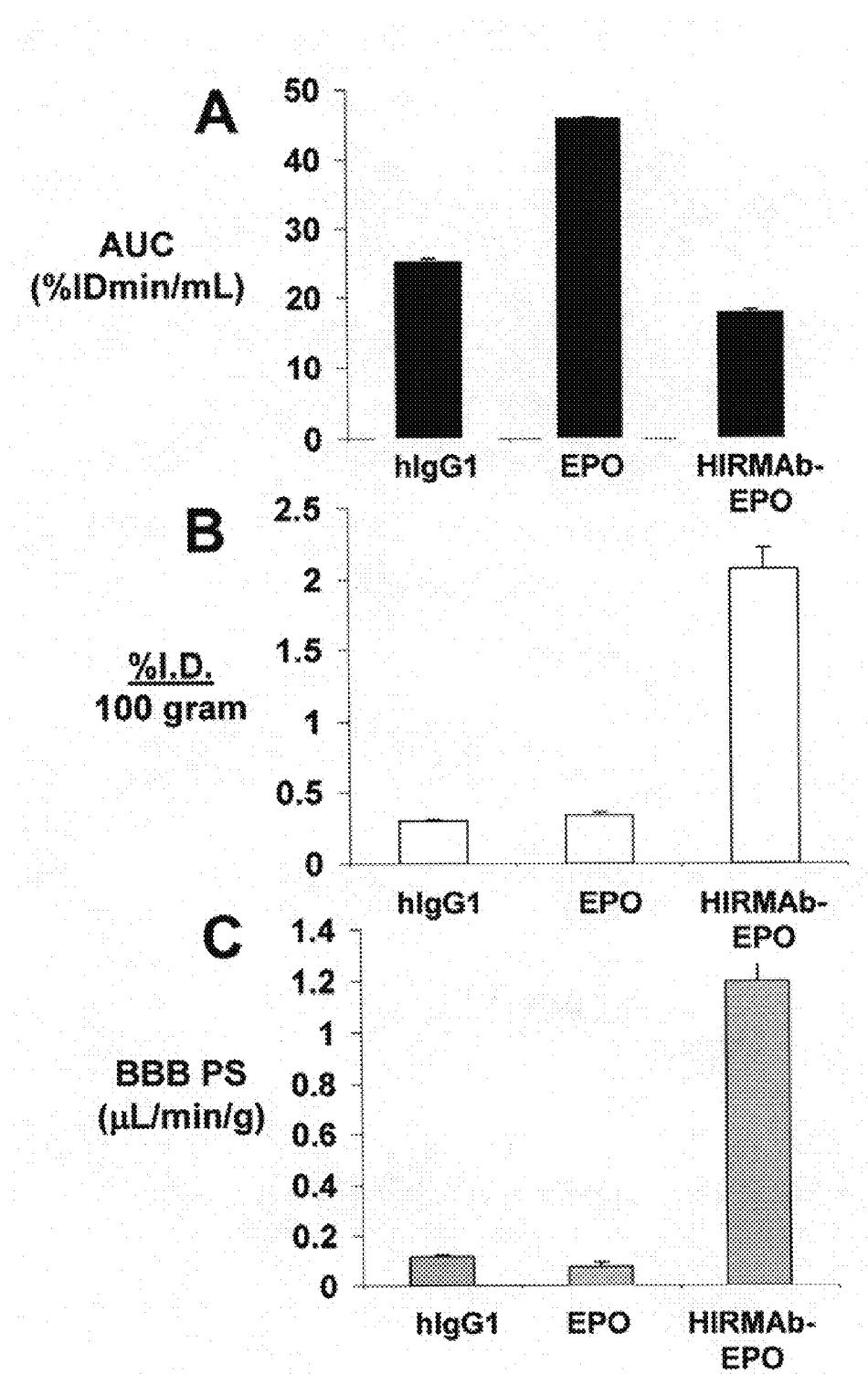
FIG. 38. The plasma area under the concentration curve or AUC (A), the brain uptake or % injected dose (ID) per 100 gram brain (B), and the BBB permeability-surface area (PS) product (C), are plotted for EPO, for the HIRMAb-EPO fusion protein, and for a brain plasma volume marker, human IgG1 (hIgG1). All measurements were made at 2 hours after intravenous administration of the protein in the Rhesus monkey. Data are mean±SE (n=3 replicates per point).

The BBB PS products for the HIRMAb-EPO fusion protein and recombinant EPO were computed from the 2 hour plasma AUC (Table 7) and the brain uptake (Table 8), and the PS products are given in FIG. 38C. For comparison, FIG. 38 also displays the AUC, the % ID/100 g, and the BBB PS product for a vascular space marker, human IgG1. The PS products were similarly computed for the HIRMAb-EPO fusion protein and recombinant EPO in peripheral organs and these data are given in Table 10. The ratio of the PS product for the HIRMAb-EPO fusion protein relative to the PS product for the recombinant EPO in each organ is plotted in FIG. 39.

TABLE 10

Organ PS products for EPO and HIRMAb-EPO fusion protein

| | PS product (uL/min/g) | |
| --- | --- | --- |
| organ | EPO | HIRMAb-EPO |
| heart | 0.49 ± 0.02 | 0.78 ± 0.11 |
| liver | 1.5 ± 0.1 | 9.9 ± 3.5 |
| spleen | 1.3 ± 0.1 | 8.9 ± 2.5 |
| lung | 2.1 ± 0.1 | 2.5 ± 0.3 |
| skeletal muscle | 0.086 ± 0.002 | 0.094 ± 0.019 |
| fat | 0.089 ± 0.010 | 0.14 ± 0.01 |
| kidney | 2.4 ± 0.1 | 2.9 ± 0.2 |

Data are mean ± SE (n = 3).

Figure 39:
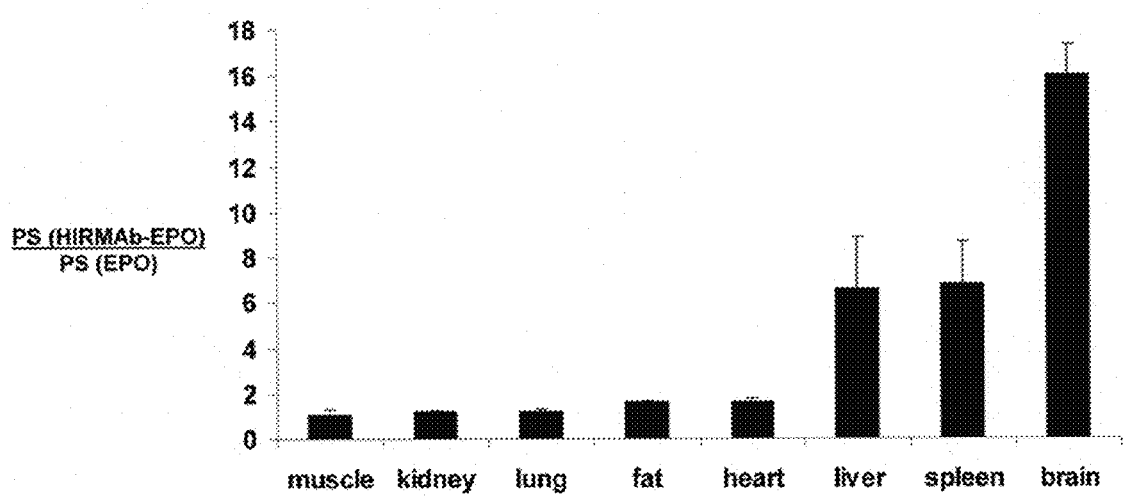
FIG. 39. Ratio of the organ PS product for the HIRMAb-EPO fusion protein, relative to the organ PS product for EPO, is plotted for each organ. Data are mean±SE (n=3 replicates per point).

Conclusions. The results of this work are consistent with the following conclusions. First, a bi-functional IgG-EPO fusion protein has been genetically engineered, wherein the amino terminus of the mature human EPO is fused to the carboxyl terminus of the heavy chain (HC) of a chimeric HIRMAb (FIG. 28), and is expressed and secreted in COS cells (Table 6), and in a stably transfected CHO cell line. Second, the HIRMAb-EPO fusion protein is bi-functional and binds the HIR and human EPOR each with high affinity (FIGS. 33 and 34). Third, the HIRMAb-EPO fusion protein has activity in a bio-assay of human TF-1 cells, and the ED50 of enhanced thymidine incorporation into the cells is comparable to the ED50 of HIRMAb-EPO fusion protein binding to the EPOR (FIG. 35). Fourth, EPO does not cross the primate BBB in vivo, as the brain uptake, or BBB PS product, for EPO is not significantly different from the same values for a brain blood volume marker, human IgG1 (FIG. 38B, C). Fifth, the brain uptake of the HIRMAb-EPO fusion protein, 2.1±0.1% I.D/100 gram brain, is high compared to the brain uptake of EPO or human IgG1 (FIG. 38B, C). Sixth, fusion of EPO to the HIRMAb results in selective targeting to the brain, relative to peripheral organs (FIG. 39).

An IgG-EPO fusion protein could be engineered by fusion of the EPO to either the amino terminus or the carboxyl terminus of either the heavy chain (HC) or light chain (LC) of the IgG, such as the HIRMAb. EPO has been fused to the amino terminus of human IgG Fc fragments. However, it is not clear if EPO can be fused to the carboxyl terminus of the IgG chain, as depicted in FIG. 28. In this construct, the heavy chain fusion protein is connected to the IgG signal peptide, and the IgG chain is translated and folded in the host cell prior to translation and folding of the EPO fused to the carboxyl terminus. The findings in this work show that fusion of the EPO to the carboxyl terminus of the IgG heavy chain allows for the retention of EPO biological activity, and the HIRMAb-EPO fusion protein binds the EPOR and activates EPO biological activity in the low nM range (FIGS. 34-35). With respect to HIRMAb-EPO fusion protein binding to the HIR, fusion of EPO to the carboxyl terminus of the IgG HC leaves free the amino terminal portions of the IgG chains, which bind to the HIR (FIG. 28). The present work shows the HIRMAb-EPO fusion protein binds to the HIR with an affinity equal to the original HIRMAb (FIG. 33).

Figure 36:
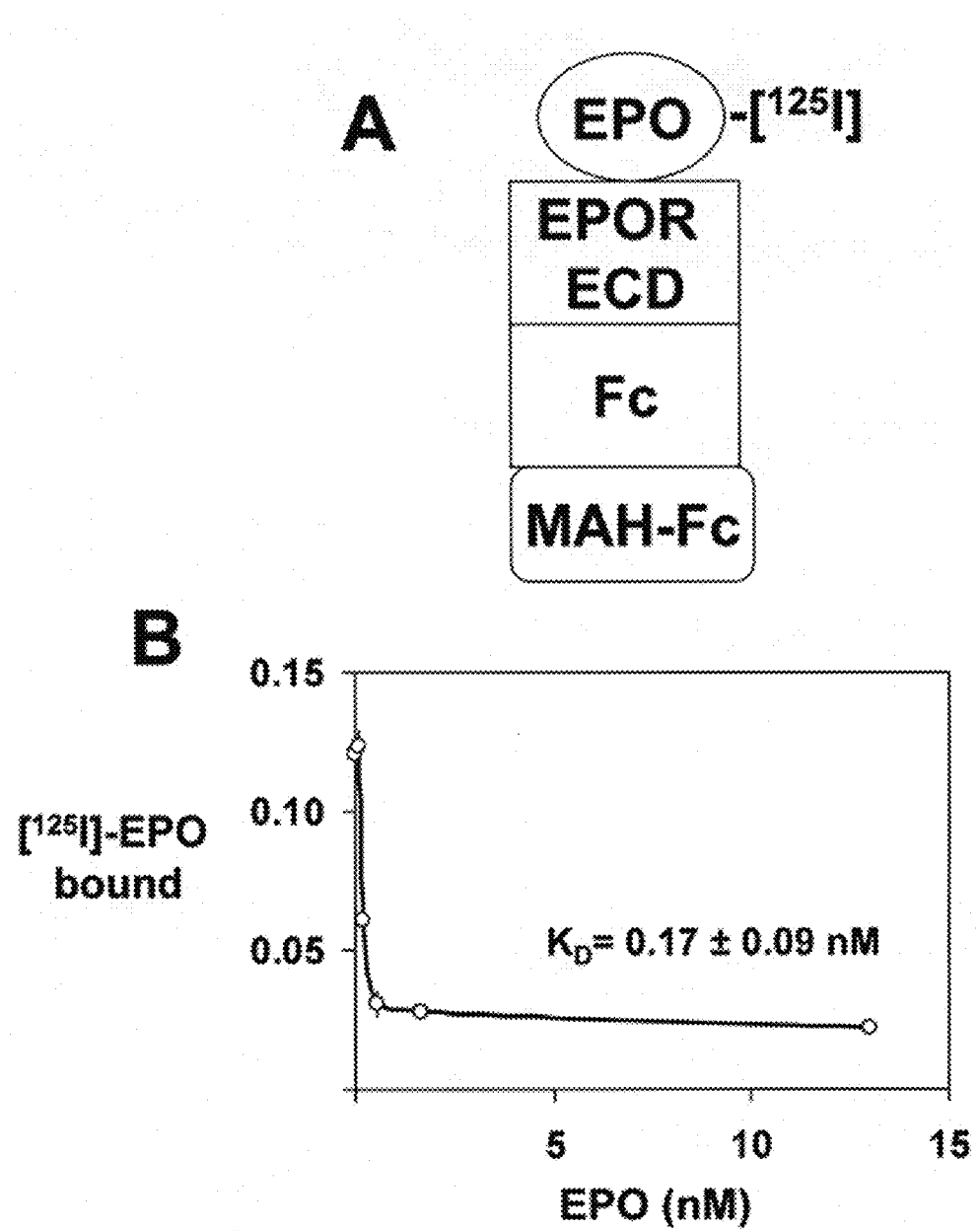
FIG. 36. (A) Outline of radio-receptor assay for measurement of the binding of Bolton-Hunter reagent-labeled [$^{125}$I]-EPO to the EPOR. A mouse anti-human (MAH) IgG1 Fc was plated, which bound the Fc region of a Fc fusion of the EPOR ECD. The EPOR binds to the [$^{125}$I]-EPO, which is displaced by the addition of unlabeled EPO. (B) The saturable binding was analyzed by a non-linear regression analysis to yield the concentration, $K_D$, which produced 50% inhibition of [$^{125}$I]-EPO binding to the EPOR.

EPO was fused to the HIRMAb molecular Trojan horse so as to produce a brain penetrating form of EPO, which is a neuroprotective peptide. In order to examine the relative brain penetrating properties of EPO and the HIRMAb-EPO fusion protein, both proteins were differentially radio-labeled for injection in the Rhesus monkey. In order to confirm that radiolabeling of EPO with the [$^{125}$I]-Bolton-Hunter reagent does not affect EPO binding to the EPOR, the [$^{125}$I]-EPO binding was evaluated with a radio-receptor assay. As shown in FIG. 36, [$^{125}$I]-EPO binds with high affinity to the EPOR with a KD of 0.17±0.09 nM.

The present work shows that, in fact, EPO does not cross the BBB in vivo. The brain uptake, or BBB PS product, of [$^{125}$I]-EPO in the primate is no different from the same parameters for a brain blood volume marker, human IgG1 (FIG. 38B, C), which indicates that EPO does not cross the BBB. In order for peripheral EPO to penetrate the brain across the BBB, it would be necessary for blood-borne EPO to access an EPOR-mediated transport system on the luminal membrane of the brain capillary endothelium, which forms the BBB in vivo. The absence of EPO transport across the BBB in vivo indicates there is no EPOR on the luminal membrane of the BBB. Evidence has been reported for EPOR immunoreactivity at the brain microvasculature, but the receptor is located in a discontinuous pattern on the abluminal side of the endothelium [Brines et al., Erythropoietin crosses the blood-brain barrier to protect against experimental brain injury, *Proc Natl Acad Sci USA* (2000) 97: 10526-10531]. These characteristics are typical of receptor expression on the astrocyte foot process that invests the brain capillary. An astrocytic EPOR could not mediate the brain uptake of circulating EPO.

The re-engineering of EPO as an IgG fusion protein with the HIRMAb molecular Trojan horse produces a brain penetrating form of EPO. The brain uptake of the HIRMAb-EPO fusion protein, 2.1% of injected dose/100 gram brain, is high relative to the brain uptake of a molecule confined to the brain plasma volume, such as EPO or human IgG1 (FIG. 38B). Brain uptake is expressed per 100 gram brain, because the brain weight in the adult Rhesus monkey is 100 grams. The HIRMAb-EPO fusion protein penetrates the BBB and enters brain parenchyma, as demonstrated by the capillary depletion method. The brain VD of the HIRMAb-EPO fusion protein in the post-vascular supernatant is 60% of the total brain homogenate VD (Table 9), which indicates the majority of the fusion protein bound by the BBB insulin receptor has penetrated brain parenchyma by 2 hours after IV administration.

Fusion of EPO to the HIRMAb selectively targets EPO to the brain compared to insulin receptor-rich peripheral organs, as demonstrated by the ratio of the organ PS product for the fusion protein, relative to the organ PS product for EPO (FIG. 39). The PS product reflects transport across the BBB, and not sequestration within the brain plasma volume. The PS product for the brain plasma volume marker, human IgG1, should be subtracted from the PS product for both EPO and the HIRMAb-EPO fusion protein. However, since the BBB PS product of the IgG1 and EPO are not significantly different (FIG. 39), the net PS product for EPO is zero, and a ratio of PS products could not be calculated. Therefore, the PS product ratio for the HIRMAb-EPO fusion protein and EPO for brain shown in FIG. 39 is a minimal estimate of the increased penetration of the BBB by the fusion protein as compared to EPO. The PS product ratio for most peripheral organs is near unity for insulin receptor-rich organs such as skeletal muscle, heart, and fat (FIG. 39). There is an intermediate level of uptake of the fusion protein by liver and spleen (FIG. 39), because these organs are perfused by a microvasculature with a highly porous endothelial barrier.

Delivery of therapeutic concentrations of EPO to brain with the HIRMAb molecular Trojan horse. The brain uptake and pharmacokinetics analysis reported here for the primate allows for initial dosing considerations with the HIRMAb-EPO fusion protein. Although EPO is expressed in brain, the concentration of EPO in the control brain, or CSF, is too low to detect quantitatively by ELISA. In those cases where EPO is detectable in human CSF, the EPO concentration is very low, 0.1 pM [Koehne et al., Vascular endothelial growth factor and erythropoietin concentrations in cerebrospinal fluid of children with hydrocephalus, *Child's Nerv. Syst.* (2002) 18: 137-141]. In peripheral tissue, the concentration of EPO that causes a 50% increase in pharmacological effect is 12 pM (Elliott et al., Control of rHuEPO biological activity: the role of carbohydrate, *Exp Hemat* (2004) 32: 1146-1155), which is equal to 0.4 ng/mL, given an EPO molecular weight of 35,000 Da. Based on the brain uptake of the HIRMAb-EPO fusion protein, 2.1% ID/100 gram brain (FIG. 38B), the peripheral injection of a very low dose of the fusion protein, 1 ug/kg, would produce a brain concentration of 1 ng/gram brain, which is a therapeutic concentration of EPO.

Selective targeting of EPO to brain, relative to peripheral tissues, with the HIRMAb molecular Trojan horse. The pharmacokinetic (PK) parameters of EPO and the HIRMAb-EPO fusion protein clearance from plasma (Table 7) were derived from the plasma clearance curves in FIG. 37A, and these data show a very different PK profile for the HIRMAb-EPO fusion protein as compared to EPO. Fusion of EPO to the HIRMAb reduces the plasma AUC of EPO over 12-fold, from 486±59% IDmin/mL to 37.5±4.6% IDmin/mL (Table 7). The markedly different PK profile for the HIRMAb-EPO fusion protein, as compared to EPO, will limit the pharmacologic properties of the fusion protein in peripheral tissues. A peripheral injection of 1 ug/kg of the HIRMAb-EPO fusion protein would be equivalent to a dose of 20 units/kg, since EPO comprises about 20% of the amino acid content of the fusion protein, and 1 unit of EPO activity is equivalent to 10 ng EPO. A dose of 20 units/kg approximates a sub-therapeutic dose of EPO with respect to hematopoiesis. However, the effect of EPO on the mass of red cells, which persist for about 120 days, is primarily a function of the plasma AUC of the EPO (Elliott et al., Control of rHuEPO biological activity: the role of carbohydrate, *Exp Hemat* (2004) 32: 1146-1155). That is, the longer the circulation time of EPO in blood, the greater the effect on hematopoiesis and hematocrit. Conversely, the shorter the circulation time of EPO, the lower the effect on hematocrit. In treatment of the brain with the HIRMAb-EPO fusion protein, it is preferred that a pharmacologic effect in brain be achieved with minimal pharmacologic effects on hematopoiesis. Fusion of EPO to the HIRMAb results in a 12-fold reduction in the plasma AUC of EPO (Table 7). Therefore, doses of the HIRMAb-EPO fusion protein that induce neuroprotection in brain are expected to have minimal effects on hematopoiesis in peripheral tissues.

Example 22

Variation of IgG-EPO Fusion Protein Domains (Prophetic Example)

This example illustrates variations of IgG-EPO fusion protein domains that can be used in the methods and compositions described herein. The HC of the HIRMAb-EPO fusion protein is comprised of the following domains: a 19 AA signal peptide (AA 1-19 of SEQ ID NO: 49), FR1 (AA 20-44 of SEQ ID NO: 49), CDR1 (AA 45-54 of SEQ ID NO: 49), FR2 (AA 55-68 of SEQ ID NO: 49), CDR2 (AA 69-85 of SEQ ID NO: 49), FR3 (AA 86-117 of SEQ ID NO: 49), CDR3 (AA 118-121 of SEQ ID NO: 49), FR4 (AA 122-132 of SEQ ID NO: 49), the constant (C)-region of the human IgG1 heavy chain (AA 133-461 of SEQ ID NO: 49), a 4 AA linker (Ser-Ser-Ser-Ser (SEQ ID NO: 58), AA 462-465 of SEQ ID NO:49), and the 166 EPO without its signal peptide (AA 466-631 of SEQ ID NO:49). The amino acid sequence of the constant-region is comprised of the following sub-domains: the CH1, hinge, CH2, and CH3 domains. The heavy chain C-region could be derived from the C-region of other human IgG isotypes, including human IgG2, IgG3, and IgG4. The different C-region isotypes each offer well known advantages or disadvantages pertaining to flexibility around the hinge region, protease sensitivity, activation of complement or binding to the Fc receptor. Any of the C-regions from IgG2, IgG3, IgG4, or any sub-domains thereof, is substituted for one or all of the IgG1 subdomains given in SEQ ID NO:49.

The LC of the HIRMAb-EPO fusion protein is comprised of the following domains: a 20 AA signal peptide (AA 1-20 of SEQ ID NO: 47), FR1 (AA 21-43 of SEQ ID NO: 47), CDR1 (AA 44-54 of SEQ ID NO: 47), FR2 (AA 55-69 of SEQ ID NO: 47), CDR2 (AA 70-76 of SEQ ID NO: 47), FR3 (AA 77-108 of SEQ ID NO: 47), CDR3 (AA 109-117 of SEQ ID NO: 47), FR4 (AA 118-128 of SEQ ID NO: 47), and the constant (C)-region of the human kappa light chain (AA 129-234 of SEQ ID NO: 47). The C-region of human lambda light chains is substituted for the C-region of the kappa light chain.

Other domains of the HC or LC of the IgG-EPO fusion protein could also be substituted. Any number of signal peptide sequences could be substituted for either the HC signal peptide (AA 1-19 of SEQ ID NO: 49), or the LC signal peptide (AA 1-20 of SEQ ID NO: 47). The linker domain between the carboxyl terminus of the HC and the mature EPO could also be substituted. The length of this linker could vary from 0, 1, 2, 3, 4, 5, 6, 7, 8, 9, 10, 11, 12, 13, 14, 15, 16, 17, 18, 19, 20, or more than 20 AA. The AA composition of this linker could also be varied, as rules for varying the composition of fusion protein linker peptide sequences are well known.

EPO variants could also be substituted for the 166 AA EPO sequence in the IgG-EPO fusion protein (AA 466-631 of SEQ ID NO:49). EPO variants may differ in the glycosylation pattern depending on the cell line used for expression of the recombinant protein. For example EPO-alpha, -beta, and -delta, or -omega, may be produced from different host cells. Or the AA sequence of the EPO moiety could be altered. For example, the carboxyl terminal arginine (AA 631 of SEQ ID NO:49) is known to be cleaved from the EPO following translation. Alternatively, portions of either the carboxyl or amino termini of the EPO protein could be deleted. Other well known variants of EPO include examples of glyco-engineering, wherein the AA sequence of EPO is mutated so as to introduce a new N-linked glycosylation site, such as Asn-Xxx-Ser/Thr. Darboepoietin-alpha was produced by SDM to yield 2 additional N-linked glycosylation sites or a total of 5 N-linked glycosylation sites on the EPO molecule. In addition to the N-linked Asn (N) residues at AA 24, 38, and 83 of EPO (SEQ ID NO:49), new N-linked sites were produced at Asn-30 and Asn-88 of Darboepoietin-alpha. Such hyper-glycosylation would produce an EPO that was differentially removed from the blood as compared to the less glycosylated EPO. Alternatively, the N-linked or O-linked glycosylation sites present in the EPO sequence (SEQ ID NO: 48) could be removed by site-directed mutagenesis (SDM), so as to reduce the EPO glycosylation. For example, the AA sequences, Asn-Ile-Thr, Asn-Ile-Thr, and Asn-Ser-Ser at AA 24-26, 38-40, and 83-85, respectively, of SEQ ID NO:48 could be altered by SDM so as to remove these consensus N-linked glycosylation sites from the EPO sequence, which would result in a EPO variant of reduced glycosylation. Similarly, the Ser at position 126 of the EPO AA sequence (SEQ ID NO: 48) could be altered by SDM so as to decrease the O-linked glycosylation of the EPO moiety of the fusion protein. Alternatively, the EPO structure of the IgG-EPO fusion protein could be modified following purification of the expressed protein. Treatment of the fusion protein with neuraminidase would produce the asialoglycoprotein form of the IgG-EPO fusion protein. Or, the EPO part of the IgG-EPO fusion protein could be modified with site-specific chemical reagents that attack particular amino acids or carbohydrate groups, and these are well known in the literature. Alternatively, polymeric compounds such as polyethyleneglycol could be attached to amino acids or carbohydrate on the fusion protein.

Example 23

Treatment of Parkinson's Disease with the HIRMAb-EPO Fusion Protein (Prophetic Example)

This example illustrates the use of the IgG-EPO fusion protein as a therapeutic for Parkinson's Disease (PD). Administering an IgG-EPO fusion protein to a subject in order to traverse the BBB has two unique advantages. First, the EPO can be given by a non-invasive systemic injection, such as an intravenous, subcutaneous, or intra-muscular injection, and no neurosurgical procedure is required. Second, the EPO enters the brain via the trans-vascular route. Since every neuron in the brain is perfused by its own blood vessel, the EPO is delivered to every cell comprising the nigra-striatal tract of brain.

Trans-BBB transport of EPO is possible following the re-engineering of EPO as a fusion protein with a BBB molecular Trojan horse (FIG. 28). The IgG-EPO fusion protein is administered intravenouslyon a weekly or bi-weekly basis to patients with PD at doses ranging from 0.1, 0.3, 1.0, 3.0, 10.0, or 30.0 ug/kg. As discussed in Example 21, a dose of 1 ug/kg is expected to generate a brain concentration of the HIRMAb-EPO fusion protein of 1 ng/gram brain. Since EPO comprises 20% of the AA content of the fusion protein, a brain concentration of 1 ng/gram of fusion protein is equivalent to a brain EPO concentration of 0.2 ng/gram. A dose of 3 ug/kg fusion protein is expected to produce a concentration in brain of fusion protein equivalent to a brain EPO concentration of 0.6 ng/gram. Thus, the 1 ug/kg and 3 ug/kg doses produce EPO concentrations in brain that border a therapeutic concentration of EPO. Higher elevations in brain EPO would be possible by further increases in the dose of fusion protein to 10, 30, or 100 ug/kg. The higher doses of fusion protein could have side effects related to stimulation of peripheral hematopoiesis by the EPO domain of the fusion protein. However, as discussed in Example 21, the fast rate of clearance of the IgG-EPO fusion protein from blood, relative to EPO clearance from blood, is expected to blunt the effect of fusion protein administration on hematopoiesis Over time, it is expected that this method would confer a therapeutic benefit to a patient with PD.

Example 24

Treatment of Parkinson's Disease with an HIRMAb-EPO-Alpha Fusion Protein (Prophetic Example)

This example illustrates the use of a HIRMAb-EPO-alpha fusion protein to treat a subject with Parkinson's Disease (PD). As an initial step, a fusion protein is engineered comprising erythropoietin alpha (EPO-alpha) fused at its amino terminal to HIRMab following the general methods described herein, except the sequence of mature EPO would be substituted with the sequence for mature EPO-alpha. The IgG-EPO-alpha fusion protein is administered intravenously on a weekly or bi-weekly basis to patients with PD at doses ranging from 0.1, 0.3, 1.0, 3.0, 10.0, or 30.0 ug/kg. As discussed in Example 21, a dose of 1 ug/kg is expected to generate a brain concentration of the HIRMAb-EPO-alpha fusion protein of 1 ng/gram brain. Since EPO-alpha comprises approximately 20% of the AA content of the fusion protein, a brain concentration of 1 ng/gram of fusion protein is equivalent to a brain EPO concentration of 0.2 ng/gram. A dose of 3 ug/kg fusion protein is expected to produce a concentration in brain of fusion protein equivalent to a brain EPO concentration of 0.6 ng/gram. Thus, the 1 ug/kg and 3 ug/kg doses produce EPO concentrations in brain that border a therapeutic concentration of EPO. Higher elevations in brain EPO would be possible by further increases in the dose of fusion protein to 10, 30, or 100 ug/kg. The higher doses of fusion protein could have side effects related to stimulation of peripheral hematopoiesis by the EPO domain of the fusion protein. However, as discussed in Example 21, the fast rate of clearance of the IgG-EPO fusion protein from blood, relative to EPO clearance from blood, is expected to blunt the effect of fusion protein administration on hematopoiesis This approach is expected to produce a therapeutic benefit to a patient with PD.

Example 25

Acute Treatment of Brain Ischemia with the HIRMAb-EPO Fusion Protein (Prophetic Example)

This example illustrates the treatment of brain ischemia with a HIRMAb-EPO fusion protein. Acute ischemia of the brain may be either regional, such as a stroke, or global, such as a cardiac arrest. In the past, studies have demonstrated that intra-cerebral injection of the EPO protein into the brain of rats with global ischemia can protect neurons from the ischemia (Catania M A, Marciano M C, Parisi A, Sturiale A, Buemi M, Grasso G. Erythropoietin prevents cognition impairment induced by transient brain ischemia in gerbils. Eur J Pharmacol. 2002; 437:147-150). In the Catania et al study, the EPO was administered by direct injection into the brain, owing to a presumed limitation of EPO transport across the BBB. Studies have also shown that peripheral administration of EPO was neuroprotective for regional ischemia and stroke. (Brines, M. L., et al., Erythropoetin crosses the blood-brain barrier to protect against experimental brain injury, *Proc Natl Acad Sci USA* (2000) 97:10526-10531). However, premature disruption of the BBB was not excluded. It is well known that the BBB in human stroke is not disrupted until at least 12 hours after stroke (Latour, L. L., Kang, D. W., Ezzeddine, M. A., Chalela, J. A. and Warach, S., Early blood-brain barrier disruption in human focal brain ischemia. *Ann Neurol*, (2004) 56: 468-477), whereas neuroprotection in human stroke is possible only during the first 5 hours after stroke (Zivin, J. A., Factors determining the therapeutic window for stroke, *Neurology* (1998) 50: 599-603). Accordingly, if recombinant human EPO is to be developed as a new therapeutic for cerebral ischemia, the neurotrophin must be re-engineered, so that the molecule can cross the BBB.

Trans-BBB transport of EPO is possible following the re-engineering of EPO as a fusion protein with a BBB molecular Trojan horse (FIG. 1). The IgG-EPO fusion protein is given acutely as soon after the ischemic attack as possible at doses ranging from 0.1, 0.3, 1.0, 3.0, 10.0, or 30.0 ug/kg. As discussed in Example 21, a dose of 1 ug/kg is expected to generate a brain concentration of the HIRMAb-EPO fusion protein of 1 ng/gram brain. Since EPO comprises 20% of the AA content of the fusion protein, a brain concentration of 1 ng/gram of fusion protein would be equivalent to a brain EPO concentration of 0.2 ng/gram. A dose of 3 ug/kg fusion protein would be expected to produce a concentration in brain of fusion protein equivalent to a brain EPO concentration of 0.6 ng/gram. Thus, the 1 ug/kg and 3 ug/kg doses produce EPO concentrations in brain that border a therapeutic concentration of EPO. Higher elevations in brain EPO would be possible by further increases in the dose of fusion protein to 10, 30, or 100 ug/kg. Since the fusion protein is administered only acutely for the treatment of stroke, there would be little concern about the risk of stimulation of hematopoiesis. This method is expected to be of therapeutic benefit to the subject.

Example 25

Treatment of Motor Neuron Disease with the HIRMAb-EPO Fusion Protein (Prophetic Example)

This example illustrates the treatment of motor neuron disease with the HIRMAb-EPO fusion protein. Motor neuron diseases such as amyotrophic lateral sclerosis (ALS) cause progressive paralysis leading to premature death. EPO is neuroprotective of spinal cord motor neurons (Iwasaki, Y, et al. 2002. Protective effect of interleukin-3 and erythropoietin on motor neuron death after neonatal axotomy. Neurol. Res., 24: 643-646).

Neurotrophins (e.g., BDNF, ciliary neurotropic factor (CNTF) with the potential to treat motor neuron disease have not been successful in the past, largely due to the lack of an efficient method of enabling the neurotrophin to access the spinal cord. However, the HIRMAb-EPO fusion proteins described herein have great potential to treat patients with ALS through systemic administration. As an initial step, a HIRMAb-EPO fusion protein would be produced. It is then administered either intravenously or subcutaneously to a subject following the dosing regimens described herein. Chronic dosing of the IgG-EPO fusion protein in motor neuron disease would be similar to dosing for Parkinson's disease discussed herein. Such method is expected to provide a therapeutic benefit to a subject with motor neuron disease.

Example 26

Treatment of Brain or Spinal Cord Injury with the HIRMAb-EPO Fusion Protein (Prophetic Example)

This example illustrates the use of the HIRMAb-EPO fusion protein to treat brain or spinal cord injuries. EPO promotes neural repair in the period following acute experimental brain injury, such as with a cryogenic brain injury, following peripheral administration when the BBB is disrupted (Grasso et al., *Brain Res.* (2007) 1182: 99-105). However, a more reliable model of traumatic brain injury (TBI) in humans is a closed head injury model, and in such models the BBB to molecules the size of EPO is not disrupted (Habgood et al., Changes in blood-brain barrier permeability to large and small molecules following traumatic brain injury in mice, *Eur. J. Neurosci.*, (2007) 25: 231-238.).

Similarly, motor neurons of the spinal cord are responsive to EPO, and EPO can promote neural repair following experimental spinal cord injury, and the intravenous administration of EPO is advocated for the acute treatment of spinal cord injury (Matis and Birbilis, Erythropoietin in spinal cord injury, *Eur. Spine J.* (2009) 18:313-323). However, the blood-spinal cord barrier (BSCB) must be disrupted in spinal cord injury in order for intravenous EPO to be neuroprotective, and the BSCB disruption in acute spinal cord injury is delayed; moreover, there is no disruption of the BSCB in regions proximal to the injury (Wetstone et al., Blood-spinal cord barrier after spinal cord injury: relation to revascularization and wound healing, *J. Neurosci. Res.* (2003) 74: 227-229).

Therefore, it is likely that for EPO to be neuroprotective in either acute traumatic brain injury, or acute spinal cord injury, the neurotrophin must be re-engineered to cross a non-disrupted BBB. In this example, the IgG-EPO fusion protein is engineered and produced according to the methods provided herein. The IgG-EPO fusion protein is then administered intravenously to a subject immediately after the subject experiences a TBI. In the early hours following TBI, the BBB may not yet be disrupted. Administration of the IgG-EPO fusion protein is expected to enable the EPO to penetrate the injured brain or spinal cord via receptor-mediated transport even when the subject still has an intact BBB. Acute dosing of the IgG-EPO fusion protein in brain or spinal cord injury would be similar to dosing for stroke discussed herein. This method is expected to provide a therapeutic benefit to a subject with TBI.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition comprising a neurotherapeutic peptide covalently linked to an antibody that is capable of crossing the blood brain barrier (BBB) on an endogenous BBB receptor, wherein the neurotherapeutic peptide is erythropoietin (EPO), an EPO biosimilar, or an antibody to the EPO receptor.

2. The composition of claim 1, wherein the endogenous BBB receptor is selected from the group consisting of the insulin receptor, transferrin receptor, leptin receptor, lipoprotein receptor, and the IGF receptor.

3. The composition of claim 2, wherein the endogenous BBB receptor is the insulin receptor.

4. The composition of claim 1, wherein the antibody is a monoclonal antibody (MAb).

5. The composition of claim 4, wherein the EPO, an EPO biosimilar, or an antibody to the EPO receptor is covalently linked at its amino terminus to the carboxy terminus of the MAb.

6. The composition of claim 5, wherein the EPO, an EPO biosimilar, or an antibody to the EPO receptor is covalently linked at its amino terminus to the carboxy terminus of the heavy chain of the MAb.

7. The composition of claim 4, wherein the MAb is a chimeric MAb.

8. The composition of claim 7, wherein the chimeric antibody contains at least 80% human sequence.

9. The composition of claim 1, wherein the EPO, an EPO biosimilar, or an antibody to the EPO receptor is covalently linked at its amino terminus to the carboxy terminus of the antibody.

10. The composition of claim 1, wherein, after peripheral administration, the EPO, an EPO biosimilar, or an antibody to the EPO receptor has a plasma area under the concentration curve (AUC) that is at least 5-fold lower than the plasma AUC of a human EPO polypeptide that is not linked to said antibody and that is capable of crossing the BBB.

11. The composition of claim 1, wherein the composition is capable of crossing the BBB in an amount that is effective in treating a neurological disorder.

12. The composition of claim 1, wherein the neurotherapeutic peptide is erythropoietin (EPO).

13. The composition of claim 1, wherein the neurotherapeutic peptide is pegylated EPO.

14. A method for ameliorating a CNS disorder in an individual comprising peripherally administering to the individual an effective amount of the composition of claim 1.

15. The method of claim 14, wherein the administering is selected from the group consisting of oral, intravenous, intramuscular, subcutaneous, intraperitoneal, rectal, transbuccal, intranasal, transdermal, and inhalation administration.

16. The method of claim 14, wherein the CNS disorder is an acute CNS disorder.

17. The method of claim 16, wherein the acute CNS disorder is selected from the group consisting of spinal cord injury, brain injury, focal brain ischemia and global brain ischemia.

18. The method of claim 14, wherein the CNS disorder is a chronic disorder.

19. The method of claim 18, wherein the chronic disorder is a chronic neurodegenerative disease.

20. The method of claim 19, wherein the chronic neurodegenerative disease is selected from the group consisting of Parkinson's disease and a motor neuron disease.

21. The method of claim 14, wherein the effective amount is about 1 ug to 10 mg.

22. A method for ameliorating a CNS disorder in an individual comprising peripherally administering to the individual an effective amount of the composition of claim 12.

* * * * *

```
                         SEQUENCE LISTING

<160> NUMBER OF SEQ ID NOS: 58

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cctgtctccg ggtaaatatt tgcgacggcc ggcaag                             36

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cttgccggcc gtcgcaaata tttacccgga gacagg                             36

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
atgctcgagg aattcccatg gatgatggct agcaagctta tg                      42

<210> SEQ ID NO 4
<211> LENGTH: 42
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 4
cataagcttg ctagccatca tccatgggaa ttcctcgagc at                          42

<210> SEQ ID NO 5
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tccggatcct cgcgagtatg cactctgacc ctgcccgtcg aggtgagctg agcgtg          56

<210> SEQ ID NO 6
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cacgctcagc tcacctcgac gggcagggtc agagtgcata ctcgcgagga tccgga          56

<210> SEQ ID NO 7
<211> LENGTH: 119
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
agtcgtacgt gcgggccctt accatggata gcaaaaagag aattggctgg cgattcataa      60
ggatagacac ttcttgtgta tgtacattga ccattaaaag gtgatcgcga ctcgagatg     119

<210> SEQ ID NO 8
<211> LENGTH: 119
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
catctcgagt cgcgatcacc ttttaatggt caatgtacat acacaagaag tgtctatcct      60
tatgaatcgc cagccaattc tcttttttgct atccatggta agggcccgca cgtacgact    119

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
atctcgcgag tatgcactct gaccctgcc                                        29

<210> SEQ ID NO 10

```
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
atctcgcgat cacctttaa tggtcaa                                          27

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
atggctagcg atatcggtac cgtatacgga tccctcgaga tg                        42

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
catctcgagg gatccgtata cggtaccgat atcgctagcc at                        42

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtgacaaaca cagacatagg atatc                                           25

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atgctcgagc taacactctc ccct                                            24

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atgaatattc caccatggaa tgcagc                                          26

<210> SEQ ID NO 16
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 16
ataggatcct cacctttaa tggtcaa                                         27

<210> SEQ ID NO 17
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aaaaggccag gaaccgaatt cagatctcgt tgctggcgtt tt                        42

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aaaacgccag caacgagatc tgaattcggt tcctggcctt tt                        42

<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
atcgaattca agcttgcggc cgcgtataca gatctatc                             38

<210> SEQ ID NO 20
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gatagatctg tatacgcggc cgcaagcttg aattcgat                             38

<210> SEQ ID NO 21
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(375)

<400> SEQUENCE: 21 ctg tct ccg ggt aaa tcg agt atg cac tct gac cct gcc cgt cga ggt      48
Leu Ser Pro Gly Lys Ser Ser Met His Ser Asp Pro Ala Arg Arg Gly
1               5                   10                  15 gag ctg agc gtg tgt gac agt att agt gag tgg gta acg gcg gca gac      96
```

```
Glu Leu Ser Val Cys Asp Ser Ile Ser Glu Trp Val Thr Ala Ala Asp
         20                  25                  30 aaa aag act gca gtg gac atg tcg ggc ggg acg gtc aca gtc ctt gaa      144
Lys Lys Thr Ala Val Asp Met Ser Gly Gly Thr Val Thr Val Leu Glu
         35                  40                  45 aag gtc cct gta tca aaa ggc caa ctg aag caa tac ttc tac gag acc      192
Lys Val Pro Val Ser Lys Gly Gln Leu Lys Gln Tyr Phe Tyr Glu Thr
 50                  55                  60 aag tgc aat ccc atg ggt tac aca aaa gaa ggc tgc agg ggc ata gac      240
Lys Cys Asn Pro Met Gly Tyr Thr Lys Glu Gly Cys Arg Gly Ile Asp
 65                  70                  75                  80 aaa agg cat tgg aac tcc cag tgc cga act acc cag tcg tac gtg cgg      288
Lys Arg His Trp Asn Ser Gln Cys Arg Thr Thr Gln Ser Tyr Val Arg
             85                  90                  95 gcc ctt acc atg gat agc aaa aag aga att ggc tgg cga ttc ata agg      336
Ala Leu Thr Met Asp Ser Lys Lys Arg Ile Gly Trp Arg Phe Ile Arg
            100                 105                 110 ata gac act tct tgt gta tgt aca ttg acc att aaa agg tga              378
Ile Asp Thr Ser Cys Val Cys Thr Leu Thr Ile Lys Arg
            115                 120                 125

<210> SEQ ID NO 22
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Leu Ser Pro Gly Lys Ser Ser Met His Ser Asp Pro Ala Arg Arg Gly
 1               5                  10                  15

Glu Leu Ser Val Cys Asp Ser Ile Ser Glu Trp Val Thr Ala Ala Asp
             20                  25                  30

Lys Lys Thr Ala Val Asp Met Ser Gly Gly Thr Val Thr Val Leu Glu
         35                  40                  45

Lys Val Pro Val Ser Lys Gly Gln Leu Lys Gln Tyr Phe Tyr Glu Thr
 50                  55                  60

Lys Cys Asn Pro Met Gly Tyr Thr Lys Glu Gly Cys Arg Gly Ile Asp
 65                  70                  75                  80

Lys Arg His Trp Asn Ser Gln Cys Arg Thr Thr Gln Ser Tyr Val Arg
             85                  90                  95

Ala Leu Thr Met Asp Ser Lys Lys Arg Ile Gly Trp Arg Phe Ile Arg
            100                 105                 110

Ile Asp Thr Ser Cys Val Cys Thr Leu Thr Ile Lys Arg
            115                 120                 125

<210> SEQ ID NO 23
<211> LENGTH: 2711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
tagtctttct cttcagtgac aaacacagac ataggatatt ccaccatgga atgcagctgg      60
gtcatgctct tcctcctgtc aggaactgca ggtgtccatt gccaggttca gctgcagcag     120
tctggacctg agctggtgaa gcctggggct tagtgaaga tatcctgcaa ggcttctggt     180
tacaccttca caaactacga tatacactgg gtgaagcaga ggcctggaca gggacttgag     240
```

```
tggattggat ggatttatcc tggagatggt agtactaagt acaatgagaa attcaagggc    300
aaggccacac tgactgcaga caaatcctcc agcacagcct acatgcacct cagcagcctg    360
acttctgaga atctgcagt ctatttctgt gcaagagagt gggcttactg gggccaaggg     420
actctggtca ctgtctctgc agctagcacc aagggcccat cggtcttccc cctggcaccc    480
tcctccaaga gcacctctgg gggcacagcg gccctgggct gcctggtcaa ggactacttc    540
cccgaaccgg tgacggtgtc gtggaactca ggcgccctga ccagcggcgt gcacaccttc    600
ccggctgtcc tacagtcctc aggactctac tccctcagca gcgtggtgac cgtgccctcc    660
agcagcttgg gcacccagac ctacatctgc aacgtgaatc acaagcccag caacaccaag    720
gtggacaaga agttggtga gaggccagca cagggaggga gggtgtctgc tggaagccag     780
gctcagcgct cctgcctgga cgcatcccgg ctatgcagcc ccagtccagg gcagcaaggc    840
aggccccgtc tgcctcttca cccggaggcc tctgcccgcc ccactcatgc tcagggagag    900
ggtcttctgg ctttttcccc aggctctggg caggcacagg ctaggtgccc ctaacccagg    960
ccctgcacac aaaggggcag gtgctgggct cagacctgcc aagagccata tccgggagga   1020
ccctgccct gacctaagcc caccccaaag gccaaactct ccactccctc agctcggaca    1080
ccttctctcc tcccagattc cagtaactcc caatcttctc tctgcagagc ccaaatcttg   1140
tgacaaaact cacacatgcc caccgtgccc aggtaagcca gcccaggcct cgccctccag   1200
ctcaaggcgg gacaggtgcc ctagagtagc ctgcatccag ggacaggccc cagccgggtg   1260
ctgacacgtc cacctccatc tcttcctcag cacctgaact cctgggggga ccgtcagtct   1320
tcctcttccc cccaaaaccc aaggacaccc tcatgatctc ccggacccct gaggtcacat   1380
gcgtggtggt ggacgtgagc cacgaagacc ctgaggtcaa gttcaactgg tacgtggacg   1440
gcgtggaggt gcataatgcc aagacaaagc cgcgggagga gcagtacaac agcacgtacc   1500
gtgtggtcag ggtcctcacc gtcctgcacc aggactggct gaatggcaag gagtacaagt   1560
gcaaggtctc caacaaagcc ctcccagccc ccatcgagaa aaccatctcc aaagccaaag   1620
gtgggacccg tggggtgcga gggccacatg gacagaggcc ggctcggccc accctctgcc   1680
ctgagagtga ccgctgtacc aacctctgtc cctacagggc agccccgaga accacaggtg   1740
tacaccctgc ccccatcccg ggatgagctg accaagaacc aggtcagcct gacctgcctg   1800
gtcaaaggct tctatcccag cgacatcgcc gtggagtggg agagcaatgg gcagccggag   1860
aacaactaca agaccacgcc tcccgtgctg gactccgacg gctccttctt cctctacagc   1920
aagctcaccg tggacaagag caggtggcag caggggaacg tcttctcatg ctccgtgatg   1980
catgaggctc tgcacaacca ctacacgcag aagagcctct ccctgtctcc gggtaaatcg   2040
agtatgcact ctgaccctgc ccgtcgaggt gagctgagcg tgtgtgacag tattagtgag   2100
tgggtaacgg cggcagacaa aaagactgca gtggacatgt cgggcgggac ggtcacagtc   2160
cttgaaaagg tccctgtatc aaaaggccaa ctgaagcaat acttctacga gaccaagtgc   2220
aatcccatgg gttacacaaa agaaggctgc aggggcatag acaaaaggca ttggaactcc   2280
cagtgccgaa ctacccagtc gtacgtgcgg gcccttacca tggatagcaa aaagagaatt   2340
ggctggcgat tcataaggat agacacttct tgtgtatgta cattgaccat taaaaggtga   2400
tcgattttgc gacggccggc aagccccgc tccccgggct ctcgcggtcg cacgaggatg    2460
cttggcacgt acccctgta catacttccc gggcgcccag catggaaata aagcacccag    2520
cgctgccctg ggccctgcg agactgtgat ggttctttcc acgggtcagg ccgagtctga   2580
ggcctgagtg gcatgaggga ggcagagcgg gtcccactgt ccccacactg gcccaggctg   2640
```

```
tgcaggtgtg cctgggccgc ctagggtggg gctcagccag gggctgccct cggcagggtg   2700
ggggatttgc c                                                        2711
```

<210> SEQ ID NO 24
<211> LENGTH: 582
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Met Glu Cys Ser Trp Val Met Leu Phe Leu Leu Ser Gly Thr Ala Gly
1               5                   10                  15

Val His Cys Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Asn Tyr Asp Ile His Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
```

```
                        340             345             350
Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
        370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys Ser Ser
    450                 455                 460

Met His Ser Asp Pro Ala Arg Arg Gly Glu Leu Ser Val Cys Asp Ser
465                 470                 475                 480

Ile Ser Glu Trp Val Thr Ala Ala Asp Lys Lys Thr Ala Val Asp Met
                485                 490                 495

Ser Gly Gly Thr Val Thr Val Leu Glu Lys Val Pro Val Ser Lys Gly
            500                 505                 510

Gln Leu Lys Gln Tyr Phe Tyr Glu Thr Lys Cys Asn Pro Met Gly Tyr
        515                 520                 525

Thr Lys Glu Gly Cys Arg Gly Ile Asp Lys Arg His Trp Asn Ser Gln
    530                 535                 540

Cys Arg Thr Thr Gln Ser Tyr Val Arg Ala Leu Thr Met Asp Ser Lys
545                 550                 555                 560

Lys Arg Ile Gly Trp Arg Phe Ile Arg Ile Asp Thr Ser Cys Val Cys
                565                 570                 575

Thr Leu Thr Ile Lys Arg
            580

<210> SEQ ID NO 25
<211> LENGTH: 582
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Glu Cys Ser Trp Val Met Leu Phe Leu Leu Ser Gly Thr Ala Gly
1               5                   10                  15

Val His Cys Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Asn Tyr Asp Ile His Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
```

```
                115                 120                 125
Thr Val Ser Ala Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
                180                 185                 190

Gly Leu Tyr Ser Leu Ser Ser Val Val Thr Val Pro Ser Ser Ser Leu
                195                 200                 205

Gly Thr Gln Thr Tyr Ile Cys Asn Val Asn His Lys Pro Ser Asn Thr
210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
                275                 280                 285

Lys Phe Asn Trp Tyr Val Asp Gly Val Glu Val His Asn Ala Lys Thr
                290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
                355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly Lys Ser Ser
                450                 455                 460

Met His Ser Asp Pro Ala Arg Arg Gly Glu Leu Ser Val Cys Asp Ser
465                 470                 475                 480

Ile Ser Glu Trp Val Thr Ala Ala Asp Lys Lys Thr Ala Val Asp Met
                485                 490                 495

Ser Gly Gly Thr Val Thr Val Leu Glu Lys Val Pro Val Ser Lys Gly
                500                 505                 510

Gln Leu Lys Gln Tyr Phe Tyr Glu Thr Lys Cys Asn Pro Met Gly Tyr
                515                 520                 525

Thr Lys Glu Gly Cys Arg Gly Ile Asp Lys Arg His Trp Asn Ser Gln
530                 535                 540
```

```
Cys Arg Thr Thr Gln Ser Tyr Val Arg Ala Leu Thr Met Asp Ser Lys
545                 550                 555                 560

Lys Arg Ile Gly Trp Arg Phe Ile Arg Ile Asp Thr Ser Cys Val Cys
            565                 570                 575

Thr Leu Thr Ile Lys Arg
            580

<210> SEQ ID NO 26
<211> LENGTH: 1757
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
attccaccat ggaatgcagc tgggtcatgc tcttcctcct gtcaggaact gcaggtgtcc      60
attgccaggt tcagctgcag cagtctggac ctgagctggt gaagcctggg gctttagtga     120
agatatcctg caaggcttct ggttacacct tcacaaacta cgatatacac tgggtgaagc     180
agaggcctgg acagggactt gagtggattg gatggattta tcctggagat ggtagtacta     240
agtacaatga gaaattcaag ggcaaggcca cactgactgc agacaaatcc tccagcacag     300
cctacatgca cctcagcagc ctgacttctg agaaatctgc agtctatttc tgtgcaagag     360
agtgggctta ctggggccaa gggactctgg tcactgtctc tgcagctagc accaagggcc     420
catcggtctt ccccctggca ccctcctcca gagcacctc tggggcaca gcggccctgg      480 gctgcctggt caaggactac ttccccgaac cggtgacggt gcgtggaac tcaggcgccc      540 tgaccagcgg cgtgcacacc ttcccggctg tcctacagtc ctcaggactc tactccctca     600
gcagcgtggt gaccgtgccc tccagcagct gggcaccca gacctacatc tgcaacgtga     660
atcacaagcc cagcaacacc aaggtggaca agaaagttga gcccaaatct tgtgacaaaa     720
ctcacacatg cccaccgtgc ccagcacctg aactcctggg gggaccgtca gtcttcctct     780
tccccccaaa acccaaggac accctcatga tctcccggac ccctgaggtc acatgcgtgg     840
tggtggacgt gagccacgaa gaccctgagg tcaagttcaa ctggtacgtg gacggcgtgg     900
aggtgcataa tgccaagaca aagccgcggg aggagcagta caacagcacg taccgtgtgg     960
tcagcgtcct caccgtcctg caccaggact ggctgaatgg caaggagtac aagtgcaagg    1020
tctccaacaa agccctccca gcccccatcg agaaaccat ctccaaagcc aaagggcagc    1080
cccgagaacc acaggtgtac accctgcccc catcccggga tgagctgacc aagaaccagg    1140
tcagcctgac ctgcctggtc aaaggcttct atcccagcga catcgccgtg gagtgggaga    1200
gcaatgggca gccggagaac aactacaaga ccacgcctcc cgtgctggac tccgacggct    1260
ccttcttcct ctacagcaag ctcaccgtgg acaagagcag gtggcagcag gggaacgtct    1320
tctcatgctc cgtgatgcat gaggctctgc acaaccacta cacgcagaag agcctctccc    1380
tgtctccggg taaatcgagt atgcactctg accctgcccg tcgaggtgag ctgagcgtgt    1440
gtgacagtat tagtgagtgg gtaacggcgg cagacaaaaa gactgcagtg gacatgtcgg    1500
gcgggacggt cacagtcctt gaaaaggtcc ctgtatcaaa aggccaactg aagcaatact    1560
tctacgagac caagtgcaat cccatggggtt acacaaaaga aggctgcagg ggcatagaca    1620
aaaggcattg gaactcccag tgccgaacta cccagtcgta cgtgcgggcc cttaccatgg    1680
atagcaaaaa gagaattggc tggcgattca taggataga cacttcttgt gtatgtacat    1740
tgaccattaa aaggtga                                                   1757
```

<210> SEQ ID NO 27
<211> LENGTH: 1749
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(1746)

<400> SEQUENCE: 27

| | | | | | | | | | | | | | | | | |
|---|---|---|---|---|---|---|---|---|---|---|---|---|---|---|---|---|
| atg | gaa | tgc | agc | tgg | gtc | atg | ctc | ttc | ctc | ctg | tca | gga | act | gca | ggt | 48 |
| Met | Glu | Cys | Ser | Trp | Val | Met | Leu | Phe | Leu | Leu | Ser | Gly | Thr | Ala | Gly | |
| 1 | | | | 5 | | | | | 10 | | | | | 15 | | |
| gtc | cat | tgc | cag | gtt | cag | ctg | cag | cag | tct | gga | cct | gag | ctg | gtg | aag | 96 |
| Val | His | Cys | Gln | Val | Gln | Leu | Gln | Gln | Ser | Gly | Pro | Glu | Leu | Val | Lys | |
| | | | 20 | | | | | 25 | | | | | 30 | | | |
| cct | ggg | gct | tta | gtg | aag | ata | tcc | tgc | aag | gct | tct | ggt | tac | acc | ttc | 144 |
| Pro | Gly | Ala | Leu | Val | Lys | Ile | Ser | Cys | Lys | Ala | Ser | Gly | Tyr | Thr | Phe | |
| | | 35 | | | | | 40 | | | | | 45 | | | | |
| aca | aac | tac | gat | ata | cac | tgg | gtg | aag | cag | agg | cct | gga | cag | gga | ctt | 192 |
| Thr | Asn | Tyr | Asp | Ile | His | Trp | Val | Lys | Gln | Arg | Pro | Gly | Gln | Gly | Leu | |
| | 50 | | | | | 55 | | | | | 60 | | | | | |
| gag | tgg | att | gga | tgg | att | tat | cct | gga | gat | ggt | agt | act | aag | tac | aat | 240 |
| Glu | Trp | Ile | Gly | Trp | Ile | Tyr | Pro | Gly | Asp | Gly | Ser | Thr | Lys | Tyr | Asn | |
| 65 | | | | | 70 | | | | | 75 | | | | | 80 | |
| gag | aaa | ttc | aag | ggc | aag | gcc | aca | ctg | act | gca | gac | aaa | tcc | tcc | agc | 288 |
| Glu | Lys | Phe | Lys | Gly | Lys | Ala | Thr | Leu | Thr | Ala | Asp | Lys | Ser | Ser | Ser | |
| | | | | 85 | | | | | 90 | | | | | 95 | | |
| aca | gcc | tac | atg | cac | ctc | agc | agc | ctg | act | tct | gag | aaa | tct | gca | gtc | 336 |
| Thr | Ala | Tyr | Met | His | Leu | Ser | Ser | Leu | Thr | Ser | Glu | Lys | Ser | Ala | Val | |
| | | | 100 | | | | | 105 | | | | | 110 | | | |
| tat | ttc | tgt | gca | aga | gag | tgg | gct | tac | tgg | ggc | caa | ggg | act | ctg | gtc | 384 |
| Tyr | Phe | Cys | Ala | Arg | Glu | Trp | Ala | Tyr | Trp | Gly | Gln | Gly | Thr | Leu | Val | |
| | | | 115 | | | | | 120 | | | | | 125 | | | |
| act | gtc | tct | gca | gct | agc | acc | aag | ggc | cca | tcg | gtc | ttc | ccc | ctg | gca | 432 |
| Thr | Val | Ser | Ala | Ala | Ser | Thr | Lys | Gly | Pro | Ser | Val | Phe | Pro | Leu | Ala | |
| | 130 | | | | | 135 | | | | | 140 | | | | | |
| ccc | tcc | tcc | aag | agc | acc | tct | ggg | ggc | aca | gcg | gcc | ctg | ggc | tgc | ctg | 480 |
| Pro | Ser | Ser | Lys | Ser | Thr | Ser | Gly | Gly | Thr | Ala | Ala | Leu | Gly | Cys | Leu | |
| 145 | | | | | 150 | | | | | 155 | | | | | 160 | |
| gtc | aag | gac | tac | ttc | ccc | gaa | ccg | gtg | acg | gtg | tcg | tgg | aac | tca | ggc | 528 |
| Val | Lys | Asp | Tyr | Phe | Pro | Glu | Pro | Val | Thr | Val | Ser | Trp | Asn | Ser | Gly | |
| | | | | 165 | | | | | 170 | | | | | 175 | | |
| gcc | ctg | acc | agc | ggc | gtg | cac | acc | ttc | ccg | gct | gtc | cta | cag | tcc | tca | 576 |
| Ala | Leu | Thr | Ser | Gly | Val | His | Thr | Phe | Pro | Ala | Val | Leu | Gln | Ser | Ser | |
| | | | 180 | | | | | 185 | | | | | 190 | | | |
| gga | ctc | tac | tcc | ctc | agc | agc | gtg | gtg | acc | gtg | ccc | tcc | agc | agc | ttg | 624 |
| Gly | Leu | Tyr | Ser | Leu | Ser | Ser | Val | Val | Thr | Val | Pro | Ser | Ser | Ser | Leu | |
| | | | 195 | | | | | 200 | | | | | 205 | | | |
| ggc | acc | cag | acc | tac | atc | tgc | aac | gtg | aat | cac | aag | ccc | agc | aac | acc | 672 |
| Gly | Thr | Gln | Thr | Tyr | Ile | Cys | Asn | Val | Asn | His | Lys | Pro | Ser | Asn | Thr | |
| | 210 | | | | | 215 | | | | | 220 | | | | | |
| aag | gtg | gac | aag | aaa | gtt | gag | ccc | aaa | tct | tgt | gac | aaa | act | cac | aca | 720 |
| Lys | Val | Asp | Lys | Lys | Val | Glu | Pro | Lys | Ser | Cys | Asp | Lys | Thr | His | Thr | |
| 225 | | | | | 230 | | | | | 235 | | | | | 240 | |
| tgc | cca | ccg | tgc | cca | gca | cct | gaa | ctc | ctg | ggg | gga | ccg | tca | gtc | ttc | 768 |
| Cys | Pro | Pro | Cys | Pro | Ala | Pro | Glu | Leu | Leu | Gly | Gly | Pro | Ser | Val | Phe | |
| | | | | 245 | | | | | 250 | | | | | 255 | | |
| ctc | ttc | ccc | cca | aaa | ccc | aag | gac | acc | ctc | atg | atc | tcc | cgg | acc | cct | 816 |
| Leu | Phe | Pro | Pro | Lys | Pro | Lys | Asp | Thr | Leu | Met | Ile | Ser | Arg | Thr | Pro | |

```
                   260                 265                 270
gag gtc aca tgc gtg gtg gtg gac gtg agc cac gaa gac cct gag gtc      864
Glu Val Thr Cys Val Val Val Asp Val Ser His Glu Asp Pro Glu Val
        275                 280                 285 aag ttc aac tgg tac gtg gac ggc gtg gag gtg cat aat gcc aag aca      912
Lys Phe Asn Trp Tyr Val Asp Gly Val Glu Val His Asn Ala Lys Thr
    290                 295                 300 aag ccg cgg gag gag cag tac aac agc acg tac cgt gtg gtc agc gtc      960
Lys Pro Arg Glu Glu Gln Tyr Asn Ser Thr Tyr Arg Val Val Ser Val
305                 310                 315                 320 ctc acc gtc ctg cac cag gac tgg ctg aat ggc aag gag tac aag tgc     1008
Leu Thr Val Leu His Gln Asp Trp Leu Asn Gly Lys Glu Tyr Lys Cys
                325                 330                 335 aag gtc tcc aac aaa gcc ctc cca gcc ccc atc gag aaa acc atc tcc     1056
Lys Val Ser Asn Lys Ala Leu Pro Ala Pro Ile Glu Lys Thr Ile Ser
            340                 345                 350 aaa gcc aaa ggg cag ccc cga gaa cca cag gtg tac acc ctg ccc cca     1104
Lys Ala Lys Gly Gln Pro Arg Glu Pro Gln Val Tyr Thr Leu Pro Pro
        355                 360                 365 tcc cgg gat gag ctg acc aag aac cag gtc agc ctg acc tgc ctg gtc     1152
Ser Arg Asp Glu Leu Thr Lys Asn Gln Val Ser Leu Thr Cys Leu Val
    370                 375                 380 aaa ggc ttc tat ccc agc gac atc gcc gtg gag tgg gag agc aat ggg     1200
Lys Gly Phe Tyr Pro Ser Asp Ile Ala Val Glu Trp Glu Ser Asn Gly
385                 390                 395                 400 cag ccg gag aac aac tac aag acc acg cct ccc gtg ctg gac tcc gac     1248
Gln Pro Glu Asn Asn Tyr Lys Thr Thr Pro Pro Val Leu Asp Ser Asp
                405                 410                 415 ggc tcc ttc ttc ctc tac agc aag ctc acc gtg gac aag agc agg tgg     1296
Gly Ser Phe Phe Leu Tyr Ser Lys Leu Thr Val Asp Lys Ser Arg Trp
            420                 425                 430 cag cag ggg aac gtc ttc tca tgc tcc gtg atg cat gag gct ctg cac     1344
Gln Gln Gly Asn Val Phe Ser Cys Ser Val Met His Glu Ala Leu His
        435                 440                 445 aac cac tac acg cag aag agc ctc tcc ctg tct ccg ggt aaa tcg agt     1392
Asn His Tyr Thr Gln Lys Ser Leu Ser Leu Ser Pro Gly Lys Ser Ser
    450                 455                 460 atg cac tct gac cct gcc cgt cga ggt gag ctg agc gtg tgt gac agt     1440
Met His Ser Asp Pro Ala Arg Arg Gly Glu Leu Ser Val Cys Asp Ser
465                 470                 475                 480 att agt gag tgg gta acg gcg gca gac aaa aag act gca gtg gac atg     1488
Ile Ser Glu Trp Val Thr Ala Ala Asp Lys Lys Thr Ala Val Asp Met
                485                 490                 495 tcg ggc ggg acg gtc aca gtc ctt gaa aag gtc cct gta tca aaa ggc     1536
Ser Gly Gly Thr Val Thr Val Leu Glu Lys Val Pro Val Ser Lys Gly
            500                 505                 510 caa ctg aag caa tac ttc tac gag acc aag tgc aat ccc atg ggt tac     1584
Gln Leu Lys Gln Tyr Phe Tyr Glu Thr Lys Cys Asn Pro Met Gly Tyr
        515                 520                 525 aca aaa gaa ggc tgc agg ggc ata gac aaa agg cat tgg aac tcc cag     1632
Thr Lys Glu Gly Cys Arg Gly Ile Asp Lys Arg His Trp Asn Ser Gln
    530                 535                 540 tgc cga act acc cag tcg tac gtg cgg gcc ctt acc atg gat agc aaa     1680
Cys Arg Thr Thr Gln Ser Tyr Val Arg Ala Leu Thr Met Asp Ser Lys
545                 550                 555                 560 aag aga att ggc tgg cga ttc ata agg ata gac act tct tgt gta tgt     1728
Lys Arg Ile Gly Trp Arg Phe Ile Arg Ile Asp Thr Ser Cys Val Cys
                565                 570                 575 aca ttg acc att aaa agg tga                                         1749
Thr Leu Thr Ile Lys Arg
```

580

<210> SEQ ID NO 28
<211> LENGTH: 582
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

Met Glu Cys Ser Trp Val Met Leu Phe Leu Leu Ser Gly Thr Ala Gly
1               5                   10                  15

Val His Cys Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Asn Tyr Asp Ile His Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro

```
                    355                 360                 365
Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys Ser Ser
    450                 455                 460

Met His Ser Asp Pro Ala Arg Arg Gly Glu Leu Ser Val Cys Asp Ser
465                 470                 475                 480

Ile Ser Glu Trp Val Thr Ala Ala Asp Lys Lys Thr Ala Val Asp Met
                485                 490                 495

Ser Gly Gly Thr Val Thr Val Leu Glu Lys Val Pro Val Ser Lys Gly
            500                 505                 510

Gln Leu Lys Gln Tyr Phe Tyr Glu Thr Lys Cys Asn Pro Met Gly Tyr
        515                 520                 525

Thr Lys Glu Gly Cys Arg Gly Ile Asp Lys Arg His Trp Asn Ser Gln
    530                 535                 540

Cys Arg Thr Thr Gln Ser Tyr Val Arg Ala Leu Thr Met Asp Ser Lys
545                 550                 555                 560

Lys Arg Ile Gly Trp Arg Phe Ile Arg Ile Asp Thr Ser Cys Val Cys
                565                 570                 575

Thr Leu Thr Ile Lys Arg
            580

<210> SEQ ID NO 29
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gatatcacca tggagacaga cacactcctg ctatggctct tgttgctcat gtttccaggt     60
accagatgtg acatccagat gacccagtct ccatcctcct tatctgcctc tctgggagaa    120
agagtcagtc tcacttgtcg ggcaagtcag gacattggtg gtaacttata ctggcttcag    180
cagggaccag atggaactat taaacgcctg atctacgcca tccagtttag attctggtgt    240
gtccccaaaa ggttcagtgg cagtaggtct gggtcagatt attctctcac catcagcagc    300
cttgagtctg aagattttgt agactattac tgtctacagt attctagttc ccgtggacg     360 ttcggtggag cgacaaagat ggaaataaaa cgaactgtgg ctgcaccatc tgtcttcatc    420
ttcccgccat ctgatgagca gttgaaatct ggaactgcct ctgttgtgtg cctgctgaat    480
aacttctatc ccagagaggc caaagtacag tggaaggtgg ataacgccct ccaatcgggt    540
aactcccagg agagtgtcac agagcaggac agcaaggaca gcacctacag cctcagcagc    600
accctgacgc tgagcaaagc agactacgag aaacacaaag tctacgcctg cgaagtcacc    660
catcagggcc tgagctcgcc cgtcacaaag agcttcaaca ggggagagtg ttag          714
```

<210> SEQ ID NO 30
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(702)

<400> SEQUENCE: 30

```
atg gag aca gac aca ctc ctg cta tgg ctc ttg ttg ctc atg ttt cca      48
Met Glu Thr Asp Thr Leu Leu Leu Trp Leu Leu Leu Leu Met Phe Pro
1               5                   10                  15 ggt acc aga tgt gac atc cag atg acc cag tct cca tcc tcc tta tct      96
Gly Thr Arg Cys Asp Ile Gln Met Thr Gln Ser Pro Ser Ser Leu Ser
            20                  25                  30 gcc tct ctg gga gaa aga gtc agt ctc act tgt cgg gca agt cag gac     144
Ala Ser Leu Gly Glu Arg Val Ser Leu Thr Cys Arg Ala Ser Gln Asp
        35                  40                  45 att ggt ggt aac tta tac tgg ctt cag cag gga cca gat gga act att     192
Ile Gly Gly Asn Leu Tyr Trp Leu Gln Gln Gly Pro Asp Gly Thr Ile
    50                  55                  60 aaa cgc ctg atc tac gcc aca tcc agt tta gat tct ggt gtc ccc aaa     240
Lys Arg Leu Ile Tyr Ala Thr Ser Ser Leu Asp Ser Gly Val Pro Lys
65                  70                  75                  80 agg ttc agt ggc agt agg tct ggg tca gat tat tct ctc acc atc agc     288
Arg Phe Ser Gly Ser Arg Ser Gly Ser Asp Tyr Ser Leu Thr Ile Ser
                85                  90                  95 agc ctt gag tct gaa gat ttt gta gac tat tac tgt cta cag tat tct     336
Ser Leu Glu Ser Glu Asp Phe Val Asp Tyr Tyr Cys Leu Gln Tyr Ser
            100                 105                 110 agt tct ccg tgg acg ttc ggt gga gcg aca aag atg gaa ata aaa cga     384
Ser Ser Pro Trp Thr Phe Gly Gly Ala Thr Lys Met Glu Ile Lys Arg
        115                 120                 125 act gtg gct gca cca tct gtc ttc atc ttc ccg cca tct gat gag cag     432
Thr Val Ala Ala Pro Ser Val Phe Ile Phe Pro Pro Ser Asp Glu Gln
    130                 135                 140 ttg aaa tct gga act gcc tct gtt gtg tgc ctg ctg aat aac ttc tat     480
Leu Lys Ser Gly Thr Ala Ser Val Val Cys Leu Leu Asn Asn Phe Tyr
145                 150                 155                 160 ccc aga gag gcc aaa gta cag tgg aag gtg gat aac gcc ctc caa tcg     528
Pro Arg Glu Ala Lys Val Gln Trp Lys Val Asp Asn Ala Leu Gln Ser
                165                 170                 175 ggt aac tcc cag gag agt gtc aca gag cag gac agc aag gac agc acc     576
Gly Asn Ser Gln Glu Ser Val Thr Glu Gln Asp Ser Lys Asp Ser Thr
            180                 185                 190 tac agc ctc agc agc acc ctg acg ctg agc aaa gca gac tac gag aaa     624
Tyr Ser Leu Ser Ser Thr Leu Thr Leu Ser Lys Ala Asp Tyr Glu Lys
        195                 200                 205 cac aaa gtc tac gcc tgc gaa gtc acc cat cag ggc ctg agc tcg ccc     672
His Lys Val Tyr Ala Cys Glu Val Thr His Gln Gly Leu Ser Ser Pro
    210                 215                 220 gtc aca aag agc ttc aac agg gga gag tgt tag                         705
Val Thr Lys Ser Phe Asn Arg Gly Glu Cys
225                 230
```

<210> SEQ ID NO 31
<211> LENGTH: 234
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

```
Met Glu Thr Asp Thr Leu Leu Leu Trp Leu Leu Leu Met Phe Pro
1               5                   10                  15

Gly Thr Arg Cys Asp Ile Gln Met Thr Gln Ser Pro Ser Ser Leu Ser
            20                  25                  30

Ala Ser Leu Gly Glu Arg Val Ser Leu Thr Cys Arg Ala Ser Gln Asp
        35                  40                  45

Ile Gly Gly Asn Leu Tyr Trp Leu Gln Gln Gly Pro Asp Gly Thr Ile
    50                  55                  60

Lys Arg Leu Ile Tyr Ala Thr Ser Ser Leu Asp Ser Gly Val Pro Lys
65                  70                  75                  80

Arg Phe Ser Gly Ser Arg Ser Gly Ser Asp Tyr Ser Leu Thr Ile Ser
                85                  90                  95

Ser Leu Glu Ser Glu Asp Phe Val Asp Tyr Tyr Cys Leu Gln Tyr Ser
            100                 105                 110

Ser Ser Pro Trp Thr Phe Gly Gly Ala Thr Lys Met Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 32
<211> LENGTH: 6505
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

| | | | | | |
|---|---|---|---|---|---|
| cgatgtacgg | gccagatata | cgcgttgaca | ttgattattg | actagttatt | aatagtaatc | 60 |
| aattacgggg | tcattagttc | atagcccata | tatggagttc | cgcgttacat | aacttacggt | 120 |
| aaatggcccg | cctggctgac | cgcccaacga | cccccgccca | ttgacgtcaa | taatgacgta | 180 |
| tgttcccata | gtaacgccaa | tagggacttt | ccattgacgt | caatgggtgg | agtatttacg | 240 |
| gtaaactgcc | cacttggcag | tacatcaagt | gtatcatatg | ccaagtacgc | cccctattga | 300 |
| cgtcaatgac | ggtaaatggc | ccgcctggca | ttatgcccag | tacatgacct | tatgggactt | 360 |
| tcctacttgg | cagtacatct | acgtattagt | catcgctatt | accatggtga | tgcggttttg | 420 |
| gcagtacatc | aatgggcgtg | gatagcggtt | tgactcacgg | ggatttccaa | gtctccaccc | 480 |
| cattgacgtc | aatgggagtt | tgttttggca | ccaaaatcaa | cgggactttc | caaaatgtcg | 540 |
| taacaactcc | gccccattga | cgcaaatggg | cggtaggcgt | gtacggtggg | aggtctatat | 600 |

```
aagcagagct ctctggctaa ctagagaacc cactgcttac tggcttatcg aaattaatac    660
gactcactat agggagaccc ttgctagcga tattccacca tggaatgcag ctgggtcatg    720
ctcttcctcc tgtcaggaac tgcaggtgtc cattgccagg ttcagctgca gcagtctgga    780
cctgagctgg tgaagcctgg ggctttagtg aagatatcct gcaaggcttc tggttacacc    840
ttcacaaact acgatataca ctgggtgaag cagaggcctg acagggact tgagtggatt    900
ggatggattt atcctggaga tggtagtact aagtacaatg agaaattcaa gggcaaggcc    960
acactgactg cagacaaatc ctccagcaca gcctacatgc acctcagcag cctgacttct   1020
gagaaatctg cagtctattt ctgtgcaaga gagtgggctt actggggcca agggactctg   1080
gtcactgtct ctgcagctag caccaagggc ccatcggtct tccccctggc accctcctcc   1140
aagagcacct ctgggggcac agcggccctg ggctgcctgg tcaaggacta cttccccgaa   1200
ccggtgacgg tgtcgtggaa ctcaggcgcc ctgaccagcg gcgtgcacac cttcccggct   1260
gtcctacagt cctcaggact ctactccctc agcagcgtgg tgaccgtgcc ctccagcagc   1320
ttgggcaccc agacctacat ctgcaacgtg aatcacaagc ccagcaacac caaggtggac   1380
aagaaagttg agcccaaatc ttgtgacaaa actcacacat gcccaccgtg cccagcacct   1440
gaactcctgg ggggaccgtc agtcttcctc ttccccccaa acccaagga caccctcatg   1500
atctcccgga cccctgaggt cacatgcgtg gtggtggacg tgagccacga agaccctgag   1560
gtcaagttca actggtacgt ggacggcgtg gaggtgcata atgccaagac aaagccgcgg   1620
gaggagcagt acaacagcac gtaccgtgtg gtcagcgtcc tcaccgtcct gcaccaggac   1680
tggctgaatg gcaaggagta caagtgcaag gtctccaaca aagccctccc agcccccatc   1740
gagaaaacca tctccaaagc caaagggcag ccccgagaac cacaggtgta caccctgccc   1800
ccatcccggg atgagctgac caagaaccag gtcagcctga cctgcctggt caaaggcttc   1860
tatcccagcg acatcgccgt ggagtgggag agcaatgggc agccggagaa caactacaag   1920
accacgcctc ccgtgctgga ctccgacggc tccttcttcc tctacagcaa gctcaccgtg   1980
gacaagagca ggtggcagca ggggaacgtc ttctcatgct ccgtgatgca tgaggctctg   2040
cacaaccact acacgcagaa gagcctctcc ctgtctccgg gtaaatcgag tatgcactct   2100
gaccctgccc gtcgaggtga gctgagcgtg tgtgacagta ttagtgagtg ggtaacggcg   2160
gcagacaaaa agactgcagt ggacatgtcg ggcgggacgg tcacagtcct tgaaaaggtc   2220
cctgtatcaa aaggccaact gaagcaatac ttctacgaga ccaagtgcaa tcccatgggt   2280
tacacaaaag aaggctgcag gggcatagac aaaaaggcatt ggaactccca gtgccgaact   2340
acccagtcgt acgtgcgggc ccttaccatg gatagcaaaa agagaattgg ctggcgattc   2400
ataaggatag acacttcttg tgtatgtaca ttgaccatta aaaggtgagg atccctcgag   2460
catgcatcta gagggcccta ttctatagtg tcacctaaat gctagagctc gctgatcagc   2520
ctcgactgtg ccttctagtt gccagccatc tgttgtttgc cctcccccg tgccttcctt   2580
gaccctggaa ggtgccactc ccactgtcct ttcctaataa aatgaggaaa ttgcatcgca   2640
ttgtctgagt aggtgtcatt ctattctggg ggtgggtg gggcaggaca gcaaggggga   2700
ggattgggaa gacaatagca ggcatgctgg ggatgcggtg gctctatgg cttctgaggc   2760
ggaaagaacc agtggcggta atacggttat ccacagaatc aggggataac gcaggaaaga   2820
acatgtgagc aaaaggccag caaaaggcca ggaaccgaat tcgatattcc atacacatac   2880
ttctgtgttc ctttgaaagc tggacttttg caggctccac cagacctctc tagatcaatt   2940
cctttgccta atttcgctta caatttacgc gcgcgttgac attgattatt gactagttat   3000
```

-continued

```
taatagtaat caattacggg gtcattagtt catagcccat atatggagtt ccgcgttaca    3060
taacttacgg taaatggccc gcctggctga ccgcccaacg accccgccc attgacgtca     3120 ataatgacgt atgttcccat agtaacgcca atagggactt tccattgacg tcaatgggtg    3180
gagtatttac ggtaaactgc ccacttggca gtacatcaag tgtatcatat gccaagtacg    3240
ccccctattg acgtcaatga cggtaaatgg cccgcctggc attatgccca gtacatgacc    3300
ttatgggact ttcctacttg gcagtacatc tacgtattag tcatcgctat taccatggtg    3360
atgcggtttt ggcagtacat caatgggcgt ggatagcggt ttgactcacg gggatttcca    3420
agtctccacc ccattgacgt caatgggagt ttgttttggc accaaaatca acgggacttt    3480
ccaaaatgtc gtaacaactc cgccccattg acgcaaatgg gcggtaggcg tgtacggtgg    3540
gaggtctata taagcagagc tctctggcta actagagaac ccactgctta ctggcttatc    3600
gaaattaata cgactcacta gggagaccc aagctggct agcgatatca ccatggagac     3660
agacacactc ctgctatggc tcttgttgct catgttttcca ggtaccagat gtgacatcca   3720
gatgacccag tctccatcct ccttatctgc ctctctggga gaaagagtca gtctcacttg    3780
tcgggcaagt caggacattg gtggtaactt atactggctt cagcagggac cagatggaac    3840
tattaaacgc ctgatctacg ccacatccag tttagattct ggtgtcccca aaaggttcag    3900
tggcagtagg tctgggtcag attattctct caccatcagc agccttgagt ctgaagattt    3960
tgtagactat tactgtctac agtattctag ttctccgtgg acgttcggtg gagcgacaaa    4020
gatgaaaata aaacgaactg tggctgcacc atctgtcttc atcttcccgc catctgatga    4080
gcagttgaaa tctggaactg cctctgttgt gtgcctgctg aataacttct atcccagaga    4140
ggccaaagta cagtggaagg tggataacgc cctccaatcg ggtaactccc aggagagtgt    4200
cacagagcag gacagcaagg acagcaccta cagcctcagc agcaccctga cgctgagcaa    4260
agcagactac gagaaacaca aagtctacgc ctgcgaagtc acccatcagg gcctgagctc    4320
gcccgtcaca aagagcttca acaggggaga gtgttagctc gagtctagag ggcccgttta    4380
aacccgctga tcagcctcga ctgtgccttc tagttgccag ccatctgttg tttgcccctc    4440
ccccgtgcct tccttgaccc tggaaggtgc cactcccact gtcctttcct aataaaatga    4500
ggaaattgca tcgcattgtc tgagtaggtg tcattctatt ctggggggtg gggtggggca    4560
ggacagcaag gggaggattg ggaagacaa tagcaggcat gctggggatg cggtgggctc     4620
tatggcttct gaggcggaaa gaaccagtgg cggtaatacg gttatccaca gaatcagggg    4680
ataacgaaat gaggacttaa cctgtggaaa tatcaagctt gcggccgcgt atcgacgctc    4740
tcccttatgc gactcctgca ttaggaagca gcccagtagt aggttgaggc cgttgagcac    4800
cgccgccgca aggaatggtg catgcaagga gatggcgccc aacagtcccc cggccacggg    4860
gcctgccacc atacccacgc cgaaacaagc gctcatgagc ccgaagtggc gagcccgatc    4920
ttccccatcg tgatgtcgg cgatataggc gccagcaacc gcacctgtgg cgccggtgat     4980
gccggccacg atgcgtccgg cgtagaggat ctctgacgga aggaaagaag tcagaaggca    5040
aaaacgagag taactccaca gtagctccaa attctttata agggtcaatg tccatgcccc    5100
aaagccaccc aaggcacagc ttggaggctt gaacagtggg acatgtacaa gagatgatta    5160
ggcagaggta aaaagttgc atggtgctgg tgcgcagacc aatttatgcc tacagcctcc     5220
taatacaaag accttttaacc taatctcctc ccccagctcc tcccagtcct aaacacaca    5280 gtctttgaag taggcctcaa ggtcggtcgt tgacattgct gggagtccaa gagtcctctt    5340
atgtaagacc ttgggcagga tctgatgggc gttcacggtg gtctccatgc aacgtgcaga    5400
```

-continued

```
ggtgaagcga agtgcacacg gaccggcaga tgagaaggca cagacgggga gaccgcgtaa      5460
agagaggtgc gccccgtggt cggctggaac ggcagacggg gaaggggacg agagagtccc      5520
aagcggcccc gcgagggtc gtccgcggga ttcagcgccg acgggacgta aacaaaggac       5580
gtcccgcgaa ggatctaaag ccagcaaaag tcccatggtc ttataaaaat gcatagcttt      5640
aggaggggag cagagaactt gaaagcatct tcctgttagt ctttcttctc gtagacttca      5700
aacttatact tgatgccttt ttcctcctgg acctcagaga ggacgcctgg gtattctggg      5760
agaagtttat atttccccaa atcaatttct gggaaaaacg tgtcactttc aaattcctgc      5820
atgatccttg tcacaaagag tctgaggtgg cctggttgat tcatggcttc ctggtaaaca      5880
gaactgcctc cgactatcca aaccatgtct actttacttg ccaattccgg ttgttcaata      5940
agtcttaagg catcatccaa acttttggca agaaaatgag ctcctcgtgg tggttctttg      6000
agttctctac tgagaactat attaattctg tcctttaaag gtcgattctt ctcaggaatg      6060
gagaaccagg ttttcctacc cataatcacc agattctgtt taccttccac tgaagaggtt      6120
gtggtcattc tttggaagta cttgaactcg ttcctgagcg gaggccaggg tcggtctccg      6180
ttcttgccaa tccccatatt ttgggacacg gcgacgatgc agttcaatgg tcgaaccatg      6240
atggcaaatt ctagaatcga taagcttttt gcaaaagcct aggcctccaa aaagcctcc      6300 tcactacttc tggaatagct cagaggccga ggcggcctcg gcctctgcat aaataaaaaa      6360
aattagtcag ccatggggcg gagaatgggc ggaactgggc ggagttaggg gcgggatggg      6420
cggagttagg ggcgggacta tggttgctga ctaattgaga tgcagatctc gagctagcac      6480
gcgtaagagc tcggtacctc cctac                                            6505
```

<210> SEQ ID NO 33
<211> LENGTH: 1749
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(1746)

<400> SEQUENCE: 33

```
atg gaa tgc agc tgg gtc atg ctc ttc ctc ctg tca gga act gca ggt        48
Met Glu Cys Ser Trp Val Met Leu Phe Leu Leu Ser Gly Thr Ala Gly
1               5                   10                  15 gtc cat tgc cag gtt cag ctg cag cag tct gga cct gag ctg gtg aag        96
Val His Cys Gln Val Gln Leu Gln Gln Ser Gly Pro Glu Leu Val Lys
            20                  25                  30 cct ggg gct tta gtg aag ata tcc tgc aag gct tct ggt tac acc ttc       144
Pro Gly Ala Leu Val Lys Ile Ser Cys Lys Ala Ser Gly Tyr Thr Phe
        35                  40                  45 aca aac tac gat ata cac tgg gtg aag cag agg cct gga cag gga ctt       192
Thr Asn Tyr Asp Ile His Trp Val Lys Gln Arg Pro Gly Gln Gly Leu
    50                  55                  60 gag tgg att gga tgg att tat cct gga gat ggt agt act aag tac aat       240
Glu Trp Ile Gly Trp Ile Tyr Pro Gly Asp Gly Ser Thr Lys Tyr Asn
65                  70                  75                  80 gag aaa ttc aag ggc aag gcc aca ctg act gca gac aaa tcc tcc agc       288
Glu Lys Phe Lys Gly Lys Ala Thr Leu Thr Ala Asp Lys Ser Ser Ser
                85                  90                  95 aca gcc tac atg cac ctc agc agc ctg act tct gag aaa tct gca gtc       336
Thr Ala Tyr Met His Leu Ser Ser Leu Thr Ser Glu Lys Ser Ala Val
            100                 105                 110
```

```
tat ttc tgt gca aga gag tgg gct tac tgg ggc caa ggg act ctg gtc      384
Tyr Phe Cys Ala Arg Glu Trp Ala Tyr Trp Gly Gln Gly Thr Leu Val
            115                 120                 125 act gtc tct gca gct agc acc aag ggc cca tcg gtc ttc ccc ctg gca      432
Thr Val Ser Ala Ala Ser Thr Lys Gly Pro Ser Val Phe Pro Leu Ala
130                 135                 140 ccc tcc tcc aag agc acc tct ggg ggc aca gcg gcc ctg ggc tgc ctg      480
Pro Ser Ser Lys Ser Thr Ser Gly Gly Thr Ala Ala Leu Gly Cys Leu
145                 150                 155                 160 gtc aag gac tac ttc ccc gaa ccg gtg acg gtg tcg tgg aac tca ggc      528
Val Lys Asp Tyr Phe Pro Glu Pro Val Thr Val Ser Trp Asn Ser Gly
                165                 170                 175 gcc ctg acc agc ggc gtg cac acc ttc ccg gct gtc cta cag tcc tca      576
Ala Leu Thr Ser Gly Val His Thr Phe Pro Ala Val Leu Gln Ser Ser
            180                 185                 190 gga ctc tac tcc ctc agc agc gtg gtg acc gtg ccc tcc agc agc ttg      624
Gly Leu Tyr Ser Leu Ser Ser Val Val Thr Val Pro Ser Ser Ser Leu
        195                 200                 205 ggc acc cag acc tac atc tgc aac gtg aat cac aag ccc agc aac acc      672
Gly Thr Gln Thr Tyr Ile Cys Asn Val Asn His Lys Pro Ser Asn Thr
    210                 215                 220 aag gtg gac aag aaa gtt gag ccc aaa tct tgt gac aaa act cac aca      720
Lys Val Asp Lys Lys Val Glu Pro Lys Ser Cys Asp Lys Thr His Thr
225                 230                 235                 240 tgc cca ccg tgc cca gca cct gaa ctc ctg ggg gga ccg tca gtc ttc      768
Cys Pro Pro Cys Pro Ala Pro Glu Leu Leu Gly Gly Pro Ser Val Phe
                245                 250                 255 ctc ttc ccc cca aaa ccc aag gac acc ctc atg atc tcc cgg acc cct      816
Leu Phe Pro Pro Lys Pro Lys Asp Thr Leu Met Ile Ser Arg Thr Pro
            260                 265                 270 gag gtc aca tgc gtg gtg gtg gac gtg agc cac gaa gac cct gag gtc      864
Glu Val Thr Cys Val Val Val Asp Val Ser His Glu Asp Pro Glu Val
        275                 280                 285 aag ttc aac tgg tac gtg gac ggc gtg gag gtg cat aat gcc aag aca      912
Lys Phe Asn Trp Tyr Val Asp Gly Val Glu Val His Asn Ala Lys Thr
    290                 295                 300 aag ccg cgg gag gag cag tac aac agc acg tac cgt gtg gtc agc gtc      960
Lys Pro Arg Glu Glu Gln Tyr Asn Ser Thr Tyr Arg Val Val Ser Val
305                 310                 315                 320 ctc acc gtc ctg cac cag gac tgg ctg aat ggc aag gag tac aag tgc     1008
Leu Thr Val Leu His Gln Asp Trp Leu Asn Gly Lys Glu Tyr Lys Cys
                325                 330                 335 aag gtc tcc aac aaa gcc ctc cca gcc ccc atc gag aaa acc atc tcc     1056
Lys Val Ser Asn Lys Ala Leu Pro Ala Pro Ile Glu Lys Thr Ile Ser
            340                 345                 350 aaa gcc aaa ggg cag ccc cga gaa cca cag gtg tac acc ctg ccc cca     1104
Lys Ala Lys Gly Gln Pro Arg Glu Pro Gln Val Tyr Thr Leu Pro Pro
        355                 360                 365 tcc cgg gat gag ctg acc aag aac cag gtc agc ctg acc tgc ctg gtc     1152
Ser Arg Asp Glu Leu Thr Lys Asn Gln Val Ser Leu Thr Cys Leu Val
    370                 375                 380 aaa ggc ttc tat ccc agc gac atc gcc gtg gag tgg gag agc aat ggg     1200
Lys Gly Phe Tyr Pro Ser Asp Ile Ala Val Glu Trp Glu Ser Asn Gly
385                 390                 395                 400 cag ccg gag aac aac tac aag acc acg cct ccc gtg ctg gac tcc gac     1248
Gln Pro Glu Asn Asn Tyr Lys Thr Thr Pro Pro Val Leu Asp Ser Asp
                405                 410                 415 ggc tcc ttc ttc ctc tac agc aag ctc acc gtg gac aag agc agg tgg     1296
Gly Ser Phe Phe Leu Tyr Ser Lys Leu Thr Val Asp Lys Ser Arg Trp
            420                 425                 430
```

```
cag cag ggg aac gtc ttc tca tgc tcc gtg atg cat gag gct ctg cac      1344
Gln Gln Gly Asn Val Phe Ser Cys Ser Val Met His Glu Ala Leu His
        435                 440                 445 aac cac tac acg cag aag agc ctc tcc ctg tct ccg ggt aaa tcg agt      1392
Asn His Tyr Thr Gln Lys Ser Leu Ser Leu Ser Pro Gly Lys Ser Ser
450                 455                 460 atg cac tct gac cct gcc cgt cga ggt gag ctg agc gtg tgt gac agt      1440
Met His Ser Asp Pro Ala Arg Arg Gly Glu Leu Ser Val Cys Asp Ser
465                 470                 475                 480 att agt gag tgg gta acg gcg gca gac aaa aag act gca gtg gac atg      1488
Ile Ser Glu Trp Val Thr Ala Ala Asp Lys Lys Thr Ala Val Asp Met
                485                 490                 495 tcg ggc ggg acg gtc aca gtc ctt gaa aag gtc cct gta tca aaa ggc      1536
Ser Gly Gly Thr Val Thr Val Leu Glu Lys Val Pro Val Ser Lys Gly
        500                 505                 510 caa ctg aag caa tac ttc tac gag acc aag tgc aat ccc atg ggt tac      1584
Gln Leu Lys Gln Tyr Phe Tyr Glu Thr Lys Cys Asn Pro Met Gly Tyr
        515                 520                 525 aca aaa gaa ggc tgc agg ggc ata gac aaa agg cat tgg aac tcc cag      1632
Thr Lys Glu Gly Cys Arg Gly Ile Asp Lys Arg His Trp Asn Ser Gln
530                 535                 540 tgc cga act acc cag tcg tac gtg cgg gcc ctt acc atg gat agc aaa      1680
Cys Arg Thr Thr Gln Ser Tyr Val Arg Ala Leu Thr Met Asp Ser Lys
545                 550                 555                 560 aag aga att ggc tgg cga ttc ata agg ata gac act tct tgt gta tgt      1728
Lys Arg Ile Gly Trp Arg Phe Ile Arg Ile Asp Thr Ser Cys Val Cys
                565                 570                 575 aca ttg acc att aaa agg tga                                          1749
Thr Leu Thr Ile Lys Arg
            580

<210> SEQ ID NO 34
<211> LENGTH: 582
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Glu Cys Ser Trp Val Met Leu Phe Leu Leu Ser Gly Thr Ala Gly
1               5                   10                  15

Val His Cys Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Asn Tyr Asp Ile His Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160
```

Val Lys Asp Tyr Phe Pro Glu Pro Val Thr Val Ser Trp Asn Ser Gly
            165                 170                 175
Ala Leu Thr Ser Gly Val His Thr Phe Pro Ala Val Leu Gln Ser Ser
            180                 185                 190
Gly Leu Tyr Ser Leu Ser Ser Val Val Thr Val Pro Ser Ser Ser Leu
            195                 200                 205
Gly Thr Gln Thr Tyr Ile Cys Asn Val Asn His Lys Pro Ser Asn Thr
            210                 215                 220
Lys Val Asp Lys Lys Val Glu Pro Lys Ser Cys Asp Lys Thr His Thr
225                 230                 235                 240
Cys Pro Pro Cys Pro Ala Pro Glu Leu Leu Gly Gly Pro Ser Val Phe
            245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser His Glu Asp Pro Glu Val
            275                 280                 285
Lys Phe Asn Trp Tyr Val Asp Gly Val Glu Val His Asn Ala Lys Thr
            290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
            325                 330                 335
Lys Val Ser Asn Lys Ala Leu Pro Ala Pro Ile Glu Lys Thr Ile Ser
            340                 345                 350
Lys Ala Lys Gly Gln Pro Arg Glu Pro Gln Val Tyr Thr Leu Pro Pro
            355                 360                 365
Ser Arg Asp Glu Leu Thr Lys Asn Gln Val Ser Leu Thr Cys Leu Val
            370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
            405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
            435                 440                 445
Asn His Tyr Thr Gln Lys Ser Leu Ser Leu Ser Pro Gly Lys Ser Ser
            450                 455                 460
Met His Ser Asp Pro Ala Arg Arg Gly Glu Leu Ser Val Cys Asp Ser
465                 470                 475                 480
Ile Ser Glu Trp Val Thr Ala Ala Asp Lys Lys Thr Ala Val Asp Met
            485                 490                 495
Ser Gly Gly Thr Val Thr Val Leu Glu Lys Val Pro Val Ser Lys Gly
            500                 505                 510
Gln Leu Lys Gln Tyr Phe Tyr Glu Thr Lys Cys Asn Pro Met Gly Tyr
            515                 520                 525
Thr Lys Glu Gly Cys Arg Gly Ile Asp Lys Arg His Trp Asn Ser Gln
            530                 535                 540
Cys Arg Thr Thr Gln Ser Tyr Val Arg Ala Leu Thr Met Asp Ser Lys
545                 550                 555                 560
Lys Arg Ile Gly Trp Arg Phe Ile Arg Ile Asp Thr Ser Cys Val Cys
            565                 570                 575
Thr Leu Thr Ile Lys Arg

<210> SEQ ID NO 35
<211> LENGTH: 705
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(702)

<400> SEQUENCE: 35

```
atg gag aca gac aca ctc ctg cta tgg ctc ttg ttg ctc atg ttt cca      48
Met Glu Thr Asp Thr Leu Leu Leu Trp Leu Leu Leu Leu Met Phe Pro
1               5                   10                  15 ggt acc aga tgt gac atc cag atg acc cag tct cca tcc tcc tta tct      96
Gly Thr Arg Cys Asp Ile Gln Met Thr Gln Ser Pro Ser Ser Leu Ser
            20                  25                  30 gcc tct ctg gga gaa aga gtc agt ctc act tgt cgg gca agt cag gac     144
Ala Ser Leu Gly Glu Arg Val Ser Leu Thr Cys Arg Ala Ser Gln Asp
        35                  40                  45 att ggt ggt aac tta tac tgg ctt cag cag gga cca gat gga act att     192
Ile Gly Gly Asn Leu Tyr Trp Leu Gln Gln Gly Pro Asp Gly Thr Ile
    50                  55                  60 aaa cgc ctg atc tac gcc aca tcc agt tta gat tct ggt gtc ccc aaa     240
Lys Arg Leu Ile Tyr Ala Thr Ser Ser Leu Asp Ser Gly Val Pro Lys
65                  70                  75                  80 agg ttc agt ggc agt agg tct ggg tca gat tat tct ctc acc atc agc     288
Arg Phe Ser Gly Ser Arg Ser Gly Ser Asp Tyr Ser Leu Thr Ile Ser
                85                  90                  95 agc ctt gag tct gaa gat ttt gta gac tat tac tgt cta cag tat tct     336
Ser Leu Glu Ser Glu Asp Phe Val Asp Tyr Tyr Cys Leu Gln Tyr Ser
            100                 105                 110 agt tct ccg tgg acg ttc ggt gga gcg aca aag atg gaa ata aaa cga     384
Ser Ser Pro Trp Thr Phe Gly Gly Ala Thr Lys Met Glu Ile Lys Arg
        115                 120                 125 act gtg gct gca cca tct gtc ttc atc ttc ccg cca tct gat gag cag     432
Thr Val Ala Ala Pro Ser Val Phe Ile Phe Pro Pro Ser Asp Glu Gln
    130                 135                 140 ttg aaa tct gga act gcc tct gtt gtg tgc ctg ctg aat aac ttc tat     480
Leu Lys Ser Gly Thr Ala Ser Val Val Cys Leu Leu Asn Asn Phe Tyr
145                 150                 155                 160 ccc aga gag gcc aaa gta cag tgg aag gtg gat aac gcc ctc caa tcg     528
Pro Arg Glu Ala Lys Val Gln Trp Lys Val Asp Asn Ala Leu Gln Ser
                165                 170                 175 ggt aac tcc cag gag agt gtc aca gag cag gac agc aag gac agc acc     576
Gly Asn Ser Gln Glu Ser Val Thr Glu Gln Asp Ser Lys Asp Ser Thr
            180                 185                 190 tac agc ctc agc agc acc ctg acg ctg agc aaa gca gac tac gag aaa     624
Tyr Ser Leu Ser Ser Thr Leu Thr Leu Ser Lys Ala Asp Tyr Glu Lys
        195                 200                 205 cac aaa gtc tac gcc tgc gaa gtc acc cat cag ggc ctg agc tcg ccc     672
His Lys Val Tyr Ala Cys Glu Val Thr His Gln Gly Leu Ser Ser Pro
    210                 215                 220 gtc aca aag agc ttc aac agg gga gag tgt tag                         705
Val Thr Lys Ser Phe Asn Arg Gly Glu Cys
225                 230
```

<210> SEQ ID NO 36
<211> LENGTH: 234
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 36

```
Met Glu Thr Asp Thr Leu Leu Leu Trp Leu Leu Leu Met Phe Pro
1               5                   10                  15

Gly Thr Arg Cys Asp Ile Gln Met Thr Gln Ser Pro Ser Ser Leu Ser
            20                  25                  30

Ala Ser Leu Gly Glu Arg Val Ser Leu Thr Cys Arg Ala Ser Gln Asp
        35                  40                  45

Ile Gly Gly Asn Leu Tyr Trp Leu Gln Gln Gly Pro Asp Gly Thr Ile
    50                  55                  60

Lys Arg Leu Ile Tyr Ala Thr Ser Ser Leu Asp Ser Gly Val Pro Lys
65                  70                  75                  80

Arg Phe Ser Gly Ser Arg Ser Gly Ser Asp Tyr Ser Leu Thr Ile Ser
                85                  90                  95

Ser Leu Glu Ser Glu Asp Phe Val Asp Tyr Tyr Cys Leu Gln Tyr Ser
            100                 105                 110

Ser Ser Pro Trp Thr Phe Gly Gly Ala Thr Lys Met Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 37
<211> LENGTH: 564
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(561)

<400> SEQUENCE: 37

```
atg gtt cga cca ttg aac tgc atc gtc gcc gtg tcc caa aat atg ggg      48
Met Val Arg Pro Leu Asn Cys Ile Val Ala Val Ser Gln Asn Met Gly
1               5                   10                  15 att ggc aag aac gga gac cga ccc tgg cct ccg ctc agg aac gag ttc      96
Ile Gly Lys Asn Gly Asp Arg Pro Trp Pro Pro Leu Arg Asn Glu Phe
            20                  25                  30 aag tac ttc caa aga atg acc aca acc tct tca gtg gaa ggt aaa cag     144
Lys Tyr Phe Gln Arg Met Thr Thr Thr Ser Ser Val Glu Gly Lys Gln
        35                  40                  45 aat ctg gtg att atg ggt agg aaa acc tgg ttc tcc att cct gag aag     192
Asn Leu Val Ile Met Gly Arg Lys Thr Trp Phe Ser Ile Pro Glu Lys
```

```
aat cga cct tta aag gac aga att aat ata gtt ctc agt aga gaa ctc    240
Asn Arg Pro Leu Lys Asp Arg Ile Asn Ile Val Leu Ser Arg Glu Leu
 65                  70                  75                  80 aaa gaa cca cca cga gga gct cat ttt ctt gcc aaa agt ttg gat gat    288
Lys Glu Pro Pro Arg Gly Ala His Phe Leu Ala Lys Ser Leu Asp Asp
                 85                  90                  95 gcc tta aga ctt att gaa caa ccg gaa ttg gca agt aaa gta gac atg    336
Ala Leu Arg Leu Ile Glu Gln Pro Glu Leu Ala Ser Lys Val Asp Met
            100                 105                 110 gtt tgg ata gtc gga ggc agt tct gtt tac cag gaa gcc atg aat caa    384
Val Trp Ile Val Gly Gly Ser Ser Val Tyr Gln Glu Ala Met Asn Gln
        115                 120                 125 cca ggc cac ctc aga ctc ttt gtg aca agg atc atg cag gaa ttt gaa    432
Pro Gly His Leu Arg Leu Phe Val Thr Arg Ile Met Gln Glu Phe Glu
    130                 135                 140 agt gac acg ttt ttc cca gaa att gat ttg ggg aaa tat aaa ctt ctc    480
Ser Asp Thr Phe Phe Pro Glu Ile Asp Leu Gly Lys Tyr Lys Leu Leu
145                 150                 155                 160 cca gaa tac cca ggc gtc ctc tct gag gtc cag gag gaa aaa ggc atc    528
Pro Glu Tyr Pro Gly Val Leu Ser Glu Val Gln Glu Glu Lys Gly Ile
                165                 170                 175 aag tat aag ttt gaa gtc tac gag aag aaa gac taa                    564
Lys Tyr Lys Phe Glu Val Tyr Glu Lys Lys Asp
                180                 185

<210> SEQ ID NO 38
<211> LENGTH: 187
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Val Arg Pro Leu Asn Cys Ile Val Ala Val Ser Gln Asn Met Gly
1               5                   10                  15

Ile Gly Lys Asn Gly Asp Arg Pro Trp Pro Pro Leu Arg Asn Glu Phe
            20                  25                  30

Lys Tyr Phe Gln Arg Met Thr Thr Thr Ser Ser Val Glu Gly Lys Gln
        35                  40                  45

Asn Leu Val Ile Met Gly Arg Lys Thr Trp Phe Ser Ile Pro Glu Lys
 50                  55                  60

Asn Arg Pro Leu Lys Asp Arg Ile Asn Ile Val Leu Ser Arg Glu Leu
 65                  70                  75                  80

Lys Glu Pro Pro Arg Gly Ala His Phe Leu Ala Lys Ser Leu Asp Asp
                 85                  90                  95

Ala Leu Arg Leu Ile Glu Gln Pro Glu Leu Ala Ser Lys Val Asp Met
            100                 105                 110

Val Trp Ile Val Gly Gly Ser Ser Val Tyr Gln Glu Ala Met Asn Gln
        115                 120                 125

Pro Gly His Leu Arg Leu Phe Val Thr Arg Ile Met Gln Glu Phe Glu
    130                 135                 140

Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Glu Lys Gly Ile
                165                 170                 175

Lys Tyr Lys Phe Glu Val Tyr Glu Lys Lys Asp
                180                 185
```

```
<210> SEQ ID NO 39

<400> SEQUENCE: 39

000

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Tyr Thr Phe Thr Asn Tyr Asp Ile His
1               5                   10

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Trp Ile Tyr Pro Gly Asp Gly Ser Thr Lys Tyr Asn Glu Lys Phe Lys
1               5                   10                  15

Gly

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Glu Trp Ala Tyr
1

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Ala Ser Gln Asp Ile Gly Gly Asn Leu Tyr
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ala Thr Ser Ser Leu Asp Ser
1               5
```

```
<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Leu Gln Tyr Ser Ser Ser Pro Trp Thr
1               5

<210> SEQ ID NO 46
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Asp Trp Thr Trp Arg Val Phe Cys Leu Leu Ala Val Ala Pro Gly
1               5                   10                  15

Ala His Ser Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Asn Tyr Asp Ile His Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
```

-continued

```
                290                 295                 300
Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
                355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly Lys
                450                 455                 460

<210> SEQ ID NO 47
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Glu Thr Pro Ala Gln Leu Leu Phe Leu Leu Leu Leu Trp Leu Pro
1               5                   10                  15

Asp Thr Thr Gly Asp Ile Gln Met Thr Gln Ser Pro Ser Ser Leu Ser
                20                  25                  30

Ala Ser Leu Gly Glu Arg Val Ser Leu Thr Cys Arg Ala Ser Gln Asp
                35                  40                  45

Ile Gly Gly Asn Leu Tyr Trp Leu Gln Gln Gly Pro Asp Gly Thr Ile
            50                  55                  60

Lys Arg Leu Ile Tyr Ala Thr Ser Ser Leu Asp Ser Gly Val Pro Lys
65                  70                  75                  80

Arg Phe Ser Gly Ser Arg Ser Gly Ser Asp Tyr Ser Leu Thr Ile Ser
                85                  90                  95

Ser Leu Glu Ser Glu Asp Phe Val Asp Tyr Tyr Cys Leu Gln Tyr Ser
                100                 105                 110

Ser Ser Pro Trp Thr Phe Gly Gly Gly Thr Lys Met Glu Ile Lys Arg
                115                 120                 125

Thr Val Ala Ala Pro Ser Val Phe Ile Phe Pro Pro Ser Asp Glu Gln
                130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
```

```
                195                 200                 205
His Lys Val Tyr Ala Cys Glu Val Thr His Gln Gly Leu Ser Ser Pro
        210                 215                 220

Val Thr Lys Ser Phe Asn Arg Gly Glu Cys
225                 230

<210> SEQ ID NO 48
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 49
<211> LENGTH: 631
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Asp Trp Thr Trp Arg Val Phe Cys Leu Leu Ala Val Ala Pro Gly
1               5                   10                  15

Ala His Ser Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Asn Tyr Asp Ile His Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95
```

```
Thr Ala Tyr Met His Leu Ser Ser Leu Thr Ser Glu Lys Ser Ala Val
            100                 105                 110
Tyr Phe Cys Ala Arg Glu Trp Ala Tyr Trp Gly Gln Gly Thr Leu Val
            115                 120                 125
Thr Val Ser Ala Ala Ser Thr Lys Gly Pro Ser Val Phe Pro Leu Ala
130                 135                 140
Pro Ser Ser Lys Ser Thr Ser Gly Gly Thr Ala Ala Leu Gly Cys Leu
145                 150                 155                 160
Val Lys Asp Tyr Phe Pro Glu Pro Val Thr Val Ser Trp Asn Ser Gly
            165                 170                 175
Ala Leu Thr Ser Gly Val His Thr Phe Pro Ala Val Leu Gln Ser Ser
            180                 185                 190
Gly Leu Tyr Ser Leu Ser Ser Val Val Thr Val Pro Ser Ser Ser Leu
            195                 200                 205
Gly Thr Gln Thr Tyr Ile Cys Asn Val Asn His Lys Pro Ser Asn Thr
            210                 215                 220
Lys Val Asp Lys Lys Val Glu Pro Lys Ser Cys Asp Lys Thr His Thr
225                 230                 235                 240
Cys Pro Pro Cys Pro Ala Pro Glu Leu Leu Gly Gly Pro Ser Val Phe
            245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser His Glu Asp Pro Glu Val
            275                 280                 285
Lys Phe Asn Trp Tyr Val Asp Gly Val Glu Val His Asn Ala Lys Thr
            290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
            325                 330                 335
Lys Val Ser Asn Lys Ala Leu Pro Ala Pro Ile Glu Lys Thr Ile Ser
            340                 345                 350
Lys Ala Lys Gly Gln Pro Arg Glu Pro Gln Val Tyr Thr Leu Pro Pro
            355                 360                 365
Ser Arg Asp Glu Leu Thr Lys Asn Gln Val Ser Leu Thr Cys Leu Val
            370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
            405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
            435                 440                 445
Asn His Tyr Thr Gln Lys Ser Leu Ser Leu Ser Pro Gly Ser Ser Ser
            450                 455                 460
Ser Ala Pro Pro Arg Leu Ile Cys Asp Ser Arg Val Leu Glu Arg Tyr
465                 470                 475                 480
Leu Leu Glu Ala Lys Glu Ala Glu Asn Ile Thr Thr Gly Cys Ala Glu
            485                 490                 495
His Cys Ser Leu Asn Glu Asn Ile Thr Val Pro Asp Thr Lys Val Asn
            500                 505                 510
Phe Tyr Ala Trp Lys Arg Met Glu Val Gly Gln Gln Ala Val Glu Val
```

```
                515                 520                 525
Trp Gln Gly Leu Ala Leu Leu Ser Glu Ala Val Leu Arg Gly Gln Ala
    530                 535                 540

Leu Leu Val Asn Ser Ser Gln Pro Trp Glu Pro Leu Gln Leu His Val
545                 550                 555                 560

Asp Lys Ala Val Ser Gly Leu Arg Ser Leu Thr Thr Leu Leu Arg Ala
                565                 570                 575

Leu Gly Ala Gln Lys Glu Ala Ile Ser Pro Pro Asp Ala Ala Ser Ala
            580                 585                 590

Ala Pro Leu Arg Thr Ile Thr Ala Asp Thr Phe Arg Lys Leu Phe Arg
            595                 600                 605

Val Tyr Ser Asn Phe Leu Arg Gly Lys Leu Lys Leu Tyr Thr Gly Glu
        610                 615                 620

Ala Cys Arg Thr Gly Asp Arg
625                 630

<210> SEQ ID NO 50
<211> LENGTH: 515
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
aggcctcagc cccaccacgc ctcatctgtg acagccgagt cctggagagg tacctcttgg      60
aggccaagga ggccgagaat atcacgacgg gctgtgctga acactgcagc ttgaatgaga     120
atatcactgt cccagacacc aaagttaatt tctatgcctg aagaggatg gaggtcgggc      180 agcaggccgt agaagtctgg cagggcctgg ccctgctgtc ggaagctgtc ctgcggggcc     240
aggccctgtt ggtcaactct tcccagccgt gggagcccct gcagctgcat gtggataaag     300
ccgtcagtgg ccttcgcagc ctcaccactc tgcttcgggc tctgggagcc agaaggaag     360 ccatctcccc tccagatgcg gcctcagctg ctccactccg aacaatcact gctgacactt     420
tccgcaaact cttccgagtc tactccaatt tcctccgggg aaagctgaag ctgtacacag     480
gggaagcctg caggacaggg gacagatgaa ggcct                               515

<210> SEQ ID NO 51
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
atggagaccc ccgcccagct gctgttcctg ttgctgcttt ggcttccaga tactaccggc      60
gacatccaga tgacccagtc tccatcctcc ttatctgcct ctctgggaga aagagtcagt     120
ctcacttgtc gggcaagtca ggacattggt ggtaacttat actggcttca gcagggacca     180
gatggaacta ttaaacgcct gatctacgcc acatccagtt tagattctgg tgtccccaaa     240
aggttcagtg gcagtaggtc tgggtcagat tattctctca ccatcagcag ccttgagtct     300
gaagattttg tagactatta ctgtctacag tattctagtt ctccgtggac gttcggtgga     360
ggcacaaagc tggaaataaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
```

```
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gttag                   705
```

<210> SEQ ID NO 52
<211> LENGTH: 1896
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

```
atggactgga cctggagggt gttctgcctg cttgcagtgg cccccggagc ccacagccag    60
gttcagctgc agcagtctgg acctgagctg gtgaagcctg ggctttagt gaagatatcc    120 tgcaaggctt ctggttacac cttcacaaac tacgatatac actgggtgaa gcagaggcct    180
ggacagggac ttgagtggat tggatggatt tatcctggag atggtagtac taagtacaat    240
gagaaattca gggcaaggc cacactgact gcagacaaat cctccagcac agcctacatg    300
cacctcagca gcctgacttc tgagaaatct gcagtctatt tctgtgcaag agagtgggct    360
tactggggcc aagggactct ggtcactgtc tctgcagcta gcaccaaggg cccatcggtc    420
ttccccctgg caccctcctc caagagcacc tctgggggca gcggccct gggctgcctg    480 gtcaaggact acttccccga accggtgacg gtgtcgtgga actcaggcgc cctgaccagc    540
ggcgtgcaca ccttcccggc tgtcctacag tcctcaggac tctactccct cagcagcgtg    600
gtgaccgtgc cctccagcag cttgggcacc cagacctaca tctgcaacgt gaatcacaag    660
cccagcaaca ccaaggtgga caagaaagtt gagcccaaat cttgtgacaa aactcacaca    720
tgcccaccgt gcccagcacc tgaactcctg ggggaccgt cagtcttcct cttccccca    780 aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagccgcg ggaggagcag tacaacagca cgtaccgtgt ggtcagcgtc    960
ctcaccgtcc tgcaccagga ctggctgaat ggcaaggagt acaagtgcaa ggtctccaac    1020
aaagccctcc cagcccccat cgagaaaacc atctccaaag ccaagggca gccccgagaa    1080 ccacaggtgt acaccctgcc cccatcccgg gatgagctga ccaagaacca ggtcagcctg    1140
acctgcctgg tcaaaggctt ctatcccagc gacatcgccg tggagtggga gagcaatggg    1200
cagccggaga caactacaa gaccacgcct cccgtgctgg actccgacgg ctccttcttc    1260
ctctacagca agctcaccgt ggacaagagc aggtggcagc aggggaacgt cttctcatgc    1320
tccgtgatgc atgaggctct gcacaaccac tacacgcaga agagcctctc cctgtctcct    1380
ggtagtagtt cctcagcccc accacgcctc atctgtgaca gccgagtcct ggagaggtac    1440
ctcttggagg ccaaggaggc cgagaatatc acgacgggct gtgctgaaca ctgcagcttg    1500
aatgagaata tcactgtccc agacaccaaa gttaatttct atgcctggaa gaggatggag    1560
gtcgggcagc aggccgtaga agtctggcag ggcctggccc tgctgtcgga agctgtcctg    1620
cggggccagg ccctgttggt caactcttcc agccgtggg agcccctgca gctgcatgtg    1680
gataaagccg tcagtggcct tcgcagcctc accactctgc ttcgggctct gggagcccag    1740
aaggaagcca tctcccctcc agatgcggcc tcagctgctc cactccgaac aatcactgct    1800
gacactttcc gcaaactctt ccgagtctac tccaatttct tccggggaaa gctgaagctg    1860
```

```
tacacagggg aagcctgcag gacagggac agatga                                      1896
```

<210> SEQ ID NO 53
<211> LENGTH: 564
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 53

```
atggttcgac cattgaactg catcgtcgcc gtgtcccaaa atatggggat tggcaagaac      60
ggagaccctac cctggcctcc gctcaggaac gagttcaagt acttccaaag aatgaccaca     120
acctcttcag tggaaggtaa acagaatctg gtgattatgg gtaggaaaac ctggttctcc     180
attcctgaga gaatcgacc tttaaaggac agaattaata tagttctcag tagaaactc       240
aaagaaccac cacgaggagc tcattttctt gccaaaagtt tggatgatgc cttaagactt     300
attgaacaac cggaattggc aagtaaagta gacatggttt ggatagtcgg aggcagttct     360
gtttaccagg aagccatgaa tcaaccaggc cacctcagac tctttgtgac aaggatcatg     420
caggaatttg aaagtgacac gttttttccca gaaattgatt tggggaaata taaacttctc     480
ccagaatacc caggcgtcct ctctgaggtc caggaggaaa aaggcatcaa gtataagttt     540
gaagtctacg agaagaaaga ctaa                                             564
```

<210> SEQ ID NO 54
<211> LENGTH: 234
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 54

```
Met Glu Thr Pro Ala Gln Leu Leu Phe Leu Leu Leu Leu Trp Leu Pro
1               5                   10                  15

Asp Thr Thr Gly Asp Ile Gln Met Thr Gln Ser Pro Ser Ser Leu Ser
            20                  25                  30

Ala Ser Leu Gly Glu Arg Val Ser Leu Thr Cys Arg Ala Ser Gln Asp
        35                  40                  45

Ile Gly Gly Asn Leu Tyr Trp Leu Gln Gln Gly Pro Asp Gly Thr Ile
    50                  55                  60

Lys Arg Leu Ile Tyr Ala Thr Ser Ser Leu Asp Ser Gly Val Pro Lys
65                  70                  75                  80

Arg Phe Ser Gly Ser Arg Ser Gly Ser Asp Tyr Ser Leu Thr Ile Ser
                85                  90                  95

Ser Leu Glu Ser Glu Asp Phe Val Asp Tyr Tyr Cys Leu Gln Tyr Ser
            100                 105                 110

Ser Ser Pro Trp Thr Phe Gly Gly Gly Thr Lys Met Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190
```

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 55
<211> LENGTH: 187
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Val Arg Pro Leu Asn Cys Ile Val Ala Val Ser Gln Asn Met Gly
1               5                   10                  15

Ile Gly Lys Asn Gly Asp Leu Pro Trp Pro Leu Arg Asn Glu Phe
            20                  25                  30

Lys Tyr Phe Gln Arg Met Thr Thr Thr Ser Ser Val Glu Gly Lys Gln
        35                  40                  45

Asn Leu Val Ile Met Gly Arg Lys Thr Trp Phe Ser Ile Pro Glu Lys
50                  55                  60

Asn Arg Pro Leu Lys Asp Arg Ile Asn Ile Val Leu Ser Arg Glu Leu
65                  70                  75                  80

Lys Glu Pro Pro Arg Gly Ala His Phe Leu Ala Lys Ser Leu Asp Asp
                85                  90                  95

Ala Leu Arg Leu Ile Glu Gln Pro Glu Leu Ala Ser Lys Val Asp Met
            100                 105                 110

Val Trp Ile Val Gly Gly Ser Ser Val Tyr Gln Glu Ala Met Asn Gln
        115                 120                 125

Pro Gly His Leu Arg Leu Phe Val Thr Arg Ile Met Gln Glu Phe Glu
    130                 135                 140

Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Glu Lys Gly Ile
                165                 170                 175

Lys Tyr Lys Phe Glu Val Tyr Glu Lys Lys Asp
            180                 185

<210> SEQ ID NO 56
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
50                  55                  60

Asn Ile Thr Val Pro Asp Thr Lys Val Asn Phe Tyr Ala Trp Lys Arg

```
                65                  70                  75                  80
Met Glu Val Gly Gln Gln Ala Val Glu Val Trp Gln Gly Leu Ala Leu
                    85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 57
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Arg Val Glu Ile Leu Glu Gly Arg Thr Glu Cys Val Lys Ser Asn
1               5                   10                  15

Leu Arg Gly Arg Thr Arg Tyr
            20

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser Ser Ser Ser
1
```